US010119147B2

(12) United States Patent
Denolf et al.

(10) Patent No.: US 10,119,147 B2
(45) Date of Patent: Nov. 6, 2018

(54) ***BRASSICA* PLANTS WITH MODIFIED SEED OIL COMPOSITION**

(71) Applicants: BAYER CROPSCIENCE NV, Diegem (BE); WASHINGTON STATE UNIVERSITY, Pullman, WA (US)

(72) Inventors: Peter Denolf, Velzeke (BE); Shuangyi Bai, Pullman, WA (US); John Browse, Palouse, WA (US)

(73) Assignees: Washington State University, Pullman, WA (US); Bayer CropScience NV, Diegem (BE)

( * ) Notice: Subject to any disclaimer, the term of this patent is extended or adjusted under 35 U.S.C. 154(b) by 731 days.

(21) Appl. No.: 14/412,815

(22) PCT Filed: Jul. 4, 2013

(86) PCT No.: PCT/EP2013/064190
§ 371 (c)(1),
(2) Date: Jan. 5, 2015

(87) PCT Pub. No.: WO2014/006162
PCT Pub. Date: Jan. 9, 2014

(65) Prior Publication Data
US 2015/0159164 A1    Jun. 11, 2015

Related U.S. Application Data

(60) Provisional application No. 61/668,529, filed on Jul. 6, 2012.

(51) Int. Cl.
| | | |
|---|---|---|
| *C12N 15/82* | (2006.01) | |
| *A01H 1/04* | (2006.01) | |
| *A01H 5/10* | (2018.01) | |
| *C12Q 1/6895* | (2018.01) | |
| *C12N 9/12* | (2006.01) | |
| *C11B 1/10* | (2006.01) | |
| *C11C 3/00* | (2006.01) | |
| *A23K 10/30* | (2016.01) | |

(52) U.S. Cl.
CPC ........... *C12N 15/8247* (2013.01); *A01H 1/04* (2013.01); *A01H 5/10* (2013.01); *A23K 10/30* (2016.05); *C11B 1/10* (2013.01); *C11C 3/003* (2013.01); *C12N 9/1288* (2013.01); *C12N 15/8218* (2013.01); *C12Q 1/6895* (2013.01); *C12Y 207/08002* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 5,985,557 A | 11/1999 | Prudent et al. | |
| 6,001,567 A | 12/1999 | Brow et al. | |
| 2005/0039233 A1 | 2/2005 | Yao et al. | |
| 2007/0022502 A1 | 1/2007 | Ohlrogge et al. | |
| 2008/0168587 A1 | 7/2008 | Yao et al. | |
| 2009/0064784 A1 | 3/2009 | Wang | |
| 2011/0131678 A1* | 6/2011 | Browse | C12N 9/1288 800/276 |

FOREIGN PATENT DOCUMENTS

| | | |
|---|---|---|
| WO | WO 89/03887 | 5/1989 |
| WO | WO 89/10396 | 11/1989 |
| WO | WO 92/13956 | 8/1992 |
| WO | WO 96/06932 | 3/1996 |
| WO | WO 97/13865 | 4/1997 |
| WO | WO 98/45461 | 10/1998 |
| WO | WO 99/53050 | 10/1999 |
| WO | WO 00/01133 | 1/2000 |
| WO | WO 02/059294 A1 | 8/2002 |
| WO | WO 03/014347 A2 | 2/2003 |
| WO | WO 03/076619 A1 | 9/2003 |
| WO | WO 2006/005807 A1 | 1/2006 |
| WO | WO 2006/074400 A2 | 7/2006 |
| WO | WO 2006/105946 A2 | 10/2006 |
| WO | WO 2009/002150 A1 | 12/2008 |
| WO | WO 2009/007091 A2 | 1/2009 |
| WO | WO 2009/064784 A1 | 5/2009 |
| WO | WO 2009/073738 A1 | 6/2009 |
| WO | WO 2009/077478 A2 | 6/2009 |
| WO | WO 2009/111587 A2 | 9/2009 |
| WO | WO 2009/125826 A1 | 11/2009 |

(Continued)

OTHER PUBLICATIONS

Lu et al (An enzyme regulating triacylglycerol composition is encoded by the ROD1 gene of *Arabidopsis*. PNAS, 106: 18837-18842, Nov. 3, 2009).*
An et al., "Conserved Expression of the *Arabidopsis* ACT1 and ACT3 Actin Subclass in Organ Primordia and Mature Pollen, " *The Plant Cell*, 8:15-30, 1996.
Azpiroz-Leehan et al., "T-DNA insertion mutagenesis in *Arabidopsis*: going back and forth," *TIG*, 13(4):152-156, 1997.
Broun et al., "Genetic Engineering of Plant Lipids," *Annu. Rev. Nutr.*, 19:197-216, 1999.
Browse, John, "Glycerolipid Synthesis: Biochemistry and Regulation," *Annu. Rev. Plant Physiol. Plant Mol. Biol.*, 42:467-506, 1991.
Chaubet et al., "Nucleotide sequences of two corn histone H3 genes. Genomic organization of the corn histone H3 and H4 genes," *Plant Molecular Biology*, 6:253-263, 1986.

(Continued)

*Primary Examiner* — Medina A Ibrahim
*Assistant Examiner* — Wayne Zhong
(74) *Attorney, Agent, or Firm* — Klarquist Sparkman, LLP

(57) ABSTRACT

The present invention relates to *Brassica* plants comprising mutant phosphatidylcholine:diacylglycerol cholinephosphotransferase encoding (ROD1) genes, ROD1 nucleic acid sequences and proteins, as well as methods for generating and identifying said plants and alleles, which can be used to plants with increased levels of C18:1 in the seeds.

8 Claims, 9 Drawing Sheets

Specification includes a Sequence Listing.

(56) References Cited

FOREIGN PATENT DOCUMENTS

| WO | WO 2011/060946 A1 | 5/2011 |
|----|-------------------|--------|
| WO | WO 2014/006162 A1 | 1/2014 |

OTHER PUBLICATIONS

Christensen et al., "Maize polyubiquitin genes: structure, thermal perturbation of expression and transcript splicing, and promoter activity following transfer to protoplasts by electroporation," *Plant Molecular Biology* 18:675-689, 1992.

De Block et al., "Transformation of *Brassica napus* and *Brassica oleracea* Using *Agrobacterium tumefaciens* and the Expression of the bar and neo Genes in the Transgenic Plants," *Plant Physiol.*, 91:694-701, 1989.

De Pater et al., "The promoter of the rice gene GOS2 is active in various different monocot tissues and binds rice nuclear factor ASF-1," *The Plant Journal*, 2(6):837-844, 1992.

Depicker et al., "Nopaline Synthase: Transcript Mapping and DNA Sequence," *Journal of Molecular and Applied Genetics*, 1(6):561-573, 1982.

Gunstone, F. D., "Movements Towards Tailor-Made Fats," *Prog. Lipid Res.*, 37(5):277-305, 1998.

Harpster et al., "Relative strengths of the 35S cauliflower mosaic virus, 1', 2', and nopaline synthase promoters in transformed tobacco sugarbeet and oilseed rape callus tissue," *Mol Gen Genet*, 212:182-190, 1988.

Henikoff et al., "TILLING. Traditional Mutagenesis Meets Functional Genomics," *Plant Physiology*, 135:630-636, 2004.

Hudspeth et al., "Structure and expression of the maize gene encoding the phosphoenolpyruvate carboxylase isozyme involved in $C_4$ photosynthesis," *Plant Molecular Biology*, 12:579-589, 1989.

Jaworski et al., "Industrial oils from transgenic plants," *Current Opinion in Plant Biology*, 6:178-184, 2003.

Keil et al., "Both wound-inducible and tuber-specific expression are mediated by the promoter of a single member of the potato proteinase inhibitor II gene family," *The EMBO Journal*, 8(5):1323-1330, 1989.

Keller et al., "Glycine-rich cell wall proteins in bean: gene structure and association of the protein with the vascular system," *The EMBO Journal*, 7(12):3625-3633, 1988.

Keller et al., "Specific expression of a novel cell wall hydroxyproline-rich glycoprotein gene in lateral root initiation," *Genes Dev.*, 3:1639-1646, 1989.

Lee et al., "Biochemical Characterization of Temperature-Induced Changes in Lipid Metabolism in a High Oleic Acid Mutant of *Brassica rapa,*" *Arch Biochem Biophys.*, 315(1):203-211, 1994.

Li et al., "A fast neutron deletion mutagenesis-based reverse genetics system for plants," *The Plant Journal*, 27:235-242, 2001.

Li et al., "Reverse genetics by fast neutron mutagenesis in higher plants," *Funct Integr Genomics*, 2:254-258, 2002.

Lu et al., "An enzyme regulating triacylglycerol composition is encoded by the ROD1 gene of *Arabidopsis*," Published online Oct. 15, 2009. doi: 10.1073/pnas.0908848106.

McCallum et al., "Targeted screening for induced mutations," *Nature Biotechnology*, 18:455-457, 2000.

McCallum et al., "Targeting Induced Local Lesions IN Genomes (TILLING) for Plant Functional Genomics," *Plant Physiology*, 123:439-442, 2000.

McElroy et al., "Isolation of an Efficient Actin Promoter for Use in Rice Transformation," *The Plant Cell*, 2:163-171, 1990.

McKenzie et al., "Tissue-culture enhanced transposition of the maize transposable element Dissociation in *Brassica oleracea* var. 'Italica'," *Theor Appl Genet*, 105:23-33, 2002.

Miquel et al., "*Arabidopsis* Mutants Deficient in Polyunsaturated Fatty Acid Synthesis," J Biol Chem., 267(3):1502-1509, 1992.

Mortazavi et al., "Mapping and quantifying mammalian transcriptomes by RNA-Seq," *Nature Methods*, 5(7):621-628, 2008.

Needleman et al., "A General Method Applicable to the Search for Similarities in the Amino Acid Sequence of Two Proteins," *J. Mol. Biol.*, 48:443-453, 1970.

Okuley et al., "*Arabidopsis* FAD2 Gene Encodes the Enzyme That Is Essential for Polyunsaturated Lipid Synthesis," *The Plant Cell*, 6:147-158, 1994.

Peleman et al., "Structure and expression analyses of the S-adenosylmethionine synthetase gene family in *Arabidopsis thaliana,*" *Gene.*, 84:359-369, 1989.

Rice et al., "EMBOSS: The European Molecular Biology Open Software Suite," *TIG*, 16(6):276-277, 2000.

Stoutjesdijk et al., "High-oleic acid Australian *Brassica napus* and *B. juncea* varieties produced by co-suppression of endogenous Δ12-desaturases," *Biochemical Society Transactions*, 28(6):938-940, 2000.

Verdaguer et al., "Isolation and expression in transgenic tobacco and rice plants, of the cassava vein mosaic virus (CVMV) promoter," *Plant Molecular Biology*, 31:1129-1139, 1996.

\* cited by examiner

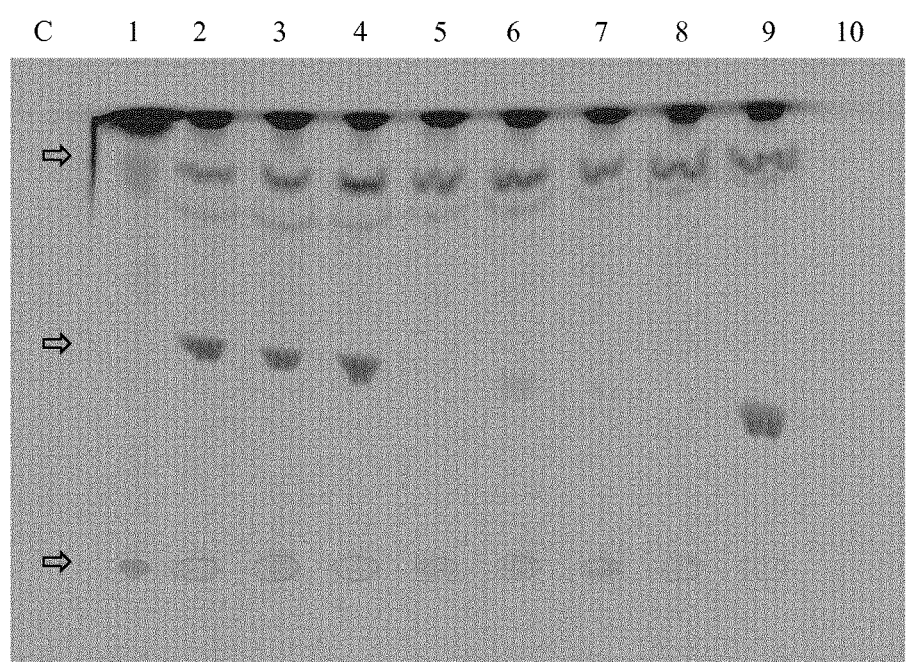
Figure 2, continued.

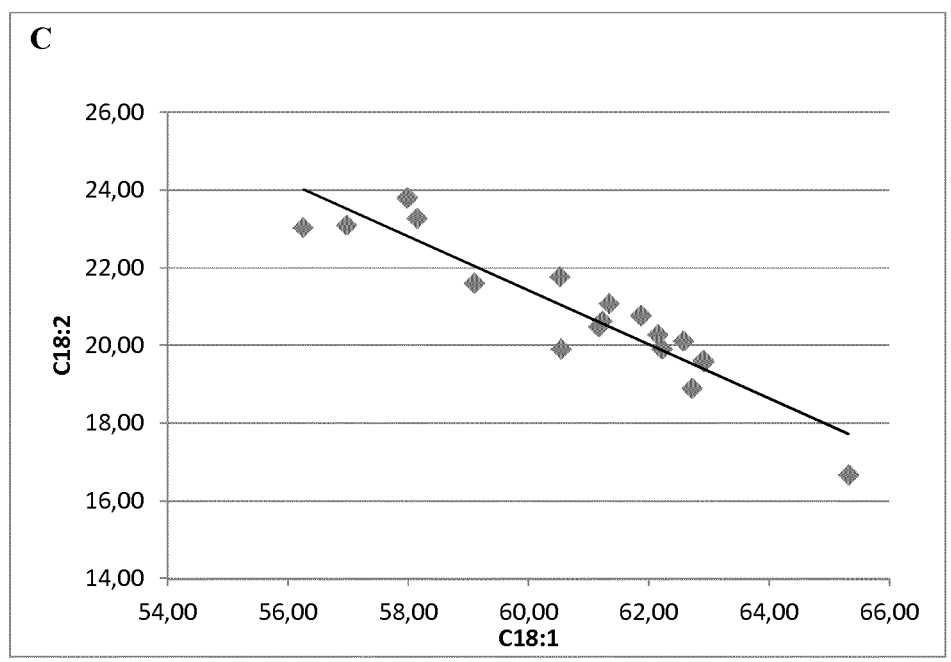
Figure 3, continued.

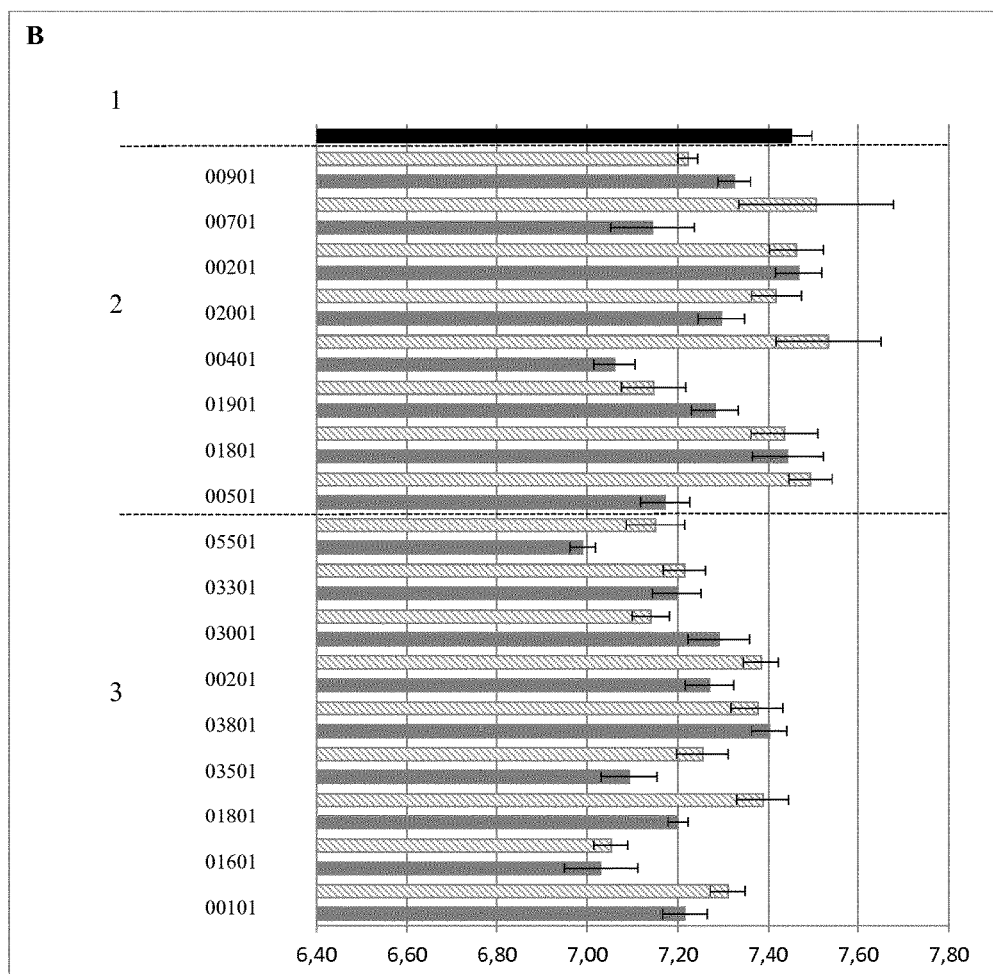
Figure 4, continued

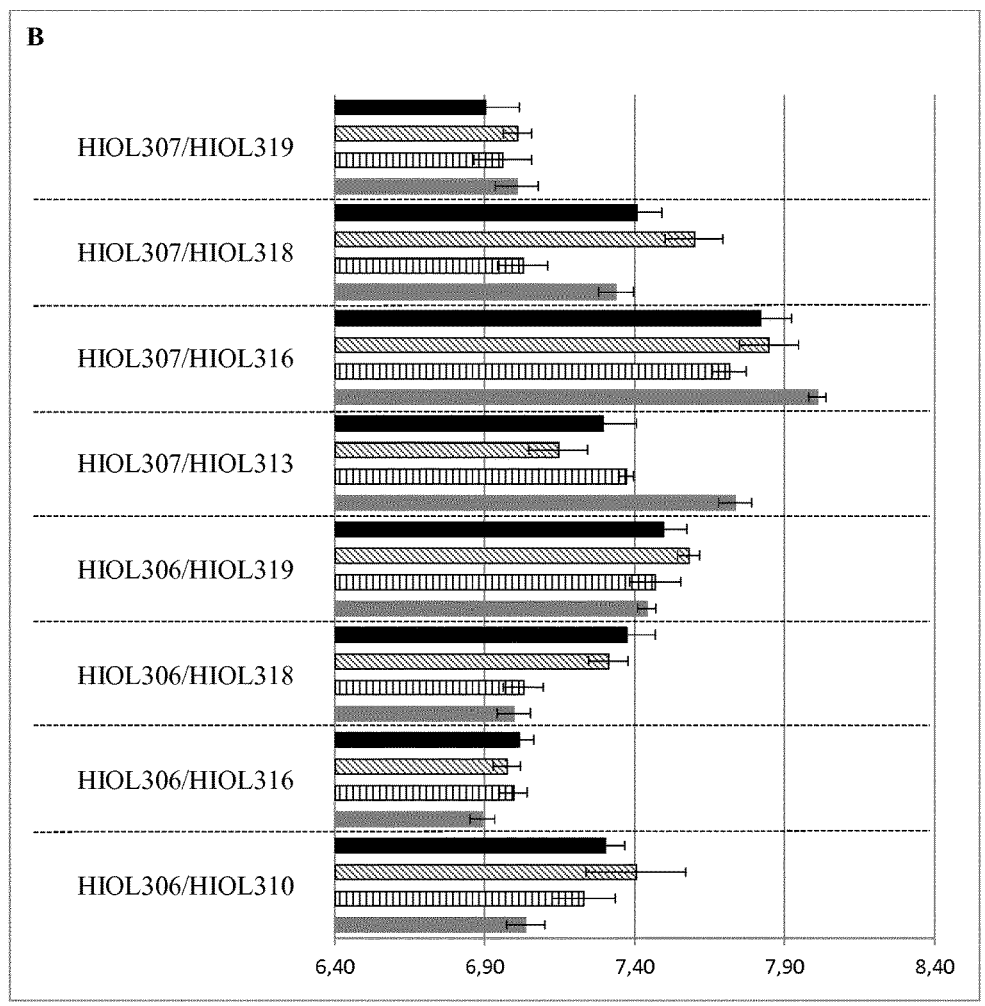
Figure 5, continued.

SEQUENCE LISTING

<160> NUMBER OF SEQ ID NOS: 91

<210> SEQ ID NO 1
<211> LENGTH: 3630
<212> TYPE: DNA
<213> ORGANISM: Brassica napus
<220> FEATURE:

```
<221> NAME/KEY: Intron
<222> LOCATION: (1027)..(1766)
<223> OTHER INFORMATION: First intron
<220> FEATURE:
<221> NAME/KEY: variation
<222> LOCATION: (1786)..(1786)
<223> OTHER INFORMATION: C to T in HIOL301
<220> FEATURE:
<221> NAME/KEY: variation
<222> LOCATION: (1802)..(1802)
<223> OTHER INFORMATION: G to A in HIOL302
<220> FEATURE:
<221> NAME/KEY: variation
<222> LOCATION: (1804)..(1804)
<223> OTHER INFORMATION: C to T in HIOL303
<220> FEATURE:
<221> NAME/KEY: variation
<222> LOCATION: (1818)..(1818)
<223> OTHER INFORMATION: G to A in HIOL304
<220> FEATURE:
<221> NAME/KEY: variation
<222> LOCATION: (1822)..(1822)
<223> OTHER INFORMATION: G to A in HIOL305
<220> FEATURE:
<221> NAME/KEY: variation
<222> LOCATION: (1834)..(1834)
<223> OTHER INFORMATION: C to T in HIOL306
<220> FEATURE:
<221> NAME/KEY: variation
<222> LOCATION: (1866)..(1866)
<223> OTHER INFORMATION: G to A in HIOL307
<220> FEATURE:
<221> NAME/KEY: Intron
<222> LOCATION: (1905)..(2760)
<223> OTHER INFORMATION: Second intron

<400> SEQUENCE: 1
aactctaggt tatgttcgaa ttcaatttct ggaatatttt gtgctaaacc gacatgtaac      60
aaactaaatg tcttcttcta tgttttttc gacaactaca ctgttatgga gggacgtgca     120
ataattatct taaaaacgtg aaacgatgtg cgccaaaagg aatcatataa tcctcaatga    180
cattataaac tagtccttat tcaacaaagg agaaaatctt ttgatattct ccataatctt    240
gaattaaagg tatatataca cattgttaat acgcacacca ctaacatgta ttagtgtgaa    300
caaaactagt tattatacta tggtaaggaa actctcgtac tcttctctat cttttttgtgt   360 gtgtttctcg tgtaaaatat tatacactta agacgtataa aaagaacaac aagtaaagcc    420
caacaaagac agatgagaaa atagcaaaga cttgcgtaaa cgtcgctctc aaacctcatc    480
tcatactcat cgttttcgta tgagttttg tagcccaaac aatcttcctt tctacagttt     540
ataatataag aaacaatact tccttcgtaa tctccgcctc gtatctctta tataactcat    600
ctctctaaac ctaaaaatg ttcctctccg ttaaatctaa cggtcatgtc aactaatacc     660
gtcgtccctc tccgtcgcag atctaacgga tatcacacta acggcgtggc ctttaacgga    720
atggataata ttgtcaagaa aaccgacgac tgctacacca acgcaacgg caacggagga     780 gtagagagaa gcaaagcctc gtttctgaca tggaccatgc gtgacgctgt ctacgtagcg    840
agataccatt ggataccgtg tttctttgcg gtcggagttc tgttctttat gggggttgag    900
tacacgctcc agatggttcc ggcgaagtct gagccgttcg atattgggtt tgtggccacg    960
cgctctctaa accgcgtctt ggcgagttca ccggatctta acacccttttt agcggctcta  1020 aacacggtat gtcgtatgag ttaatttagg ttaaaactat atttaatggt tatcttcaat   1080
tcttcatgcc acacctaaca ttttgtattt tttctttgtc atttaattcg taataatata   1140
ttgaattagt caaaataaaa taggtggggt tagtgatgga tatacataaa tctcagatct   1200 tttccttat tttgtgtggt attaactatc cagctggagt ttttccgtcc agggtatcat    1260
```

```
gcaacgatat ttaagagttg atttgagttt agaacgcatt tttataaaga tacatgtttt    1320
acaaaaataa atttatttca aaaatatatt ttctatgtat taattatact tattaatttt    1380
ttgttaattt taatttgtga aaatagataa tcataacaat aatgtattta taatcaaaat    1440
ttaatatttt aataagtata gaaactctaa aacatatata ttgtgaaaca cacagaaatag   1500 gtagtgggca aaaatgtatt taatgtaatc tcagctatca aagtagttgt ataattttat    1560
ttttaacaac tgccattttt ttttgtttt ctttataaag aagtagtaca ataatagatt     1620
agattgcttt taactttaaa gtttcaaccc aatgaaaagg gacacatggt gatgagttgg    1680
agacatgatc acatgcaatg caaagagatt ggttagattc gatttggtac ttgtaactat    1740
ttaatattgg tggatggtgg ggacaggtat tcgtagcgat gcaaacgacg tatattgtat    1800
ggacatggtt gatggaagga agaccacgag ccactatctc ggcttgcttc atgtttactt    1860
gtcgcggcat tcttggttac tctactcagc tccctctacc acaggtctct cacctctta    1920 cataaatatt agtatattat actctactca gctccctcta ccttactctt ataatatatt    1980
tatattggca ttgtagtaaa tatatttaat tatgtcaagt ctttagatat tgttggacat    2040
gtgattttcc cttggccgtt tccatataga aaacagttgt aactttatag gccccaaata    2100
ttttgaactt tttattttca ttataacaaa agactatata ttataataat ttactcttaa    2160
aattaatata tagatattgt accaaatcga tgtatttatg tagtccctat atattgttgg    2220
acgtgtgatt tccccttggc cactaccgta cagaggacag ctgtaattac agtccccaaa    2280
tattctttta atccggacat ctaaactaca aaattattgt ttcacaaaac acctgatttc    2340
tttaacaaaa gcaaaacaat ttaatttatg aatgttcgtt ttataccttt tatttatagg    2400
gttaaattat ttattatatt tcaaaattta tattgaaata ctaaataaca ctttgaaaaac   2460 agaaagatgt aaatgataac tcattctgaa atggaaagag caatctggtt gttagcatag    2520
agagggaggg taatttgcag tggattgtat tttactgttt tgttttgttt ttgtttgcta    2580
ccgactaccg aggaccgaac tttttttctat ctatcaaaaa atgttccacg ggatgattga    2640
ctggacataa atcacattgt ctcactcctc tgcgttctac agttctagtt ttttttaaag    2700
actactttct tatgttcaag gatacaatga ttgaaggtaa ttatttgact cttttttacag   2760 gattttttag gatcaggagt tgattttccg gtgggaaacg tctcattctt cctcttctat    2820
tctggccacg tagccggttc aatgatcgca tccttggaca tgaggagaat gcagaggttg    2880
agactagcga tgcttttgga catcctcaac atattacaat cgatcagact gctcgggacg    2940
agaggacact acacgatcga tcttgcggtc ggagttggcg ctgggattct ctttgactca    3000
ttggccggga agtacgaaga gatgatgagc aagagacaca atttagccaa tggttttagt    3060
ttgatttcta aagactcgct agtcaattaa tcttttgttt tcattttaaa tgattagttg    3120
aacttgaaca tatttgattt agttaaagac ttaaagtcca atgaattaca ttttttttct    3180
ttcaacttta attgaatagg gtttcattag tttacttgaa cctaattaaa tgtgtacgtt    3240
attgtgaaat atagaggttt gttgtggcct tcctacaact atttcattca attcaatgtt    3300
agcagttgca tgtgagtcca tccgaaattc ataggctcta caacttagta aaaacattgc    3360
catataaatt tgataaaaaa ttataactta aacagataaa tcacaataaa atcatttat    3420 tcaactgaat ggtgttttat aacattctga tataagtata aaagtattca aattgaaaaa    3480
tcattcgacc atattggtat tgcgtatact gccaatatgc aaaatttaat gatacaaaaa    3540
atccggcatt aaattattaa tgtacttcct tcaccatttt tggtgcaaca tgtgtttgt     3600
```

-continued

```
tttccaagag taggtcaaga tggttttcgt                                    3630
```

<210> SEQ ID NO 2
<211> LENGTH: 1415
<212> TYPE: DNA
<213> ORGANISM: Brassica napus
<220> FEATURE:
<221> NAME/KEY: CDS
<222> LOCATION: (252)..(1100)
<220> FEATURE:
<221> NAME/KEY: variation
<222> LOCATION: (652)..(652)
<223> OTHER INFORMATION: C to T in HIOL301
<220> FEATURE:
<221> NAME/KEY: variation
<222> LOCATION: (668)..(668)
<223> OTHER INFORMATION: G to A in HIOL302
<220> FEATURE:
<221> NAME/KEY: variation
<222> LOCATION: (670)..(670)
<223> OTHER INFORMATION: C to T in HIOL303
<220> FEATURE:
<221> NAME/KEY: variation
<222> LOCATION: (684)..(684)
<223> OTHER INFORMATION: G to A in HIOL304
<220> FEATURE:
<221> NAME/KEY: variation
<222> LOCATION: (688)..(688)
<223> OTHER INFORMATION: G to A in HIOL305
<220> FEATURE:
<221> NAME/KEY: variation
<222> LOCATION: (700)..(700)
<223> OTHER INFORMATION: C to T in HIOL306
<220> FEATURE:
<221> NAME/KEY: variation
<222> LOCATION: (732)..(732)
<223> OTHER INFORMATION: G to A in HIOL307

<400> SEQUENCE: 2

```
gtataaaaag aacaacaagt aaagcccaac aaagacagat gagaaaatag caaagacttg      60
cgtaaacgtc gctctcaaac ctcatctcat actcatcgtt ttcgtatgag ttttttgtagc    120 ccaaacaatc ttcctttcta cagtttataa tataagaaac aatacttcct tcgtaatctc    180
cgcctcgtat ctcttatata actcatctct ctaaacctaa aaaatgttcc tctccgttaa    240
atctaacggt c atg tca act aat acc gtc gtc cct ctc cgt cgc aga tct     290
            Met Ser Thr Asn Thr Val Val Pro Leu Arg Arg Arg Ser
              1               5                  10 aac gga tat cac act aac ggc gtg gcc ttt aac gga atg gat aat att      338
Asn Gly Tyr His Thr Asn Gly Val Ala Phe Asn Gly Met Asp Asn Ile
         15                  20                  25 gtc aag aaa acc gac gac tgc tac acc aac ggc aac ggc aac gga gga      386
Val Lys Lys Thr Asp Asp Cys Tyr Thr Asn Gly Asn Gly Asn Gly Gly
 30                  35                  40                  45 gta gag aga agc aaa gcc tcg ttt ctg aca tgg acc atg cgt gac gct      434
Val Glu Arg Ser Lys Ala Ser Phe Leu Thr Trp Thr Met Arg Asp Ala
                 50                  55                  60 gtc tac gta gcg aga tac cat tgg ata ccg tgt ttc ttt gcg gtc gga      482
Val Tyr Val Ala Arg Tyr His Trp Ile Pro Cys Phe Phe Ala Val Gly
             65                  70                  75 gtt ctg ttc ttt atg ggg gtt gag tac acg ctc cag atg gtt ccg gcg      530
Val Leu Phe Phe Met Gly Val Glu Tyr Thr Leu Gln Met Val Pro Ala
         80                  85                  90 aag tct gag ccg ttc gat att ggg ttt gtg gcc acg cgc tct cta aac      578
Lys Ser Glu Pro Phe Asp Ile Gly Phe Val Ala Thr Arg Ser Leu Asn
     95                 100                 105 cgc gtc ttg gcg agt tca ccg gat ctt aac acc ctt tta gcg gct cta      626
Arg Val Leu Ala Ser Ser Pro Asp Leu Asn Thr Leu Leu Ala Ala Leu
```

```
                 110              115              120             125
    aac acg gta ttc gta gcg atg caa acg acg tat att gta tgg aca tgg    674
    Asn Thr Val Phe Val Ala Met Gln Thr Thr Tyr Ile Val Trp Thr Trp
                     130              135             140 ttg atg gaa gga aga cca cga gcc act atc tcg gct tgc ttc atg ttt    722
    Leu Met Glu Gly Arg Pro Arg Ala Thr Ile Ser Ala Cys Phe Met Phe
                 145              150             155 act tgt cgc ggc att ctt ggt tac tct act cag ctc cct cta cca cag    770
    Thr Cys Arg Gly Ile Leu Gly Tyr Ser Thr Gln Leu Pro Leu Pro Gln
                 160              165             170 gat ttt tta gga tca gga gtt gat ttt ccg gtg gga aac gtc tca ttc    818
    Asp Phe Leu Gly Ser Gly Val Asp Phe Pro Val Gly Asn Val Ser Phe
                 175              180             185 ttc ctc ttc tat tct ggc cac gta gcc ggt tca atg atc gca tcc ttg    866
    Phe Leu Phe Tyr Ser Gly His Val Ala Gly Ser Met Ile Ala Ser Leu
    190              195              200             205 gac atg agg aga atg cag agg ttg aga cta gcg atg ctt ttt gac atc    914
    Asp Met Arg Arg Met Gln Arg Leu Arg Leu Ala Met Leu Phe Asp Ile
                         210              215             220 ctc aac ata tta caa tcg atc aga ctg ctc ggg acg aga gga cac tac    962
    Leu Asn Ile Leu Gln Ser Ile Arg Leu Leu Gly Thr Arg Gly His Tyr
                 225              230             235 acg atc gat ctt gcg gtc gga gtt ggc gct ggg att ctc ttt gac tca   1010
    Thr Ile Asp Leu Ala Val Gly Val Gly Ala Gly Ile Leu Phe Asp Ser
                 240              245             250 ttg gcc ggg aag tac gaa gag atg atg agc aag aga cac aat tta gcc   1058
    Leu Ala Gly Lys Tyr Glu Glu Met Met Ser Lys Arg His Asn Leu Ala
                 255              260             265 aat ggt ttt agt ttg att tct aaa gac tcg cta gtc aat taa           1100
    Asn Gly Phe Ser Leu Ile Ser Lys Asp Ser Leu Val Asn
    270              275              280 tcttttgttt tcattttaaa tgattagttg aacttgaaca tatttgattt agttaaagac 1160
ttaaagtcca atgaattaca tttttttct  ttcaacttta attgaatagg gtttcattag 1220
tttacttgaa cctaattaaa tgtgtacgtt attgtgaaat atagaggttt gttgtggcct 1280
tcctacaact atttcattca attcaatgtt agcagttgca tgtgagtcca tccgaaattc 1340
ataggctcta caacttagta aaaacattgc catataaatt tgataaaaaa ttataactta 1400
aacagataaa tcaca                                                  1415

<210> SEQ ID NO 3
<211> LENGTH: 282
<212> TYPE: PRT
<213> ORGANISM: Brassica napus

<400> SEQUENCE: 3

Met Ser Thr Asn Thr Val Val Pro Leu Arg Arg Arg Ser Asn Gly Tyr
1               5                   10                  15

His Thr Asn Gly Val Ala Phe Asn Gly Met Asp Asn Ile Val Lys Lys
                20                  25                  30

Thr Asp Asp Cys Tyr Thr Asn Gly Asn Gly Asn Gly Gly Val Glu Arg
            35                  40                  45

Ser Lys Ala Ser Phe Leu Thr Trp Thr Met Arg Asp Ala Val Tyr Val
        50                  55                  60

Ala Arg Tyr His Trp Ile Pro Cys Phe Phe Ala Val Gly Val Leu Phe
65                  70                  75                  80

Phe Met Gly Val Glu Tyr Thr Leu Gln Met Val Pro Ala Lys Ser Glu
                85                  90                  95
```

```
Pro Phe Asp Ile Gly Phe Val Ala Thr Arg Ser Leu Asn Arg Val Leu
            100                 105                 110

Ala Ser Ser Pro Asp Leu Asn Thr Leu Leu Ala Ala Leu Asn Thr Val
            115                 120                 125

Phe Val Ala Met Gln Thr Thr Tyr Ile Val Trp Thr Trp Leu Met Glu
130                 135                 140

Gly Arg Pro Arg Ala Thr Ile Ser Ala Cys Phe Met Phe Thr Cys Arg
145                 150                 155                 160

Gly Ile Leu Gly Tyr Ser Thr Gln Leu Pro Leu Pro Gln Asp Phe Leu
                165                 170                 175

Gly Ser Gly Val Asp Phe Pro Val Gly Asn Val Ser Phe Phe Leu Phe
            180                 185                 190

Tyr Ser Gly His Val Ala Gly Ser Met Ile Ala Ser Leu Asp Met Arg
            195                 200                 205

Arg Met Gln Arg Leu Arg Leu Ala Met Leu Phe Asp Ile Leu Asn Ile
210                 215                 220

Leu Gln Ser Ile Arg Leu Leu Gly Thr Arg Gly His Tyr Thr Ile Asp
225                 230                 235                 240

Leu Ala Val Gly Val Gly Ala Gly Ile Leu Phe Asp Ser Leu Ala Gly
                245                 250                 255

Lys Tyr Glu Glu Met Met Ser Lys Arg His Asn Leu Ala Asn Gly Phe
            260                 265                 270

Ser Leu Ile Ser Lys Asp Ser Leu Val Asn
            275                 280

<210> SEQ ID NO 4
<211> LENGTH: 10695
<212> TYPE: DNA
<213> ORGANISM: Brassica napus
<220> FEATURE:
<221> NAME/KEY: Intron
<222> LOCATION: (1597)..(2907)
<223> OTHER INFORMATION: First intron
<220> FEATURE:
<221> NAME/KEY: variation
<222> LOCATION: (2907)..(2907)
<223> OTHER INFORMATION: G to A in HIOL317
<220> FEATURE:
<221> NAME/KEY: variation
<222> LOCATION: (2917)..(2917)
<223> OTHER INFORMATION: G to A in HIOL308
<220> FEATURE:
<221> NAME/KEY: variation
<222> LOCATION: (2930)..(2930)
<223> OTHER INFORMATION: C to T in HIOL309
<220> FEATURE:
<221> NAME/KEY: variation
<222> LOCATION: (2956)..(2956)
<223> OTHER INFORMATION: G to A in HIOL310
<220> FEATURE:
<221> NAME/KEY: variation
<222> LOCATION: (2963)..(2963)
<223> OTHER INFORMATION: G to A in HIOL311
<220> FEATURE:
<221> NAME/KEY: variation
<222> LOCATION: (2968)..(2968)
<223> OTHER INFORMATION: C to T in HIOL318 and HIOL319
<220> FEATURE:
<221> NAME/KEY: variation
<222> LOCATION: (2981)..(2981)
<223> OTHER INFORMATION: C to T in HIOL312
<220> FEATURE:
<221> NAME/KEY: variation
<222> LOCATION: (3004)..(3004)
<223> OTHER INFORMATION: G to A in HIOL313
<220> FEATURE:
```

```
<221> NAME/KEY: variation
<222> LOCATION: (3007)..(3007)
<223> OTHER INFORMATION: G to A in HIOL314
<220> FEATURE:
<221> NAME/KEY: variation
<222> LOCATION: (3040)..(3040)
<223> OTHER INFORMATION: C to T in HIOL315
<220> FEATURE:
<221> NAME/KEY: Intron
<222> LOCATION: (3046)..(9944)
<223> OTHER INFORMATION: Second intron
<220> FEATURE:
<221> NAME/KEY: variation
<222> LOCATION: (3046)..(3046)
<223> OTHER INFORMATION: G to A in HIOL316

<400> SEQUENCE: 4
```

| | | | | | |
|---|---|---|---|---|---|
| tgtaaaaaca | aatagaggag | gtaacatggc | aaaaatatag | tttcttattg | accaattatt | 60 |
| ttcgcctacg | tggacattct | atctacggct | tatatcatct | ttttattact | tgttttgata | 120 |
| ttgtcaggat | aaaattaagc | ccattattta | cgatactagg | aaaaaagtgt | ccaaagattt | 180 |
| aaaatattgt | tttattgatc | aaatagcaaa | cattcaatgc | ataagagtga | aaaacttaga | 240 |
| tttagatgtt | tgtttgttgt | ataagtaggt | tggtaggttc | gtttcatctc | ttcgagtttt | 300 |
| gagtttgtat | ttataaagac | aatcgaatat | atctttaat | atcataaaaa | aattgtgtat | 360 |
| attctagata | ttataatata | tttatctaca | agacttttt | tatcattaaa | cacgagtttc | 420 |
| ctctagtcca | atagacatta | tgaattcttc | ctagctatga | aactggcgtt | tggtgtattg | 480 |
| atttttaacca | aaataacatc | ttctgaatta | atttatgtcc | aacatctaat | ataaatatac | 540 |
| gaaacctaca | gtaattatat | gatattgaac | agttaaaact | cttggttatg | ttcgaattca | 600 |
| atttctcgaa | tattttgtgc | taaaccgaca | tgtaacaaac | taaatgtctt | cttctatgtt | 660 |
| ttttttcgaca | actacactgt | tatggaggga | cgtgcaataa | ttgtcttaaa | aacgtgaaac | 720 |
| gatgtgcgcc | aaaaggaatc | atataatcct | caatgacatt | ataaactagt | ccttattcaa | 780 |
| caaaggagaa | aatctttga | tattctccat | tatcttgaat | taaaggtata | tatacacatt | 840 |
| gttaatacgc | acaccactaa | catgtattag | tgtgaacaaa | actagtcatt | atactatggt | 900 |
| aaggaaactc | tcatactctt | ctctatcttt | ttgtgtgtgt | ttttcgtgta | aaatattata | 960 |
| cacttaagac | atataaaaag | aacaacaagt | aaagcccaac | aaagacagat | gagaaaatag | 1020 |
| caaagacttg | cgtaaacgtc | gctctcaaac | ctcatctcat | actcatcgtt | tcgtatgag | 1080 |
| tttctgtagc | ccaaacaatc | ttcctttcta | cggtttataa | tataagaaac | aatacttcct | 1140 |
| tcgtaatctc | cgccttgtat | ctcttatata | actcatctct | ctaaacctaa | aaaatgttcc | 1200 |
| tctccgttaa | atctaacggt | catgtcaact | aataccgtcg | tccctctccg | tcgcagatct | 1260 |
| aacggatatc | acactaacgg | cgtggccttc | aacggaatgg | agaacattgt | caagaaaacc | 1320 |
| gacgactgct | acaccaatgg | caacggagta | ggagggaaga | gcaaggcgtc | gtttctgaca | 1380 |
| tggaccatgc | gtgacgctgt | ctacgtagcg | agataccatt | ggataccgtg | tttctttgcg | 1440 |
| gtcggagttc | tgttctttat | ggggttgag | tacacgctcc | agatggttcc | ggcgaagtct | 1500 |
| gagccgttcg | atattgggtt | tgtggccacg | cgctctctga | accgcgtctt | ggcgagttca | 1560 |
| ccggatctta | acacccttt | ggcggctcta | aacacggtat | gtcgtatgag | ttaatttagg | 1620 |
| ttaaaactat | atttaatgat | tatcttcaat | tcttcatgcc | acacggccca | caccaaacat | 1680 |
| tttgtatttt | tcctttgtca | tttaattcgt | aataatatat | tgaattagtc | aaaataaaat | 1740 |
| aggtgggggtt | agtgatggat | atacataaat | ctccagatctt | ttcctttatt | gtgtgtggta | 1800 |
| ttaaactatc | cagctggagt | tttgccgtcc | agggtatcat | gcaatgttta | agagttgatt | 1860 |

```
tgagtttaga actcattttt tataaagata catgttttac aaaaataaat ttatttcaaa    1920
aatacatttt ctatgtatta attatactta ttattatttt gttaatttta atttgtgaaa    1980
gtagataatc ataacaataa tgtatttata atcaaaattt aatattttt aataagtata     2040
gaaactccaa aacatatata tatcgtgaaa cacacagagt aggtagtggt aggtctggga    2100
cggatcgggt atccgggcaa ttttaaggta tccggattcg gatccttatc cggcggatcc    2160
atgatttac tatccttatc cggatccggg gttctcggat atccgggtgt cggatatcct    2220
tctaaaaatt gtaatatccg gcggatatcc ggatccggat ttggatcctt aaaataaata    2280
aaaaataata ttaaaattta taaaatatta aaataaaaaa atatataatg ttttaatta     2340
tttctatgta taatattaca aaatttacat acaatttata tatactctta taaaaatgaa    2400
aatatattaa ataaaattaa tttttatata tagatattac tattttttgaa atagttatta   2460
gtaaaactta cggatccgga tatccggact aaaaaataaa gatatccgga tccggatccg    2520
tcaacaacat tttactatcc ggatccagat tcggccactc cggatatccg gattttcgga    2580
tcggatccgg atcaaatctc ggatcgaatc cggatctcgg ataaaaatcc caggcctagg    2640
tagtgggcat aaatgtattt aatgtaatct cagctatcaa agtagttgta taatttttatt   2700
tttaacaact gccatatttt ttgtttgttt tctttataaa gaagtagtac aataatagat    2760
tagattgctt ttaactttaa agtttcaacc caatgaaaag ggacacatgg tgatgagttg    2820
gagacatgat cacatgcaat gtaaagagat tggttagatt cgatttggta cttgtaacta    2880
tttaatattg gtggatgatg gggacaggta ttcgtagcga tgcaaacgac gtatattgta    2940
tggacatggt tgatggaagg aagaccacga gccactatct cggcttgctt catgtttact    3000
tgtcgcggta ttcttggtta ctctactcag ctccctctac cacaggtctc ccacctcttt    3060
acacaaatat tatattatac tacctctcac tcttataata tatttatatt ggcattgtag    3120
taaatatatt taattatgtc aagtctctag atattgttgg acatgtgatt ttccctttgg    3180
cgtttccata tagaaaacag ttgtaacttt ataggcccca aatattttga acttttttatt   3240
ttcattaaaa caaagactaa tatattataa taatttactc ttaaaattaa tatatagata    3300
ttgtaccaaa tcgatatatt tatgtagtcc ctatatattg ttggacgtgt gatttcccct    3360
tggccactac cgtacggatg acagctgtaa ttacagtccc caaatattct tttaatccgg    3420
acatctaaac tacaaattat tgtttcacaa aacacctgat ttctataaca aaagcaaaac    3480
aatttgattt atgaatgttc gttttatacc ttttatttat agggtaaat tattattatt      3540
ttttcaaaat ttatattgaa atgttgtgaa cttaatgatt tcgagtctct aagttctttt    3600
tattattaat cataacataa agtgccctta tatatgagaa ttacaaagag ataaagaaa     3660
atacataaat atgaaagtg tacagataca agaaaaatga actaggatt tcttttctct      3720
aagtcgcctc tctctctctc tcttgcggcc gcctctctct ctctaggtat tgggccggtt    3780
ctggaccggg ccggttatgg acatccacaa tatgatttat aacactctcc cttggatgcc    3840
ataaccatac atggattgta atacgctttg gatgttgtct cattaaaacc ttaccaggaa    3900
aacccagtgg gacaaaacca tggtgaagga aaaagagtac aacacgtatt actccctctg    3960
ttctgatcat cactgaagat ccttcaattt acccatccca atctgatgcg tgagcttcct    4020
gaatgtagaa gtcggaagtg acttggtgaa taggtaggct aatttgtcgc tggaacgtac    4080
ttggaccctct ccagccttt gcaaatcgtg agtgaagaag aatttcaggc agaatatgct    4140
tcgtcctcga acatgatagt tggtccttct ttaccatcgg ccatgccaca atctgattga    4200
```

```
acatattgag tcatcgacct caaatacaca cacacgaaat cttggatgat gttgctgtga    4260
tatgcgtgta ccaccatgtg taaaacataa ctgtctgaaa aacaaatcaa caaaaccaga    4320
taactcctct ttgggctggt tagtataaaa taaaccaaaa tcaaagactt cttcatcgtc    4380
cttcttatgg accaaacaga tcaatgtcta aaacaagact tctgcatcgt ccatctcagg    4440
aataaatgga cttctttatc gtccacctt t ggactgaatg gatcagtgtc caaaacaagt    4500
gatctcacgc ccatgtacta gataatgggt gaggctgatc catattaaat ctcttgagta    4560
ccctttctg tatatactag ttgatgcaca aggatttcat tgttaatgta ctcaagctgt     4620
aatcccaaac aaaactttgt tttccaagat ctttcatctc aaactctttc ttgagatatt    4680
caactgtttg agaaattgta tccagagttt cctatgatat tcagatcata cactttgatg    4740
atttatcaat attgttctcg agaacttgct gtactttcag ctcaataccc tctagtactt    4800
tcattatcca gtggaccata taaatatgca gtcactacat caatttgctg caagtctaat    4860
tttctctctt atatagccag acttatgaga atctaaaag tagttgcatc caccacatga     4920
gagtatgtct cctcataatc tattactggt ctttgtgaga atccttgtgc aacatcagct    4980
ttatatctca caatttgtat tcttcacaag acccatttat atccactggt tttaacatca    5040
tatgcgtct taatcatatg gccaaatatg cctttcttct ttaaactatt taaccccatg     5100
tttccattca atccaatctg ttctacgagt gcgcactctt atattgacgt gggttcatga    5160
tcctcgctta tattcataaa ttcaagtgct acattgtatg caaataaatc atcttatgtc    5220
gacatttctt attggttcca ttatgttcca gacatgatat aatcgattga gatttattat    5280
tatcaggacc tttaatactt tgcagcttgg cgtcccaagc tacattgttt tggtacctgt    5340
accttagagc cggtcggcct tatcttcatg tctgggatgg tttccttagt aacctcggat    5400
ttggattttg attatcattc tttgcacctt ttttttgttt ccgaggattc ttatcttttg    5460
gaacctattg gtctaccacg tttcatacgt tgtctagact ctgtagcaac ttgactgtgt    5520
ctcttcttgg acatcaaatt cgttggtgct ttacaagctg gtttatatat gacttagtca    5580
ttcttttcg ggtcagcaaa tgtgtctggc atttgattag ctagctttgt aaatgtataa     5640
tctttggacg tccatttcac attctttagc ccgaggatct tgccaagaca ttgatgattg    5700
attccattat atttctttta ccagctttat tattttctc ctcatggtct aaaataatc      5760
tgtgtaccta gcctcaaata taatcacccg tagttggttc aatgtacttt attattgtgg    5820
gagaatcata tccaacatat atccccatcc tccttttgat gtctcatctt agttctctgt    5880
ggtggagcaa ttagtacata gacagcacat ccaaatgtct tatgatggag tatgtctggc    5940
tcttgacctg ttaataattg tgatatggga tatctatgct cactaaatgg cctgatgtgt    6000
attaacttag gtgcatgtaa atttcgtgtg gcccaagctg tgaacgggag ttttaaactc    6060
ataagttatg gtctatcaat cagctatttg cgttttaaaa gatttcggcc aagctgttct    6120
tggtatgaac atgtatcaca gaattgtcca cacttacccc catggacata ccataatcat    6180
ttaaacgctt gggacatgta ttcaccagta ttatctagac atatagtctt tattatgaaa    6240
aagggctcgt agccgtttta ctggtgatgg cctaatgagt ttcccttgtg tacatgctac    6300
acacgtgaga ttctttggga taacttttct tatcttttaa tgtgtgcatt ttgaatatca    6360
attttcgcat catgtttgga ccaggatggc caatccggtc gtgccataaa gtgtatattt    6420
agcaggcttt tagcctttat catactgatc tatgcatagt ctaggtcagt agagaatgca    6480
ggtatagtct ttaggactta ttatggcctt ggacgatttt atacatatat ctgaaggaac    6540
tatttgtttc cttcgcccat tgtttcaata tggaaaccat tcattctttt atctttaaaa    6600
```

```
ctcaatagac tgctcttact cttagagctg ggtgaatata aggcatcact gatttctaga    6660
tgcatacsct tagggaataa tatattagcc taaccatagt cttctttcag actggcgata    6720
cctgctttag tacttatatt ggcgtttttc agtgtactca tatagaaaaa tcattcattc    6780
atttaatcta agcagacaat gtaatagaaa taaattcaag gagataaaaa tcagagaaaa    6840
catacaagca aagcaatcac acaagtttga tgtcgaaatc agattatcaa cttgattctt    6900
ttaggcaatc ataagtctca tattccataa gatcatcttg atcatgttcg aaattatttt    6960
caccatcttt atagaccaag tgggtttcag gattcttccc tttcagactc actttgatag    7020
aggtcacata aatttttgga agtccttcat atcttagtcc aatggttccc cattccacat    7080
ctatgacaca atgatttggt cgagctttgt ggtttaaagg ataccaca accactgtct      7140 tgaccatggc tcaaattggg tatcccaca gcctctgcca tagtgattct cacggccaaa     7200
tgtgttgtag tggccatggc catgtccttt ttaccctcca cggccatggc cgtgtggtct    7260
atcatcctgg acgtggttag attctttgga ttttttcttt tcctttgcgg ccttattggc    7320
ttcaggtaat ggggttgatc caggaggtct caattcattg tttcttatta gctagcaata    7380
gactcatcca cggacttgta gtcctggatt ttgagattcc tccatagctt ttggtaataa    7440
cacctttctt tggtgatcat atctcgattt gaattatgtc caaaggtcta gaggattctc    7500
aattgtcaaa tactgatctt tgagactctc aataagatga tggcgaataa ttaatatttc    7560
cctgtatcaa ttttctcat ttggcattat cgtcttttg tgattcattc accaagtctt      7620
ttgactttag gataaactca gtatccagtg cccatttcaa ataattatct tctgagagat    7680
ttggggcagc aaaatccaag ttgattttcg acatctcaaa tcaaatatca atcaatttta    7740
gatctcataa aatatttaac atacaaccat aaacaagaca tgctatcaag tcaatacatt    7800
tctaataagc aaacaagcca cacgaccaaa ggtgatataa tgcaataagg ccacacggcc    7860
aaagtgatat atgatgcata ataagtcaca cagatttatc aagcaagagt atcgaccaaa    7920
caagatattt ctatatgttt tcatgcggcc atatggttat aatgcaaacc tagcatactg    7980
attctatatg tacatgagtg gaattatgga acctcaattt aaaacaatca gattcaatta    8040
ggttttatca agactagcaa ttagatcaat aacctaaaat aatcaaacgg attcaagcat    8100
tacacaattt agggtttcga tccaaaaata gggtttcaat catgaaaaac caaacaatc    8160 agtttcaagg ctgattctat caattttatt aatcagtttc aaggctgata tttatcagtt    8220
tcaaggctga tattagcaag atggaatcaa gcaatctgat tttaggaata cgcaaattag    8280
ggtttagggt ttcaattcta aattagggtt ttatcaatca atcagcttct agcaaataat    8340
cttaaacctg agaacagttg attatatcat gaaactatca acgtagtata atatgaaacc    8400
tcaaaacatt caattcagat tatgcaaata cactgattct attttagggt ttatcaattc    8460
gaattagggt ttatattata acagattcta acatgcaata ttaaacctca aatcattcaa    8520
tcaggttata aaactatca atcctaactc acacggattt aaacctcaaa gaacattca     8580 atcaatcaaa taaacaatc catgcacacg taatttaggg tttacatatt ttaaaacaag    8640
caaagcaatt tcaattcatt cagattcgag tttaaacaat cttagcaaca gttctaggtg    8700
atcaaaacaa tcaatgaaga ttcaaattca acaatcaaa atcgattttc aaattagggt    8760
ttagggtttc gaatttgatc attagatcaa aggggtttga tttgagattc aaaaccatta    8820 atgatttga ttttaattga tcaatagatc aatctcgatt tagggtttgg ggtatcgaac     8880
ttttgagctt cgatttactc aatagggttt tgatctatta ccctatggtt ttcataaaga    8940
```

```
ttaggatttt agggtttcat tctttatcaa caatccaaat tcgattatag gttcttaggt    9000
tttgaattac ctttaactta gatgattgtt gaaacaggac caccaaagat tatgaaccgc    9060
gagctgcaac acaaacggga atgaacgcga gctattcgcg agctggacac gagctgatcc    9120
ggaacgcctt gatcgtcggg aacgcgaatg gtatgtttgc gcaccaatcg ctatcggctt    9180
gcggacgtct gatcgggaat gcgggctgag gctgagatcg gactgaaatc atctgaagct    9240
gagactggga cgcgagctgg aacagacgcg gaacaagag gcgcgatcgg attagggttc    9300
gtcggttcgc cggctagggt tagggtttta gggttttgtt cttttggttt cttagcttag    9360
ggatttttaga gtttcgtgct gataacgtgt tgtgaactta atgatttaga gtctgtaagt    9420
tcttcttatt attaatcata acataaggtg cccttatata tgagaattac aaagagataa    9480
aatgaaagac ataaatatgg aaagtgtaca aatacaagga aaggaaacta gagtttcctt    9540
tctctaagtc gcctctctct ctctctctct cttgcggccg cctctctctc tctaggtatt    9600
gggccggttc tagaccgggc cggttatgga catccacaat atgatttata acatgtaata    9660
ataaataaca ctttgaaaac agaaagatgt aaatgataac tcattttgaa atgaaagagc    9720
aatctggttg ttagcgtaga gagggagggt aaatgataac tcattttgta ccgagtaccg    9780
aacttttttc tatctatcaa aaaatgttcc acgggatgat tgacaggaca tatatcacat    9840
tgtctcactc atctgcgttc tacagttcta gtttcttttta aaagactact ttcttatgtt    9900
caaggataca atgattgaag gtaattattt gactcttttt acaggatttt ttaggatcag    9960
gagttgattt tccggtggga aacgtctcat tcttcctctt ctattctggc cacgtagccg   10020
gttcaatgat cgcatccttg gacatgagga gaatgcagag gttgagacta gcgatgcttt   10080
ttgacatcct caacatatta caatcgatca ggctgctcgg gacgagagga cactacacga   10140
tcgatcttgc ggtcggagtt ggcgctggga ttctctttga ctcattggcc gggaagtacg   10200
aagagatgat gagcaagaga cacaatttag ccaatggttt tagtttgatt tctaaagact   10260
cgctagtcaa ttaatctttt gttttcattt taaatgatta gttgaactta aaacatattt   10320
gatttagtta aagtccaatg aattacattt ttttctttca actttaattg aatagggttt   10380
cattagttta cttgaaccta attaaatgtg tacgttattg tgaaatatat aagtttcttg   10440
tggccttcct acaactattt cattctattc aatgttagca gttgcatgtg agtccatccg   10500
aaattcatag gctctacaac ttagtaaaaa cattgccata taaatttgat aaaaatatat   10560
aactaaaaca gataaatcac aagaaaatca tttttattcga ctgaatggtg ttttataaca   10620
ttctgatata atataaatgt attcaaattg aaaaatcatt cgaccatatt ggtattgcgt   10680
aaactgccaa tatgc                                                    10695
```

<210> SEQ ID NO 5
<211> LENGTH: 1220
<212> TYPE: DNA
<213> ORGANISM: Brassica napus
<220> FEATURE:
<221> NAME/KEY: CDS
<222> LOCATION: (252)..(1094)
<220> FEATURE:
<221> NAME/KEY: variation
<222> LOCATION: (636)..(636)
<223> OTHER INFORMATION: G to A in HIOL308
<220> FEATURE:
<221> NAME/KEY: variation
<222> LOCATION: (649)..(649)
<223> OTHER INFORMATION: C to T in HIOL309
<220> FEATURE:
<221> NAME/KEY: variation
<222> LOCATION: (675)..(675)

<223> OTHER INFORMATION: G to A in HIOL310
<220> FEATURE:
<221> NAME/KEY: variation
<222> LOCATION: (682)..(682)
<223> OTHER INFORMATION: G to A in HIOL311
<220> FEATURE:
<221> NAME/KEY: variation
<222> LOCATION: (687)..(687)
<223> OTHER INFORMATION: C to T in HIOL318 and HIOL319
<220> FEATURE:
<221> NAME/KEY: variation
<222> LOCATION: (700)..(700)
<223> OTHER INFORMATION: C to T in HIOL312
<220> FEATURE:
<221> NAME/KEY: variation
<222> LOCATION: (724)..(724)
<223> OTHER INFORMATION: G to A in HIOL313
<220> FEATURE:
<221> NAME/KEY: variation
<222> LOCATION: (727)..(727)
<223> OTHER INFORMATION: G to A in HIOL314
<220> FEATURE:
<221> NAME/KEY: variation
<222> LOCATION: (759)..(759)
<223> OTHER INFORMATION: C to T in HIOL315

<400> SEQUENCE: 5

```
atataaaaag aacaacaagt aaagcccaac aaagacagat gagaaaatag caaagacttg    60
cgtaaacgtc gctctcaaac ctcatctcat actcatcgtt ttcgtatgag tttctgtagc   120
ccaaacaatc ttcctttcta cggtttataa tataagaaac aatacttcct tcgtaatctc   180
cgccttgtat ctcttatata actcatctct ctaaacctaa aaatgttcc tctccgttaa    240 atctaacggt c atg tca act aat acc gtc gtc cct ctc cgt cgc aga tct   290
          Met Ser Thr Asn Thr Val Val Pro Leu Arg Arg Arg Ser
            1               5                  10 aac gga tat cac act aac ggc gtg gcc ttc aac gga atg gag aac att   338
Asn Gly Tyr His Thr Asn Gly Val Ala Phe Asn Gly Met Glu Asn Ile
 15                  20                  25 gtc aag aaa acc gac gac tgc tac acc aat ggc aac gga gta gga ggg   386
Val Lys Lys Thr Asp Asp Cys Tyr Thr Asn Gly Asn Gly Val Gly Gly
 30                  35                  40                  45 aag agc aag gcg tcg ttt ctg aca tgg acc atg cgt gac gct gtc tac   434
Lys Ser Lys Ala Ser Phe Leu Thr Trp Thr Met Arg Asp Ala Val Tyr
                 50                  55                  60 gta gcg aga tac cat tgg ata ccg tgt ttc ttt gcg gtc gga gtt ctg   482
Val Ala Arg Tyr His Trp Ile Pro Cys Phe Phe Ala Val Gly Val Leu
             65                  70                  75 ttc ttt atg ggg gtt gag tac acg ctc cag atg gtt ccg gcg aag tct   530
Phe Phe Met Gly Val Glu Tyr Thr Leu Gln Met Val Pro Ala Lys Ser
         80                  85                  90 gag ccg ttc gat att ggg ttt gtg gcc acg cgc tct ctg aac cgc gtc   578
Glu Pro Phe Asp Ile Gly Phe Val Ala Thr Arg Ser Leu Asn Arg Val
     95                 100                 105 ttg gcg agt tca ccg gat ctt aac acc ctt ttg gcg gct cta aac acg   626
Leu Ala Ser Ser Pro Asp Leu Asn Thr Leu Leu Ala Ala Leu Asn Thr
110                 115                 120                 125 gta ttc gta gcg atg caa acg acg tat att gta tgg aca tgg ttg atg   674
Val Phe Val Ala Met Gln Thr Thr Tyr Ile Val Trp Thr Trp Leu Met
                130                 135                 140 gaa gga aga cca cga gcc act atc tcg gct tgc ttc atg ttt act tgt   722
Glu Gly Arg Pro Arg Ala Thr Ile Ser Ala Cys Phe Met Phe Thr Cys
            145                 150                 155 cgc ggt att ctt ggt tac tct act cag ctc cct cta cca cag gat ttt   770
Arg Gly Ile Leu Gly Tyr Ser Thr Gln Leu Pro Leu Pro Gln Asp Phe
        160                 165                 170
```

```
tta gga tca gga gtt gat ttt ccg gtg gga aac gtc tca ttc ttc ctc      818
Leu Gly Ser Gly Val Asp Phe Pro Val Gly Asn Val Ser Phe Phe Leu
175                 180                 185 ttc tat tct ggc cac gta gcc ggt tca atg atc gca tcc ttg gac atg      866
Phe Tyr Ser Gly His Val Ala Gly Ser Met Ile Ala Ser Leu Asp Met
190                 195                 200                 205 agg aga atg cag agg ttg aga cta gcg atg ctt ttt gac atc ctc aac      914
Arg Arg Met Gln Arg Leu Arg Leu Ala Met Leu Phe Asp Ile Leu Asn
            210                 215                 220 ata tta caa tcg atc agg ctg ctc ggg acg aga gga cac tac acg atc      962
Ile Leu Gln Ser Ile Arg Leu Leu Gly Thr Arg Gly His Tyr Thr Ile
            225                 230                 235 gat ctt gcg gtc gga gtt ggc gct ggg att ctc ttt gac tca ttg gcc     1010
Asp Leu Ala Val Gly Val Gly Ala Gly Ile Leu Phe Asp Ser Leu Ala
240                 245                 250 ggg aag tac gaa gag atg atg agc aag aga cac aat tta gcc aat ggt     1058
Gly Lys Tyr Glu Glu Met Met Ser Lys Arg His Asn Leu Ala Asn Gly
255                 260                 265 ttt agt ttg att tct aaa gac tcg cta gtc aat taa tcttttgttt          1104
Phe Ser Leu Ile Ser Lys Asp Ser Leu Val Asn
270                 275                 280 tcattttaaa tgattagttg aacttaaaac atatttgatt tagttaaagt ccaatgaatt   1164 acatttttt ctttcaactt taattgaata gggtttcatt agtttacttg aaccta        1220

<210> SEQ ID NO 6
<211> LENGTH: 280
<212> TYPE: PRT
<213> ORGANISM: Brassica napus

<400> SEQUENCE: 6

Met Ser Thr Asn Thr Val Val Pro Leu Arg Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Val Gly Gly Lys Ser Lys
        35                  40                  45

Ala Ser Phe Leu Thr Trp Thr Met Arg Asp Ala Val Tyr Val Ala Arg
    50                  55                  60

Tyr His Trp Ile Pro Cys Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205
```

Gln Arg Leu Arg Leu Ala Met Leu Phe Asp Ile Leu Asn Ile Leu Gln
        210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280

<210> SEQ ID NO 7
<211> LENGTH: 3950
<212> TYPE: DNA
<213> ORGANISM: Brassica napus
<220> FEATURE:
<221> NAME/KEY: Intron
<222> LOCATION: (1972)..(2541)
<223> OTHER INFORMATION: First intron
<220> FEATURE:
<221> NAME/KEY: Intron
<222> LOCATION: (2680)..(3203)
<223> OTHER INFORMATION: Second intron

<400> SEQUENCE: 7

```
ctctacttct ttttatcttt cttgtataag acttccttaa ggcttttttt actttgagtt      60
gttgttgatt gttttttgttt ccttgctgta ataagttgtt taaaaacaat agtgtaacct    120
ttcaaaaatt gataatctta gcatcttacc aaaaaaataa caaatattga cttatttatg    180
tgaatatgta ttttatttta aatctttata gtggacgaag aaaacaccat aatttgtaca    240
acaaattttc ttagattcac gtcatcatac tcaccatttt accatttaa ttacataatt     300
ttagatgagc ttcttcacct tccccgatta ttttttgcttt atttataact acaatataaa   360
gttataaact atatatatta taaattaata atttatttat ccttgaagtc taacgattaa    420
aaatagaaca taattcaata tagatatatg attctattag taaattagta gttacaaatt    480
tgaaattttt agaaatatca aaagttgtat gttagttaat tatcttataa atgacattta    540
tttctaattt tttttggatg agaatatttt ggctgaggtg gatagtctca aaaactttga    600
atttagtccc ttttatatag taggatgtgt aattagataa tgtgagtatc taactttttat   660
ataaaattct taagacttat ctattgtcga tgagccagcc tctagatgat taatcagagg    720
ctttcgcggt ttggagaact taaaaaaaac ttaaatctttt ttttttcaata cttatcttaa   780
aaaagcgtca agatgattg cgcccaaaaa aaaaaaaata ctcagttgaa taaactaatg    840
tctgatgcgt acaacgaagc atcaaatctc ttgatattct ccataatctt gaattagagt    900
atatacacat tgttaacact taatatgcat acacgcacca ctaacatgtt tttgtctgaa    960
aactagaatt attttagtaa cgagagaatc tcatagtctt ttatatctat attctcttca   1020
tttcattttt aagtgtcatt ttaaatttgt gtatgcagtt ttttttgtat attttccaaa   1080
taaaatatca ttaactatat acatttaatc atatgtttga ccaatccaaa ataaaataaa   1140
aaatataaat aattatatag catagaaaat cgataaattt tgcattaaaa ttccataaca   1200
ataattattt tgtatcaaaa gttttacttt acaacaacat tgattataaa aattagggaa   1260
catttctttt ggtcgtctaa aatatcaaac ttgacatata aaaattaggg aacatttcat   1320
ttggtcgtct aaaatatcaa acttaaaata taaaagaac ttaacaacat gttggtacaa    1380
aattaaagta aagcccaaca aagagagaaa acaaagaaaa aaaataataa ggcaaagact   1440
```

```
ttgcgtaaac gtagctctcg aaactcaata ctcatcgttt tcgtatgaat ttttgtagac   1500
caaacaatct tccttccaca gttcacaaaa taaaaacaat acctccttcg aaatctctgc   1560
ctcttataga actcatctct gacgcttatg tcaactgaaa ctagcgtccc tctccgtcgc   1620
agatctacct ctcttaacgg acatcactct aacgacgtcg cctttgacgg aaccgtccca   1680
ttaatggaga acaacattgt taagaaaaca gacgacggct acgccaatgg aggaggaaag   1740
gcgtcgttta tgacatggac ggcgcgtgac gctatctacg tggcgagagt ccattggata   1800
ccgtgtgtgt tcgcggttgg agttctcttc ttcatgggcg tcgagtatac gcttcaaatg   1860
attcccgcga ggtctgagcc gttcgatatt gggtttgtgg tcacgcgctc tctgaaccgc   1920
gtcttggcaa attcaccggg tcttaacacc gttttagccg cactaaacac ggtatgcaga   1980
gagagagatt aacttagggg ttaaaacaac tattaaatga tttatcatca attccccatg   2040
cctcacctaa cttttttttt ctttatcatt taaatcgtaa gtaataaatt attgaattag   2100
tcaaataaat taaattgtgg tagtgatggg aaacaaatct cagatctttt cctttatttt   2160
gtgagtaatt aattctccag ctggaatatt gctgtcaact gtaaacatca acatgcaatg   2220
gaatttccta agagtggaat aatggtgtta gtagataaac tagtgacac aaatgtattt   2280 aatgtaatcg ctttgtttag tagttaagtc taatcttctt tttaacaact gccattttgt   2340
ttgtttgttt cttataacg aaatagttgc actatagtag tataatagaa tgctttataa   2400
ctttaaagtt aaaacccatt aaaaagtaac acatgggtga tatggagacg tgatcacatg   2460
caatgcaaag tgattggata gatttgactt ttgtactttt taactattta aaacttttgt   2520
ttggatggtg gtgggagaca ggtgttcgta gggatgcaaa ctacgtatat tgtatggaca   2580
tggttgatgg aaggaagacc acgagccacc atctcggctt gcttcatgtt tacttgtcgc   2640
ggtatccttg gttactctac tcagctccct ctccctcagg tccccaatct ttacatctca   2700
ctctctttga aaattatata ttatattaat aaccaaatga tattgtaaca aatagatgaa   2760
ttatgcaaag tcgccaaata ttgttgggcg tgtgattttc tcccttggcc actaccgtat   2820
aggaatcagg ttgtaacttt atatgaatat atagtatata cccaaatgtt ttgataacct   2880
ggactctaat taaagattaa tatctcacaa aacaattagt ttatgaattt tatgttcatt   2940
ttgaataggg ttaagatatt tagtatgatg tcaaatacag tagtatattg aaaacgatag   3000
tatttaattt gaaataaaag gagtaatttg attataagca agagggtaat tgtagtggtt   3060
tgtatttact tctttaactt gcgggagtta ggttaattaa ttagtagtat catcataatt   3120
aggcattact atgtctcgtt gcggttaaca tgttgtatta aaaagtgtca aaagcatcac   3180
taattatttg acttttctta caggagtttt taggatcagg agtcgatttt cctgtgggaa   3240
acgtctcatt cttccttttc tactcgggtc acgtcgccgg ttcgatgata gcatccttag   3300
acatgaggag aatgcagagg ttgagactag caatgctttt tgacatcctc aatgtattac   3360
aatcgatacg gctgctcggg acgagaggac attacaccat cgatcttgcg gtcggagttg   3420
gcgctgggat tctctttgac tcgttggccg ggaagtacga agagatgatg agcaaaagac   3480
acaatttagg caatggtttt agtttgattt ctaaagactc gctagacaat taattttgtt   3540
ttctttttaa atgttttgtt ggacttgaac atattgaatt taattgatgt ccagtgaatt   3600
aaatttattt tctttccgat gattctgact gaaaaggatt agatagcagt ttaacctaac   3660
taaactgtac gttgttgtga agttataggt gtttcttatg gtatttctac aactatttca   3720
ttcaagtcaa tgttattgtt aggagttaca ggtgggggtga gtcttccaaa actcattggc   3780
```

```
tctaccacgt agtgaacttt gaatgtactt cttcactatt tttagtgagc atgtgtcttg    3840
ttttccattg gtaggtgaag tggatttcgt ataagttaac gggacaggta caccgatcca    3900
tgatcattat tcattaatag tttggtcgag ggaaagcaat agatcatact              3950
```

<210> SEQ ID NO 8
<211> LENGTH: 1406
<212> TYPE: DNA
<213> ORGANISM: Brassica napus
<220> FEATURE:
<221> NAME/KEY: CDS
<222> LOCATION: (242)..(1093)

<400> SEQUENCE: 8

```
aatataaaaa gaacttaaca acatgttggt acaaaattaa agtaaagccc aacaaagaga    60
gaaaacaaag aaaaaaaata ataaggcaaa gactttgcgt aaacgtagct ctcgaaactc    120
aatactcatc gttttcgtat gaattttgt agaccaaaca atcttcottc cacagttcac    180 aaaataaaaa caatacctcc ttcgaaatct ctgcctctta tagaactcat ctctgacgct    240 t atg tca act gaa act agc gtc cct ctc cgt cgc aga tct acc tct ctt    289
  Met Ser Thr Glu Thr Ser Val Pro Leu Arg Arg Arg Ser Thr Ser Leu
  1               5                   10                  15 aac gga cat cac tct aac gac gtc gcc ttt gac gga acc gtc cca tta    337
Asn Gly His His Ser Asn Asp Val Ala Phe Asp Gly Thr Val Pro Leu
            20                  25                  30 atg gag aac aac att gtt aag aaa aca gac gac ggc tac gcc aat gga    385
Met Glu Asn Asn Ile Val Lys Lys Thr Asp Asp Gly Tyr Ala Asn Gly
        35                  40                  45 gga gga aag gcg tcg ttt atg aca tgg acg gcg cgt gac gct atc tac    433
Gly Gly Lys Ala Ser Phe Met Thr Trp Thr Ala Arg Asp Ala Ile Tyr
    50                  55                  60 gtg gcg aga gtc cat tgg ata ccg tgt gtg ttc gcg gtt gga gtt ctc    481
Val Ala Arg Val His Trp Ile Pro Cys Val Phe Ala Val Gly Val Leu
65                  70                  75                  80 ttc ttc atg ggc gtc gag tat acg ctt caa atg att ccc gcg agg tct    529
Phe Phe Met Gly Val Glu Tyr Thr Leu Gln Met Ile Pro Ala Arg Ser
                85                  90                  95 gag ccg ttc gat att ggg ttt gtg gtc acg cgc tct ctg aac cgc gtc    577
Glu Pro Phe Asp Ile Gly Phe Val Val Thr Arg Ser Leu Asn Arg Val
            100                 105                 110 ttg gca aat tca ccg ggt ctt aac acc gtt tta gcc gca cta aac acg    625
Leu Ala Asn Ser Pro Gly Leu Asn Thr Val Leu Ala Ala Leu Asn Thr
        115                 120                 125 gtg ttc gta ggg atg caa act acg tat att gta tgg aca tgg ttg atg    673
Val Phe Val Gly Met Gln Thr Thr Tyr Ile Val Trp Thr Trp Leu Met
    130                 135                 140 gaa gga aga cca cga gcc acc atc tcg gct tgc ttc atg ttt act tgt    721
Glu Gly Arg Pro Arg Ala Thr Ile Ser Ala Cys Phe Met Phe Thr Cys
145                 150                 155                 160 cgc ggt atc ctt ggt tac tct act cag ctc cct ctc cct cag gag ttt    769
Arg Gly Ile Leu Gly Tyr Ser Thr Gln Leu Pro Leu Pro Gln Glu Phe
                165                 170                 175 tta gga tca gga gtc gat ttt cct gtg gga aac gtc tca ttc ttc ctt    817
Leu Gly Ser Gly Val Asp Phe Pro Val Gly Asn Val Ser Phe Phe Leu
            180                 185                 190 ttc tac tcg ggt cac gtc gcc ggt tcg atg ata gca tcc tta gac atg    865
Phe Tyr Ser Gly His Val Ala Gly Ser Met Ile Ala Ser Leu Asp Met
        195                 200                 205 agg aga atg cag agg ttg aga cta gca atg ctt ttt gac atc ctc aat    913
Arg Arg Met Gln Arg Leu Arg Leu Ala Met Leu Phe Asp Ile Leu Asn
```

```
              210                 215                 220
gta tta caa tcg ata cgg ctg ctc ggg acg aga gga cat tac acc atc      961
Val Leu Gln Ser Ile Arg Leu Leu Gly Thr Arg Gly His Tyr Thr Ile
225                 230                 235                 240 gat ctt gcg gtc gga gtt ggc gct ggg att ctc ttt gac tcg ttg gcc     1009
Asp Leu Ala Val Gly Val Gly Ala Gly Ile Leu Phe Asp Ser Leu Ala
                245                 250                 255 ggg aag tac gaa gag atg atg agc aaa aga cac aat tta ggc aat ggt     1057
Gly Lys Tyr Glu Glu Met Met Ser Lys Arg His Asn Leu Gly Asn Gly
            260                 265                 270 ttt agt ttg att tct aaa gac tcg cta gac aat taa ttttgttttc           1103
Phe Ser Leu Ile Ser Lys Asp Ser Leu Asp Asn
        275                 280 tttttaaatg ttttgttgga cttgaacata ttgaatttaa ttgatgtcca gtgaattaaa    1163
tttattttct ttccgatgat tctgactgaa aaggattaga tagcagttta acctaactaa    1223
actgtacgtt gttgtgaagt tataggtgtt tcttatggta tttctacaac tatttcattc    1283
aagtcaatgt tattgttagg agttacaggt ggggtgagtc ttccaaaact cattggctct    1343
accacgtagt gaactttgaa tgtacttctt cactattttt agtgagcatg tgtcttgttt    1403
tcc                                                                  1406
```

<210> SEQ ID NO 9
<211> LENGTH: 283
<212> TYPE: PRT
<213> ORGANISM: Brassica napus

<400> SEQUENCE: 9

```
Met Ser Thr Glu Thr Ser Val Pro Leu Arg Arg Arg Ser Thr Ser Leu
1               5                   10                  15

Asn Gly His His Ser Asn Asp Val Ala Phe Asp Gly Thr Val Pro Leu
            20                  25                  30

Met Glu Asn Asn Ile Val Lys Lys Thr Asp Asp Gly Tyr Ala Asn Gly
        35                  40                  45

Gly Gly Lys Ala Ser Phe Met Thr Trp Thr Ala Arg Asp Ala Ile Tyr
    50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Ile Gly Phe Val Thr Arg Ser Leu Asn Arg Val
            100                 105                 110

Leu Ala Asn Ser Pro Gly Leu Asn Thr Val Leu Ala Ala Leu Asn Thr
        115                 120                 125

Val Phe Val Gly Met Gln Thr Thr Tyr Ile Val Trp Thr Trp Leu Met
    130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
            180                 185                 190

Phe Tyr Ser Gly His Val Ala Gly Ser Met Ile Ala Ser Leu Asp Met
        195                 200                 205

Arg Arg Met Gln Arg Leu Arg Leu Ala Met Leu Phe Asp Ile Leu Asn
    210                 215                 220
```

```
Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
            245                 250                 255

Gly Lys Tyr Glu Glu Met Met Ser Lys Arg His Asn Leu Gly Asn Gly
        260                 265                 270

Phe Ser Leu Ile Ser Lys Asp Ser Leu Asp Asn
        275                 280

<210> SEQ ID NO 10
<211> LENGTH: 4943
<212> TYPE: DNA
<213> ORGANISM: Brassica napus
<220> FEATURE:
<221> NAME/KEY: Intron
<222> LOCATION: (1706)..(3195)
<223> OTHER INFORMATION: First intron
<220> FEATURE:
<221> NAME/KEY: Intron
<222> LOCATION: (3334)..(3855)
<223> OTHER INFORMATION: Second intron

<400> SEQUENCE: 10 atagggtca aattaccccc tccctaaagg ctatctctgc caatgtgcct actttaaatg      60
ttttctaggt tttcgtttac tacattgtta agttcgatac ttatagtctc taaaccaagc     120
gatatgagcc gggagtttct aggacaggtg gtctgcgtac cacgtcaatt tcccaggtat     180
ctcggattcg atccgcgcct cctgcgatga ggctgatggg ccaactgaac cggcccgttg     240
tggtccagta ataaagttga caaaaaaaac catgcgatat gattgtgggt ggtacggcgg     300
gttcggaaag attctaaacg ttttaagttt gaaatctacc atttagattt atttatatgt     360
atgattagat aatgtgaata tctaactttt atataaaata ctcagactta tctatttata     420
gatgagccag cctctagatg attaatcaga ggctttcgcg gtttggatac tcgaggaatt     480
agaaaaaaaa ttaatctctt tttcaatact tatcttaaaa agcgtcaaag atgattgccc     540
aagaaaatta cagtatataa tactcaattg aataaactaa tgtctgatgc atacaacgaa     600
gcatcgaatc tatattctcc ataatcttga attagagtat atacacattg ttaacactta     660
attagtatgc atacacacac cgctaacatg tttttgtctg aaaactataa ttattatagt     720
aacgagagaa tctcatagtc ttatatctat attctcttca ttttatttta agtgtgattt     780
taaatttgtt tacacagttt ttgtatattt tccaataaaa atatcattaa gcatacattt     840
aatcatattt ttgaccaatc aaaaataaaa tggaaaatat aaatatttat aaagcataga     900
aaatcgataa attttgcatt aaaattctat aacataatt attttgtatc aaaaatttta     960
ctttacaaca atatttatta taaaaattag ggaacagttc ttttggtcgt ctaaaatatc    1020
aaacttgaca tataaaaatt agggaacatt tcatttggtc gtctaaaata tcaaacttaa    1080
catataaaaa gaacttaaca acatgttggt acaaagtaa agtaaagccc aacaaagaga    1140
gaaaacagag aaaaaaataa taaggcaaag actttgcgta aacgtagctc tcgaaactca    1200
atactcatcg ttttcgtatg aattttttgta gaccaaacaa tcttccttcc acagttcaca    1260
aaatataaaa caataccctcc ttcgaaatct ctgcctctta tataacccat ctctgacgct    1320
tatgtcaact gaaactggcg tccctctccg tcgcagatct aactctctta acggacatca    1380
ctctaacgac gtcgcctttg acggaaccgt cccatcaatg gagaacaaca ttgttaagaa    1440
aacagacgac ggctacgcca atggaggagg aaggcgtcg tttatgacat ggacggcgcg    1500
```

```
tgacgctatc tacgtggcga gagtccattg gataccgtgt gtgttcgcgg ttggagttct    1560
gttcttcatg ggcgtcgagt atacgcttca gatgattccc gcgaggtctg agccgttcga    1620
tgttgggttt gtggccacgc gctctctgaa ccgcgtcttg gcaaattcac cgggtcttaa    1680
caccgtttta gccgcactaa acacggtatt gcagagagag agattaactt aggggttaaa    1740
acaactatta aatgatttat catcaattcc tcatgcctca cctaacttt tgttttttct    1800
ttctttatca tttaaatcgt aagtaataaa ttattgaatt agtcaaataa attaaattgt    1860
ggtagtgatg ggaacaaatc tcagatcttt tcctttattt tgtgaggtga ttagggctgt    1920
taaatatggt aaaaccgaac cgtaccgaac cgaaatagat aatatggttt ggttttaata    1980
tataccatat aaatcgaatg gatataattt tataaaaact gtaggatttg gatatggttt    2040
ggtatataac cgattaaaac gaataaaccg aacaaaaccg attaaaagta gaaacatgta    2100
aatatgtatc tatttatata caatgcatga aaatctattt gttatataag ttaaattagt    2160
gttaataact attaccataa tgttatagta ataagaact ttatataatt tgtaaaacac    2220
ttgaatacat cgcaattcag acatcttatt ttctaagtct tttttttat cctttgctt    2280
tattttagta tccactaaat taatacgaag atgataaatt tgatagaaaa taattaatga    2340
aaaatttca caactttttt cttatctata acaaacaga gttgcgtgtt caattgaaaa    2400
acatgacttt aatgaacact aaatatggaa gagtggaaaa acttttcttt catgtttctg    2460
ttttgtttca tattttatt ttcaaaattt cagactctga ttaattat agatttgatg    2520
attttatttg atggtagaag cattttacg tcttattca tttatttgaa catgtaatat    2580
atttttaata aatgaatgtg ttgacaatat gactctaaaa ttcattttat atgatctcaa    2640
actaaataat tatgtttttt ggtataaaac cgaataaacc aaaaaccgac ggtatataaa    2700
ccgaaccgaa ccgaagtaaa tatggattta gaatggtagt tatattttac taaccgaaat    2760
accgaaaacc gaaaaaaacc gaacctaaac cgaaccgata tccggattga acaccctaga    2820
ggtgattaat tctccagctg gaattttgct gtcaattgta aacatcaaca tgcaatgaaa    2880
tttcctaaga gtggaataat ggtgttagta gataaactag tggacacaaa tgtatttaat    2940
gtaatcgctt tgtttagtag ttaagtatct tcttttaac aactgccatt tgtttgttt    3000
gtttctttat aacgaaatag tcgcactata gtagtataat agaatgcttt ataactttaa    3060
agttaaaacc ccttaaaaag taacacatgg gtgatatgga gacgtgatca catgcaatgc    3120
aaagagattg gatagatttg acttttgtac ttttaacta tttaaaactt tgtttggat    3180
ggtggtggga gacaggtgtt cgtagggatg caaactacgt atattgtatg gacatggttg    3240
atggaaggaa gaccacgagc caccatctcg gcttgcttca tgtttacttg tcgcggtatt    3300
cttggttact ctactcagct ccctctccct caggtcccaa tctttacatc tcactctctc    3360
tatgaaaaat atatattata ataactaaat gatgttgtaa caaatagat gaattatgta    3420
aagtcgccaa atattgttgg gcgtgtgatt ttctcccttg gccactaccg tataggaaac    3480
aggttgtaac tttatatgaa tatatacccca aatgttttga taacctggac tctaattaaa    3540
gattaatatc tcacaaaaca attagtttat gaattttatg ttcatttgta ataggttaa    3600
gttatttagt atgatgtcaa atacagtact agtatattga aaacgatagt atttaatttg    3660
aaataaaagc agtaatttga ttataagcaa tgagagggta attgtactgg tttgtatta    3720
cttcttaac ttgcgggggt taggttagtt aattagtagt atcatcataa ttaggcatta    3780
ctatgtctcg ttgctgttaa catgttgtat taaaaagtgt caaaagcatc aataattatt    3840
tgactttttt tacaggagtt tttaggatca ggagtcgatt ttcctgtggg aaacgtctca    3900
```

-continued

```
ttcttcctttt tctactcggg tcacgtcgcc ggttcgatga tagcatcctt agacatgagg    3960
agaatgcaga ggttgagact agcaatgctt tttgacatcc tcaatgtttt acaatcgata    4020
aggctgctcg ggacgagagg acattacacc atcgatcttg cggtcggagt tggcgctggg    4080
attctctttg actcgttggc cgggaagtac aagagagatga tgagcaaaag acacaattta    4140
ggcaatggtt ttagtttgat ttctaaagac tcgctagtca attaattttg ttttcttttt    4200
aaatgtttag ttgaacttga acatatatta aatttaattg atgtccaatg aattaaattt    4260
attttctttc cgatgattct gactgaaaag gattagatag cagtttaacc taactaaacc    4320
tgtacgtttt tgcgaagtta taggagtttc ttatggtctt tctacaacta tttcattcaa    4380
gtcaatgtta ggagttacag gtgaggtgag actgccaaaa ctcattggct ctaccactta    4440
gtgaactttg aatgtacttc ttcactattt ttagtgagca tgtgtcttgt tttccattgg    4500
tgaagtggat ttcgtataag ttaacgggac aggtacaccg atccatgatt attattcatt    4560
aatagtttgg tccacggaaa gcaatagatc atactttatt tacggtcttt ttgttgttca    4620
gaagtttccc caatgtatgt tagttcaact aataaataga tcaacatgtt aacatttcta    4680
aatagtcggt ggctaaagag agtcagatat tttaagtatc aagctctttt ataagtaaat    4740
aaaaatcatt gagtgacatt tcagttactg catgtatact agcatactat taaataccga    4800
accacacatc tgtggtcgtg gcacaaggcg ttttgtggat ctctaagaaa cccgaattta    4860
aatccactgc taacccagat aaatacggcg cgtggccacc agaacttttc acattctttc    4920
tccagaagaa aggtttacct tgt                                            4943
```

<210> SEQ ID NO 11
<211> LENGTH: 1558
<212> TYPE: DNA
<213> ORGANISM: Brassica napus
<220> FEATURE:
<221> NAME/KEY: CDS
<222> LOCATION: (241)..(1092)

<400> SEQUENCE: 11

```
atataaaaag aacttaacaa catgttggta caaaagtaaa gtaaagccca acaaagagag    60
aaaacagaga aaaaaataat aaggcaaaga ctttgcgtaa acgtagctct cgaaactcaa    120
tactcatcgt tttcgtatga attttttgtag accaaacaat cttccttcca cagttcacaa    180
aatataaaac aatacctcct tcgaaatctc tgcctcttat ataacccatc tctgacgctt    240
```

| atg tca act gaa act ggc gtc cct ctc cgt cgc aga tct aac tct ctt | 288 |
|---|---|
| Met Ser Thr Glu Thr Gly Val Pro Leu Arg Arg Arg Ser Asn Ser Leu | |
| 1               5                   10                  15 | |

| aac gga cat cac tct aac gac gtc gcc ttt gac gga acc gtc cca tca | 336 |
|---|---|
| Asn Gly His His Ser Asn Asp Val Ala Phe Asp Gly Thr Val Pro Ser | |
|             20                  25                  30 | |

| atg gag aac aac att gtt aag aaa aca gac gac ggc tac gcc aat gga | 384 |
|---|---|
| Met Glu Asn Asn Ile Val Lys Lys Thr Asp Asp Gly Tyr Ala Asn Gly | |
|         35                  40                  45 | |

| gga gga aag gcg tcg ttt atg aca tgg acg gcg cgt gac gct atc tac | 432 |
|---|---|
| Gly Gly Lys Ala Ser Phe Met Thr Trp Thr Ala Arg Asp Ala Ile Tyr | |
|     50                  55                  60 | |

| gtg gcg aga gtc cat tgg ata ccg tgt gtg ttc gcg gtt gga gtt ctg | 480 |
|---|---|
| Val Ala Arg Val His Trp Ile Pro Cys Val Phe Ala Val Gly Val Leu | |
| 65                  70                  75                  80 | |

| ttc ttc atg ggc gtc gag tat acg ctt cag atg att ccc gcg agg tct | 528 |
|---|---|
| Phe Phe Met Gly Val Glu Tyr Thr Leu Gln Met Ile Pro Ala Arg Ser | |
|                 85                  90                  95 | |

| | | |
|---|---|---|
| gag ccg ttc gat gtt ggg ttt gtg gcc acg cgc tct ctg aac cgc gtc<br>Glu Pro Phe Asp Val Gly Phe Val Ala Thr Arg Ser Leu Asn Arg Val<br>100 105 110 | | 576 |
| ttg gca aat tca ccg ggt ctt aac acc gtt tta gcc gca cta aac acg<br>Leu Ala Asn Ser Pro Gly Leu Asn Thr Val Leu Ala Ala Leu Asn Thr<br>115 120 125 | | 624 |
| gtg ttc gta ggg atg caa act acg tat att gta tgg aca tgg ttg atg<br>Val Phe Val Gly Met Gln Thr Thr Tyr Ile Val Trp Thr Trp Leu Met<br>130 135 140 | | 672 |
| gaa gga aga cca cga gcc acc atc tcg gct tgc ttc atg ttt act tgt<br>Glu Gly Arg Pro Arg Ala Thr Ile Ser Ala Cys Phe Met Phe Thr Cys<br>145 150 155 160 | | 720 |
| cgc ggt att ctt ggt tac tct act cag ctc cct ctc cct cag gag ttt<br>Arg Gly Ile Leu Gly Tyr Ser Thr Gln Leu Pro Leu Pro Gln Glu Phe<br>165 170 175 | | 768 |
| tta gga tca gga gtc gat ttt cct gtg gga aac gtc tca ttc ttc ctt<br>Leu Gly Ser Gly Val Asp Phe Pro Val Gly Asn Val Ser Phe Phe Leu<br>180 185 190 | | 816 |
| ttc tac tcg ggt cac gtc gcc ggt tcg atg ata gca tcc tta gac atg<br>Phe Tyr Ser Gly His Val Ala Gly Ser Met Ile Ala Ser Leu Asp Met<br>195 200 205 | | 864 |
| agg aga atg cag agg ttg aga cta gca atg ctt ttt gac atc ctc aat<br>Arg Arg Met Gln Arg Leu Arg Leu Ala Met Leu Phe Asp Ile Leu Asn<br>210 215 220 | | 912 |
| gtt tta caa tcg ata agg ctg ctc ggg acg aga gga cat tac acc atc<br>Val Leu Gln Ser Ile Arg Leu Leu Gly Thr Arg Gly His Tyr Thr Ile<br>225 230 235 240 | | 960 |
| gat ctt gcg gtc gga gtt ggc gct ggg att ctc ttt gac tcg ttg gcc<br>Asp Leu Ala Val Gly Val Gly Ala Gly Ile Leu Phe Asp Ser Leu Ala<br>245 250 255 | | 1008 |
| ggg aag tac gaa gag atg atg agc aaa aga cac aat tta ggc aat ggt<br>Gly Lys Tyr Glu Glu Met Met Ser Lys Arg His Asn Leu Gly Asn Gly<br>260 265 270 | | 1056 |
| ttt agt ttg att tct aaa gac tcg cta gtc aat taa ttttgttttc<br>Phe Ser Leu Ile Ser Lys Asp Ser Leu Val Asn<br>275 280 | | 1102 |
| tttttaaatg tttagttgaa cttgaacata tattaaattt aattgatgtc caatgaatta | | 1162 |
| aatttatttt ctttccgatg attctgactg aaaaggatta gatagcagtt taacctaact | | 1222 |
| aaacctgtac gttttttgcga agttatagga gtttcttatg gtctttctac aactatttca | | 1282 |
| ttcaagtcaa tgttaggagt tacaggtgag gtgagactgc caaaactcat tggctctacc | | 1342 |
| acttagtgaa ctttgaatgt acttcttcac tattttagt gagcatgtgt cttgttttcc | | 1402 |
| attggtgaag tggatttcgt ataagttaac gggacaggta caccgatcca tgattattat | | 1462 |
| tcattaatag tttggtccac ggaaagcaat agatcatact ttatttacgg tcttttttgtt | | 1522 |
| gttcagaagt ttcccccaatg tatgttagtt caacta | | 1558 |

<210> SEQ ID NO 12
<211> LENGTH: 283
<212> TYPE: PRT
<213> ORGANISM: Brassica napus

<400> SEQUENCE: 12

Met Ser Thr Glu Thr Gly Val Pro Leu Arg Arg Arg Ser Asn Ser Leu
1               5                   10                  15

Asn Gly His His Ser Asn Asp Val Ala Phe Asp Gly Thr Val Pro Ser
            20                  25                  30

Met Glu Asn Asn Ile Val Lys Lys Thr Asp Asp Gly Tyr Ala Asn Gly
 35                  40                  45

Gly Gly Lys Ala Ser Phe Met Thr Trp Thr Ala Arg Asp Ala Ile Tyr
 50                  55                  60

Val Ala Arg Val His Trp Ile Pro Cys Val Phe Ala Val Gly Val Leu
 65                  70                  75                  80

Phe Phe Met Gly Val Glu Tyr Thr Leu Gln Met Ile Pro Ala Arg Ser
                 85                  90                  95

Glu Pro Phe Asp Val Gly Phe Val Ala Thr Arg Ser Leu Asn Arg Val
                100                 105                 110

Leu Ala Asn Ser Pro Gly Leu Asn Thr Val Leu Ala Ala Leu Asn Thr
                115                 120                 125

Val Phe Val Gly Met Gln Thr Thr Tyr Ile Val Trp Thr Trp Leu Met
130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Phe Leu
                180                 185                 190

Phe Tyr Ser Gly His Val Ala Gly Ser Met Ile Ala Ser Leu Asp Met
                195                 200                 205

Arg Arg Met Gln Arg Leu Arg Leu Ala Met Leu Phe Asp Ile Leu Asn
                210                 215                 220

Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
                245                 250                 255

Gly Lys Tyr Glu Glu Met Met Ser Lys Arg His Asn Leu Gly Asn Gly
                260                 265                 270

Phe Ser Leu Ile Ser Lys Asp Ser Leu Val Asn
                275                 280

<210> SEQ ID NO 13
<211> LENGTH: 3635
<212> TYPE: DNA
<213> ORGANISM: Brassica rapa
<220> FEATURE:
<221> NAME/KEY: Intron
<222> LOCATION: (1261)..(1997)
<223> OTHER INFORMATION: First intron
<220> FEATURE:
<221> NAME/KEY: Intron
<222> LOCATION: (2136)..(2989)
<223> OTHER INFORMATION: Second intron

<400> SEQUENCE: 13
ttttaatatc ataaaaaaat tgtgtatatt ctagatatta gaatatattt atctacaaga     60 cttttttat cattaaacat gagtttcctc tagtccaata gacattatga attcttcccg    120
gctatgaaac tggcgtttgg tgtatattga ttttaaccaa aataacatct cctgaattaa    180
tttatgtcca acatctataa atatacgaaa cctacagtaa ctatatgatt ttaaaacagt    240
taaaactctt ggttatgttc gaattcaatt tctcgaatat tttgtgctaa accgacatgt    300
aacaaactaa atgtcttctt ctctttttttt ttgacaacta cactattatg gagggacgtg    360
caataattat cttaaaaacg tgaaacgatg tgcgccaaaa ggaatcatat aatcctcaat    420
gacattataa actagtactt attcaacaaa ggagaaaatc ttttgatatt ctccataatc    480

```
ttgaattaag gtatatatac acattgttaa tacgcacacc actaacatgt attagtgtga    540
acaaaactag ttattatact atggtaagga aactctcgta ctctctctat cttttttgtgt   600 gtgtttctcg tgtaaaatat tatacactta agacgtataa aaagaacaac aagtaaagcc    660
caacaaagac agatgagaaa atagcaaaga cttgcgtaaa cgtcgctctc aaacctcatc    720
tcatactcat cgttttcgta tgagttttg tagcccaaac aatcttcctt tctacagttt    780
ataatataag aaacaatact tccttcgtaa tctccgcctc gtatctctta tataactcat    840
ctctctaaac ctaaaaaatg ttcctctccg ttaaatctaa cggtcatgtc aactaatacc    900
gtcgttcctc tccgtcgcag atctaacgga tatcacacta acggcgtggc ctttaacgga    960
atggagaaca ttgtcaagaa aaccgacgac tgctacacca acggcaacgg aggagtagag   1020
agaagcaaag cctcgtttct gacatggacc atgcgtgacg ctgtctacgt agcgagatac   1080
cattggatac cgtgtttctt tgcggtcgga gttctgttct ttatgggggt tgagtacacg   1140
ctccagatgg ttccggcgaa gtctgagccg ttcgatattg ggtttgtggc cacgcgctct   1200
ctgaaccgcg tcttggcgag ttcaccggat cttaacaccc ttttagcggc tctaaacacg   1260
gtatgtcgta tgagttaatt taggttaaaa ctatatttaa tgattatctt caattcttca   1320
tgccacacct aacattttgt attttttctt tgtcatttaa ttcgtaataa tatattgaat   1380
tagtcaaaat aaaataggtg gggttagtga tggatataca taaatctcag atcttttcct   1440
ttattttgtg tggtattaac tatccagctg gagttttcc gtccagggta tcatgcaacg    1500
atatttaaga gttgatttga gtttagaacg cattttttata aagatacatg ttttacaaaa   1560
ataaatttat ttcaaaaata catttttctat gtattaatta tacttattaa ttttttgtta   1620 atttttaattt gtgaaaatag ataatcataa caataatgta tttataatca aaatttaata   1680
ttttaataag tatagaaact ctaaaacata tatattgtga aacacacaga ataggtagtg   1740
ggcaaaaatg tatttaatgt aatctcagct atcaaagtag ttgtataatt ttattttttaa   1800 caactgccat ttttttttt tctttataaa gaagtagtac aataatagat tagattgctt    1860
ttaactttaa agtttcaacc caatgaaaag ggacacatgg tgatgagttg gagacatgat   1920
cacatgcaat gcaaagagat tggttagatt cgatttggta cttgtaacta tttaatattg   1980
gtggatggtg gggacaggta ttcgtagcga tgcaaacgac gtatattgta tggacatggt   2040
tgatggaagg aagaccacga gccactatct cggcttgctt catgtttact tgtcgcggca   2100
ttcttggtta ctctactcag ctccctctac cacaggtctc tcacctcttt acataaatat   2160
tatattatac tctactcagc tccctctacc ttactcttat aatatattta tattggcatt   2220
gtagtaaata tatttaatta tgtcaagtct ttagatattg ttgtacatgt gatttttccct   2280 tggccgtttc catatagaaa acagttgtaa ctttataggc cccaaatatt ttgaactttt   2340
tattttcatt ataacaaaag actatatatt ataataattt actcttaaaa ttaatatata   2400
gatattgtac caaatcgatg tatttatgta gtccctatat attgttggac gtgtgatttc   2460
cccttggcca ctaccgtaca gaggacagct gtaattacag tccccaaata ttcttttaat   2520
ccggacatct aaactacaaa attattgttt cacaaaacac ctgatttctt taacaaaagc   2580
aaaacaattt gatttatgaa tgttcgtttt ataccttta tttatagggt taaattattt    2640
attatatttc aaaatttata ttgaaatact aaataacact ttgaaaacag aaagatgtaa   2700
atgataactc attctgaaat ggaaagagca atctggttgt tagcttagag agggagggta   2760
atttgcagtg gattgtattt tactgttttg ttttgttttt gtttgctacc gactaccgag   2820
```

-continued

```
gaccgaacttt ttttctatct atcaaaaaat gttccacggg atgattgact ggacataaat      2880
cacattgtct cactcatctg cgttctacag ttctagtttt tttttaaaga ctactttctt      2940
atgttcaagg atacaatgat tgaaggtaat tatttgactc tttttacagg atttttttagg     3000 atcaggagtt gattttcctg tgggaaacgt ctcattcttc ctcttctatt ctggccacgt      3060
agccggttca atgatcgcat ccttggacat gaggagaatg cagaggttga gactagcgat      3120 gcttttgac atcctcaaca tattacaatc gatcagactg ctcgggacga gaggacacta      3180
cacgatcgat cttgcggtcg gagttggcgc tgggattctc tttgactcat ggccgggaa       3240 gtacgaagag atgatgagca agagacacaa tttagccaat ggttttagtt tgatttctaa      3300
agactcgcta gtcaattaat cttttgtttt cattttaaat gattagttga acttgaacat      3360
atttgattta gttaaagtcc aatgaattac atttttttct ttcaacttta attgaatagg      3420
atttcattag tttacttgaa cctaattaaa tgtgtacgtt attgtgaaat aaagaagttt      3480
gttgtggcct tcctacaact atttcattca attcaatgtt agcagttgca tgtgagtcca      3540
tccgaaattc ataggctcta caacttagta aaaacattgc catataaatt tgattaaaaa      3600
ttataactaa aacagataaa tcacaataaa atcat                                 3635
```

```
<210> SEQ ID NO 14
<211> LENGTH: 1243
<212> TYPE: DNA
<213> ORGANISM: Brassica rapa
<220> FEATURE:
<221> NAME/KEY: CDS
<222> LOCATION: (252)..(1094)

<400> SEQUENCE: 14
```

```
gtataaaaag aacaacaagt aaagcccaac aaagacagat gagaaaatag caaagacttg      60
cgtaaacgtc gctctcaaac ctcatctcat actcatcgtt ttcgtatgag ttttttgtagc     120 ccaaacaatc ttcctttcta cagtttataa tataagaaac aatacttcct tcgtaatctc     180
cgcctcgtat ctcttatata actcatctct ctaaacctaa aaaatgttcc ctctccgttaa     240 atctaacggt c atg tca act aat acc gtc gtt cct ctc cgt cgc aga tct      290
            Met Ser Thr Asn Thr Val Val Pro Leu Arg Arg Arg Ser
            1               5                   10 aac gga tat cac act aac ggc gtg gcc ttt aac gga atg gag aac att      338
Asn Gly Tyr His Thr Asn Gly Val Ala Phe Asn Gly Met Glu Asn Ile
 15                  20                  25 gtc aag aaa acc gac gac tgc tac acc aac ggc aac gga gga gta gag      386
Val Lys Lys Thr Asp Asp Cys Tyr Thr Asn Gly Asn Gly Gly Val Glu
 30              35                  40                  45 aga agc aaa gcc tcg ttt ctg aca tgg acc atg cgt gac gct gtc tac      434
Arg Ser Lys Ala Ser Phe Leu Thr Trp Thr Met Arg Asp Ala Val Tyr
                 50                  55                  60 gta gcg aga tac cat tgg ata ccg tgt ttc ttt gcg gtc gga gtt ctg      482
Val Ala Arg Tyr His Trp Ile Pro Cys Phe Phe Ala Val Gly Val Leu
             65                  70                  75 ttc ttt atg ggg gtt gag tac acg ctc cag atg gtt ccg gcg aag tct      530
Phe Phe Met Gly Val Glu Tyr Thr Leu Gln Met Val Pro Ala Lys Ser
         80                  85                  90 gag ccg ttc gat att ggg ttt gtg gcc acg cgc tct ctg aac cgc gtc      578
Glu Pro Phe Asp Ile Gly Phe Val Ala Thr Arg Ser Leu Asn Arg Val
     95                  100                 105 ttg gcg agt tca ccg gat ctt aac acc ctt tta gcg gct cta aac acg      626
Leu Ala Ser Ser Pro Asp Leu Asn Thr Leu Leu Ala Ala Leu Asn Thr
 110                 115                 120                 125
```

```
gta ttc gta gcg atg caa acg acg tat att gta tgg aca tgg ttg atg      674
Val Phe Val Ala Met Gln Thr Thr Tyr Ile Val Trp Thr Trp Leu Met
            130                 135                 140 gaa gga aga cca cga gcc act atc tcg gct tgc ttc atg ttt act tgt      722
Glu Gly Arg Pro Arg Ala Thr Ile Ser Ala Cys Phe Met Phe Thr Cys
        145                 150                 155 cgc ggc att ctt ggt tac tct act cag ctc cct cta cca cag gat ttt      770
Arg Gly Ile Leu Gly Tyr Ser Thr Gln Leu Pro Leu Pro Gln Asp Phe
        160                 165                 170 tta gga tca gga gtt gat ttt cct gtg gga aac gtc tca ttc ttc ctc      818
Leu Gly Ser Gly Val Asp Phe Pro Val Gly Asn Val Ser Phe Phe Leu
    175                 180                 185 ttc tat tct ggc cac gta gcc ggt tca atg atc gca tcc ttg gac atg      866
Phe Tyr Ser Gly His Val Ala Gly Ser Met Ile Ala Ser Leu Asp Met
190                 195                 200                 205 agg aga atg cag agg ttg aga cta gcg atg ctt ttt gac atc ctc aac      914
Arg Arg Met Gln Arg Leu Arg Leu Ala Met Leu Phe Asp Ile Leu Asn
                210                 215                 220 ata tta caa tcg atc aga ctg ctc ggg acg aga gga cac tac acg atc      962
Ile Leu Gln Ser Ile Arg Leu Leu Gly Thr Arg Gly His Tyr Thr Ile
                225                 230                 235 gat ctt gcg gtc gga gtt ggc gct ggg att ctc ttt gac tca ttg gcc     1010
Asp Leu Ala Val Gly Val Gly Ala Gly Ile Leu Phe Asp Ser Leu Ala
            240                 245                 250 ggg aag tac gaa gag atg atg agc aag aga cac aat tta gcc aat ggt     1058
Gly Lys Tyr Glu Glu Met Met Ser Lys Arg His Asn Leu Ala Asn Gly
        255                 260                 265 ttt agt ttg att tct aaa gac tcg cta gtc aat taa tcttttgttt          1104
Phe Ser Leu Ile Ser Lys Asp Ser Leu Val Asn
270                 275                 280 tcattttaaa tgattagttg aacttgaaca tatttgattt agttaaagtc caatgaatta   1164
catttttttc tttcaacttt aattgaatag gatttcatta gtttacttga acctaattaa   1224
atgtgtacgt tattgtgaa                                                1243

<210> SEQ ID NO 15
<211> LENGTH: 280
<212> TYPE: PRT
<213> ORGANISM: Brassica rapa

<400> SEQUENCE: 15

Met Ser Thr Asn Thr Val Val Pro Leu Arg Arg Ser Asn Gly Tyr
1               5                   10                  15

His Thr Asn Gly Val Ala Phe Asn Gly Met Glu Asn Ile Val Lys Lys
                20                  25                  30

Thr Asp Asp Cys Tyr Thr Asn Gly Asn Gly Val Glu Arg Ser Lys
            35                  40                  45

Ala Ser Phe Leu Thr Trp Thr Met Arg Asp Ala Val Tyr Val Ala Arg
    50                  55                  60

Tyr His Trp Ile Pro Cys Phe Phe Ala Val Gly Val Leu Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
```

```
                 130                 135                 140
Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
                180                 185                 190

Gly His Val Ala Gly Ser Met Ile Ala Ser Leu Asp Met Arg Arg Met
                195                 200                 205

Gln Arg Leu Arg Leu Ala Met Leu Phe Asp Ile Leu Asn Ile Leu Gln
        210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
                260                 265                 270

Ile Ser Lys Asp Ser Leu Val Asn
        275                 280

<210> SEQ ID NO 16
<211> LENGTH: 3519
<212> TYPE: DNA
<213> ORGANISM: Brassica rapa
<220> FEATURE:
<221> NAME/KEY: Intron
<222> LOCATION: (1518)..(2088)
<223> OTHER INFORMATION: First intron
<220> FEATURE:
<221> NAME/KEY: Intron
<222> LOCATION: (2227)..(2750)
<223> OTHER INFORMATION: Second intron

<400> SEQUENCE: 16
tttctaagat atgagtgttt aaaaaaattt aacacgggat gtttagaata cagaattatg     60
cttatgagag agtggctcgg gaatgagctt caagatgggt cgaataggct ctgaaaatag    120 cttttttattt tgactcaagc ccaatccgga tgacatggca tcttggttgg ttcataatat    180
tttgtccatg tggcatggct tagaaagaag ggatttagtc ccttttatat agtaggattc    240
ttagacttat ctattgtcga tgagccagcc tctagatgat taatcagagg ctttcgcggt    300
ttggagaact taaaaaaaaa acttaaatct ttttttcaat acttaaaaaa gcgtcgaaga    360
tgattgcgcc caaaaaaaat aataatactc agttgaataa actaatgtct gatgcataca    420
acgaagcatc aaatctcttg atattctcca aatcttgaa ttagagtatt tacacattgt     480
taacacttaa tatgcataca cacaccacta acatgttttt gtctgaaaac tataattatt    540
ttagtaacga gagaatctca tagtcttata tctatattct cttcatttta ttttaagtat    600
cattttaaat ttatatacac agttttgta tattttccaa ataaaatatc attaactata     660
tacatttaat catattttg acaaatcaaa ataaaatag aaatataaa taattataaa      720 gcatagaaaa tcgataaaag ttttgcatta aaattctata acaataatta ttttgtatca    780 aaaatttttac tttacaacaa catttattat aaaaattagg gaacatttct tttggtcgtc   840
taaaatatca aacttgacat ataaaaatta gggaacattt catttggtcg tctaaaatat    900
caaacttaac atataaaact taacaacatg ttggtacaaa agtaaagtaa agcccaacaa    960 agaaaaaat aacaaggcaa agactttgcg taaacgtagc tctcgaaact caatactcat   1020
```

-continued

```
cgttttcgta tgaattttig tagaccaaac aatcttcctt ccacagttca taaaatataa    1080
aacaatacct ccttcgaaat ctctgcctct tatataaccc atctctgacg cttatgtcaa    1140
ctgaaactgg cgtccctctc cgtcgcagat ctacctctct taacggatac cactctaacg    1200
acgtctcctt tgacggaacc gtcccattaa tggagcacaa cattgttaag aaaacagacg    1260
acggctacgc caatggagga ggaaaggcgt cgtttatgac atggacagcg cgtgacgcta    1320
tctacgtggc gagagtccat tggataccgt gtgtgttcgc ggttggagtt ctgttcttca    1380
tgggcgtcga gtatacgctt caaatgattc ccgcgaggtc tgagccgttc gatattgggt    1440
ttgtggtcac cgcgctctctg aaccgcgtct tggcaaattc accgggtctt aacaccgttt    1500
tagccgcact aaacacggta tgcagagaga gagattaact taggggttaa aacaactatt    1560
aaatgattta tcatcaattc cccatgcctc acctaacttt ttttttttctt tatcatttaa    1620 atcgtaagta ataaattatt gaattagtca aataaattaa attgtggtag tgatgggaaa    1680
caaatctcag atcttttcct ttattttgtg agtaattaat tctccagctg gaatattgct    1740
gtcaactgta aacatcaaca tgcaatgaaa tttcctaaga gtggaataat ggtgttagta    1800
gataaactag tggacacaaa tgtatttaat gtaatcgctt tgtttagtag ttaagtctaa    1860
tcttcttttt aacaactgcc attttgtttg tttgtttctt tataacgaaa tagttgcact    1920
atagtagtat aatagaatgc tttataactt taaagttaaa acccattaaa aagtaacaca    1980
tgggtgatat ggagacgtga tcacatgcaa tgcaaagtga ttggatagat ttgacttttg    2040
tactttttaa ctatttaaaa cttttgtttg gatggtggtg ggagacaggt gttcgtaggg    2100
atgcaaacta cgtatattgt atggacatgg ttgatggaag gaagaccacg agccaccatc    2160
tcggcttgct tcatgtttac ttgtcgcggt attcttggtt actctactca gctccctctc    2220
cctcaggtcc ccaatcttta catctcactc tctttgaaaa ttatatatta tattaataac    2280
caaatgatat tgtaacaaat agatgaatta tgcaaagtcg ccaaatattg ttgggcgtgt    2340
gattttctcc cttggccact accgtatagg aatcaggttg taactttata tgaatatata    2400
gtatataccc aaatgttttg ataacctgga ctctaattaa agattaatat ctcacaaaac    2460
aattagttta tgaattttat gttcattttg aataggggtta agatatttag tatgatgtca    2520
aatacagtag tatattgaaa acgatagtat ttaatttgaa ataaaaggag taatttgatt    2580
ataagcaaga gggtaattgt agtggtttgt atttacttct ttaacttgcg ggagttaggt    2640
taattaatta gtagtatcat cataattagg cattactatg tctcgttgcg gttaacatgt    2700
tgtattaaaa agtgtcaaaa gcatcactaa ttatttgact ttttttacag gagtttttag    2760
gatcaggagt cgatttttcct gtgggaaacg tctcattctt cctttttctac tcgggtcacg    2820 tcgccggttc gatgatagca tccttagaca tgaggagaat gcagaggttg agactagcaa    2880 tgcttttttga catcctcaat gtattacaat cgatacggct gctcgggacg agaggacatt    2940
acaccatcga tcttgcggtc ggagttggcg ctgggattct ctttgactcg ttggccggga    3000
agtacgaaga gatgatgagc aaaagacaca atttaggcaa tggttttagt ttgatttcta    3060
aagactcgct agacaattaa ttttgttttc ttttaaatg tttagttgga cttgaacata    3120
ttgaatttaa ttgatgtcca gtgaattaaa tttatttctc ttccgatgat tctgactgaa    3180
aaggattaga tagcagttta acctaactaa actgtacgtt gttgtgaagt tataggtgtt    3240
tcttatggta tttctacaac tatttcattc aagtcaatgt tattgttagg agttacaggt    3300
ggggtgagtc ttccaaaact cattggctct accacgtagt gaactttgaa tgtacttctt    3360
cactattttt agtgagcatg tgtcttgttt tccattggta ggtgaagtgg atttcgtata    3420
```

-continued

```
agttaacggg acaggtacac cgatccatga tcatcctact atataaaagg gactaaatta    3480
gaagatttct aggcatgcca catcagcaaa aatattcag                           3519

<210> SEQ ID NO 17
<211> LENGTH: 1462
<212> TYPE: DNA
<213> ORGANISM: Brassica rapa
<220> FEATURE:
<221> NAME/KEY: CDS
<222> LOCATION: (298)..(1149)

<400> SEQUENCE: 17
cgtctaaaat atcaaacttg acatataaaa attagggaac atttcatttg gtcgtctaaa      60
atatcaaact taacatataa aacttaacaa catgttggta caaaagtaaa gtaaagccca     120
acaaagaaaa aaataacaag gcaaagactt tgcgtaaacg tagctctcga aactcaatac     180
tcatcgtttt cgtatgaatt tttgtagacc aaacaatctt ccttccacag ttcataaaat     240
ataaaacaat acctccttcg aaatctctgc ctcttatata acccatctct gacgcctt       297 atg tca act gaa act ggc gtc cct ctc cgt cgc aga tct acc tct ctt      345
Met Ser Thr Glu Thr Gly Val Pro Leu Arg Arg Arg Ser Thr Ser Leu
1               5                   10                  15 aac gga tac cac tct aac gac gtc tcc ttt gac gga acc gtc cca tta      393
Asn Gly Tyr His Ser Asn Asp Val Ser Phe Asp Gly Thr Val Pro Leu
                20                  25                  30 atg gag cac aac att gtt aag aaa aca gac gac ggc tac gcc aat gga      441
Met Glu His Asn Ile Val Lys Lys Thr Asp Asp Gly Tyr Ala Asn Gly
            35                  40                  45 gga gga aag gcg tcg ttt atg aca tgg aca gcg cgt gac gct atc tac      489
Gly Gly Lys Ala Ser Phe Met Thr Trp Thr Ala Arg Asp Ala Ile Tyr
        50                  55                  60 gtg gcg aga gtc cat tgg ata ccg tgt gtg ttc gcg gtt gga gtt ctg      537
Val Ala Arg Val His Trp Ile Pro Cys Val Phe Ala Val Gly Val Leu
65                  70                  75                  80 ttc ttc atg ggc gtc gag tat acg ctt caa atg att ccc gcg agg tct      585
Phe Phe Met Gly Val Glu Tyr Thr Leu Gln Met Ile Pro Ala Arg Ser
                85                  90                  95 gag ccg ttc gat att ggg ttt gtg gtc acg cgc tct ctg aac cgc gtc      633
Glu Pro Phe Asp Ile Gly Phe Val Val Thr Arg Ser Leu Asn Arg Val
            100                 105                 110 ttg gca aat tca ccg ggt ctt aac acc gtt tta gcc gca cta aac acg      681
Leu Ala Asn Ser Pro Gly Leu Asn Thr Val Leu Ala Ala Leu Asn Thr
        115                 120                 125 gtg ttc gta ggg atg caa act acg tat att gta tgg aca tgg ttg atg      729
Val Phe Val Gly Met Gln Thr Thr Tyr Ile Val Trp Thr Trp Leu Met
130                 135                 140 gaa gga aga cca cga gcc acc atc tcg gct tgc ttc atg ttt act tgt      777
Glu Gly Arg Pro Arg Ala Thr Ile Ser Ala Cys Phe Met Phe Thr Cys
145                 150                 155                 160 cgc ggt att ctt ggt tac tct act cag ctc cct ctc cct cag gag ttt      825
Arg Gly Ile Leu Gly Tyr Ser Thr Gln Leu Pro Leu Pro Gln Glu Phe
                165                 170                 175 tta gga tca gga gtc gat ttt cct gtg gga aac gtc tca ttc ttc ctt      873
Leu Gly Ser Gly Val Asp Phe Pro Val Gly Asn Val Ser Phe Phe Leu
            180                 185                 190 ttc tac tcg ggt cac gtc gcc ggt tcg atg ata gca tcc tta gac atg      921
Phe Tyr Ser Gly His Val Ala Gly Ser Met Ile Ala Ser Leu Asp Met
        195                 200                 205 agg aga atg cag agg ttg aga cta gca atg ctt ttt gac atc ctc aat      969
```

```
Arg Arg Met Gln Arg Leu Arg Leu Ala Met Leu Phe Asp Ile Leu Asn
        210                 215                 220 gta tta caa tcg ata cgg ctg ctc ggg acg aga gga cat tac acc atc    1017
Val Leu Gln Ser Ile Arg Leu Leu Gly Thr Arg Gly His Tyr Thr Ile
225                 230                 235                 240 gat ctt gcg gtc gga gtt ggc gct ggg att ctc ttt gac tcg ttg gcc    1065
Asp Leu Ala Val Gly Val Gly Ala Gly Ile Leu Phe Asp Ser Leu Ala
                245                 250                 255 ggg aag tac gaa gag atg atg agc aaa aga cac aat tta ggc aat ggt    1113
Gly Lys Tyr Glu Glu Met Met Ser Lys Arg His Asn Leu Gly Asn Gly
                260                 265                 270 ttt agt ttg att tct aaa gac tcg cta gac aat taa ttttgttttc          1159
Phe Ser Leu Ile Ser Lys Asp Ser Leu Asp Asn
                275                 280 tttttaaatg tttagttgga cttgaacata ttgaatttaa ttgatgtcca gtgaattaaa   1219
tttattttct ttccgatgat tctgactgaa aaggattaga tagcagttta acctaactaa   1279
actgtacgtt gttgtgaagt tataggtgtt tcttatggta tttctacaac tatttcattc   1339
aagtcaatgt tattgttagg agttacaggt ggggtgagtc ttccaaaact cattggctct   1399
accacgtagt gaactttgaa tgtacttctt cactattttt agtgagcatg tgtcttgttt   1459
tcc                                                                  1462

<210> SEQ ID NO 18
<211> LENGTH: 283
<212> TYPE: PRT
<213> ORGANISM: Brassica rapa

<400> SEQUENCE: 18

Met Ser Thr Glu Thr Gly Val Pro Leu Arg Arg Ser Thr Ser Leu
1               5                   10                  15

Asn Gly Tyr His Ser Asn Asp Val Ser Phe Asp Gly Thr Val Pro Leu
                20                  25                  30

Met Glu His Asn Ile Val Lys Lys Thr Asp Asp Gly Tyr Ala Asn Gly
            35                  40                  45

Gly Gly Lys Ala Ser Phe Met Thr Trp Thr Ala Arg Asp Ala Ile Tyr
50                  55                  60

Val Ala Arg Val His Trp Ile Pro Cys Val Phe Ala Val Gly Val Leu
65                  70                  75                  80

Phe Phe Met Gly Val Glu Tyr Thr Leu Gln Met Ile Pro Ala Arg Ser
                85                  90                  95

Glu Pro Phe Asp Ile Gly Phe Val Thr Arg Ser Leu Asn Arg Val
                100                 105                 110

Leu Ala Asn Ser Pro Gly Leu Asn Thr Val Leu Ala Ala Leu Asn Thr
            115                 120                 125

Val Phe Val Gly Met Gln Thr Thr Tyr Ile Val Trp Thr Trp Leu Met
130                 135                 140

Glu Gly Arg Pro Arg Ala Thr Ile Ser Ala Cys Phe Met Phe Thr Cys
145                 150                 155                 160

Arg Gly Ile Leu Gly Tyr Ser Thr Gln Leu Pro Leu Pro Gln Glu Phe
                165                 170                 175

Leu Gly Ser Gly Val Asp Phe Pro Val Gly Asn Val Ser Phe Leu
                180                 185                 190

Phe Tyr Ser Gly His Val Ala Gly Ser Met Ile Ala Ser Leu Asp Met
            195                 200                 205

Arg Arg Met Gln Arg Leu Arg Leu Ala Met Leu Phe Asp Ile Leu Asn
```

```
                210                 215                 220
Val Leu Gln Ser Ile Arg Leu Leu Gly Thr Arg Gly His Tyr Thr Ile
225                 230                 235                 240

Asp Leu Ala Val Gly Val Gly Ala Gly Ile Leu Phe Asp Ser Leu Ala
            245                 250                 255

Gly Lys Tyr Glu Glu Met Met Ser Lys Arg His Asn Leu Gly Asn Gly
                260                 265                 270

Phe Ser Leu Ile Ser Lys Asp Ser Leu Asp Asn
            275                 280

<210> SEQ ID NO 19
<211> LENGTH: 4140
<212> TYPE: DNA
<213> ORGANISM: Brassica rapa
<220> FEATURE:
<221> NAME/KEY: Intron
<222> LOCATION: (1523)..(2001)
<223> OTHER INFORMATION: First intron
<220> FEATURE:
<221> NAME/KEY: Intron
<222> LOCATION: (2140)..(2396)
<223> OTHER INFORMATION: Second intron

<400> SEQUENCE: 19
tttcttcttc ttcaccgttt cgtgtgagtg ttgtggtttt cgatgattta aattgacccc      60
tttggtttat gtatatgtat taaatctaac cccgtaattc ttgatttgtt tgtgattaat     120
cacttcttaa gttttaagcg ttacattgtt atcataagaa cttatttttta tctttgtgtt    180 tatattggag tgtatggttt agaaaacttg aaatgatagt ttttttttata caagctcttt    240 atatacgtca taagaaattt cggaagttac aaacacaaat tgaagatact aatttttaatc    300 taattgaatg aacaaatgtt gtgaaactaa agatgacgtt tgttttgttt atggttggta    360
tacaagtaca cagctaatca actataatgg aaggactctc tgagtatata tgattgatta    420
tctctatatt atttagttgt gtatttgttt aagtaattta tgtacaattg tatatatcta    480
atatttgatg aatgtcaaga ttttgtatat actaaaataa agttatattc aaatctaatt    540
tctcgaatat tttacaccaa ttcaacatgt tttggatttta tgcattatga atccaataag    600
agcaatagtt atcttaaaaa gtgtgaaaga aaatttgcgc ccaagggaac tatatagtcc    660
ttaatgcaaa agtagtaatg tattcaagga agcaccaaat cttcgacat cctccataat     720 cttgaattag accagagtag agttatctac atattgttaa tacttaatat accactgaag    780 tgttctgtg tgaaaaacta gtgttattaa ttcattataa ataatgaaat ctcatactct     840
ttatctctat ttttctttgg ctgtctcaag gccatactgg aatacaaaat gaataacatg    900
ccgatacaaa acgtacctcc caacaaagag aaaaacaaaa caaaactttg cgtaaacgta    960
gctctcaaat ctcatattca tcgttttcgt atgaactttt gtagcccaaa caaccttcct   1020
ttccttccac aagtttcata taatatctct tatataaccc atctctctaa gcctctcaaa   1080
acgttcttct ccgttaaatc taacggtcat gtcaactaca acaatcgtcc ctctccgtcg   1140
cacttctaac tctctcaatg aataccacac taacgcagtc gcctttgacg gaatcgtcgg   1200
gtcagcaagt actagccaaa tggaggagat tgttacgcaa accgacgact gctacgccaa   1260
ccccaacgga gatggaggga aagcaagac gtcgttaatg acgtggagga tgtgcaatcc    1320
tgtccacgtg gtgagagtcc attggatacc gtgtttgtta gcggtaggag ttctgttctt   1380
cacgtgcgta gaggagtaca tgctccagat gattccggcg agttctgagc cgttcgatat   1440
tggttttgtg gcgacgggct ctctgtatcg cctcttggct tcttcaccgg atcttaatac   1500
```

```
cgttttagct gctctcaaca cggtatgtcg taagaaactt cggggttaaaa atatatatat    1560 tgagtatcct caattctgca tgcttcacct aacaaatgag attttgtttg tttgcttctt    1620
tataaagaag taacacaata tacatttact cctatatgac cgtttttagc tttaaaagtt    1680
ttaaatacaa ttaaaaggca tacatggtga taggttggga aacatcacaa accatatgaa    1740
aattctatcc tggacatatg aaaatttgaa aggaaaaaaa cagcataaag ctcataatat    1800
ttttaagaga taatgtatag aaacataagt tctgaaattg ttaaaaacca aaaaaaaaac    1860
taaaatctct tactaaattg tctatagtaa aattttctag gtccgtctat tctgaccgca    1920
tgcaatataa tgaatttggt tagttgtgtt cgacatatcg tatagttta actatataaa     1980 tttgtggggc tgtggagaca ggtgtttgta gggatgcaaa cgacgtatat tttatggaca    2040
tggttggtgg aaggacgacc acgagcgacc atctcggctt gcttcatgtt tacttgccgt    2100
ggcattctgg gttactctac tcagctccct cttcctcagg ttcaaatcat catatttctc    2160
tcttttatat attatatagc attttgttta gtgatgttct accaatttag ttattttct    2220 tttttgtga tgtaacatcg acacatgatt ttatttatgt gtcgtcttgt tatactatgt     2280
attaacacgt tcaaaataaa aactggttta accaaaactg gtttaaagtt aatttgctct    2340
agtgcgtgat taagatatat acaatcctga aaattattta actattttca taacaggatt    2400
ttctaggatc aggggtagat tttccggtag gaaacgtctc gttcttcctc ttctactcag    2460
gccatgtcgc agggtcgacg atagcatcct tggatatgag gagaatgaag aggttgagac    2520
ttgccttgct ttttgacatc ctcaatgtat tacaatcgat caggcttctc gggacgagag    2580
gacaatacac gatcgatctc gctgtcggag ttggcgctgg ggttctcttt gactcactgg    2640
ctggaaaata cgaagagatg atgagcaaga gacacaatgt aggcaatggt tttagtttga    2700
tttcgtctcg ctagttatta attttgttt tttttttatg ttttagtct ggacatattt       2760 aatttagttg aaatctaatg acttaatttt actttctttc aaaatggtct aactgaatac    2820
ggacctaact aaatgtgtac gttattgtgt agttaccata gaggtttcgt attgtcttga    2880
gcctgatatt ttgattttag agctcgttta tacggtagct aataaaaaaa aaaaaaaaag    2940
ctcgtttata cggtagctaa taataaaaaa gaatcaacat gtgacattta tcgtacattc    3000
gtactcaact accatgcaca tgtatacatt ttttaattca gatgctgata ttaacatatc    3060
tatattatat ttacatgaat aatgattagt tttattaact agaatcaggg ccggcttaac    3120
cgatttatag gtcctggggc aatttttcaa aataggccct taacttataa atattgttt    3180 attcatagca taattgtaca atttatcaag aacatgaaac caaatgctta aaatattatc    3240
aggctcatat aagggattag aagtgattag agtcgtattt ttttggacaa aatgatttag    3300
agtcatatta aaacaattat ctcaaagaaa atgtttgtat accatcagat ttcaatttt    3360 caaatttgta ttaccacttg ttttcaaaaa tttgttaaaa tgttcaacaa atctaattg    3420 tcaagtacta aaatgaagtg acatgtatta actattaaaa ttttgatctg tctaaaatac    3480 taaaagttt actcaagaaa atagaacaac attaaattag aaatatttat ggggaaatga    3540
aattttaatg gggaaaatga aattctaatg gggaaagaga atcactaaa tacgaatatc    3600 tttgacaaaa agaaaacata cgaacatcat tgacttcttt ttaactctag ttgttctgtc    3660
acttaaattt ttaatagtca gaaaaatatt atgggcccct cttgctcttg ggccctgggc    3720
cgtcgccttg ctcgccctg tacctgagcc ggcactgact agaatcagat accctctaaa    3780
ctgatttcat ttccaaagtt ctattgaatt caaaagactt ttacggaaca tcttgtaagt    3840
```

```
aaacacatat taaactgaat gaaagttttt ctctttcaaa gaataaactg aaaattatga    3900
aagtcttgat tacataaact aatgaaacca aaaacaaaag aagaaaatat aaaatcaaaa    3960
aaaaaatcat taaactagaa aaacaaatta gtggccttgt gcagttttgc gataatcttg    4020
tttgaggttt gaaccgcatc ctcaacccct gaagactcaa catatgcacc aatcaatgtt    4080
ttataggttc aacatctggt ttagaagcga taatcttgtt tgagctaata tctattttgg    4140

<210> SEQ ID NO 20
<211> LENGTH: 1227
<212> TYPE: DNA
<213> ORGANISM: Brassica rapa
<220> FEATURE:
<221> NAME/KEY: CDS
<222> LOCATION: (151)..(1020)

<400> SEQUENCE: 20
tagctctcaa atctcatatt catcgttttc gtatgaactt ttgtagccca acaaccttc     60 ctttccttcc acaagtttca tataatatct cttatataac ccatctctct aagcctctca    120
aaacgttctt ctccgttaaa tctaacggtc atg tca act aca aca atc gtc cct    174
                                 Met Ser Thr Thr Thr Ile Val Pro
                                   1               5 ctc cgt cgc act tct aac tct ctc aat gaa tac cac act aac gca gtc    222
Leu Arg Arg Thr Ser Asn Ser Leu Asn Glu Tyr His Thr Asn Ala Val
 10                  15                  20 gcc ttt gac gga atc gtc ggg tca gca agt act agc caa atg gag gag    270
Ala Phe Asp Gly Ile Val Gly Ser Ala Ser Thr Ser Gln Met Glu Glu
 25                  30                  35                  40 att gtt acg caa acc gac gac tgc tac gcc aac ccc aac gga gat gga    318
Ile Val Thr Gln Thr Asp Asp Cys Tyr Ala Asn Pro Asn Gly Asp Gly
                 45                  50                  55 ggg aga agc aag acg tcg tta atg acg tgg agg atg tgc aat cct gtc    366
Gly Arg Ser Lys Thr Ser Leu Met Thr Trp Arg Met Cys Asn Pro Val
         60                  65                  70 cac gtg gtg aga gtc cat tgg ata ccg tgt tta gcg gta gga gtt        414
His Val Val Arg Val His Trp Ile Pro Cys Leu Leu Ala Val Gly Val
 75                  80                  85 ctg ttc ttc acg tgc gta gag gag tac atg ctc cag atg att ccg gcg    462
Leu Phe Phe Thr Cys Val Glu Glu Tyr Met Leu Gln Met Ile Pro Ala
 90                  95                 100 agt tct gag ccg ttc gat att ggt ttt gtg gcg acg ggc tct ctg tat    510
Ser Ser Glu Pro Phe Asp Ile Gly Phe Val Ala Thr Gly Ser Leu Tyr
105                 110                 115                 120 cgc ctc ttg gct tct tca ccg gat ctt aat acc gtt tta gct gct ctc    558
Arg Leu Leu Ala Ser Ser Pro Asp Leu Asn Thr Val Leu Ala Ala Leu
                125                 130                 135 aac acg gtg ttt gta ggg atg caa acg acg tat att tta tgg aca tgg    606
Asn Thr Val Phe Val Gly Met Gln Thr Thr Tyr Ile Leu Trp Thr Trp
        140                 145                 150 ttg gtg gaa gga cga cca cga gcg acc atc tcg gct tgc ttc atg ttt    654
Leu Val Glu Gly Arg Pro Arg Ala Thr Ile Ser Ala Cys Phe Met Phe
    155                 160                 165 act tgc cgt ggc att ctg ggt tac tct act cag ctc cct ctt cct cag    702
Thr Cys Arg Gly Ile Leu Gly Tyr Ser Thr Gln Leu Pro Leu Pro Gln
170                 175                 180 gat ttt cta gga tca ggg gta gat ttt ccg gta gga aac gtc tcg ttc    750
Asp Phe Leu Gly Ser Gly Val Asp Phe Pro Val Gly Asn Val Ser Phe
185                 190                 195                 200 ttc ctc ttc tac tca ggc cat gtc gca ggg tcg acg ata gca tcc ttg    798
Phe Leu Phe Tyr Ser Gly His Val Ala Gly Ser Thr Ile Ala Ser Leu
```

```
                    205                 210                 215
gat atg agg aga atg aag agg ttg aga ctt gcc ttg ctt ttt gac atc      846
Asp Met Arg Arg Met Lys Arg Leu Arg Leu Ala Leu Leu Phe Asp Ile
        220                 225                 230 ctc aat gta tta caa tcg atc agg ctt ctc ggg acg aga gga caa tac      894
Leu Asn Val Leu Gln Ser Ile Arg Leu Leu Gly Thr Arg Gly Gln Tyr
            235                 240                 245 acg atc gat ctc gct gtc gga gtt ggc gct ggg gtt ctc ttt gac tca      942
Thr Ile Asp Leu Ala Val Gly Val Gly Ala Gly Val Leu Phe Asp Ser
    250                 255                 260 ctg gct gga aaa tac gaa gag atg atg agc aag aga cac aat gta ggc      990
Leu Ala Gly Lys Tyr Glu Glu Met Met Ser Lys Arg His Asn Val Gly
265                 270                 275                 280 aat ggt ttt agt ttg att tcg tct cgc tag ttattaattt ttgttttttt       1040
Asn Gly Phe Ser Leu Ile Ser Ser Arg
                285 tttatgtttt tagtctggac atatttaatt tagttgaaat ctaatgactt aattttactt   1100 tctttcaaaa tggtctaact gaatacggac ctaactaaat gtgtacgtta ttgtgtagtt   1160 accatagagg tttcgtattg tcttgagcct gatattttga ttttagagct cgtttatacg   1220 gtagcta                                                              1227

<210> SEQ ID NO 21
<211> LENGTH: 289
<212> TYPE: PRT
<213> ORGANISM: Brassica rapa

<400> SEQUENCE: 21

Met Ser Thr Thr Thr Ile Val Pro Leu Arg Arg Thr Ser Asn Ser Leu
1               5                   10                  15

Asn Glu Tyr His Thr Asn Ala Val Ala Phe Asp Gly Ile Val Gly Ser
                20                  25                  30

Ala Ser Thr Ser Gln Met Glu Glu Ile Val Thr Gln Thr Asp Asp Cys
            35                  40                  45

Tyr Ala Asn Pro Asn Gly Asp Gly Arg Ser Lys Thr Ser Leu Met
        50                  55                  60

Thr Trp Arg Met Cys Asn Pro Val His Val Arg Val His Trp Ile
65                  70                  75                  80

Pro Cys Leu Leu Ala Val Gly Val Leu Phe Phe Thr Cys Val Glu Glu
                85                  90                  95

Tyr Met Leu Gln Met Ile Pro Ala Ser Ser Glu Pro Phe Asp Ile Gly
            100                 105                 110

Phe Val Ala Thr Gly Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220
```

```
Arg Leu Ala Leu Leu Phe Asp Ile Leu Asn Val Gln Ser Ile Arg
225                 230                 235                 240

Leu Leu Gly Thr Arg Gly Gln Tyr Thr Ile Asp Leu Ala Val Gly Val
            245                 250                 255

Gly Ala Gly Val Leu Phe Asp Ser Leu Ala Gly Lys Tyr Glu Glu Met
        260                 265                 270

Met Ser Lys Arg His Asn Val Gly Asn Gly Phe Ser Leu Ile Ser Ser
        275                 280                 285

Arg

<210> SEQ ID NO 22
<211> LENGTH: 6109
<212> TYPE: DNA
<213> ORGANISM: Brassica rapa
<220> FEATURE:
<221> NAME/KEY: Intron
<222> LOCATION: (2109)..(2978)
<223> OTHER INFORMATION: First intron
<220> FEATURE:
<221> NAME/KEY: Intron
<222> LOCATION: (3117)..(3744)
<223> OTHER INFORMATION: Second intron

<400> SEQUENCE: 22
tcccgtttgt gctttccttc aagttcttcc tcttttttc acttctcttc atctctctag      60
ttgcttagct gttttccttt catgtctcgc taatgcaaaa ctcatactat tctctttcga     120
tcaaggttct cttttcccac ttccctcaaa tatcttccgg ttcatctgct tcacttgctt     180
gcccatcaag gctcaacaaa cccctaatcc taaaaaccaa atccccaaat ggcttttccc     240
cattaaagtt gctatattcg ccgtggtgtt acatatgtat gattacaaac aatatatgtc     300
tccagttgtg ttattggttc tctatgtttt ccacgtatac ttggagctag acattacctt     360
gatgcttgtc aaacttttcg tctttatcac tcttggatgc gatctagagc cgcaggccaa     420
tgaaccatac ttagccacct ctcttcaaga cttctggggt cgccggtgga atcttatggt     480
cccggcaatc cttaggccgg ctatatacat ccccgtgcgg cagttttgta gaggtctaat     540
gagctctgat tgggcgacat tattggcggt tttggcaacg ttcgttgcct ctggtgtagc     600
tcacgaggtg ttcttcctta ctttgacctt tgagatgcct acaggagaag tggcttgctt     660
ctttgtatta catggagttt gcactactgt cgaggtagct gtgaagagga cagactttgt     720
gcggcgttgg agggtgagtc cagcagtgtc gcgactgctt acggtggggt ttgtggttgt     780
gactagtggc tggttgcttt tccctactct tgcaagaagc gacatgctgg agaaactcgc     840
taacgaagcc ttgctgtcca ttgatttcgt caagcgcacg ttttatagtt tttggtgata     900
gtaaatggtt aaatcatgat tttttataaa aaaataaatg gttaaatcat gatttgtgga     960
tttatgtgct tcttgataag atcgttttat gctgttaatc gtgtttcgac gagagtatta    1020
taaatttata atactgcgtg agaagtaata atctctccta ttgtgaactt tcctataaga    1080
cgttaaaaca aaataaaacg ttgattatct tgggtataaa aaaatatttt acatggatga    1140
atggtagtct atgaatgaaa caatatgata tgttatactc catatgtttc atattaagca    1200
tcactttaga tttgtgcacg cagattaata aaacatttaa ttttttcatt atccatacac    1260
ttaaccatat ttcaaccaat agaaaaataa actggaaaat aaaattaata aattttgtat    1320
caaaatgata aaacgaaact tattttgcaa cgaaattttt tttctatacc gaagaggagt    1380
actatcgtag atcccactga tacaattgat atcacgaacg aaagagagac atcggaacct    1440
```

```
gcctcagaaa aaaaaacaat ctctttttt ggtaaaaaaa tcaatattgg tacgcatatt    1500
ttcaaacttt ctattttggg tgaaatggtt taattaattc attcgaaaca accaacataa    1560
aaagaacaca tgtcgaaaca aaatgtccac aaacaccctg ttgtaataac ttccatatct    1620
aatcgtcacc tatgattggg gatctgtat aattacacat aagtcaaatc gtcacagttt    1680
tggtagtaaa tcgaagcgct catttgtgta ataaagttgt acgttattat gttctagaaa    1740
aaatataaga aatcttctct ctctctctct ctctctctct ctctaaactc ttcagaccca    1800
aaaaaaagac aaggaataat aaaatgtctc aaatggacat ttctacgaga actgaggaag    1860
gaggatggag aagcaagcct tcgtttatga cgtggagagc gcgcgacgtt gtctacgtga    1920
tgagacacca ttggataccg tgtctgttcg cggccggatt cttgttcgtc gtaagcgtgg    1980
agtcctcgat caagatggtt tccgagagtt ctccaccgtt cgatattggg tttgtggcca    2040
cggagtctct gcatcatatc ttggcttctt caccggatct gaacaccggt ttggccgctc    2100
taaactcggt atgtcctaag aattggtttg agtgaattcg atagatgatg atgtgtggat    2160
gtgcaattac caaaataaat tattttggt caaaagaatt aatataaatg tgatttgata    2220
ccataaatag tgttgttttc ttaacaattc ccaactttct ttttatttta actctaataa    2280
aagctctgat ttcttataaa atattatatt atgtccatat ttattttca tagtgtagta    2340 gattagatac aaacgagatg atgattatat atgttttgtt atgaagatgt gcaatttatc    2400
atagacggcc aaagaaaact aaaaccctaa ggccatttca ctatctctat tttatatcat    2460
aagttagatg tctttttat aatttatcat caaatagaag ttcttaaagc atatttcata    2520
aactattctt attcctgatt attgcaaatt aattttggaa aaaaatcttt tcacatcacc    2580
taatattttg tttccttcta tgtcatttaa ctcttactag tatattaatg gatatgtatc    2640
caaccacata tcttgactga tttgagtttg gtatttttt catgattttc aatgcattta    2700
gggatactag tgattcgttg ctaaattcat ttgagatatc atcacttgca accatgaacg    2760 taaaagaat tctataatat tttcagtgtt agcatctttc aaagttttt tttataaaac    2820 ttgacccttc gatttaata acatttacaa atattagaaa tatgaaaata tggattttag    2880
gatatacctt ttacaaaatt gtgattcatt gttcaaaaag agaacattgt atgttcttat    2940
ttactgatag atttacttgt attgatgtgg acatgcaggt gttaggagtg atgcaagtat    3000
cgtatattgc atggacatgg ttaatagaag gacggccacg agccaccatc acggctttat    3060
tcctcttcac ttgtcgcggt gttctcggtt actgtacgca gcttcctctt tcaaaggttc    3120
ccatctacat atctatatac caattattct tttgatagtt tagtgatgtt caatcaaatt    3180
agatgtccaa gtactgacca attaatatca gatactagaa cgttataggc acatatgatt    3240
ccccccttga ccattattga aaaagcagtt ttatagatta tttggtctaa atgttaagca    3300
gttttatagt tcccaaatat tttgacatcc tggactctcg atataaaagt gttagattgt    3360
attatcatag agaggtttaa tttgtacgta gtagttttac ttaaaaatat tgtacgtaag    3420
tccatattgt atatattaat taatttgact taaggcgttt aggctaagta taatcatcaa    3480
ataataaaac tattttgggt ccccaattgt tacttaactt tcttcatctt taaaaattaa    3540
ataaaattct atgaggtgat tgactggaca taagaacaag atttataacg taagccaaac    3600
tctatgtata gataaattat ttatgtatct cgtctaggta tactagttag tatttacatg    3660
cccaaacaat agattgaatt gaggttgatt agctcctcta ttcagatata taatcttgta    3720 tattttttc aatcttgttt acaggagtat ctaggatcag caatcgattt cccgctagga    3780
aacctctcgt tcttctattt tttctcgggt cacgtggcag gcgcgactat cgcatctttg    3840
```

```
gacatgagga ggatgcagag gttgagactt gcgatgattt ttgacatcct caatgtatta    3900
cagtcgatca ggctgcttgc gacgagagga cactacacga tcgatctcgc aggtggagtt    3960
gccgccgcga ttctctttga ctcattggcc ggcaagtacg aagctaatac aagaaagagg    4020
caattgtagg aacaggtttc agcttgatta ccaaaaaact tcaaagattt cattaattca    4080
acatgtttag ttgctgttga attaagtcta ctgtggtttg gcaattattc tccccatgag    4140
ccagtggctt ggacttcttc gaccctagtg ttcatggtca gactgtatat gttgtttatt    4200
tctcattttt tcattcgact ccgcaatttg tgatatgggt ttggttaaca ctagttggtt    4260
cagttgtttt caattggttt tactctgaaa gttataaacg ttttgtaata ccagatttta    4320
cccaacaacg ctcttattaa catcccagtt caatgttgac cggatcatag aaacggataa    4380
gaaaaaaatg agtaagataa aattttaaaa atgacgagga atgatgattt tttatcaaaa    4440
ttaataagga ataaatttgt tttataattc tttacaaaca acaaaagaat gaagatgaat    4500
gaataaaaaa atttattctt cgtgaatgat aaaaaattta aggaatgcta agaatatag    4560 tgttcctcat cattctcttg gtggggtggg gtggccagag agaccgcttg gttcacggtt    4620
gctcacggtg ggttttgtgt gtattagcag taattgttat ttttcctcag ttaaaacgaa    4680
gcaacgtgat agagagacga ggccgtgaat cgttgttttt cattgattct ttaagcgaca    4740
gttttcgtaa ggtcggatta attgttcaaa acgtacatat tcattaataa ttattctatt    4800
gcgttgagtt atggattaaa ttttaaaca tcgctggtat ggaactatgg attttagtt    4860 tgataaagta aacacaacta tatatatctt tgaactggta acaagtatat agacctttta   4920
aacatgaaga atgaggaacc accagatttt gacaaacatg ataacattgt tttttttttt   4980
tttgcagtgt gccattcact gcgctataaa catgagtttt gagtcaatgc ttcatgcaaa   5040
tcatgaaaat agttggattg gatcattagc ctatataaca gcaatcaaaa tacacactta   5100
attggatttc agactggac ttaggttctt agccctttat ttaaaccaat atacatgata   5160
acattattct ttatgaacta tatcattcac tatattttca gttacaagtt gagaattgtg    5220
tttgcacttt tgtgttagccg aaaaataata cttgattttt tcatatcttc caaataatta   5280
gtatggattt cactccataa tttccagtca ttagaaaata aaatgatcat gaaatattgt    5340
tttcatcctg acccttgagt tctcttttat gtttaacatt aactatatac ataagggtgt    5400
caatcgggct aatccggtct ggtacaaaat ccacaaagat cataaatatc taaccctggt    5460
ttagtccggt ccgtgttta aacctccggt cggcgctaaa agggctatta agctacttgg    5520
gattttcagg tttaaaaaaa atctgatatc caatgctttt tttttggtc aaagatatac    5580 aatgcgaaaa aaaagattc gtgatctaaa ccctaaacta agtatccgca actcatatct    5640
ctatcattat aaccctcgaa acttcttatc ctccttttac aaaccaatcc tctgaaacac    5700
aagaaacgag aggtaagaga cccatgagga gtgtcctctg attaatcgtg gccgaaagta    5760
gttgtgtcaa tttgattttg aatggatcga tataagctca attgttacaa aactctttta    5820 tttattttt caaaagttag ggtttctcgt tatatcttca tcattctttc ctcatatcca   5880
attcattgac tcacaaaact tgtgaagttt gacatgattg ttacggtctt aaaataagat    5940
gtagcacgtt cccttttgt ttgatccgga ctgttgaatg tgttgatgct tttgtttcga    6000
accgaatctc aacagtttcc aaaataatct gtattagttc agttctggtt gaccaaaaaa    6060
aaattaagtt ctgttgcaat tatatatttt tcctttttca tttgttgat                6109

<210> SEQ ID NO 23
```

```
<211> LENGTH: 1422
<212> TYPE: DNA
<213> ORGANISM: Brassica rapa
<220> FEATURE:
<221> NAME/KEY: CDS
<222> LOCATION: (270)..(977)

<400> SEQUENCE: 23
acataaaaag aacacatgtc gaaacaaaat gtccacaaac accctgttgt ataacttcc      60 atatctaatc gtcacctatg attggggatc tgatataatt acacataagt caaatcgtca    120
cagttttggt agtaaatcga agcgctcatt tgtgtaataa agttgtacgt tattatgttc    180
tagaaaaaat ataagaaatc ttctctctct ctctctctct ctctctctct aaactcttca    240
```
gacccaaaaa aagacaagg aataataaa atg tct caa atg gac att tct acg          293
                                  Met Ser Gln Met Asp Ile Ser Thr
                                   1               5 aga act gag gaa gga gga tgg aga agc aag cct tcg ttt atg acg tgg         341
Arg Thr Glu Glu Gly Gly Trp Arg Ser Lys Pro Ser Phe Met Thr Trp
 10              15                  20 aga gcg cgc gac gtt gtc tac gtg atg aga cac cat tgg ata ccg tgt         389
Arg Ala Arg Asp Val Val Tyr Val Met Arg His His Trp Ile Pro Cys
25                  30                  35                  40 ctg ttc gcg gcc gga ttc ttg ttc gtc gta agc gtg gag tcc tcg atc         437
Leu Phe Ala Ala Gly Phe Leu Phe Val Val Ser Val Glu Ser Ser Ile
                45                  50                  55 aag atg gtt tcc gag agt tct cca ccg ttc gat att ggg ttt gtg gcc         485
Lys Met Val Ser Glu Ser Ser Pro Pro Phe Asp Ile Gly Phe Val Ala
            60                  65                  70 acg gag tct ctg cat cat atc ttg gct tct tca ccg gat ctg aac acc         533
Thr Glu Ser Leu His His Ile Leu Ala Ser Ser Pro Asp Leu Asn Thr
        75                  80                  85 ggt ttg gcc gct cta aac tcg gtg tta gga gtg atg caa gta tcg tat         581
Gly Leu Ala Ala Leu Asn Ser Val Leu Gly Val Met Gln Val Ser Tyr
    90                  95                 100 att gca tgg aca tgg tta ata gaa gga cgg cca cga gcc acc atc acg         629
Ile Ala Trp Thr Trp Leu Ile Glu Gly Arg Pro Arg Ala Thr Ile Thr
105                 110                 115                 120 gct tta ttc ctc ttc act tgt cgc ggt gtt ctc ggt tac tgt acg cag         677
Ala Leu Phe Leu Phe Thr Cys Arg Gly Val Leu Gly Tyr Cys Thr Gln
                125                 130                 135 ctt cct ctt tca aag gag tat cta gga tca gca atc gat ttc ccg cta         725
Leu Pro Leu Ser Lys Glu Tyr Leu Gly Ser Ala Ile Asp Phe Pro Leu
            140                 145                 150 gga aac ctc tcg ttc ttc tat ttt ttc tcg ggt cac gtg gca ggc gcg         773
Gly Asn Leu Ser Phe Phe Tyr Phe Phe Ser Gly His Val Ala Gly Ala
        155                 160                 165 act atc gca tct ttg gac atg agg agg atg cag agg ttg aga ctt gcg         821
Thr Ile Ala Ser Leu Asp Met Arg Arg Met Gln Arg Leu Arg Leu Ala
    170                 175                 180 atg att ttt gac atc ctc aat gta tta cag tcg atc agg ctg ctt gcg         869
Met Ile Phe Asp Ile Leu Asn Val Leu Gln Ser Ile Arg Leu Leu Ala
185                 190                 195                 200 acg aga gga cac tac acg atc gat ctc gca ggt gga gtt gcc gcc gcg         917
Thr Arg Gly His Tyr Thr Ile Asp Leu Ala Gly Gly Val Ala Ala Ala
                205                 210                 215 att ctc ttt gac tca ttg gcc ggc aag tac gaa gct aat aca aga aag         965
Ile Leu Phe Asp Ser Leu Ala Gly Lys Tyr Glu Ala Asn Thr Arg Lys
            220                 225                 230 agg caa ttg tag gaacaggttt cagcttgatt accaaaaaac ttcaaagatt          1017
Arg Gln Leu

```
                                                                      235 tcattaattc aacatgttta gttgctgttg aattaagtct actgtggttt ggcaattatt       1077 ctccccatga gccagtggct tggacttctt cgaccctagt gttcatggtc agactgtata       1137 tgttgtttat ttctcatttt ttcattcgac tccgcaattt gtgatatggg tttggttaac       1197 actagttggt tcagttgttt tcaattggtt ttactctgaa agttataaac gttttgtaat       1257 accagatttt acccaacaac gctcttatta acatcccagt tcaatgttga ccggatcata       1317 gaaacggata agaaaaaaat gagtaagata aaattttaaa aatgacgagg aatgatgatt       1377 ttttatcaaa attaataagg aataaatttg ttttataatt cttta                      1422

<210> SEQ ID NO 24
<211> LENGTH: 235
<212> TYPE: PRT
<213> ORGANISM: Brassica rapa

<400> SEQUENCE: 24

Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Ala Thr Ile Ala Ser Leu Asp Met Arg
                165                 170                 175

Arg Met Gln Arg Leu Arg Leu Ala Met Ile Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ile Leu Phe Asp Ser Leu Ala Gly
    210                 215                 220

Lys Tyr Glu Ala Asn Thr Arg Lys Arg Gln Leu
225                 230                 235

<210> SEQ ID NO 25
<211> LENGTH: 6189
<212> TYPE: DNA
<213> ORGANISM: Brassica oleracea
<220> FEATURE:
<221> NAME/KEY: Intron
<222> LOCATION: (2188)..(2916)
<223> OTHER INFORMATION: First intron
<220> FEATURE:
```

<221> NAME/KEY: Intron
<222> LOCATION: (3055)..(4133)
<223> OTHER INFORMATION: Second intron

<400> SEQUENCE: 25

```
gaaaactgtc atttaatata taaatttaat caattacaca gtaatttaca taatttaatt      60
ggccacacaa tatccaataa atataaagtt acattgaaat ataaaaacaa tttatatagt     120
gaaacaaaaa tacttttaaa ccattatatt ataaaacaaa tggaatattc aaattatatt     180
gaaacattag aatagtaaga atcagacaag ctgaaatctc aacgtcgatc atttacgtag     240
gccatgcctt agaccatctc caatgtattc ctctactttt ttctctaaaa tagaggaatt     300
tcataaaaga gatggttttt tctccgatgt attttttctat tttctctcct gaaaaagaat    360
attcttgata tattcttttc taagtttaca aataatactt tttatttgtg aaagttgaaa     420
accaacccaa tttattttag tattttataa aattatgata ctatttacac taaatatttt     480
ctttacaaac tattatgtaa ataaaaaaat atattatatt tatataaaca atatatttca     540
ctaaaaaaat attttcggtt ataattgttt aagtaaaaag ttaaaggatc attttgtaaa     600
aataagtaga ggaggtaata tggcaaaaat atagttttt attggtcgat tattttcgtc      660
tacgtggaca ctctatataa ggcttatatc ctcttttat tactttgata ttgttaggat      720
aaaattaagc ggattattta cgatactagg aaaaaagtgt ccaaagattt aaaatattgt     780
tttattgatc aaatagcaaa catccaatgc ataagagtga aaaacttaga tttagatgtt     840
tgtttgttgt ataagtaggt tggtaggtta gtttcatctc ttcgagtttt gagtttgtat     900
ttataaagac aatcgaatat atcttttaat atcataaaaa aattgtgtat attctagata     960
ttataatata tttatctaca agacttttt ttatcattaa acacgagttt cctctagtcc     1020
aatagacatt atgaattctt cctagctatg aaactggcgt ttggtgtatt gattttaacc    1080
aaaataacat ctcctgaatt aatttatgtc caacatctaa tataaatata cgaaacctac    1140
agtaattata tgatattgaa cagttgaaac tcttggttat gttcgaattc aatttctcga    1200
atattttgtg ctaaaccgac atgtaacaaa ctaaatgtcg tcttctatgt tttttcgac     1260
aactacactg ttatggaggg acgtgaaata attatcttaa aaacgtgaaa cgatgtgcgc    1320
caaaaagaat catataatcc tcaatgacat tataaactag tccttattca acaaaggaga    1380
aaatcttttg atattctcca ttatcttgaa ttaaaggtat atatacacat tgttaatacg    1440
cacaccacta acatgtatta gtgtgaacaa aactagtcat tatactatgg taaggaaact    1500
ctcatactct tctctatctt tttgtgtgtg tttctcgtgt aaaatattat acacttaaga    1560
catataaaaa gaacaacaag taaagcccaa caaagacaga tgagaaaata gcaaagactt    1620
gcgtaaacgt cgctctcaaa tctcatctca tactcatcgt tttcgtatga gttttttgtag   1680
cccaaacaat cttcctttct acggtttata atataagaaa caatacttcc ttcgtaatct    1740
ccgccttgta tctcttatat aactcatctc tctaaaccta aaaaatgttc ctctccgtta    1800
aatctaacgg tcatgtcaac taataccgtc gtccctctcc gtcgcagatc taacggatat    1860
cacactaacg gcgtggcctt caacggaatg gagaacattg tcaagaaaac cgacgactgc    1920
tacaccaatg gcaacggagt aggagggaag agcaaggcgt catttctgac atggaccatg    1980
cgtgacgctg tcttcgtagc gagataccat tggataccat gtttctttgc tgtcggagtt    2040
ctgttcttta tgggggttga gtacacgctc cagatggttc cggcgaagtc tgagccgttc    2100
gatattgggt ttgtggccac gcgctctctg aaccgcgtct tggcgagttc accggatctt    2160
aacacccttt tagcggctct aaacacggta tgtcgtatga gttaatttag gttaaaacta    2220
```

```
tatttaatga ttatcttcaa ttcttcatgc ccacacctaa cattttgtat tttttctttt   2280
tcatttaatt cgtaataata tattgaatta gtcaaaataa aataggtggg gttagtgatg   2340
gatatacata aatctcagat cttttccttt attttgtgtg gtattaacta tccagctgga   2400
gttttgccgt ccagggtatc atgcaatgat atttaagagt tgatttgagt ttagaactca   2460
ttttttataaa gatatacatg ttttccaaaa atacatttgc tatgtattaa ttatatttat   2520
tatttttgtt aattttaatt tgtgaaaaca gataatcata acaataatgt atttataatc   2580
aaaatttaaa tttattttaa taagtataga aactctaaaa catatatatt gtgaaacaca   2640
gagtaggtag tgggcaaaaa tgtatttatt aatggaatct cagctatcaa agtagttgta   2700
taattttatt ttaacaactg ccattttttt tgtttgtttt ctttataaag aagtagtaca   2760
ataatagatt agattgcttt taactttaaa gtttcaaccc catgaaaagg gacacatggt   2820
gatgagtcgg agacatgatc acatgcaatg caaagagatt ggttagattc gatttggtac   2880
ttgtaactat ttaatattgg tagatggtgg ggacaggtat tcgtagcgat gcaaacgacg   2940
tatattgtat ggacatggtt gatggaagga aggccacgag ccactatctc ggcttgcttc   3000
atgtttactt gtcgcggcat tcttggttac tctactcagc tccctctacc acaggtctcc   3060
cacctctttta cataaatatt atattatact accttactct tttttttttgt cactgatact   3120
accttactct tataaatata tttaattatg tcaagtctct agatattgtt ggacatgtga   3180
ttttcccttg gccgtttcca tatagaaaac agttgtaact ttataggccc caaatatttt   3240
gaacttttta ttttcattat aacaaaaaga ctatatatta taataattta ctcttaaaat   3300
taatatatag atattgtatc aaatcgatgt atttatgtag tccctatata tagttggacg   3360
tgtgatttcc ccttggccac taccgtacag aggacagctg taattacagt ccccaaaatat   3420
tcttttaatc cggacatcta aactacaaaa ttgttgtttc acaaaacacc tgatttcttt   3480
aacaaaagca aaacaatttg attttttgaat gtttgtttta taatctctcc gttcaacaaa   3540
gatagtcttt taatatttttt atacatatta aaaaaacaca ttaaactact ataataaatg   3600
tatcgttttt tgtaattttc aataacttttt aatcaatagt aatttaataa atttaattaa   3660
ttttttttgaa atttacaaat ttttcataga aaacacaaaa aatacatatt tctgaaacaa   3720
atttttattct aaaaaatata tcttaatgga acggagggag taccttttat ttatagggtt   3780
aaattatttta ttattttttca aaatttatat tgaaatacta aataacactt tgaaaacaga   3840
aagatgtaaa tgataactca ttttgaatgg aaagagcaat ctggttgtta gcatagagag   3900
ggagggtaat ttgcagtgga ttgtattttta ctgttttgtt atgttttttgt ttgctaccga   3960
ctaccgagta ccgaactttt ttctatctat caaaaaatgt tccacgggat gattgactgg   4020
acataaatca cattcactca tctgcgttct acagttctag tttttttttta aagactactt   4080
tcttatgttc aaggatacaa tgattgaagg taattatttg actcttttta caggattttt   4140
taggatcagg agttgatttt ccggtgggaa acgtctcatt cttcctcttc tattctggcc   4200
acgtagccgg ttcaatgatc gcatccttgg acatgaggag aatgcagagg ttgagactag   4260
cgatgctttt tgcatccctc aacatattac aatcgatcag gctgctcggg acgagaggac   4320
actacacgat cgatcttgcg gtcggagttg gcgctgggat tctctttgac tcattggctg   4380
ggaagtacga agagatgatg agcaagagac acaatttagc caatggtttt agtttgattt   4440
ctaaagactc gctagtcaat taatcttttg ttttcatttt aaatgattag ttgaacttga   4500
acatatttga tttagttaaa gtccaatgaa ttacattttt ttatttcaac tttaattgaa   4560
```

```
tagggtttca ttagtttact tgaacctaat taaatgtgta cgtcaagttt cttgtggccg    4620
tcctacaact aattcattcg attcaatgtt agcagttgca tgtgagtcca tccgaaattc    4680
ataggctcta caacttagta aaaacattgc catataaatt tgaaaaaaaa attataacta    4740
aaagtctaaa acagataaat cacaagaaaa tcattttatt cgactgaatg gtgttttata    4800
acattctgat ataagtataa aagtattcaa tttgaaaaat cattcgacca tattggtatt    4860
gcgtaaactg acaatatgca aaatctaatg atacaaaaaa tccggcatta aattattaat    4920
gtacttcctt caccattttt ggtgcaacat gtgttttgtt ttccaagagt aggtcaagat    4980
ggttttcgtg taagttaacg agacaggtac accaatccat gatcattaat agtagtttgg    5040
tccaggggaa agcaacagat cataatctat ttactttgtc tttttgttga gaaaattctc    5100
caatataata atgtacttag cctttaaata tgttagttca actaaatata tgatttacta    5160
gtattcagtg gctaagaaga gtaaaataat ttaagtgtaa agctcttata taactaagta    5220
aaaatcaagg gacacttaaa atattcagtt accacatgta tacatattca aatactgatt    5280
ttaacatatc tgtgtttata tatttattat tttttttttt tgaactgatt cttgcattaa    5340
attaaaaata tgatgagtag caaaagtggc tctcagccca ctttaataca aacctaaaca    5400
aaaaccaatt agaacctagt acacttctaa ggagaaagcc caaactagca tctcacttta    5460
taataaaaga ttcatccctt ctaaccagaa gaagattaac gagataaaaa aaaaacgatt    5520
aggaccctag ttagaatcag acaagacgag aaagatgacg gggtaataga cagcgatcac    5580
gcaggaaaca gagagaacca gagctgtatt aattcgctgg ccagggggtt attctcaggt    5640
ctgagagctg atattctgtt cttgattgtg gaggagattt tcttaatggt cagatcggga    5700
gatcagtgat tacctctgtg tagacgatca ttccgttccc accagagatc gtagatcgtg    5760
gcttgccaag tgactatgga caggtagtta cggtgtctac ttcccgattg agacaggaga    5820
gagtgagcga cgtcatccca ggaagccgat ggagaattga tacccaaccc tatagagaag    5880
tgattccaaa cagatgcaga gtaggcacaa gagaagaaga gatggttttcg tgattcgttc    5940 tcccgattac acaagaggca tagaggatca gtttggaggc cccaagaaag taaacggtct    6000
ctggtcgggc tccgattaag aagcattaac caggcaagag tcttatgctt cggaataacct    6060 tttttgatcc aaatgagtgg ataccaaggg actttaggag tatgcgccaa caaggagtga    6120
tagacatagg agctagagaa ggatctctgg gtctttccat tgtttatcca gcgagcagta    6180
ctcggcgcg                                                            6189

<210> SEQ ID NO 26
<211> LENGTH: 1219
<212> TYPE: DNA
<213> ORGANISM: Brassica oleracea
<220> FEATURE:
<221> NAME/KEY: CDS
<222> LOCATION: (252)..(1094)

<400> SEQUENCE: 26
atataaaaag aacaacaagt aaagcccaac aaagacagat gagaaaatag caaagacttg      60
cgtaaacgtc gctctcaaat ctcatctcat actcatcgtt ttcgtatgag tttttgtagc     120
ccaaacaatc ttcctttcta cggtttataa tataagaaac aatacttcct tcgtaatctc     180
cgccttgtat ctcttatata actcatctct ctaaacctaa aaaatgttcc tctccgttaa     240
atctaacggt c atg tca act aat acc gtc gtc cct ctc cgt cgc aga tct      290
            Met Ser Thr Asn Thr Val Val Pro Leu Arg Arg Arg Ser
              1               5                  10
```

| | | | | | | | | | | | | | | | |
|---|---|---|---|---|---|---|---|---|---|---|---|---|---|---|---|
| aac | gga | tat | cac | act | aac | ggc | gtg | gcc | ttc | aac | gga | atg | gag | aac | att | 338 |
| Asn | Gly | Tyr | His | Thr | Asn | Gly | Val | Ala | Phe | Asn | Gly | Met | Glu | Asn | Ile |
| 15 | | | | 20 | | | | | 25 | | | | | | |

| gtc | aag | aaa | acc | gac | gac | tgc | tac | acc | aat | ggc | aac | gga | gta | gga | ggg | 386 |
| Val | Lys | Lys | Thr | Asp | Asp | Cys | Tyr | Thr | Asn | Gly | Asn | Gly | Val | Gly | Gly |
| 30 | | | | 35 | | | | 40 | | | | | 45 | | |

| aag | agc | aag | gcg | tca | ttt | ctg | aca | tgg | acc | atg | cgt | gac | gct | gtc | ttc | 434 |
| Lys | Ser | Lys | Ala | Ser | Phe | Leu | Thr | Trp | Thr | Met | Arg | Asp | Ala | Val | Phe |
| | | | | 50 | | | | 55 | | | | | 60 | | |

| gta | gcg | aga | tac | cat | tgg | ata | cca | tgt | ttc | ttt | gct | gtc | gga | gtt | ctg | 482 |
| Val | Ala | Arg | Tyr | His | Trp | Ile | Pro | Cys | Phe | Phe | Ala | Val | Gly | Val | Leu |
| | | | 65 | | | | 70 | | | | 75 | | | | |

| ttc | ttt | atg | ggg | gtt | gag | tac | acg | ctc | cag | atg | gtt | ccg | gcg | aag | tct | 530 |
| Phe | Phe | Met | Gly | Val | Glu | Tyr | Thr | Leu | Gln | Met | Val | Pro | Ala | Lys | Ser |
| | | 80 | | | | | 85 | | | | | 90 | | | |

| gag | ccg | ttc | gat | att | ggg | ttt | gtg | gcc | acg | cgc | tct | ctg | aac | cgc | gtc | 578 |
| Glu | Pro | Phe | Asp | Ile | Gly | Phe | Val | Ala | Thr | Arg | Ser | Leu | Asn | Arg | Val |
| | 95 | | | | | 100 | | | | | 105 | | | | |

| ttg | gcg | agt | tca | ccg | gat | ctt | aac | acc | ctt | tta | gcg | gct | cta | aac | acg | 626 |
| Leu | Ala | Ser | Ser | Pro | Asp | Leu | Asn | Thr | Leu | Leu | Ala | Ala | Leu | Asn | Thr |
| 110 | | | | | 115 | | | | | 120 | | | | | 125 |

| gta | ttc | gta | gcg | atg | caa | acg | acg | tat | att | gta | tgg | aca | tgg | ttg | atg | 674 |
| Val | Phe | Val | Ala | Met | Gln | Thr | Thr | Tyr | Ile | Val | Trp | Thr | Trp | Leu | Met |
| | | | | 130 | | | | | 135 | | | | | 140 | |

| gaa | gga | agg | cca | cga | gcc | act | atc | tcg | gct | tgc | ttc | atg | ttt | act | tgt | 722 |
| Glu | Gly | Arg | Pro | Arg | Ala | Thr | Ile | Ser | Ala | Cys | Phe | Met | Phe | Thr | Cys |
| | | | 145 | | | | | 150 | | | | | 155 | | |

| cgc | ggc | att | ctt | ggt | tac | tct | act | cag | ctc | cct | cta | cca | cag | gat | ttt | 770 |
| Arg | Gly | Ile | Leu | Gly | Tyr | Ser | Thr | Gln | Leu | Pro | Leu | Pro | Gln | Asp | Phe |
| | | | 160 | | | | | 165 | | | | | 170 | | |

| tta | gga | tca | gga | gtt | gat | ttt | ccg | gta | gga | aac | gtc | tca | ttc | ttc | ctc | 818 |
| Leu | Gly | Ser | Gly | Val | Asp | Phe | Pro | Val | Gly | Asn | Val | Ser | Phe | Phe | Leu |
| | 175 | | | | | 180 | | | | | 185 | | | | |

| ttc | tat | tct | ggc | cac | gta | gcc | ggt | tca | atg | atc | gca | tcc | ttg | gac | atg | 866 |
| Phe | Tyr | Ser | Gly | His | Val | Ala | Gly | Ser | Met | Ile | Ala | Ser | Leu | Asp | Met |
| 190 | | | | | 195 | | | | | 200 | | | | | 205 |

| agg | aga | atg | cag | agg | ttg | aga | cta | gcg | atg | ctt | ttt | gac | atc | ctc | aac | 914 |
| Arg | Arg | Met | Gln | Arg | Leu | Arg | Leu | Ala | Met | Leu | Phe | Asp | Ile | Leu | Asn |
| | | | 210 | | | | | 215 | | | | | 220 | | |

| ata | tta | caa | tcg | atc | agg | ctg | ctc | ggg | acg | aga | gga | cac | tac | acg | atc | 962 |
| Ile | Leu | Gln | Ser | Ile | Arg | Leu | Leu | Gly | Thr | Arg | Gly | His | Tyr | Thr | Ile |
| | | | 225 | | | | | 230 | | | | | 235 | | |

| gat | ctt | gcg | gtc | gga | gtt | ggc | gct | ggg | att | ctc | ttt | gac | tca | ttg | gct | 1010 |
| Asp | Leu | Ala | Val | Gly | Val | Gly | Ala | Gly | Ile | Leu | Phe | Asp | Ser | Leu | Ala |
| | | 240 | | | | | 245 | | | | | 250 | | | |

| ggg | aag | tac | gaa | gag | atg | atg | agc | aag | aga | cac | aat | tta | gcc | aat | ggt | 1058 |
| Gly | Lys | Tyr | Glu | Glu | Met | Met | Ser | Lys | Arg | His | Asn | Leu | Ala | Asn | Gly |
| | 255 | | | | | 260 | | | | | 265 | | | | |

| ttt | agt | ttg | att | tct | aaa | gac | tcg | cta | gtc | aat | taa | tcttttgttt | | | | 1104 |
| Phe | Ser | Leu | Ile | Ser | Lys | Asp | Ser | Leu | Val | Asn | | | | | |
| 270 | | | | 275 | | | | | 280 | | | | | | | tcattttaaa tgattagttg aacttgaaca tatttgattt agttaaagtc caatgaatta    1164 cattttttta tttcaacttt aattgaatag ggtttcatta gtttacttga accta          1219

<210> SEQ ID NO 27
<211> LENGTH: 280
<212> TYPE: PRT
<213> ORGANISM: Brassica oleracea

<400> SEQUENCE: 27

Met Ser Thr Asn Thr Val Val Pro Leu Arg Arg Ser Asn Gly Tyr
1               5                   10                  15

His Thr Asn Gly Val Ala Phe Asn Gly Met Glu Asn Ile Val Lys Lys
            20                  25                  30

Thr Asp Asp Cys Tyr Thr Asn Gly Asn Gly Val Gly Gly Lys Ser Lys
        35                  40                  45

Ala Ser Phe Leu Thr Trp Thr Met Arg Asp Ala Val Phe Val Ala Arg
    50                  55                  60

Tyr His Trp Ile Pro Cys Phe Phe Ala Val Gly Val Leu Phe Phe Met
65                  70                  75                  80

Gly Val Glu Tyr Thr Leu Gln Met Val Pro Ala Lys Ser Glu Pro Phe
                85                  90                  95

Asp Ile Gly Phe Val Ala Thr Arg Ser Leu Asn Arg Val Leu Ala Ser
            100                 105                 110

Ser Pro Asp Leu Asn Thr Leu Leu Ala Ala Leu Asn Thr Val Phe Val
        115                 120                 125

Ala Met Gln Thr Thr Tyr Ile Val Trp Thr Trp Leu Met Glu Gly Arg
    130                 135                 140

Pro Arg Ala Thr Ile Ser Ala Cys Phe Met Phe Thr Cys Arg Gly Ile
145                 150                 155                 160

Leu Gly Tyr Ser Thr Gln Leu Pro Leu Pro Gln Asp Phe Leu Gly Ser
                165                 170                 175

Gly Val Asp Phe Pro Val Gly Asn Val Ser Phe Phe Leu Phe Tyr Ser
            180                 185                 190

Gly His Val Ala Gly Ser Met Ile Ala Ser Leu Asp Met Arg Arg Met
        195                 200                 205

Gln Arg Leu Arg Leu Ala Met Leu Phe Asp Ile Leu Asn Ile Leu Gln
    210                 215                 220

Ser Ile Arg Leu Leu Gly Thr Arg Gly His Tyr Thr Ile Asp Leu Ala
225                 230                 235                 240

Val Gly Val Gly Ala Gly Ile Leu Phe Asp Ser Leu Ala Gly Lys Tyr
                245                 250                 255

Glu Glu Met Met Ser Lys Arg His Asn Leu Ala Asn Gly Phe Ser Leu
            260                 265                 270

Ile Ser Lys Asp Ser Leu Val Asn
        275                 280

<210> SEQ ID NO 28
<211> LENGTH: 4233
<212> TYPE: DNA
<213> ORGANISM: Brassica oleracea
<220> FEATURE:
<221> NAME/KEY: Intron
<222> LOCATION: (2232)..(2807)
<223> OTHER INFORMATION: First intron
<220> FEATURE:
<221> NAME/KEY: Intron
<222> LOCATION: (2946)..(3466)
<223> OTHER INFORMATION: Second intron

<400> SEQUENCE: 28 aaaaagaaa ctggaaattg atggatgtgg tgagtgcata attctaaatc agaatctata      60
ttattgtgag atctatttgt acgtcgatac tttttattaa agttaagaaa taatgaatca    120
aagaaacatc aacaatggcc caaatccaag catagaccat tttagacaaa cccgtctgat    180
tgagtgatta gacaggcacg tagtagtcta gtttgtgtga aaaacataca aaatcaccat    240

```
cgccttgagt ttcgttaata tgtagacaat tacatgattt acattttgta tacctttgag     300
aatttaaata attatcttaa atctgtatga atctataaaa tttaaaattc ttctatacaa     360
ctaaatttca gagtttattc tataaccgat tatgtttata tgcataccta ctataaacgt     420
cttctatgtt ttcgtttact acattgtgga agttcaatac ttagtcccga attgggtaat     480
tggaataagt attggaattt aagtatgcaa gtactttgat ggaaaagata tccaagtctc     540
gtttttttca aagtattgat aaaaaaaata ggatttgttt tagttaaaaa gatacattga     600
attccattaa aattcaccat aactgaattc taattaaatt taaaaaatat cgaataacat     660
tggttttcaa tggatttaaa ttttatttac caaatactca atccaataac actgaattta     720
ggtatggatt taaattccac tcaattctat aaaataactc aattcaataa caccctctaa     780
accaccgata tgattttggg tggtacggtg ggttccagaa agattctaaa cgttttaagt     840
tttttttttt tttgacagca aacgtttaa gtttgaaatc taccatttag atttatttat     900
atgtgtgatt agataatgtg agtatctaac ttttatataa aattcttaga cttatttatt     960
gtcgatacta gatgattaat cagaggcttt cgcggtttgg agaactaaaa aaacttaaat    1020
cttttttttt caatacttat cttaaaaaag cgtcaaagat gattgcgccc aaaaaataaa    1080
atataatact cagttgaata aactaatgtc tgatgcatac aacgaagcat caaatctctt    1140
gatattctcc ataatcttga attagagtat atacacattg ttagcactta atatgcatac    1200
acacaccact aacatgtttt tgtctgaaaa ctataattat tttagtaacg agagaatctc    1260
atagtcttat atctataatc tcttcatttt attttaagtg tcattttaaa tttgtttaca    1320
cagattttgt atattttcca aataaaaatat cattaagtat acatttaatc atattttga    1380
ccaatcaaaa ataaaatgga aaatataaat atttataaag catagaaaat cgataaattt    1440
tgcattaaaa ttctataaca ataattattt tgtatcaaaa aatttacttt acaacaatat    1500
ttattataaa aattagggaa caattctttt ggtcgtctaa aatatcaaac ttgacatata    1560
aaaattaggg aacatttcat ttggtcgtct aaaaatatcaa acttaacata taaaaagaac    1620
ttaacaacat gttggtacaa aagtaaagta aagcccaaca aagagagaaa acagagaaaa    1680
aaataataag gcaaagactt tgcgtaaacg tagctctcga aactcaatac tcatcgtttt    1740
cgtatgaatt tttgtagacc aaacaatctt ccttccacag ttcacaaaat ataaaacaat    1800
acctccttcg aaatctctgc ctcttatata acccatctct gacgcttatg tcaactgaaa    1860
ctggcgtccc tctccgtcgc agatctaact ctcttaacgg acatcactct aacgacgtcg    1920
cctttgacgg aaccgtccca tcaatggaga acaacattgt taagaaaaca gacgacggct    1980
acgccaatgg aggaggaaag gcgtcgttta tgacatggac ggcgcgtgac gctatctacg    2040
tggcgagagt ccattggata ccgtgtgtgt tcgcggttgg agttctgttc ttcatgggcg    2100
tcgagtatac gcttcagatg attcccgcga ggtctgagcc gttcgatgtt gggtttgtgg    2160
ccacgcgctc tctgaacagc gtcttggcaa attcaccggg tcttaacacc gttttagccg    2220
cactaaacac ggtatgcaga gagagagatt aacttagggg ttaaaacaac tattaaatga    2280
tttatcatca attcctcatg cctcacctaa cttttttgttt ttttttctttt atcatttaaa    2340
tcgtaagtaa taaattattg aattagtcaa ataaattaaa ttgtggtagt gatgggaaca    2400
aatctcagat cttttccttt attttgtgag gtgattaatt ctccagctgg aattttgctg    2460
tcaactgtaa acatcaacat gcaatgaaat ttcctaagag tggaataatg gtgttagtag    2520
ataaactagt ggacacaaat gtatttaatg taatcgcttt gtttagtagt taagtctaat    2580
cttctttta acaactgcca ttttgtttgt ttgtttcttt ataacgaaat agttgcacta    2640
```

-continued

```
tagtagtata atagaatgct ttataacttt aaagttaaaa cccattaaaa agtaacacat    2700
gggtgatatg gagacgtgat cacatgcaat gcgaagagat tggatagatt tgactttttgt   2760 acttttttaac tatttaaaac ttttgtttgg atggtggtgg gagacaggtg ttcgtaggga   2820
tgcaaactac gtatattgta tggacatggt tgatggaagg aagaccacga gccaccatct    2880
cggcttgctt catgtttact tgtcgcggta ttcttggtta ctctactcag ctccctctcc    2940
ctcaggtccc aatctttaca tctcactctc tctatgaaaa atatagatta taataactaa    3000
atgatgttgt aacaaaatag atgaattatg taaagtcgcc aaatattgtt gggcgtctga    3060 tttttctccct tggccactac cgtataggaa acaggttgta actttatatg aatatatacc   3120 caaatgttttt gataacctgg actctaatta aagattaata tctcacaaaa caattagttt   3180
atgaatttta tgttcatttt gaataggggtt aagttattta gtatgatgtc aaatacagta   3240
ctagtatatt gaaaacgata gtatttaatt tgaaataaaa gcagtaattt gattataagc    3300
aacgagaggg caattgtagt ggtttgtatt tacttcttta acttgcgggg gttaagttag    3360
ttaattagta gtatcatcat aattaggcat tactatgtct cgttgctgtt aacatgttgt    3420
attaaaaagt gtcaaaagca tcaataatta tttgactttt ttacaggagt ttttaggatc    3480
aggagtcgat tttcctgtgg gaaacgtctc attcttcctt ttctactcgg gtcacgtcgc    3540
cggttcgatg atagcatcct tagacatgag gagaatgcag aggttgagac tagcaatgct    3600
ttttgacatc ctcaatgtat tacaatcgat aaggctgctc gggacgagag gacattacac    3660
catcgatctt gcggtcggag ttggcgctgg gattctcttt gactcgttgg ccgggaagta    3720
cgaagagatg atgagcaaaa gacacaattt aggcaatggt tttagtttga tttctaaaga    3780
ctcgctagtc aattaatttt gttttctttt taaatgttta gttgaacttg aacatatatt    3840
aaatttaatt gatgtccaat gaattaaatt tatttctttt ccgatgattc tgactgaaaa    3900
ggattagata gcagtttaac ctaactaaac ctgtacgttt ttgcgaagtt ataggagttt    3960
cttatggtct ttctacaact atttcattca agtcaatgtt aggagttaaa ggtgaggtga    4020
gactgccaaa actcattggc tctaccactt agtgaacttt gaatgtactt cttcactatg    4080
tttagtgagc atgtgtcttg ttttccattg gtaggtgaag tggatttcgt ataaattaac    4140
gggacaggta caccgatcca tgattattat tcattaatag tttggtccac ggaaagcaat    4200
agatcatact ttatttacgg tcttttttgtt gtt                                 4233
```

<210> SEQ ID NO 29
<211> LENGTH: 1299
<212> TYPE: DNA
<213> ORGANISM: Brassica oleracea
<220> FEATURE:
<221> NAME/KEY: CDS
<222> LOCATION: (241)..(1092)

<400> SEQUENCE: 29

```
atataaaaag aacttaacaa catgttggta caaaagtaaa gtaaagccca acaaagagag    60
aaaacagaga aaaaaataat aaggcaaaga ctttgcgtaa acgtagctct cgaaactcaa   120
tactcatcgt tttcgtatga attttttgtag accaaacaat cttccttcca cagttcacaa   180
aatataaaac aatacctcct tcgaaatctc tgcctcttat ataacccatc tctgacgctt    240 atg tca act gaa act ggc gtc cct ctc cgt cgc aga tct aac tct ctt     288
Met Ser Thr Glu Thr Gly Val Pro Leu Arg Arg Arg Ser Asn Ser Leu
1               5                   10                  15 aac gga cat cac tct aac gac gtc gcc ttt gac gga acc gtc cca tca     336
```

|  |  |  |  |  |  |  |  |  |  |  |  |
|---|---|---|---|---|---|---|---|---|---|---|---|
| Asn | Gly | His | His | Ser | Asn | Asp | Val | Ala | Phe | Asp | Gly | Thr | Val | Pro | Ser |
|  |  |  | 20 |  |  |  | 25 |  |  |  | 30 |  |  |  |  |

```
atg gag aac aac att gtt aag aaa aca gac gac ggc tac gcc aat gga     384
Met Glu Asn Asn Ile Val Lys Lys Thr Asp Asp Gly Tyr Ala Asn Gly
        35                  40                  45 gga gga aag gcg tcg ttt atg aca tgg acg gcg cgt gac gct atc tac     432
Gly Gly Lys Ala Ser Phe Met Thr Trp Thr Ala Arg Asp Ala Ile Tyr
 50                  55                  60 gtg gcg aga gtc cat tgg ata ccg tgt gtg ttc gcg gtt gga gtt ctg     480
Val Ala Arg Val His Trp Ile Pro Cys Val Phe Ala Val Gly Val Leu
 65                  70                  75                  80 ttc ttc atg ggc gtc gag tat acg ctt cag atg att ccc gcg agg tct     528
Phe Phe Met Gly Val Glu Tyr Thr Leu Gln Met Ile Pro Ala Arg Ser
                     85                  90                  95 gag ccg ttc gat gtt ggg ttt gtg gcc acg cgc tct ctg aac agc gtc     576
Glu Pro Phe Asp Val Gly Phe Val Ala Thr Arg Ser Leu Asn Ser Val
                100                 105                 110 ttg gca aat tca ccg ggt ctt aac acc gtt tta gcc gca cta aac acg     624
Leu Ala Asn Ser Pro Gly Leu Asn Thr Val Leu Ala Ala Leu Asn Thr
            115                 120                 125 gtg ttc gta ggg atg caa act acg tat att gta tgg aca tgg ttg atg     672
Val Phe Val Gly Met Gln Thr Thr Tyr Ile Val Trp Thr Trp Leu Met
130                 135                 140 gaa gga aga cca cga gcc acc atc tcg gct tgc ttc atg ttt act tgt     720
Glu Gly Arg Pro Arg Ala Thr Ile Ser Ala Cys Phe Met Phe Thr Cys
145                 150                 155                 160 cgc ggt att ctt ggt tac tct act cag ctc cct ctc cct cag gag ttt     768
Arg Gly Ile Leu Gly Tyr Ser Thr Gln Leu Pro Leu Pro Gln Glu Phe
                165                 170                 175 tta gga tca gga gtc gat ttt cct gtg gga aac gtc tca ttc ttc ctt     816
Leu Gly Ser Gly Val Asp Phe Pro Val Gly Asn Val Ser Phe Phe Leu
                180                 185                 190 ttc tac tcg ggt cac gtc gcc ggt tcg atg ata gca tcc tta gac atg     864
Phe Tyr Ser Gly His Val Ala Gly Ser Met Ile Ala Ser Leu Asp Met
            195                 200                 205 agg aga atg cag agg ttg aga cta gca atg ctt ttt gac atc ctc aat     912
Arg Arg Met Gln Arg Leu Arg Leu Ala Met Leu Phe Asp Ile Leu Asn
210                 215                 220 gta tta caa tcg ata agg ctg ctc ggg acg aga gga cat tac acc atc     960
Val Leu Gln Ser Ile Arg Leu Leu Gly Thr Arg Gly His Tyr Thr Ile
225                 230                 235                 240 gat ctt gcg gtc gga gtt ggc gct ggg att ctc ttt gac tcg ttg gcc    1008
Asp Leu Ala Val Gly Val Gly Ala Gly Ile Leu Phe Asp Ser Leu Ala
                245                 250                 255 ggg aag tac gaa gag atg atg agc aaa aga cac aat tta ggc aat ggt    1056
Gly Lys Tyr Glu Glu Met Met Ser Lys Arg His Asn Leu Gly Asn Gly
                260                 265                 270 ttt agt ttg att tct aaa gac tcg cta gtc aat taa ttttgttttc         1102
Phe Ser Leu Ile Ser Lys Asp Ser Leu Val Asn
            275                 280 tttttaaatg tttagttgaa cttgaacata tattaaattt aattgatgtc caatgaatta  1162
aatttatttt ctttccgatg attctgactg aaaaggatta gatagcagtt taacctaact  1222
aaacctgtac gttttgcga agttatagga gtttcttatg gtctttctac aactatttca   1282
ttcaagtcaa tgttagg                                                 1299
```

<210> SEQ ID NO 30
<211> LENGTH: 283
<212> TYPE: PRT

<213> ORGANISM: Brassica oleracea

<400> SEQUENCE: 30

```
Met Ser Thr Glu Thr Gly Val Pro Leu Arg Arg Ser Asn Ser Leu
1               5                   10                  15
Asn Gly His His Ser Asn Asp Val Ala Phe Asp Gly Thr Val Pro Ser
            20                  25                  30
Met Glu Asn Asn Ile Val Lys Lys Thr Asp Asp Gly Tyr Ala Asn Gly
        35                  40                  45
Gly Gly Lys Ala Ser Phe Met Thr Trp Thr Ala Arg Asp Ala Ile Tyr
    50                  55                  60
Val Ala Arg Val His Trp Ile Pro Cys Val Phe Ala Val Gly Val Leu
65                  70                  75                  80
Phe Phe Met Gly Val Glu Tyr Thr Leu Gln Met Ile Pro Ala Arg Ser
                85                  90                  95
Glu Pro Phe Asp Val Gly Phe Val Ala Thr Arg Ser Leu Asn Ser Val
            100                 105                 110
Leu Ala Asn Ser Pro Gly Leu Asn Thr Val Leu Ala Ala Leu Asn Thr
        115                 120                 125
Val Phe Val Gly Met Gln Thr Thr Tyr Ile Val Trp Thr Trp Leu Met
    130                 135                 140
Glu Gly Arg Pro Arg Ala Thr Ile Ser Ala Cys Phe Met Phe Thr Cys
145                 150                 155                 160
Arg Gly Ile Leu Gly Tyr Ser Thr Gln Leu Pro Leu Pro Gln Glu Phe
                165                 170                 175
Leu Gly Ser Gly Val Asp Phe Pro Val Gly Asn Val Ser Phe Phe Leu
            180                 185                 190
Phe Tyr Ser Gly His Val Ala Gly Ser Met Ile Ala Ser Leu Asp Met
        195                 200                 205
Arg Arg Met Gln Arg Leu Arg Leu Ala Met Leu Phe Asp Ile Leu Asn
    210                 215                 220
Val Leu Gln Ser Ile Arg Leu Leu Gly Thr Arg Gly His Tyr Thr Ile
225                 230                 235                 240
Asp Leu Ala Val Gly Val Gly Ala Gly Ile Leu Phe Asp Ser Leu Ala
                245                 250                 255
Gly Lys Tyr Glu Glu Met Met Ser Lys Arg His Asn Leu Gly Asn Gly
            260                 265                 270
Phe Ser Leu Ile Ser Lys Asp Ser Leu Val Asn
        275                 280
```

<210> SEQ ID NO 31
<211> LENGTH: 5140
<212> TYPE: DNA
<213> ORGANISM: Brassica oleracea
<220> FEATURE:
<221> NAME/KEY: Intron
<222> LOCATION: (1500)..(2001)
<223> OTHER INFORMATION: First intron
<220> FEATURE:
<221> NAME/KEY: Intron
<222> LOCATION: (2140)..(2383)
<223> OTHER INFORMATION: Second intron

<400> SEQUENCE: 31

```
atctcaccgt tggatttacc aaacacccaa gactgctctg ctgaagaact atggcgacca      60
gcttcaagaa aacccagaca acagaagatc caaccgttga aaaccaaatc ccttcggtga     120
acctctaacc cactgactga agaagcttcc cacaaaatat cagcccaatc aggatccgtt     180
```

```
tgaccctcca aatccagtct tgaaaacacc ttacgagttt tctccttctt ctctcttctt      240
tctctctttt gtctctttct ctaaactcta ttattgtgag tctacagtgc aaaggggaac      300
atcattaatt acttaaggtc accccaattg gtcctctcca tctaggaggg acccaacagt      360
acacagctaa tcaactataa tgaaggactc tctgagtata tatgattatc tctatattat      420
ttagttgtgt atttgtttaa gtaatttatg tacaattgca tatatcgaat atttgatgaa      480
tgtcaagatt ttgtatataa taaaataaag ttatattcaa atctaatttc tcgaatattt      540
tacaccaatt caacatgttt tggatttatg cattatgaat ccaataagag caatagttat      600
cttaaaaagt gtgaaagaaa atttgcgccc aagggaacta tatagtcctt aatgcaaaag      660
tagtaatgta ttcaaggaaa caccaaatct ttcgacatcc tccataatct tgaattagac      720
cagagtagag ttctacatat tgttaatact taatatacca ctaacgtgtt tctgtatgaa      780
aaactagtgt tattataaat aatgaaatct catactcttt atctctattt ttctttggtt      840
gtctcaaggc aatactggaa atataaagtg aacaacatgc cggtacaaaa cgtacctccc      900
aacaaagaga aaacaaaac aaaaccttgc gtaaacgtag ctctcaaatc tcatattcat      960
cgttttcgta tgaacttttg tagcccaaac aaccttcctt tccttccaca agtttcataa     1020
tatctcttat ataacccata tctccaagcc tctcgaaatg ttcttctccg ttaaatctaa     1080
cggtcatgtc aactacaaca atcgtccctc tccgtcgcag ttctaactct ctcaatgaat     1140
accacactaa cgcagtcgcc tttgacggaa tcgtcgggtc aacaagtact agccaaatgg     1200
aggagattgt tacgcaaacc gacgactgct acgccaatca caacggagat ggagggagaa     1260
gcaaggcatc gtttatgacg tggaggatgt gcaatcctgt ccaggtggcg agagtccatt     1320
ggataccgtg tttgctagcg gtaggagttc tgttcttcac gggcgtagag gagtacatgc     1380
tccagatgat tccggcgagt tctgagccgt tcgatattgg ttttgtggcg acgcgctctc     1440
tgtatcgact cttggcttct tcaccggatc ttaataccgt tttagctgct ctcaacacgg     1500
tatgtcttaa gaaacttagg gttaaaaata tatttattga gtatcctcaa ttctgcatgc     1560
ttcacctaac aaatgagatt ttgtttgttt gcttctttat aaagaagtta acaatataa     1620 atttattcgt atatgaccgt ttttagcttt aaaagtctta aacacaatga aaaggcacac     1680
ttggtgatag gttggggaaa caccacgaac catatgaaaa gtcgatcctg gacatatgaa     1740
aattaaaaaa gatgcataaa gctcataata ttcttaagag aaaaaaataa taatattttt     1800
tagagataat gtatagaaac ataagttctt aaattgttaa aaaccaaaat ttttttttta     1860
atctcttact aaattgtgta tagtaaaatc ttttaggtcc gtctattctg acctcatgca     1920
atatatataa tgaatctggt taactgtatt cgacatatcg tatagtttta actatataaa     1980
tttgtggggc tgtggagaca ggtgtttgta gggatgcaaa cgacgtatat tttatggaca     2040
tggttggtgg aaggacgacc acgagcgacc atctcggctt gcttcatgtt tacttgtcgt     2100
ggcattcttg gttactctac tcagctccct cttcctcagg ttcaaatcat catatttctc     2160
tcttttatat attatatagc attttgttta gtgatgttct accaatttag ttattttcc      2220 tttttttgtg atgtaacatc gacacatgat tttatttatg tgtcgtcttg ttatactatg     2280
tatttacatg ttcaagaata aaaactggtt taaggttaat ttgctctagt gcgtgattaa     2340
gatatataca atcctgaaaa ttatttaact attttcataa caggatttc taggatcagg      2400 ggtagatttt ccgtaggaa acgtctcgtt cttcctcttc tactcaggcc atgtcgcagg      2460
gtcgacgata gcatccttgg atatgaggag aatgaagagg ttgagactag ccttgctttt     2520
```

```
tgacatcctc aatgtattac aatcgatcag gcttctcggg acgagaggac aatacacgat    2580
cgatctcgct gtcggagttg gcgctggggt tctctttgac tcactggctg aaaatacga     2640 agagatgatg agcaagagac gcaatgtagg caatggtttt agtttgattt cgtctcgcta    2700
gttattaatt tttgttttt ttttatgtt tttagtctgg acatatttaa tttagttgaa      2760
atctaatgac ttaaatttgc tttctttcaa aatgctctaa ctgacggacc taactaaatg    2820
tgtacgttat tgtgtagtta ccatagaggt ttcgtattgt cttgagcctg atattttgat    2880
tttagagctc gtttatacgg tagctaataa taaaaagaa tcaacatgtg acatttatcg     2940
tactcaatta ccatgcacat gtatatatgt ttttgttgga gtaagcttga aagaaaagga    3000
aacttgagtt ataagtttct aacctaatcc taccgagtta tggaaatagg aatactaaca    3060
tatttaggag tcatctaaat gtattaccta taaggattag gaaatatcaa tctctatata    3120
agaagatgtc aagatgtgac atagcttatg agtttagaga ttgagagctt aagttttga    3180 gttagttttc ttaagcatta ataaagtgag ttatacttta tacattcttt gaactctaga   3240
tttggtatca aaatattgcg acgaagaagg gatatcacaa ggcatctaac agctccgtat   3300
actccacaac agaatggagt ggtggaaaga agaaatcgaa cgttaatgga gatgacgaga   3360
agcctgctta agcatatgca catgcctaat tatttgtggg gtgaagcaat aagacatgca   3420
acttacttga taaacaggat agccacacga tccttgctgc ttcagacgcc atacgaagtg   3480
ctacgaagga gaaagccaaa tataagtcac ctacggatat ttggatgttt gagttatgcc   3540
aaagttgata aggcgcacct aagaaagctc gacgacaggt caagaatgct agttcatctc   3600
ggaacagagc cgggatccaa ggcctacaga ttgttcgatg ttgaaacacg gagagttgta   3660
gtaagtcgcg acgtcgtatt tgacgagaca aaaggcttga actggaaaaa atatgatgcg   3720
aaggtagaaa actatgatga cttcacggtc acgatgggtg agttcggtaa tcatgggatc   3780
actgaacact caaaccacga caagcttgca gaaattcaag cgtcgcacga tgaggaagaa   3840
aacaaagatg atgatgatga tgaagctcaa aactcgggaa cagatatttt tggaccagtc   3900
agcgaaggag aacaagaaac aagagtgttg agaagaagtg agagacaaac ttccacacca   3960
aaataccttg aagattacgt gatggtagct gaagaagaag gagaggtgct gctaatgtgt   4020
ataaacaacg aaccaagaaa cttttgtggag gctagtatgc taaagaatg gatagacgcg   4080 tgcaaggatg agatacagtc catcgagaag aatgaggtat ggaaactagt tgacttacca   4140
gttggagcta aacccattgg tctcagatgg atattcaaga taaaacgcaa ttctgatgga   4200
tcgatcaata agtataaagc tcgtctagtg gcaaaagggt atgtacaaca acaagggatc   4260
gatttcgatg aggttttttgc tcccgtagca cgccttgaaa ctatcagact actcatcggt   4320
gttgcagcta cgaacggatg gcaagttcac cacctcgacg ttaagacggc cttccttcat   4380
ggagagttaa agaaatcgt ttatgttaca cagcctgaag gtttcgaggt gaagggaagt   4440
gagagaaagg tatacaagct caacaaagca ttgtacggac tgcgacaggc accgagggct   4500
tggaacaaca agttgaatcg gatactactc gagtttgggt tcgaaaagtg ctccaaggaa   4560
cactctgtat acaggaaaac cgtgggacag agcattctcg tcgtggctgt ttatgtagat   4620
gacttgttcg tgtgtggagc aagcgagaag atcattggag atttttaaaag agagatgggg   4680 tcaaagtttg atatgagtga cttgggtaaa ctaagttact atcttgggat tgaagttcat   4740
caagaagaag gatatataag cctaaaccaa actaagttac tatcttggga ttgaagttca   4800
tcaagaagaa ggatatataa gcctaaacca aactaagtta ctatcttggg attgaagttc   4860
atcaagaaga aggatatata agcctaaacc aaactaagtt actatcttgg gattgaagtt   4920
```

```
catttgcctt agatatcttc gaggaactac gtcacttggt ctcacgtttg ctagatcatc    4980
gctagggatt ccaaagctca ttgggtacag tgatagcagt cacaatgtgg acatagatga    5040
tggaagaagc actgcaggtc acatattcta cttgagtgat agcatgatta cgtggtgctc    5100
aagtaagtag gacacagttg ctctctcttc ctgcgaggca                          5140

<210> SEQ ID NO 32
<211> LENGTH: 1230
<212> TYPE: DNA
<213> ORGANISM: Brassica oleracea
<220> FEATURE:
<221> NAME/KEY: CDS
<222> LOCATION: (153)..(1022)

<400> SEQUENCE: 32
aacgtagctc tcaaatctca tattcatcgt tttcgtatga acttttgtag cccaaacaac      60
cttcctttcc ttccacaagt ttcataatat ctcttatata acccatatct ccaagcctct     120
cgaaatgttc ttctccgtta aatctaacgg tc atg tca act aca aca atc gtc      173
                                    Met Ser Thr Thr Thr Ile Val
                                     1               5 cct ctc cgt cgc agt tct aac tct ctc aat gaa tac cac act aac gca      221
Pro Leu Arg Arg Ser Ser Asn Ser Leu Asn Glu Tyr His Thr Asn Ala
         10                  15                  20 gtc gcc ttt gac gga atc gtc ggg tca aca agt act agc caa atg gag      269
Val Ala Phe Asp Gly Ile Val Gly Ser Thr Ser Thr Ser Gln Met Glu
 25                  30                  35 gag att gtt acg caa acc gac gac tgc tac gcc aat cac aac gga gat      317
Glu Ile Val Thr Gln Thr Asp Asp Cys Tyr Ala Asn His Asn Gly Asp
 40                  45                  50                  55 gga ggg aga agc aag gca tcg ttt atg acg tgg agg atg tgc aat cct      365
Gly Gly Arg Ser Lys Ala Ser Phe Met Thr Trp Arg Met Cys Asn Pro
                 60                  65                  70 gtc cag gtg gcg aga gtc cat tgg ata ccg tgt ttg cta gcg gta gga      413
Val Gln Val Ala Arg Val His Trp Ile Pro Cys Leu Leu Ala Val Gly
         75                  80                  85 gtt ctg ttc ttc acg ggc gta gag gag tac atg ctc cag atg att ccg      461
Val Leu Phe Phe Thr Gly Val Glu Glu Tyr Met Leu Gln Met Ile Pro
     90                  95                 100 gcg agt tct gag ccg ttc gat att ggt ttt gtg gcg acg cgc tct ctg      509
Ala Ser Ser Glu Pro Phe Asp Ile Gly Phe Val Ala Thr Arg Ser Leu
105                 110                 115 tat cga ctc ttg gct tct tca ccg gat ctt aat acc gtt tta gct gct      557
Tyr Arg Leu Leu Ala Ser Ser Pro Asp Leu Asn Thr Val Leu Ala Ala
120                 125                 130                 135 ctc aac acg gtg ttt gta ggg atg caa acg acg tat att tta tgg aca      605
Leu Asn Thr Val Phe Val Gly Met Gln Thr Thr Tyr Ile Leu Trp Thr
            140                 145                 150 tgg ttg gtg gaa gga cga cca cga gcg acc atc tcg gct tgc ttc atg      653
Trp Leu Val Glu Gly Arg Pro Arg Ala Thr Ile Ser Ala Cys Phe Met
                155                 160                 165 ttt act tgt cgt ggc att ctt ggt tac tct act cag ctc cct ctt cct      701
Phe Thr Cys Arg Gly Ile Leu Gly Tyr Ser Thr Gln Leu Pro Leu Pro
        170                 175                 180 cag gat ttt cta gga tca ggg gta gat ttt ccg gta gga aac gtc tcg      749
Gln Asp Phe Leu Gly Ser Gly Val Asp Phe Pro Val Gly Asn Val Ser
    185                 190                 195 ttc ttc ctc ttc tac tca ggc cat gtc gca ggg tcg acg ata gca tcc      797
Phe Phe Leu Phe Tyr Ser Gly His Val Ala Gly Ser Thr Ile Ala Ser
200                 205                 210                 215
```

| | | | | | | | | | | | | | | |
|---|---|---|---|---|---|---|---|---|---|---|---|---|---|---|
| ttg | gat | atg | agg | aga | atg | aag | agg | ttg | aga | cta | gcc | ttg | ctt | ttt | gac | 845 |
| Leu | Asp | Met | Arg | Arg | Met | Lys | Arg | Leu | Arg | Leu | Ala | Leu | Leu | Phe | Asp |
| | | | 220 | | | | | 225 | | | | | 230 | | |

| atc | ctc | aat | gta | tta | caa | tcg | atc | agg | ctt | ctc | ggg | acg | aga | gga | caa | 893 |
| Ile | Leu | Asn | Val | Leu | Gln | Ser | Ile | Arg | Leu | Leu | Gly | Thr | Arg | Gly | Gln |
| | | | 235 | | | | | 240 | | | | | 245 | | |

| tac | acg | atc | gat | ctc | gct | gtc | gga | gtt | ggc | gct | ggg | gtt | ctc | ttt | gac | 941 |
| Tyr | Thr | Ile | Asp | Leu | Ala | Val | Gly | Val | Gly | Ala | Gly | Val | Leu | Phe | Asp |
| | | 250 | | | | | 255 | | | | | 260 | | | |

| tca | ctg | gct | gga | aaa | tac | gaa | gag | atg | atg | agc | aag | aga | cgc | aat | gta | 989 |
| Ser | Leu | Ala | Gly | Lys | Tyr | Glu | Glu | Met | Met | Ser | Lys | Arg | Arg | Asn | Val |
| | | 265 | | | | | 270 | | | | | 275 | | | |

| ggc | aat | ggt | ttt | agt | ttg | att | tcg | tct | cgc | tag | ttattaattt | ttgttttttt | 1042 |
| Gly | Asn | Gly | Phe | Ser | Leu | Ile | Ser | Ser | Arg |
| 280 | | | | | 285 | | | | |

| | | |
|---|---|---|
| ttttatgttt | ttagtctgga | catatttaat | ttagttgaaa | tctaatgact | taaatttgct | 1102 |
| ttctttcaaa | atgctctaac | tgacggacct | aactaaatgt | gtacgttatt | gtgtagttac | 1162 |
| catagaggtt | tcgtattgtc | ttgagcctga | tattttgatt | ttagagctcg | tttatacggt | 1222 |
| agctaata | | | | | | 1230 |

<210> SEQ ID NO 33
<211> LENGTH: 289
<212> TYPE: PRT
<213> ORGANISM: Brassica oleracea

<400> SEQUENCE: 33

Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Asp Cys
        35                  40                  45

Tyr Ala Asn His Asn Gly Asp Gly Gly Arg Ser Lys Ala Ser Phe Met
    50                  55                  60

Thr Trp Arg Met Cys Asn Pro Val Gln Val Ala Arg Val His Trp Ile
65                  70                  75                  80

Pro Cys Leu Leu Ala Val Gly Val Leu Phe Phe Thr Gly Val Glu Glu
                85                  90                  95

Tyr Met Leu Gln Met Ile Pro Ala Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220

```
Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
            245                 250                 255

Gly Ala Gly Val Leu Phe Asp Ser Leu Ala Gly Lys Tyr Glu Glu Met
            260                 265                 270

Met Ser Lys Arg Arg Asn Val Gly Asn Gly Phe Ser Leu Ile Ser Ser
            275                 280                 285

Arg

<210> SEQ ID NO 34
<211> LENGTH: 6109
<212> TYPE: DNA
<213> ORGANISM: Brassica oleracea
<220> FEATURE:
<221> NAME/KEY: Intron
<222> LOCATION: (2104)..(2978)
<223> OTHER INFORMATION: First intron
<220> FEATURE:
<221> NAME/KEY: Intron
<222> LOCATION: (3117)..(3668)
<223> OTHER INFORMATION: Second intron

<400> SEQUENCE: 34
aaatcgaagg gagtgagaag tgtgaggatc ggagaagtta ccgtagaagg atcattgatc      60
ggcgaaatcg tgataggctt gagactgagg gatgctggga gtgaatcatc agaacgagga    120
agataacaat cgctgctcca catgagtaaa tcttccgtct tctgagagat tcaggggttt    180
gacttctctc tttctctggt ccgtctagga gagcaagaaa gagacgctac gaattacgga    240
cactgtctca taagagagac ctatcttttg acccttaatt aagagacgtt caattttctt    300
ttttttaaaa aaattctaaa aacattaaaa accccaccta agcatctgcc tccttgttcg    360
gaaattcgct aggcactacg cgtacgacac attaagacct agcgatttat taaaaaatcg    420
aaaaaaatca ggaaatacgc gtagagaatt tttttatact tttatatgta ttatatctta    480
tttatatgta taatacaaaa tattcttggt actaaaatta tagatttgta aatacatacc    540
aaattttttc acagcaatac aattatgtta tttacaattc aaatttagta gtataaaata    600
taaaaataaa tcacatatag gaggaaaaaa aagttgttag aacacctcca taattaaaat    660
aatggggtca aatactaaca ataaatactt tatcgggatc aatatgcaaa tttacatgaa    720
acaattgtca cgtgttacgt agctactgac accacacgct tcaaccataa ctttatgact    780
agagtcagtg agtcaccttc ttcttcttct gtattttcta gtgattttat tttgactgaa    840
tcttgttctt atgttaaaac acataaacct aatcacgggc aaagaaaaaa agcttttgtt    900
tcaggccaat cctctcacca aaaatgcttt gtcagcctcc gttaactatc actgcgtatg    960
aaacgaaaat tcaccgtgaa ataaccgatt ttaaccaagc gattttgtcc attacgcggc   1020
cgagttttat aaatctacac agtccacgct cgttactcgg ctcaccgcgt aatgcaaccg   1080
aagtggccca tttcgccacg gtgcctaacc gaatcacgtg taatcggccg attaaacgtc   1140
tccgcggccg agttttagaa cgaggatctg cgttaatgtc gtgctctaat actgcgtgag   1200
aagtaataat ctctcctatt gtgaactttt ctatataaag acgttaaaac aagataaaaa   1260
gttgattatc tttggaataa aaaaaatatt tacatggatg aatggtagtt tatgatttgt   1320
tattacttgg gatctatgaa tgaaacaata tgatatgtta taccctcgta gatcccactg   1380
attcaattga tatcacgaac gaaagagatc ggaacctgcc tcaggaaaaa aaaaaaaaa    1440
aaaaagcgca atcttttttt tggtaaaaaa atcaatcttg gtacgcatat tttcaaactt   1500
```

```
tctatttttgg gtaattggtt taattaattc attcgaaaca gccaacataa aaagaaccaa    1560
tgtcgggaca aaatgtccac aaagaccctg ttgtaataac ttccatatct aatcgtcacc    1620
tatgattggg gatctgatat aattacacat aagtcaaatc gtcacagttt tggtagtaaa    1680
tcgaagcgct catttgtgta ataaagttgt acgttattat gtttctagaa aaaatataag    1740
aaatcttctc aattctttct gtctctctct ctctctctct aaactcttca gacccaaaaa    1800
aagacaagga ataataaaat gtctcaaatg gacatttcta cgagaactga ggaaggagga    1860
tggagaagca agccttcgtt tatgacgtgg agagcgcgcg acgttgtcta cgtgatgaga    1920
caccattgga taccgtgtct gttcgcggcc ggattcttgt tcgtcgtaag cgtggagtcc    1980
tcgatcaaga tggtttccga gagttctcca ccgttcgata ttgggtttgt ggccacggag    2040
tctctgcatc atatcttggc ttcttcaccg gatctgaaca ccggtttggc cgctctaaac    2100
tcggtatgtc ctaagaattg gtttgagtga attcgataga tgatgatgat gtgtggatgt    2160
acaattacca aaataaatta tttttagtca aaagaattaa tataaatgtg atttgatacc    2220
ataaatagtg ttgttttctt aacaattccc aaatttcttt ttatttaac tctaataaaa     2280 gttatgattt gttataaaat atgatattat gtccatattt attttcata gtgtagtaga     2340 ttagatacaa atgaaatgat gattatctat gttttgttat gaagatgtgc aatttatcat    2400
agacggccaa agaaaactaa aaccctaagg ccatttcact acctctattt tatatcataa    2460
gttagatgtc ttttttataat ttatcatcaa atagaagtcc ttaaagcata tttcataaac   2520
tattcttctt cctgattatt gcaaattaat tttggaaaaa aatcttttca catcacctaa    2580
tattttgttt ccttctatgt catttaactc atactgatat taatggatat gtatccaacc    2640
acatatcttg actgatttga gtttggtaat ttttttcatg atttttcaatg catttaggga    2700 tactagtgat tcgttactaa attcatttga gatatcacca cttgcaacca tgaacgtaaa    2760
aaaaaattct atagcatttt cagtattagc atctttcaaa gttctttta ttaaacttga     2820 cccttcgatt ttaataacat ttacaaatat tagaaatatg aaaatatgga ttttaggata    2880
tatcttttac aaaattgtga ttctttgttc aaaaagagaa cattgtatgt ttttatttac    2940
tgatagattt acttgtattg atggatgtgg acatgcaggt gttaggagtg atgcaagtat    3000
cgtatattgc atggacatgg ttaatagaag gacggccccg agccaccatc acggctttat    3060
tcctcttcac ttgtcgcggt gttctcggtt actgtactca gctccctctt tcaaaggttc    3120
ccatctacat atctatatac caattattcc tttgatagtt tagtgatgtt caatcaaatt    3180
agatgtccaa gtactgacca attaatatca gatactagaa cgttataggc acatatgatt    3240
ccatatattc tgacatcttg gactctcgat ataaaagtgt tagattgtat tatcatagag    3300
aggtttaatt tgtacgtagt agttttactt caaaaatatt gtacgtagtc cattgtatat    3360
actgattatg acttaaggcg tttaggctaa gtataatcat caaataataa aactattttg    3420
tgtccccagt tgttacttaa ctttcttcat ctttaaaata aaataaaatt caatgaggtg    3480
attgactgga cataaggaca caatttataa cgtaagccaa actctatacg tatagataaa    3540
ttatttatgt atctcgtcta ggtatactag ttagtattta catgcccaaa caatagattg    3600
aattgaggtt gattagctcc tctattgaga tatataatct tgtatattgt tttcaatctt    3660
gtttacagga gtatctagga tcagcaatcg atttcccgct aggaaatctc tcgttcttct    3720
attttttctc gggtcacgtg gcaggcgcga ccatcgcatc tttggacatg aggaggatgc    3780
agaggttgag atttgcgatg gttttttgaca tcctcaatgt attacagtcg atcaggctgc    3840
```

```
ttgcgacgag aggacactac acgatcgatc tcgcaggtgg agttgccgct gcgattctct    3900
ttgactcatt ggccggaaag tacgaagcta atacaagaaa gaggcaattg taggaacagg    3960
tttcagcttg attaccaaaa gacttcaaag atttcattca acatgtttag ttgctgttga    4020
attctactgt ggttcggcaa ttattctccc catgagccag tggcttggac ttcttcgacc    4080
ctaatgttca tggtcagact gtatatgttg tttatttctc attttttcat tcgactccgc    4140
aatttgtgat atgggtttgg ttaacactag ttggttcaat tgttttcaat tggttttact    4200
ctgaaagttg taaacgttgt gtaataccag attacccaac aacgctagct cttattaaca    4260
tcccagttag ttgtgaaaaa aaaaactcaa aactactagc ttaattaatt aattaaaatag   4320
tggaagcact gtaacttaat ggtacgaggt tcgcagtaaa tgtagaatct taatttgact    4380
agtgttgaca aaaaattaat tggttagcct tatttaagag cacttttagt ggtaaaaatt    4440
tcaaaaagta taactcaaac aaaaggatta gtaatattta ataatgttca tttaattatt    4500
tttttgcgta agaaaaaaaa tcattagatg aaaaacatgt gatatttgaa gttctcatga    4560
gtatttagt tctcaaacga gttaggttat ttttttcaca ttaacacaat ttgacatctc      4620
atacaaaaga taccttaatg ttacttaaac ttatacgatg tgcattacaa tactaaactg    4680
aacttggatt aatgttgaag caaaagctag ttcgactttg ttctccgaat attcatccac    4740
tatcttcctg cagtaaaacc acatgcctta tattttattt caattgctta tcatccaagt    4800
aacaaacaac ttaaaacata ggtgatttca aaacatcagc aactcaaaaa ggaagaagat    4860
ctaggatatg aaagaagaac gcaagaactt caacaatgta tgggtttcac caataatctc    4920
agtatcttac tgctacttct tatcaactag aatcaaagct gaagtttttc gattactatt    4980
tgttcttcca atgtgtgcta tgttccccaa tgtcgagaaa atacgttttt gaattttttgg   5040
cgaaaaaatg taattttgta gtttgttaaa aaaatatgat tttgcgggaa aatatgattt    5100
gcagttttga cggaaaatgc gattttgcaa ttttggtgaa aaaatgtgtt ttgcgatttt    5160
tcagaaataa aattttgatg gatatgactg aaaaatataa atataattta acgatttga    5220
tgtaatttta cgggttttat ggaaaaaaat acaatatttc agttgaaaaa aatatatcat    5280
aatttatttg tttgtctaga tttgatcta aatatttat ttggataaga gtatttgaag     5340
tttgttattt tgtatagatt catctccatc tagatgcacc catttgattc atcaagatga    5400
gtctactaaa attctaaaac tcatttggat aaatcatgtc agtgtgctca ttttaacata    5460
aaacaaatat cattctcacc ttatgaaatg ccctaaattt taaactaact ttatggtggc    5520
ataaaacccg atcgatcgag tcttccacta tattttcagt tacagttgag aactgggttt    5580
gcactttgtg ttagccgaaa aataatactt gattttttca tatcctctaa agaattagta    5640
tggatttcat ccataatttt cagtcattag aaaaaaacaa tcatgaaata ttgcttcgtt    5700
ctgaccgtta attgagttct cttttatgtt taacattaac tatatactgt ataggggtgt    5760
aaatcgggat aacccggtct ggtccggtcc aaaacccaca aagctcatag ctatctaggt    5820
ctggtttaat ccggtccata aaaaaattgg gcctatattt caaatctggt tcagattttt    5880
aaaaatttta aaattaaaaa attaagttta aaccaaaat taattcaatt ctaaatttaa     5940
acaatcatca atatatgttt ataaaagagt caattagctc aaaatcctaa aataaattag    6000
aaattaggaa actacctatg agacattttg tgtggacttt atgttgcaag tagtacaaag    6060
caaattacca acagtcatt ctgtcgattt aaaaaaaact taaaatatg                  6109
```

<210> SEQ ID NO 35
<211> LENGTH: 1306

```
<212> TYPE: DNA
<213> ORGANISM: Brassica oleracea
<220> FEATURE:
<221> NAME/KEY: CDS
<222> LOCATION: (276)..(983)

<400> SEQUENCE: 35
aacataaaaa gaaccaatgt cgggacaaaa tgtccacaaa gaccctgttg taataacttc      60
catatctaat cgtcacctat gattggggat ctgatataat tacacataag tcaaatcgtc     120
acagttttgg tagtaaatcg aagcgctcat ttgtgtaata aagttgtacg ttattatgtt     180
tctagaaaaa atataagaaa tcttctcaat tctttctgtc tctctctctc tctctctaaa     240
ctcttcagac ccaaaaaaag acaaggaata ataaa atg tct caa atg gac att         293
                                      Met Ser Gln Met Asp Ile
                                        1               5 tct acg aga act gag gaa gga gga tgg aga agc aag cct tcg ttt atg        341
Ser Thr Arg Thr Glu Glu Gly Gly Trp Arg Ser Lys Pro Ser Phe Met
             10                  15                  20 acg tgg aga gcg cgc gac gtt gtc tac gtg atg aga cac cat tgg ata        389
Thr Trp Arg Ala Arg Asp Val Val Tyr Val Met Arg His His Trp Ile
         25                  30                  35 ccg tgt ctg ttc gcg gcc gga ttc ttg ttc gtc gta agc gtg gag tcc        437
Pro Cys Leu Phe Ala Ala Gly Phe Leu Phe Val Val Ser Val Glu Ser
     40                  45                  50 tcg atc aag atg gtt tcc gag agt tct cca ccg ttc gat att ggg ttt        485
Ser Ile Lys Met Val Ser Glu Ser Ser Pro Pro Phe Asp Ile Gly Phe
 55                  60                  65                  70 gtg gcc acg gag tct ctg cat cat atc ttg gct tct tca ccg gat ctg        533
Val Ala Thr Glu Ser Leu His His Ile Leu Ala Ser Ser Pro Asp Leu
                 75                  80                  85 aac acc ggt ttg gcc gct cta aac tcg gtg tta gga gtg atg caa gta        581
Asn Thr Gly Leu Ala Ala Leu Asn Ser Val Leu Gly Val Met Gln Val
             90                  95                 100 tcg tat att gca tgg aca tgg tta ata gaa gga cgg ccc cga gcc acc        629
Ser Tyr Ile Ala Trp Thr Trp Leu Ile Glu Gly Arg Pro Arg Ala Thr
        105                 110                 115 atc acg gct tta ttc ctc ttc act tgt cgc ggt gtt ctc ggt tac tgt        677
Ile Thr Ala Leu Phe Leu Phe Thr Cys Arg Gly Val Leu Gly Tyr Cys
    120                 125                 130 act cag ctc cct ctt tca aag gag tat cta gga tca gca atc gat ttc        725
Thr Gln Leu Pro Leu Ser Lys Glu Tyr Leu Gly Ser Ala Ile Asp Phe
135                 140                 145                 150 ccg cta gga aat ctc tcg ttc ttc tat ttt ttc tcg ggt cac gtg gca        773
Pro Leu Gly Asn Leu Ser Phe Phe Tyr Phe Phe Ser Gly His Val Ala
                155                 160                 165 ggc gcg acc atc gca tct ttg gac atg agg agg atg cag agg ttg aga        821
Gly Ala Thr Ile Ala Ser Leu Asp Met Arg Arg Met Gln Arg Leu Arg
            170                 175                 180 ttt gcg atg gtt ttt gac atc ctc aat gta tta cag tcg atc agg ctg        869
Phe Ala Met Val Phe Asp Ile Leu Asn Val Leu Gln Ser Ile Arg Leu
        185                 190                 195 ctt gcg acg aga gga cac tac acg atc gat ctc gca ggt gga gtt gcc        917
Leu Ala Thr Arg Gly His Tyr Thr Ile Asp Leu Ala Gly Gly Val Ala
    200                 205                 210 gct gcg att ctc ttt gac tca ttg gcc gga aag tac gaa gct aat aca        965
Ala Ala Ile Leu Phe Asp Ser Leu Ala Gly Lys Tyr Glu Ala Asn Thr
215                 220                 225                 230 aga aag agg caa ttg tag gaacaggttt cagcttgatt accaaaagac              1013
Arg Lys Arg Gln Leu
                235
```

| ttcaaagatt tcattcaaca tgtttagttg ctgttgaatt ctactgtggt tcggcaatta | 1073 |
| ttctccccat gagccagtgg cttggacttc ttcgacccta atgttcatgg tcagactgta | 1133 |
| tatgttgttt atttctcatt ttttcattcg actccgcaat ttgtgatatg ggtttggtta | 1193 |
| acactagttg gttcaattgt tttcaattgg ttttactctg aaagttgtaa acgttgtgta | 1253 |
| ataccagatt acccaacaac gctagctctt attaacatcc cagttagttg tga | 1306 |

```
<210> SEQ ID NO 36
<211> LENGTH: 235
<212> TYPE: PRT
<213> ORGANISM: Brassica oleracea

<400> SEQUENCE: 36
```

Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Ala Thr Ile Ala Ser Leu Asp Met Arg
                165                 170                 175

Arg Met Gln Arg Leu Arg Phe Ala Met Val Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235

```
<210> SEQ ID NO 37
<211> LENGTH: 51
<212> TYPE: DNA
<213> ORGANISM: artificial
<220> FEATURE:
<223> OTHER INFORMATION: primer

<400> SEQUENCE: 37
```

| gtttcgacgg attctagaac tagtggatcc atgtcaacta ataccgtcgt c | 51 |

```
<210> SEQ ID NO 38
<211> LENGTH: 50
```

-continued

<212> TYPE: DNA
<213> ORGANISM: artificial
<220> FEATURE:
<223> OTHER INFORMATION: primer

<400> SEQUENCE: 38
ggtatcgata agcttgatat cgaattctta attgactagc gagtctttag          50

<210> SEQ ID NO 39
<211> LENGTH: 51
<212> TYPE: DNA
<213> ORGANISM: artificial
<220> FEATURE:
<223> OTHER INFORMATION: primer

<400> SEQUENCE: 39
gtttcgacgg attctagaac tagtggatcc atgtctactg aaacttctgt c        51

<210> SEQ ID NO 40
<211> LENGTH: 50
<212> TYPE: DNA
<213> ORGANISM: artificial
<220> FEATURE:
<223> OTHER INFORMATION: primer

<400> SEQUENCE: 40
ggtatcgata agcttgatat cgaattctta gttatccaat gaatccttgg          50

<210> SEQ ID NO 41
<211> LENGTH: 51
<212> TYPE: DNA
<213> ORGANISM: artificial
<220> FEATURE:
<223> OTHER INFORMATION: primer

<400> SEQUENCE: 41
gtttcgacgg attctagaac tagtggatcc atgtctactg aaactggtgt c        51

<210> SEQ ID NO 42
<211> LENGTH: 50
<212> TYPE: DNA
<213> ORGANISM: artificial
<220> FEATURE:
<223> OTHER INFORMATION: primer

<400> SEQUENCE: 42
ggtatcgata agcttgatat cgaattctta gttaaccaat gaatccttgg          50

<210> SEQ ID NO 43
<211> LENGTH: 29
<212> TYPE: DNA
<213> ORGANISM: artificial
<220> FEATURE:
<223> OTHER INFORMATION: primer

<400> SEQUENCE: 43
caccgtcgca gatctaacgg atatcacac                                 29

<210> SEQ ID NO 44
<211> LENGTH: 25
<212> TYPE: DNA
<213> ORGANISM: artificial
<220> FEATURE:
<223> OTHER INFORMATION: primer

<400> SEQUENCE: 44
aatatcgaac ggctcagact tcgcc                                           25

<210> SEQ ID NO 45
<211> LENGTH: 25
<212> TYPE: DNA
<213> ORGANISM: artificial
<220> FEATURE:
<223> OTHER INFORMATION: primer

<400> SEQUENCE: 45
caccccgttc gatattgggt ttgtg                                           25

<210> SEQ ID NO 46
<211> LENGTH: 23
<212> TYPE: DNA
<213> ORGANISM: artificial
<220> FEATURE:
<223> OTHER INFORMATION: primer

<400> SEQUENCE: 46
ttaattgact agcgagtctt tag                                             23

<210> SEQ ID NO 47
<211> LENGTH: 3365
<212> TYPE: DNA
<213> ORGANISM: Artificial
<220> FEATURE:
<223> OTHER INFORMATION: Expression cassette pTCO363
<220> FEATURE:
<221> NAME/KEY: P35S
<222> LOCATION: (1)..(1353)
<223> OTHER INFORMATION: Sequence including the promoter region of the
      Cauliflower Mosaic Virus 35S transcript
<220> FEATURE:
<221> NAME/KEY: ROD1Bn
<222> LOCATION: (1405)..(1676)
<223> OTHER INFORMATION: nt 29-300 of the coding sequence of the
      BnROD1-A1 gene
<220> FEATURE:
<221> NAME/KEY: intron cat
<222> LOCATION: (1735)..(1930)
<223> OTHER INFORMATION: Fragment of the first intron from the
      catalase-1 gene of Ricinus communis
<220> FEATURE:
<221> NAME/KEY: intron2 pdk
<222> LOCATION: (1965)..(2737)
<223> OTHER INFORMATION: Second intron of the pyruvate orthophosphate
      dikinase gene from Flaveria trinervia (antisense)
<220> FEATURE:
<221> NAME/KEY: ROD1Bn
<222> LOCATION: (2801)..(3072)
<223> OTHER INFORMATION: nt 29-300 of the coding sequence of the
      BnROD1-A1 gene (antisense)
<220> FEATURE:
<221> NAME/KEY: 3'g7
<222> LOCATION: (3162)..(3365)
<223> OTHER INFORMATION: sequence including the 3' untranslated region
      of gene 7 of the A. tumefaciens octopine Ti plasmid

<400> SEQUENCE: 47
cggccgctcg acgaattaat tccaatccca caaaaatctg agcttaacag cacagttgct     60
cctctcagag cagaatcggg tattcaacac cctcatatca actactacgt tgtgtataac   120
ggtccacatg ccggtatata cgatgactgg ggttgtacaa aggcggcaac aaacggcgtt   180
cccggagttg cacacaagaa atttgccact attacagagg caagagcagc agctgacgcg   240
tacacaacaa gtcagcaaac agacaggttg aacttcatcc ccaaaggaga agctcaactc   300
aagcccaaga gctttgctaa ggccctaaca agcccaccaa gcaaaaaagc ccactggctc   360
acgctaggaa ccaaaaggcc cagcagtgat ccagccccaa aagagatctc ctttgccccg   420

```
gagattacaa tggacgattt cctctatctt tacgatctag gaaggaagtt cgaaggtgaa    480
ggtgacgaca ctatgttcac cactgataat gagaaggtta gcctcttcaa tttcagaaag    540
aatgctgacc cacagatggt tagagaggcc tacgcagcag gtctcatcaa gacgatctac    600
ccgagtaaca atctccagga gatcaaatac cttcccaaga aggttaaaga tgcagtcaaa    660
agattcagga ctaattgcat caagaacaca gagaaagaca tatttctcaa gatcagaagt    720
actattccag tatggacgat tcaaggcttg cttcataaac caaggcaagt aatagagatt    780
ggagtctcta aaaaggtagt tcctactgaa tctaaggcca tgcatggagt ctaagattca    840
aatcgaggat ctaacagaac tcgccgtgaa gactggcgaa cagttcatac agagtctttt    900
acgactcaat gacaagaaga aaatcttcgt caacatggtg gagcacgaca ctctggtcta    960
ctccaaaaat gtcaaagata cagtctcaga agaccaaagg gctattgaga cttttcaaca   1020
aaggataatt tcgggaaacc tcctcggatt ccattgccca gctatctgtc acttcatcga   1080
aaggacagta gaaaaggaag gtggctccta caaatgccat cattgcgata aggaaaggc    1140 tatcattcaa gatctctctg ccgacagtgg tcccaaagat ggaccccac ccacgaggag    1200 catcgtggaa aaagaagacg ttccaaccac gtcttcaaag caagtggatt gatgtgacat   1260
ctccactgac gtaagggatg acgcacaatc ccactatcct tcgcaagacc cttcctctat   1320
ataaggaagt tcatttcatt tggagaggac acgctcgaga caagtttgta caaaaaagca   1380
ggctccgcgg ccgccccctt caccgtcgca gatctaacgg atatcacact aacggcgtgg   1440
cctttaacgg aatggataat attgtcaaga aaaccgacga ctgctacacc aacggcaacg   1500
gcaacggagg agtagagaga agcaaagcct cgtttctgac atggaccatg cgtgacgctg   1560
tctacgtagc gagataccat tggataccgt gtttctttgc ggtcggagtt ctgttcttta   1620 tggggggttga gtacacgctc cagatggttc cggcgaagtc tgagccgttc gatattaagg   1680
gtgggcgcgc cgacccagct ttcttgtaca aagtggtcta gaggatccaa gcttgtgcag   1740
gtaaatttct agttttttctc cttcatttttc ttggttagga ccctttttctc tttttatttt   1800 tttgagcttt gatctttctt taaactgatc tatttttttaa ttgattggtt atggtgtaaa   1860
tattacatag ctttaactga taatctgatt actttatttc gtgtgtctat gatgatgatg   1920
ataactgcag cgcaagctta tcgatttcga acccagcttc ccaactgtaa tcaatccaaa   1980
tgtaagatca atgataacac aatgacatga tctatcatgt taccttgttt attcatgttc   2040
gactaattca tttaattaat agtcaatcca tttagaagtt aataaaacta caagtattat   2100
ttagaaatta ataagaatgt tgattgaaaa ataatactat ataaaattga tagatcttgc   2160
gctttgttat attagcatta gattatgttt tgttacatta gattactgtt tctattagtt   2220
tgatattatt tgttactttta gcttgttatt taatattttg tttattgata aattacaagc   2280
agattggaat ttctaacaaa atatttatta acttttaaac taaaatattt agtaatggta   2340
tagatattta attatataat aaactattaa tcataaaaaa atattatttt aatttattta   2400
ttcttatttt tactatagta ttttatcatt gatatttaat tcatcaaacc agctagaatt   2460
actattatga ttaaaacaaa tattaatgct agtatatcat cttacatgtt cgatcaaatt   2520
cattaaaaat aatatactta ctctcaactt ttatcttctt cgtcttacac atcacttgtc   2580
atattttttt acattactat gttgtttatg taaacaatat atttataaat tattttttca   2640
caattataac aactatatta ttataatcat actaattaac atcacttaac tattttatac   2700
taaaaggaaa aagaaaata attatttcct taccaagctg gggtaccgaa ttcctcgaga   2760
```

```
ccactttgta caagaaagct gggtcggcgc gcccacccct aatatcgaac ggctcagact    2820
tcgccggaac catctggagc gtgtactcaa cccccataaa gaacagaact ccgaccgcaa    2880
agaaacacgg tatccaatgg tatctcgcta cgtagacagc gtcacgcatg gtccatgtca    2940
gaaacgaggc tttgcttctc tctactcctc cgttgccgtt gccgttggtg tagcagtcgt    3000
cggttttctt gacaatatta tccattccgt taaaggccac gccgttagtg tgatatccgt    3060
tagatctgcg acggtgaagg gggcggccgc ggagcctgct ttttgtaca aacttgtcta    3120 gagtcctgct ttaatgagat atgaaatacg cgtggcgcgc ctaagctagc tatatcatca    3180
atttatgtat tacacataat atcgcactca gtctttcatc tacggcaatg taccagctga    3240
tataatcagt tattgaaata tttctgaatt taaacttgca tcaataaatt tatgtttttg    3300
cttggactat aatacctgac ttgttatttt atcaataaat atttaaacta tatttctttc    3360
aagat                                                                3365

<210> SEQ ID NO 48
<211> LENGTH: 3921
<212> TYPE: DNA
<213> ORGANISM: artificial
<220> FEATURE:
<223> OTHER INFORMATION: Expression cassette pTCO364
<220> FEATURE:
<221> NAME/KEY: P35S
<222> LOCATION: (1)..(1353)
<223> OTHER INFORMATION: Sequence including the promoter region of the
      Cauliflower Mosaic Virus 35S transcript
<220> FEATURE:
<221> NAME/KEY: ROD1Bn
<222> LOCATION: (1405)..(1965)
<223> OTHER INFORMATION: nt 289-849 of the coding sequence of the
      BnROD1-A1 gene
<220> FEATURE:
<221> NAME/KEY: intron cat
<222> LOCATION: (2024)..(2219)
<223> OTHER INFORMATION: Fragment of the first intron from the
      catalase-1 gene of Ricinus communis
<220> FEATURE:
<221> NAME/KEY: intron2 pdk
<222> LOCATION: (2254)..(3022)
<223> OTHER INFORMATION: Second intron of the pyruvate orthophosphate
      dikinase gene from Flaveria trinervia (antisense)
<220> FEATURE:
<221> NAME/KEY: ROD1Bn
<222> LOCATION: (3090)..(3650)
<223> OTHER INFORMATION: nt 29-300 of the coding sequence of the
      BnROD1-A1 gene (antisense)
<220> FEATURE:
<221> NAME/KEY: 3'g7
<222> LOCATION: (3718)..(3921)
<223> OTHER INFORMATION: Sequence including the 3' untranslated regino
      of gene 7 of the A. tumefaciens octopine Ti plasmid

<400> SEQUENCE: 48
cggccgctcg acgaattaat tccaatccca caaaaatctg agcttaacag cacagttgct      60
cctctcagag cagaatcggg tattcaacac cctcatatca actactacgt tgtgtataac     120
ggtccacatg ccggtatata cgatgactgg ggttgtacaa aggcggcaac aaacggcgtt     180
cccggagttg cacacaagaa atttgccact attacagagg caagagcagc agctgacgcg     240
tacacaacaa gtcagcaaac agacaggttg aacttcatcc ccaaaggaga agctcaactc     300
aagcccaaga gctttgctaa ggccctaaca agcccaccaa agcaaaaagc ccactggctc     360
acgctaggaa ccaaaaggcc cagcagtgat ccagccccaa aagagatctc ctttgccccg     420
gagattacaa tggacgattt cctctatctt tacgatctag gaaggaagtt cgaaggtgaa     480
ggtgacgaca ctatgttcac cactgataat gagaaggtta gcctcttcaa tttcagaaag     540
```

```
aatgctgacc cacagatggt tagagaggcc tacgcagcag gtctcatcaa gacgatctac    600
ccgagtaaca atctccagga gatcaaatac cttcccaaga aggttaaaga tgcagtcaaa    660
agattcagga ctaattgcat caagaacaca gagaaagaca tatttctcaa gatcagaagt    720
actattccag tatggacgat tcaaggcttg cttcataaac caaggcaagt aatagagatt    780
ggagtctcta aaaaggtagt tcctactgaa tctaaggcca tgcatggagt ctaagattca    840
aatcgaggat ctaacagaac tcgccgtgaa gactggcgaa cagttcatac agagtctttt    900
acgactcaat gacaagaaga aaatcttcgt caacatggtg gagcacgaca ctctggtcta    960
ctccaaaaat gtcaaagata cagtctcaga agaccaaagg ctattgagac ttttcaaca   1020 aaggataatt tcgggaaacc tcctcggatt ccattgccca gctatctgtc acttcatcga   1080
aaggacagta gaaaaggaag gtggctccta caaatgccat cattgcgata aaggaaaggc   1140
tatcattcaa gatctctctg ccgacagtgg tcccaaagat ggaccccccac ccacgaggag   1200 catcgtggaa aaagaagacg ttccaaccac gtcttcaaag caagtggatt gatgtgacat   1260
ctccactgac gtaagggatg acgcacaatc ccactatcct tcgcaagacc cttcctctat   1320
ataaggaagt tcatttcatt tggagaggac acgctcgaga caagtttgta caaaaaagca   1380
ggctccgcgg ccgccccctt caccccgttc gatattgggt ttgtggccac gcgctctcta   1440
aaccgcgtct tggcgagttc accggatctt aacacccttt tagcggctct aaacacggta   1500
ttcgtagcga tgcaaacgac gtatattgta tggacatggt tgatggaagg aagaccacga   1560
gccactatct cggcttgctt catgtttact tgtcgcggca ttcttggtta ctctactcag   1620
ctccctctac cacaggattt tttaggatca ggagttgatt ttccggtggg aaacgtctca   1680
ttcttcctct tctattctgg ccacgtagcc ggttcaatga tcgcatcctt ggacatgagg   1740
agaatgcaga ggttgagact agcgatgctt tttgacatcc tcaacatatt acaatcgatc   1800
agactgctcg ggacgagagg acactacacg atcgatcttg cggtcggagt tggcgctggg   1860
attctctttg actcattggc cgggaagtac gaagagatga tgagcaagag acacaattta   1920
gccaatggtt ttagtttgat ttctaaagac tcgctagtca attaaaaggg tgggcgcgcc   1980
gacccagctt tcttgtacaa agtggtctag aggatccaag cttgtgcagg taaatttcta   2040 gttttttctcc ttcatttttct tggttaggac ccttttctct tttttatttttt ttgagctttg   2100 atctttcttt aaactgatct atttttttaat tgattggtta tggtgtaaat attacatagc   2160
tttaactgat aatctgatta ctttatttcg tgtgtctatg atgatgatga taactgcagc   2220
gcaagcttat cgatttcgaa cccagcttcc caactgtaat caatccaaat gtaagatcaa   2280
tgataacaca atgacatgat ctatcatgtt accttgttta ttcatgttcg actaattcat   2340
ttaattaata gtcaatccat ttagaagtta ataaaactac aagtattatt tagaaattaa   2400
taagaatgtt gattgaaaaa taatactata taaaattgat agatcttgcg ctttgttata   2460
ttagcattag attatgtttt gttacattag attactgttt ctattagttt gatattattt   2520
gttactttag cttgttattt aatattttgt ttattgataa attacaagca gattggaatt   2580
tctaacaaaa tatttattaa ctttaaact aaaatattta gtaatggtat agatattaa   2640 ttatataata aactattaat cataaaaaaa tattatttta atttatttat tcttattttt   2700
actatagtat tttatcattg atatttaatt catcaaacca gctagaatta ctattatgat   2760
taaaacaaat attaatgcta gtatatcatc ttacatgttc gatcaaattc attaaaaata   2820
atatacttac tctcaacttt tatcttcttc gtcttacaca tcacttgtca tattttttta   2880
```

```
cattactatg ttgtttatgt aaacaatata tttataaatt atttttttcac aattataaca    2940 actatattat tataatcata ctaattaaca tcacttaact attttatact aaaaggaaaa    3000
aagaaaataa ttatttcctt accaagctgg ggtaccgaat tcctcgagac cactttgtac    3060
aagaaagctg ggtcggcgcg cccacccttt taattgacta gcgagtcttt agaaatcaaa    3120
ctaaaaccat tggctaaatt gtgtctcttg ctcatcatct cttcgtactt cccggccaat    3180
gagtcaaaga gaatcccagc gccaactccg accgcaagat cgatcgtgta gtgtcctctc    3240
gtcccgagca gtctgatcga ttgtaatatg ttgaggatgt caaaaagcat cgctagtctc    3300
aacctctgca ttctcctcat gtccaaggat gcgatcattg aaccggctac gtggccagaa    3360
tagaagagga agaatgagac gtttcccacc ggaaaatcaa ctcctgatcc taaaaaatcc    3420
tgtggtagag ggagctgagt agagtaacca agaatgccgc gacaagtaaa catgaagcaa    3480
gccgagatag tggctcgtgg tcttccttcc atcaaccatg tccatacaat atacgtcgtt    3540
tgcatcgcta cgaataccgt gtttagagcg ctaaaaggg tgttaagatc cggtgaactc    3600
gccaagacgc ggtttagaga gcgcgtggcc acaaacccaa tatcgaacgg ggtgaagggg    3660
gcggccgcgg agcctgcttt tttgtacaaa cttgtctaga aatacgcgtg gcgcgcctaa    3720
gctagctata tcatcaattt atgtattaca cataatatcg cactcagtct ttcatctacg    3780
gcaatgtacc agctgatata atcagttatt gaaatatttc tgaatttaaa cttgcatcaa    3840
taaatttatg ttttgcttg gactataata cctgacttgt tattttatca ataaatattt    3900
aaactatatt tctttcaaga t                                              3921
```

<210> SEQ ID NO 49
<211> LENGTH: 24
<212> TYPE: DNA
<213> ORGANISM: artificial
<220> FEATURE:
<223> OTHER INFORMATION: FAM primer HIOL302

<400> SEQUENCE: 49
gtcttccttc catcaaccat gtcg                                            24

<210> SEQ ID NO 50
<211> LENGTH: 25
<212> TYPE: DNA
<213> ORGANISM: artificial
<220> FEATURE:
<223> OTHER INFORMATION: VIC primer HIOL302

<400> SEQUENCE: 50
ggtcttcctt ccatcaacca tgtta                                           25

<210> SEQ ID NO 51
<211> LENGTH: 28
<212> TYPE: DNA
<213> ORGANISM: artificial
<220> FEATURE:
<223> OTHER INFORMATION: Reverse primer HIOL302

<400> SEQUENCE: 51
gtagcgatgc aaacgacgta tattgtat                                        28

<210> SEQ ID NO 52
<211> LENGTH: 27
<212> TYPE: DNA
<213> ORGANISM: artificial
<220> FEATURE:
<223> OTHER INFORMATION: FAM primer HIOL303

<400> SEQUENCE: 52
atgcaaacga cgtatattgt atggacc                                              27

<210> SEQ ID NO 53
<211> LENGTH: 28
<212> TYPE: DNA
<213> ORGANISM: artificial
<220> FEATURE:
<223> OTHER INFORMATION: VIC primer HIOL303

<400> SEQUENCE: 53
gatgcaaacg acgtatattg tatggatt                                             28

<210> SEQ ID NO 54
<211> LENGTH: 25
<212> TYPE: DNA
<213> ORGANISM: artificial
<220> FEATURE:
<223> OTHER INFORMATION: Reverse primer HIOL303

<400> SEQUENCE: 54
tcgtggtctt ccttccatca accat                                                25

<210> SEQ ID NO 55
<211> LENGTH: 23
<212> TYPE: DNA
<213> ORGANISM: artificial
<220> FEATURE:
<223> OTHER INFORMATION: FAM primer HIOL304

<400> SEQUENCE: 55
agatagtggc tcgtggtctt ccg                                                  23

<210> SEQ ID NO 56
<211> LENGTH: 24
<212> TYPE: DNA
<213> ORGANISM: artificial
<220> FEATURE:
<223> OTHER INFORMATION: VIC primer HIOL304

<400> SEQUENCE: 56
gagatagtgg ctcgtggtct tcta                                                 24

<210> SEQ ID NO 57
<211> LENGTH: 29
<212> TYPE: DNA
<213> ORGANISM: artificial
<220> FEATURE:
<223> OTHER INFORMATION: Reverse primer HIOL304

<400> SEQUENCE: 57
cgtatattgt atggacatgg ttgatggaa                                            29

<210> SEQ ID NO 58
<211> LENGTH: 42
<212> TYPE: DNA
<213> ORGANISM: artificial
<220> FEATURE:
<223> OTHER INFORMATION: FAM primer HIOL306

<400> SEQUENCE: 58
gaaggtgacc aagttcatgc tggaaggaag accacgagcc ac                             42

<210> SEQ ID NO 59

<211> LENGTH: 42
<212> TYPE: DNA
<213> ORGANISM: artificial
<220> FEATURE:
<223> OTHER INFORMATION: VIC primer HIOL306

<400> SEQUENCE: 59
gaaggtcgga gtcaacggat tggaaggaag accacgagcc at        42

<210> SEQ ID NO 60
<211> LENGTH: 25
<212> TYPE: DNA
<213> ORGANISM: artificial
<220> FEATURE:
<223> OTHER INFORMATION: Reverse primer HIOL306

<400> SEQUENCE: 60
gagctgagta gagtaaccaa gaatg        25

<210> SEQ ID NO 61
<211> LENGTH: 23
<212> TYPE: DNA
<213> ORGANISM: artificial
<220> FEATURE:
<223> OTHER INFORMATION: FAM primer HIOL307

<400> SEQUENCE: 61
tgcttcatgt ttacttgtcg cgg        23

<210> SEQ ID NO 62
<211> LENGTH: 26
<212> TYPE: DNA
<213> ORGANISM: artificial
<220> FEATURE:
<223> OTHER INFORMATION: VIC primer HIOL307

<400> SEQUENCE: 62
gcttgcttca tgtttacttg tcgcaa        26

<210> SEQ ID NO 63
<211> LENGTH: 25
<212> TYPE: DNA
<213> ORGANISM: artificial
<220> FEATURE:
<223> OTHER INFORMATION: Reverse primer HIOL307

<400> SEQUENCE: 63
gggagctgag tagagtaacc aagaa        25

<210> SEQ ID NO 64
<211> LENGTH: 27
<212> TYPE: DNA
<213> ORGANISM: artificial
<220> FEATURE:
<223> OTHER INFORMATION: FAM primer HIOL308

<400> SEQUENCE: 64
catacaatat acgtcgtttg catcgcg        27

<210> SEQ ID NO 65
<211> LENGTH: 27
<212> TYPE: DNA
<213> ORGANISM: artificial
<220> FEATURE:
<223> OTHER INFORMATION: VIC primer HIOL308

<400> SEQUENCE: 65
catacaatat acgtcgtttg catcgta                                          27

<210> SEQ ID NO 66
<211> LENGTH: 25
<212> TYPE: DNA
<213> ORGANISM: artificial
<220> FEATURE:
<223> OTHER INFORMATION: Reverse primer HIOL308

<400> SEQUENCE: 66
tggatgatgg ggacaggtat tcgta                                            25

<210> SEQ ID NO 67
<211> LENGTH: 24
<212> TYPE: DNA
<213> ORGANISM: artificial
<220> FEATURE:
<223> OTHER INFORMATION: FAM primer HIOL309

<400> SEQUENCE: 67
gtattcgtag cgatgcaaac gacc                                             24

<210> SEQ ID NO 68
<211> LENGTH: 26
<212> TYPE: DNA
<213> ORGANISM: artificial
<220> FEATURE:
<223> OTHER INFORMATION: VIC primer HIOL309

<400> SEQUENCE: 68
aggtattcgt agcgatgcaa acgatt                                           26

<210> SEQ ID NO 69
<211> LENGTH: 29
<212> TYPE: DNA
<213> ORGANISM: artificial
<220> FEATURE:
<223> OTHER INFORMATION: Reverse primer HIOL309

<400> SEQUENCE: 69
ccttccatca accatgtcca tacaatata                                        29

<210> SEQ ID NO 70
<211> LENGTH: 47
<212> TYPE: DNA
<213> ORGANISM: artificial
<220> FEATURE:
<223> OTHER INFORMATION: FAM primer HIOL310

<400> SEQUENCE: 70
gaaggtgacc aagttcatgc tgtatattgt atggacatgg ttgatgg                    47

<210> SEQ ID NO 71
<211> LENGTH: 48
<212> TYPE: DNA
<213> ORGANISM: artificial
<220> FEATURE:
<223> OTHER INFORMATION: VIC primer HIOL310

<400> SEQUENCE: 71
gaaggtcgga gtcaacggat tcgtatattg tatggacatg gttgatga                   48

<210> SEQ ID NO 72
<211> LENGTH: 39
<212> TYPE: DNA

```
<213> ORGANISM: artificial
<220> FEATURE:
<223> OTHER INFORMATION: Reverse primer HIOL310

<400> SEQUENCE: 72
aatataaata tattataaga gtgagaggta gtataatat                              39

<210> SEQ ID NO 73
<211> LENGTH: 25
<212> TYPE: DNA
<213> ORGANISM: artificial
<220> FEATURE:
<223> OTHER INFORMATION: FAM primer HIOL311

<400> SEQUENCE: 73
atggacatgg ttgatggaag gaagg                                            25

<210> SEQ ID NO 74
<211> LENGTH: 27
<212> TYPE: DNA
<213> ORGANISM: artificial
<220> FEATURE:
<223> OTHER INFORMATION: VIC primer HIOL311

<400> SEQUENCE: 74
gtatggacat ggttgatgga aggaaaa                                          27

<210> SEQ ID NO 75
<211> LENGTH: 25
<212> TYPE: DNA
<213> ORGANISM: artificial
<220> FEATURE:
<223> OTHER INFORMATION: FAM primer HIOL313

<400> SEQUENCE: 75
ggcttgcttc atgtttactt gtcgg                                            25

<210> SEQ ID NO 76
<211> LENGTH: 26
<212> TYPE: DNA
<213> ORGANISM: artificial
<220> FEATURE:
<223> OTHER INFORMATION: VIC primer HIOL313

<400> SEQUENCE: 76
cggcttgctt catgtttact tgtcaa                                           26

<210> SEQ ID NO 77
<211> LENGTH: 22
<212> TYPE: DNA
<213> ORGANISM: artificial
<220> FEATURE:
<223> OTHER INFORMATION: FAM primer HIOL315

<400> SEQUENCE: 77
aaagaggtgg gagacctgtg gc                                               22

<210> SEQ ID NO 78
<211> LENGTH: 24
<212> TYPE: DNA
<213> ORGANISM: artificial
<220> FEATURE:
<223> OTHER INFORMATION: VIC primer HIOL315

<400> SEQUENCE: 78
gtaaagaggt gggagacctg tgat                                             24
```

<210> SEQ ID NO 79
<211> LENGTH: 25
<212> TYPE: DNA
<213> ORGANISM: artificial
<220> FEATURE:
<223> OTHER INFORMATION: Reverse primer HIOL315

<400> SEQUENCE: 79
tggttactct actcagctcc ctcta                                      25

<210> SEQ ID NO 80
<211> LENGTH: 27
<212> TYPE: DNA
<213> ORGANISM: artificial
<220> FEATURE:
<223> OTHER INFORMATION: FAM primer HIOL316

<400> SEQUENCE: 80
aatatttgtg taaagaggtg ggagacg                                    27

<210> SEQ ID NO 81
<211> LENGTH: 31
<212> TYPE: DNA
<213> ORGANISM: artificial
<220> FEATURE:
<223> OTHER INFORMATION: VIC primer HIOL316

<400> SEQUENCE: 81
atataatatt tgtgtaaaga ggtgggagat a                               31

<210> SEQ ID NO 82
<211> LENGTH: 24
<212> TYPE: DNA
<213> ORGANISM: artificial
<220> FEATURE:
<223> OTHER INFORMATION: FAM primer HIOL318-319

<400> SEQUENCE: 82
atggttgatg gaaggaagac cacc                                       24

<210> SEQ ID NO 83
<211> LENGTH: 26
<212> TYPE: DNA
<213> ORGANISM: artificial
<220> FEATURE:
<223> OTHER INFORMATION: VIC primer HIOL318-319

<400> SEQUENCE: 83
acatggttga tggaaggaag accatt                                     26

<210> SEQ ID NO 84
<211> LENGTH: 1026
<212> TYPE: DNA
<213> ORGANISM: Brassica napus
<220> FEATURE:
<221> NAME/KEY: CDS
<222> LOCATION: (127)..(996)

<400> SEQUENCE: 84
gttttcgtat gaacttttgt agcccaaaca accttccttt ccttccacaa gtttcatata    60
atatctctta tataacccat ctctctaagc ctctcaaaac gttcttctcc gttaaatcta   120 acggtc atg tca act aca aca atc gtc cct ctc cgt cgc agt tct aac      168
       Met Ser Thr Thr Thr Ile Val Pro Leu Arg Arg Ser Ser Asn
        1               5                   10

```
tct ctc aat gaa tac cac act aac gca gtc gcc ttt gac gga atc gtc      216
Ser Leu Asn Glu Tyr His Thr Asn Ala Val Ala Phe Asp Gly Ile Val
 15          20                  25                  30 ggg tca aca agt act agc caa atg gag gag att gtt acg caa acc gac      264
Gly Ser Thr Ser Thr Ser Gln Met Glu Glu Ile Val Thr Gln Thr Asp
             35                  40                  45 gac tgc tac gcc aac ccc aac gga gat ggg aga agc aag acg tcg          312
Asp Cys Tyr Ala Asn Pro Asn Gly Asp Gly Arg Ser Lys Thr Ser
                 50                  55                  60 tta atg acg tgg agg atg tgc aat cct gtc cag gtg gtg aga gtc cat      360
Leu Met Thr Trp Arg Met Cys Asn Pro Val Gln Val Val Arg Val His
                 65                  70                  75 tgg ata ccg tgt ttg tta gcg gta gga gtt ctg ttc ttc acg tgc gta      408
Trp Ile Pro Cys Leu Leu Ala Val Gly Val Leu Phe Phe Thr Cys Val
 80                  85                  90 gag gag tac atg ctc cag atg att ccg gcg agt tct gag ccg ttc gat      456
Glu Glu Tyr Met Leu Gln Met Ile Pro Ala Ser Ser Glu Pro Phe Asp
 95          100                 105                 110 att ggt ttt gtg gcg acg ggc tct ctg tat cgc ctc ttg gct tct tca      504
Ile Gly Phe Val Ala Thr Gly Ser Leu Tyr Arg Leu Leu Ala Ser Ser
             115                 120                 125 ccg gat ctt aat acc gtt tta gct gct ctc aac acg gtg ttt gta ggg      552
Pro Asp Leu Asn Thr Val Leu Ala Ala Leu Asn Thr Val Phe Val Gly
                 130                 135                 140 atg caa acg acg tat att tta tgg aca tgg ttg gtg gaa gga cga cca      600
Met Gln Thr Thr Tyr Ile Leu Trp Thr Trp Leu Val Glu Gly Arg Pro
                 145                 150                 155 cga gcg acc atc tcg gct tgc ttc atg ttt act tgc cgt ggc att ctg      648
Arg Ala Thr Ile Ser Ala Cys Phe Met Phe Thr Cys Arg Gly Ile Leu
                 160                 165                 170 ggt tac tct act cag ctc cct ctt cct cag gat ttt cta gga tca ggg      696
Gly Tyr Ser Thr Gln Leu Pro Leu Pro Gln Asp Phe Leu Gly Ser Gly
175                 180                 185                 190 gta gat ttt ccg gta gga aac gtc tcg ttc ttc ctc ttc tac tca ggc      744
Val Asp Phe Pro Val Gly Asn Val Ser Phe Phe Leu Phe Tyr Ser Gly
                 195                 200                 205 cat gtc gca ggg tcg acg ata gca tcc ttg gat atg agg aga atg aag      792
His Val Ala Gly Ser Thr Ile Ala Ser Leu Asp Met Arg Arg Met Lys
                 210                 215                 220 agg ttg aga ctt gcc ttg ctt ttt gac atc ctc aat gta tta caa tcg      840
Arg Leu Arg Leu Ala Leu Leu Phe Asp Ile Leu Asn Val Leu Gln Ser
                 225                 230                 235 atc agg ctt ctc ggg acg aga gga caa tac acg atc gat ctc gct gtc      888
Ile Arg Leu Leu Gly Thr Arg Gly Gln Tyr Thr Ile Asp Leu Ala Val
 240                 245                 250 gga gtt ggc gct ggg gtt ctc ttt gac tca ctg gct gga aaa tac gaa      936
Gly Val Gly Ala Gly Val Leu Phe Asp Ser Leu Ala Gly Lys Tyr Glu
255                 260                 265                 270 gag atg atg agc aag aga cac aat gta ggc aat ggt ttt agt ttg att      984
Glu Met Met Ser Lys Arg His Asn Val Gly Asn Gly Phe Ser Leu Ile
                 275                 280                 285 tcg tct cgc tag ttattaattt ttgttttttt tttatgtttt                    1026
Ser Ser Arg
```

<210> SEQ ID NO 85
<211> LENGTH: 289
<212> TYPE: PRT
<213> ORGANISM: Brassica napus

<400> SEQUENCE: 85

```
Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Glu Ile Val Thr Gln Thr Asp Asp Cys
        35                  40                  45

Tyr Ala Asn Pro Asn Gly Asp Gly Gly Arg Ser Lys Thr Ser Leu Met
    50                  55                  60

Thr Trp Arg Met Cys Asn Pro Val Gln Val Val Arg Val His Trp Ile
65                  70                  75                  80

Pro Cys Leu Leu Ala Val Gly Val Leu Phe Phe Thr Cys Val Glu Glu
                85                  90                  95

Tyr Met Leu Gln Met Ile Pro Ala Ser Ser Glu Pro Phe Asp Ile Gly
            100                 105                 110

Phe Val Ala Thr Gly Ser Leu Tyr Arg Leu Leu Ala Ser Ser Pro Asp
        115                 120                 125

Leu Asn Thr Val Leu Ala Ala Leu Asn Thr Val Phe Val Gly Met Gln
    130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
    210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg His Asn Val Gly Asn Gly Phe Ser Leu Ile Ser Ser
        275                 280                 285

Arg

<210> SEQ ID NO 86
<211> LENGTH: 1230
<212> TYPE: DNA
<213> ORGANISM: Brassica napus
<220> FEATURE:
<221> NAME/KEY: CDS
<222> LOCATION: (153)..(1022)

<400> SEQUENCE: 86
aacgtagctc tcaaatctca tattcatcgt tttcgtatga actttttgtag cccaaacaac     60 cttcctttcc ttccacaagt ttcataatat ctcttatata acccatatct ccaagcctct    120
cgaaatgttc ttctccgtta aatctaacgg tc atg tca act aca aca atc gtc     173
                                    Met Ser Thr Thr Thr Ile Val
                                    1               5 cct ctc cgt cgc agt tct aac tct ctc aat gaa tac cac act aac gca    221
Pro Leu Arg Arg Ser Ser Asn Ser Leu Asn Glu Tyr His Thr Asn Ala
        10                  15                  20
```

```
gtc gcc ttt gac gga atc gtc ggg tca aca agt act agc caa atg gag    269
Val Ala Phe Asp Gly Ile Val Gly Ser Thr Ser Thr Ser Gln Met Glu
    25                  30                  35 gag att gtt acg caa acc gac gac tgc tac gcc aat ccc aac gga gat    317
Glu Ile Val Thr Gln Thr Asp Asp Cys Tyr Ala Asn Pro Asn Gly Asp
40                  45                  50                  55 gga ggg aga agc aag gcg tcg ttt atg acg tgg agg atg tgc aat cct    365
Gly Gly Arg Ser Lys Ala Ser Phe Met Thr Trp Arg Met Cys Asn Pro
                60                  65                  70 gtc cag gtg gtg aga gtc cat tgg ata ccg tgt tta gcg gta gga        413
Val Gln Val Val Arg Val His Trp Ile Pro Cys Leu Leu Ala Val Gly
            75                  80                  85 gtt ctg ttc ttc acg ggc gta gag gag tac atg ctc cag atg att ccg    461
Val Leu Phe Phe Thr Gly Val Glu Glu Tyr Met Leu Gln Met Ile Pro
        90                  95                  100 gcg agt tct gag ccg ttc gat att ggt ttt gtg gcg acg cgc tct ctg    509
Ala Ser Ser Glu Pro Phe Asp Ile Gly Phe Val Ala Thr Arg Ser Leu
    105                 110                 115 tat cgc ctc ttg gct tct tca ccg gat ctt aat acc gtt tta gct gct    557
Tyr Arg Leu Leu Ala Ser Ser Pro Asp Leu Asn Thr Val Leu Ala Ala
120                 125                 130                 135 ctc aac acg gtg ttt gta ggg atg caa acg acg tat att tta tgg aca    605
Leu Asn Thr Val Phe Val Gly Met Gln Thr Thr Tyr Ile Leu Trp Thr
                140                 145                 150 tgg ttg gtg gaa gga cga cca cga gcg acc atc tcg gct tgc ttc atg    653
Trp Leu Val Glu Gly Arg Pro Arg Ala Thr Ile Ser Ala Cys Phe Met
            155                 160                 165 ttt act tgt cgt ggc att ctt ggt tac tct act cag ctc cct ctt cct    701
Phe Thr Cys Arg Gly Ile Leu Gly Tyr Ser Thr Gln Leu Pro Leu Pro
        170                 175                 180 cag gat ttt cta gga tca ggg gta gat ttt ccg gta gga aac gtc tcg    749
Gln Asp Phe Leu Gly Ser Gly Val Asp Phe Pro Val Gly Asn Val Ser
    185                 190                 195 ttc ttc ctc ttc tac tca ggc cat gtc gca ggg tcg acg ata gca tcc    797
Phe Phe Leu Phe Tyr Ser Gly His Val Ala Gly Ser Thr Ile Ala Ser
200                 205                 210                 215 ttg gat atg agg aga atg aag agg ttg aga cta gcc ttg ctt ttt gac    845
Leu Asp Met Arg Arg Met Lys Arg Leu Arg Leu Ala Leu Leu Phe Asp
                220                 225                 230 atc ctc aat gta tta caa tcg atc agg ctt ctc ggg acg aga gga caa    893
Ile Leu Asn Val Leu Gln Ser Ile Arg Leu Leu Gly Thr Arg Gly Gln
            235                 240                 245 tac acg atc gat ctc gct gtc gga gtt ggc gct ggg gtt ctc ttt gac    941
Tyr Thr Ile Asp Leu Ala Val Gly Val Gly Ala Gly Val Leu Phe Asp
        250                 255                 260 tca ctg gct gga aaa tac gaa gag atg atg agc aag aga cgc aat gta    989
Ser Leu Ala Gly Lys Tyr Glu Glu Met Met Ser Lys Arg Arg Asn Val
    265                 270                 275 ggc aat ggt ttt agt ttg att tcg tct cgc tag ttattaattt tgtttttttt 1042
Gly Asn Gly Phe Ser Leu Ile Ser Ser Arg
280                 285 ttttatgttt ttagtctgga catatttaat ttagttgaaa tctaatgact taaatttgct 1102 ttctttcaaa atgctctaac tgacggacct aactaaatgt gtacgttatt gtgtagttac 1162 catagaggtt tcgtattgtc ttgagcctga tattttgatt ttagagctcg tttatacggt 1222 agctaata                                                          1230

<210> SEQ ID NO 87
```

<211> LENGTH: 289
<212> TYPE: PRT
<213> ORGANISM: Brassica napus

<400> SEQUENCE: 87

```
Met Ser Thr Thr Thr Ile Val Pro Leu Arg Arg Ser Ser Asn Ser Leu
1               5                   10                  15

Asn Glu Tyr His Thr Asn Ala Val Ala Phe Asp Gly Ile Val Gly Ser
            20                  25                  30

Thr Ser Thr Ser Gln Met Glu Ile Val Thr Gln Thr Asp Asp Cys
        35                  40                  45

Tyr Ala Asn Pro Asn Gly Asp Gly Arg Ser Lys Ala Ser Phe Met
50                  55                  60

Thr Trp Arg Met Cys Asn Pro Val Gln Val Val Arg Val His Trp Ile
65                  70                  75                  80

Pro Cys Leu Leu Ala Val Gly Val Leu Phe Phe Thr Gly Val Glu Glu
                85                  90                  95

Tyr Met Leu Gln Met Ile Pro Ala Ser Ser Glu Pro Phe Asp Ile Gly
            100                 105                 110

Phe Val Ala Thr Arg Ser Leu Tyr Arg Leu Leu Ala Ser Ser Pro Asp
        115                 120                 125

Leu Asn Thr Val Leu Ala Ala Leu Asn Thr Val Phe Val Gly Met Gln
130                 135                 140

Thr Thr Tyr Ile Leu Trp Thr Trp Leu Val Glu Gly Arg Pro Arg Ala
145                 150                 155                 160

Thr Ile Ser Ala Cys Phe Met Phe Thr Cys Arg Gly Ile Leu Gly Tyr
                165                 170                 175

Ser Thr Gln Leu Pro Leu Pro Gln Asp Phe Leu Gly Ser Gly Val Asp
            180                 185                 190

Phe Pro Val Gly Asn Val Ser Phe Phe Leu Phe Tyr Ser Gly His Val
        195                 200                 205

Ala Gly Ser Thr Ile Ala Ser Leu Asp Met Arg Arg Met Lys Arg Leu
210                 215                 220

Arg Leu Ala Leu Leu Phe Asp Ile Leu Asn Val Leu Gln Ser Ile Arg
225                 230                 235                 240

Leu Leu Gly Thr Arg Gly Gln Tyr Thr Ile Asp Leu Ala Val Gly Val
                245                 250                 255

Gly Ala Gly Val Leu Phe Asp Ser Leu Ala Gly Lys Tyr Glu Glu Met
            260                 265                 270

Met Ser Lys Arg Arg Asn Val Gly Asn Gly Phe Ser Leu Ile Ser Ser
        275                 280                 285

Arg
```

<210> SEQ ID NO 88
<211> LENGTH: 1422
<212> TYPE: DNA
<213> ORGANISM: Brassica napus
<220> FEATURE:
<221> NAME/KEY: CDS
<222> LOCATION: (270)..(977)

<400> SEQUENCE: 88

```
acataaaaag aacacatgtc gaaacaaaat gtccacaaac accctgttgt ataacttcc      60 atatctaatc gtcacctatg attggggatc tgatataatt acacataagt caaatcgtca    120
cagttttggt agtaaatcga agcgctcatt tgtgtaataa agttgtacgt tattatgttc    180
```

```
tagaaaaaat ataagaaatc ttctctctct ctctctctct ctctctctct aaactcttca        240
gacccaaaaa aaagacaagg aataataaaa atg tct caa atg gac att tct acg        293
                                 Met Ser Gln Met Asp Ile Ser Thr
                                  1               5 aga act gag gaa gga gga tgg aga agc aag cct tcg ttt atg acg tgg         341
Arg Thr Glu Glu Gly Gly Trp Arg Ser Lys Pro Ser Phe Met Thr Trp
 10              15                  20 aga gcg cgc gac gtt gtc tac gtg atg aga cac cat tgg ata ccg tgt         389
Arg Ala Arg Asp Val Val Tyr Val Met Arg His His Trp Ile Pro Cys
 25              30                  35                  40 ctg ttc gcg gcc gga ttc ttg ttc gtc gta agc gtg gag tcc tcg atc         437
Leu Phe Ala Ala Gly Phe Leu Phe Val Val Ser Val Glu Ser Ser Ile
                 45                  50                  55 aag atg gtt tcc gag agt tct cca ccg ttc gat att ggg ttt gtg gcc         485
Lys Met Val Ser Glu Ser Ser Pro Pro Phe Asp Ile Gly Phe Val Ala
                     60                  65                  70 acg gag tct ctg cat cat atc ttg gct tct tca ccg gat ctg aac acc         533
Thr Glu Ser Leu His His Ile Leu Ala Ser Ser Pro Asp Leu Asn Thr
                 75                  80                  85 ggt ttg gcc gct cta aac tcg gtg tta gga gtg atg caa gta tcg tat         581
Gly Leu Ala Ala Leu Asn Ser Val Leu Gly Val Met Gln Val Ser Tyr
 90                  95                 100 att gca tgg aca tgg tta ata gaa gga cgg cca cga gcc acc atc acg         629
Ile Ala Trp Thr Trp Leu Ile Glu Gly Arg Pro Arg Ala Thr Ile Thr
105             110                 115                 120 gct tta ttc ctc ttc act tgt cgc ggt gtt ctc ggt tac tgt acg cag         677
Ala Leu Phe Leu Phe Thr Cys Arg Gly Val Leu Gly Tyr Cys Thr Gln
                125                 130                 135 ctt cct ctt tca aag gag tat cta gga tca gca atc gat ttc ccg cta         725
Leu Pro Leu Ser Lys Glu Tyr Leu Gly Ser Ala Ile Asp Phe Pro Leu
                140                 145                 150 gga aac ctc tcg ttc ttc tat ttt ttc tcg ggt cac gtg gca ggc gcg         773
Gly Asn Leu Ser Phe Phe Tyr Phe Phe Ser Gly His Val Ala Gly Ala
                155                 160                 165 act atc gca tct ttg gac atg agg agg atg cag agg ttg aga ctt gcg         821
Thr Ile Ala Ser Leu Asp Met Arg Arg Met Gln Arg Leu Arg Leu Ala
170                 175                 180 atg att ttt gac atc ctc aat gta tta cag tcg atc agg ctg ctt gcg         869
Met Ile Phe Asp Ile Leu Asn Val Leu Gln Ser Ile Arg Leu Leu Ala
185                 190                 195                 200 acg aga gga cac tac acg atc gat ctc gca ggt gga gtt gcc gcc gcg         917
Thr Arg Gly His Tyr Thr Ile Asp Leu Ala Gly Gly Val Ala Ala Ala
                    205                 210                 215 att ctc ttt gac tca ttg gcc ggc aag tac gaa gct aat aca aga aag         965
Ile Leu Phe Asp Ser Leu Ala Gly Lys Tyr Glu Ala Asn Thr Arg Lys
                220                 225                 230 agg caa ttg tag gaacaggttt cagcttgatt accaaaaaac ttcaaagatt            1017
Arg Gln Leu
        235 tcattaattc aacatgttta gttgctgttg aattaagtct actgtggttt ggcaattatt      1077 ctccccatga gccagtggct tggacttctt cgaccctagt gttcatggtc agactgtata      1137 tgttgtttat ttctcatttt ttcattcgac tccgcaattt gtgatatggg tttggttaac      1197 actagttggt tcagttgttt tcaattggtt ttactctgaa agttataaac gttttgtaat      1257 accagatttt acccaacaac gctcttatta acatcccagt tcaatgttga ccggatcata      1317 gaaacggata agaaaaaaat gagtaagata aaatttaaa aatgacgagg aatgatgatt       1377 ttttatcaaa attaataagg aataaatttg ttttataatt cttta                      1422
```

<210> SEQ ID NO 89
<211> LENGTH: 235
<212> TYPE: PRT
<213> ORGANISM: Brassica napus

<400> SEQUENCE: 89

```
Met Ser Gln Met Asp Ile Ser Thr Arg Thr Glu Glu Gly Gly Trp Arg
1               5                   10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe
        35                  40                  45

Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
        115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Ala Thr Ile Ala Ser Leu Asp Met Arg
                165                 170                 175

Arg Met Gln Arg Leu Arg Leu Ala Met Ile Phe Asp Ile Leu Asn Val
            180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

<210> SEQ ID NO 90
<211> LENGTH: 1200
<212> TYPE: DNA
<213> ORGANISM: Brassica napus
<220> FEATURE:
<221> NAME/KEY: CDS
<222> LOCATION: (24)..(731)

<400> SEQUENCE: 90

```
aaaaaaagac aaggaataat aaa atg tct caa atg gac att tct acg aga act        53
                        Met Ser Gln Met Asp Ile Ser Thr Arg Thr
                        1               5                   10 gag gaa gga gga tgg aga agc aag cct tcg ttt atg acg tgg aga gcg         101
Glu Glu Gly Gly Trp Arg Ser Lys Pro Ser Phe Met Thr Trp Arg Ala
            15                  20                  25 cgc gac gtt gtc tac gtg atg aga cac cat tgg ata ccg tgt ctg ttc        149
Arg Asp Val Val Tyr Val Met Arg His His Trp Ile Pro Cys Leu Phe
        30                  35                  40 gcg gcc gga ttc ttg ttc gtc gta agc gtg gag tcc tcg atc aag atg        197
Ala Ala Gly Phe Leu Phe Val Val Ser Val Glu Ser Ser Ile Lys Met
    45                  50                  55
```

```
gtt tcc gag agt tct cca ccg ttc gat att ggg ttt gtg gcc acg gag    245
Val Ser Glu Ser Ser Pro Pro Phe Asp Ile Gly Phe Val Ala Thr Glu
         60                  65                  70 tct ctg cat cat atc ttg gct tct tca ccg gat ctg aac acc ggt ttg    293
Ser Leu His His Ile Leu Ala Ser Ser Pro Asp Leu Asn Thr Gly Leu
 75                  80                  85                  90 gcc gct cta aac tcg gtg tta gga gtg atg caa gta tcg tat att gca    341
Ala Ala Leu Asn Ser Val Leu Gly Val Met Gln Val Ser Tyr Ile Ala
                 95                 100                 105 tgg aca tgg tta ata gaa gga cgg ccc cga gcc acc atc acg gct tta    389
Trp Thr Trp Leu Ile Glu Gly Arg Pro Arg Ala Thr Ile Thr Ala Leu
            110                 115                 120 ttc ctc ttc act tgt cgc ggt gtt ctc ggt tac tgt act cag ctc cct    437
Phe Leu Phe Thr Cys Arg Gly Val Leu Gly Tyr Cys Thr Gln Leu Pro
        125                 130                 135 ctt tca aag gag tat cta gga tca gca atc gat ttc ccg cta gga aat    485
Leu Ser Lys Glu Tyr Leu Gly Ser Ala Ile Asp Phe Pro Leu Gly Asn
    140                 145                 150 ctc tcg ttc ttc tat ttt ttc tcg ggt cac gtg gca ggc gcg acc atc    533
Leu Ser Phe Phe Tyr Phe Phe Ser Gly His Val Ala Gly Ala Thr Ile
155                 160                 165                 170 gca tct ttg gac atg agg agg atg cag agg ttg aga ttt gcg atg gtt    581
Ala Ser Leu Asp Met Arg Arg Met Gln Arg Leu Arg Phe Ala Met Val
                175                 180                 185 ttt gac atc ctc aat gta tta cag tcg atc agg ctg ctt gcg acg aga    629
Phe Asp Ile Leu Asn Val Leu Gln Ser Ile Arg Leu Leu Ala Thr Arg
            190                 195                 200 gga cac tac acg atc gat ctc gca ggt gga gtt gcc gct gcg att ctc    677
Gly His Tyr Thr Ile Asp Leu Ala Gly Gly Val Ala Ala Ala Ile Leu
        205                 210                 215 ttt gac tca ttg gcc gga aag tac gaa gct aat aca aga aag agg caa    725
Phe Asp Ser Leu Ala Gly Lys Tyr Glu Ala Asn Thr Arg Lys Arg Gln
    220                 225                 230 ttg tag gaacaggttt cagcttgatt accaaaagac ttcaaagatt tcattcaaca    781
Leu
235 tgtttagttg ctgttgaatt ctactgtggt tcggcaatta ttctccccat gagccagtgg    841 cttggacttc ttcgacccta atgttcatgg tcagactgta tatgttgttt atttctcatt    901 ttttcattcg actccgcaat tgtgatatg ggtttggtta cactagttg gttcaattgt    961 tttcaattgg ttttactctg aaagttgtaa acgttgtgta ataccagatt acccaacaac    1021 gctagctctt attaacatcc cagttagttg tgaaaaaaaa aaactcaaaa ctactagctt    1081 aattaattaa ttaaatagtg gaagcactgt aacttaatgg tacgaggttc gcagtaaatg    1141 tagaatctta atttgactag tgttgacaaa aattaatttg gttagcctta tttaagtag     1200
```

<210> SEQ ID NO 91
<211> LENGTH: 235
<212> TYPE: PRT
<213> ORGANISM: Brassica napus

<400> SEQUENCE: 91

Met Ser Gln Met Asp Ile Ser Thr Arg Thr Glu Glu Gly Gly Trp Arg
 1               5                  10                  15

Ser Lys Pro Ser Phe Met Thr Trp Arg Ala Arg Asp Val Val Tyr Val
            20                  25                  30

Met Arg His His Trp Ile Pro Cys Leu Phe Ala Ala Gly Phe Leu Phe

-continued

```
                35                  40                  45
Val Val Ser Val Glu Ser Ser Ile Lys Met Val Ser Glu Ser Ser Pro
    50                  55                  60

Pro Phe Asp Ile Gly Phe Val Ala Thr Glu Ser Leu His His Ile Leu
65                  70                  75                  80

Ala Ser Ser Pro Asp Leu Asn Thr Gly Leu Ala Ala Leu Asn Ser Val
                85                  90                  95

Leu Gly Val Met Gln Val Ser Tyr Ile Ala Trp Thr Trp Leu Ile Glu
            100                 105                 110

Gly Arg Pro Arg Ala Thr Ile Thr Ala Leu Phe Leu Phe Thr Cys Arg
            115                 120                 125

Gly Val Leu Gly Tyr Cys Thr Gln Leu Pro Leu Ser Lys Glu Tyr Leu
    130                 135                 140

Gly Ser Ala Ile Asp Phe Pro Leu Gly Asn Leu Ser Phe Phe Tyr Phe
145                 150                 155                 160

Phe Ser Gly His Val Ala Gly Ala Thr Ile Ala Ser Leu Asp Met Arg
                165                 170                 175

Arg Met Gln Arg Leu Arg Phe Ala Met Val Phe Asp Ile Leu Asn Val
                180                 185                 190

Leu Gln Ser Ile Arg Leu Leu Ala Thr Arg Gly His Tyr Thr Ile Asp
        195                 200                 205

Leu Ala Gly Gly Val Ala Ala Ala Ile Leu Phe Asp Ser Leu Ala Gly
    210                 215                 220

Lys Tyr Glu Ala Asn Thr Arg Lys Arg Gln Leu
225                 230                 235
```

BRASSICA PLANTS WITH MODIFIED SEED OIL COMPOSITION

CROSS-REFERENCE TO RELATED APPLICATIONS

This application is the U.S. National Phase of International Patent Application No. PCT/EP2013/064190, filed Jul. 4, 2013, which claims the benefit of priority to Provisional Application No. 61/668,529, filed Jul. 6, 2012.

FIELD OF THE INVENTION

The invention relates to the field of agronomy. Methods and means are provided to modulate fatty acid composition in *Brassica* seeds, such as to increase levels of unsaturated fatty acids in *Brassica* seeds by modulation of expression of ROD1 genes in various manners, including provision of knock-out ROD1 alleles or providing inhibitory RNAs to the ROD1 genes.

BACKGROUND OF THE INVENTION

Many plant species store triacylglycerols (TAGs) in their seeds as a carbon reserve. These TAGs are the major source of energy and carbon material that supports seedling development during the early stages of plant life. Vegetable oils from soybean (*Glycine max*), *Brassica* (*Brassica napus* or *B. rapa*), sunflower (*Helianthus annuus*) and many other oilseed crops are also an important source of oil for the human diet or industrial applications including, but not limited to biofuels, biolubricants, nylon precursors, and detergent feedstocks. The degree and/or amount of polyunsaturated fatty acids of vegetable oils are characteristic and determinative properties with respect to oil uses in food or non-food industries. More specifically, the characteristic properties and utilities of vegetable oils are largely determined by their fatty acyl compositions in TAG.

Major vegetable oils are comprised primarily of palmitic (16:0), stearic (18:0), oleic (18:1cis $\Delta^9$), linoleic (18:2cis $\Delta^{9,12}$), and α-linolenic (18:3cis $\Delta^{9,12,15}$ or C18:3) acids. Palmitic and stearic acids are, respectively, 16 and 18 carbon-long, saturated fatty acids. Oleic, linoleic, and linolenic acids are 18-carbon-long, unsaturated fatty acids containing one, two, and three double bonds, respectively. Oleic acid is referred to as a monounsaturated fatty acid, while linoleic and linolenic acids are referred to as polyunsaturated fatty acids. Modifications of the fatty acid compositions have been sought after for at least a century in order to provide optimal oil products for human nutrition and chemical (e.g., oleochemical) uses (Gunstone, 1998, Prog Lipid Res 37:277; Broun et al., 1999, Annu Rev Nutr 19:107; Jaworski et al, 2003, Curr Opin Plant Biol 6:178). In particular, the polyunsaturated fatty acids (18:2 and 18:3) have received considerable attention because they are major factors that affect nutritional value and oil stability. However, while these two fatty acids provide essential nutrients for humans and animals, they increase oil instability because they comprise multiple double bonds that may be easily oxidized during processing and storage.

The desaturation of 18:1 into 18:2 is a critical step for synthesizing polyunsaturated fatty acids. During storage lipid biosynthesis, this reaction is known to be catalyzed by the fatty acid desaturase, FAD2, a membrane-bound enzyme located on the endoplasmic reticulum (ER) (Browse and Somerville, 1991, Annu Rev Plant Physiol Plant Mol Biol 42:467). The FAD2 substrate 18:1 must be esterified on the sn-2 position of phosphatidylcholine (PC) (Miguel and Browse, 1992, J Biol Chem 267:1502; Okuley et al., 1994, Plant Cell 6:147), which is the major membrane phospholipid of plant cells. Not surprisingly, therefore, down-regulation of FAD2 (and FAD3) genes has become a preferred strategy for avoiding the need to hydrogenate vegetable oils and the concomitant production of undesirable trans fatty acids. For example, soybean has both seed-specific and constitutive FAD2 desaturases, so that gene silencing of the seed-specific isoform has allowed the production of high-oleate cultivars (>88% 18:1 in the oil) in which membrane unsaturation and plant performance are largely unaffected. Significantly, however, such FAD2 gene-silencing strategies are substantially limited because, for example, canola and other oilseed plants have only constitutive FAD2 enzymes. Therefore, in canola and other such constitutive FAD2 crops, silencing or down-regulation of FAD2 not only alters the fatty acid composition of the storage triacylglycerol (TAG) in seeds, but also of the cellular membranes, which severely compromises growth and yield of the plant. For example, the defective FAD2 in the *Arabidopsis* mutant fad2 alters fatty acid compositions of seeds as well as vegetable tissues, and severely compromises plant growth (Browse and Somerville, supra). FAD2 mutations and silencing that produce the highest 18:1 levels in the oil also reduce membrane unsaturation in vegetative and seed tissues, resulting in plants that germinate and grow poorly. As a result, only partial downregulation of FAD2 expression is possible, producing approximately 70-75% 18:1 in the oil of commercial cultivars such as Nexera/Natreon (Dow Agro-Sciences) and Clear Valley 75 (Cargill). Lu et al (2009, Proc Natl Acad Sci USA 106:18837) and WO2009/111587 describe the identification of phosphatidylcholine:diacylglycerol cholinephosphotransferase (PDCT) from *Arabidopsis*, which is endoced by the ROD1 gene, which is involved in the transfer of 18:1 into phosphatidylcholine for desaturation and also for the reverse transfer of 18:2 and 18:3 into the triacylglycerol synthesis pathway. The PDCT enzyme catalyzes transfer of 18:2 and 18:3 into the triacylglycerol synthesis pathway. Seeds of an *Arabidopsis* rod1 mutant have a decrease in 18:2 and 18:3 polyunsaturated fatty acids and a concomitant increase in 18:1 relative to wild-type, whereas there is no effect on the fatty acid compositions of leaf or root tissues. identified in *Arabidopsis*. WO2009/111587 further describes ROD1 homologs from *Brassica napus, Brassica rapa*, and *Brassica oleracea*.

In order to use the ROD1 gene to increase 18:1 levels and reduce 18:2 and 18:3 levels in *Brassica*, a need remains for knowing all ROD1 gene sequences and the functionality of the encoded proteins in the *Brassica* genome. The isolation of mutant alleles corresponding to rod1 in economically important Brassicaceae plants, such as oilseed rape, may be complicated by the amphidiploidy in oilseed rape and the consequent functional redundancy of the corresponding genes.

Thus, the prior art is deficient in teaching how many ROD1 genes exist in *Brassica*, and which of the ROD1 genes encode a functional protein or need to be inactivated in order to increase the levels of 18:1 in seeds. As described hereinafter, this problem has been solved, allowing to modulate expression of PDCT with the aim to modulate the 18:1 levels in *Brassica* seeds, as will become apparent from the different embodiments and the claims.

SUMMARY OF THE INVENTION

It is a first embodiment of the invention to provide a *Brassica* plant or plant cell, part, seed or progeny thereof, comprising at least one ROD1 gene, characterized in that at least one ROD1 gene is an inactivated or knock-out rod1 gene. In a further embodiment, said *Brassica* plant is *Brassica rapa*, and said inactivated or knock-out rod1 gene is a knock-out allele of the ROD1 gene encoding a protein having at least 90% sequence identity to SEQ ID No. 15, SEQ ID No. 18, SEQ ID No. 21, or SEQ ID No. 24. In yet a further embodiment, said *Brassica* plant is *Brassica oleracea*, and said knock-out rod1 gene is a knock-out allele of the ROD1 gene encoding a protein having at least 90% sequence identity to SEQ ID No. 27, SEQ ID No. 30, SEQ ID No. 33, or SEQ ID No. 36. In yet another embodiment, said *Brassica* plant is *Brassica napus*, and said knock-out rod1 gene is a knock-out allele of a ROD1 gene encoding a protein having at least 90% sequence identity to SEQ ID No. 3 or SEQ ID No. 6, such as *Brassica napus* which is obtainable from seeds obtainable from seeds selected from the group consisting of seed comprising HIOL306 having been deposited at NCIMB under accession number NCIMB 41995, seed comprising HIOL307 having been deposited at NCIMB under accession number NCIMB 42000, seed comprising HIOL310 having been deposited at NCIMB under accession number NCIMB 41996, seed comprising HIOL313 having been deposited at NCIMB under accession number NCIMB 42001, seed comprising HIOL316 having been deposited at NCIMB under accession number NCIMB 41997, seed comprising HIOL318 having been deposited at NCIMB under accession number NCIMB 41998, and seed comprising HIOL319 having been deposited at NCIMB under accession number NCIMB 41999, or such as *Brassica napus* comprising two knock-out ROD1 alleles, one of said knock-out alleles being a knock-out allele of a ROD1 gene encoding a protein having at least 90% sequence identity to SEQ ID No. 3, and one of said knock-out alleles being a knock-out allele of a ROD1 gene encoding a protein having at least 90% sequence identity to SEQ ID No. 6.

In a further embodiment, said *Brassica* plant in homozygous for said knock-out rod1 gene.

In a further embodiment, a transgenic *Brassica* plant is provided comprising a chimeric gene, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells. In another embodiment, said transgenic *Brassica* plant is *Brassica napus*, and said RNA molecule is inhibitory to a ROD1 gene encoding a protein having at least 90% sequence identity to SEQ ID No. 3 or SEQ ID No. 6.

In a further embodiment, seeds are provided from the plants according to the invention, i.e. plants comprising a knock-out ROD1 gene or an RNA inhibitory to a ROD1 gene. In yet another embodiment, oil from the seeds of the plants according to the invention is provided.

In another embodiment, a method is provided for increasing the C18:1 levels in seed oil, comprising modulating the expression of a ROD1 gene. In yet another embodiment, a method is provided for increasing the C18:1 levels in seed oil, comprising the steps of introducing or providing an chimeric gene to a *Brassica* plant cell, to create transgenic cells, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells; and regenerating transgenic plants from said transgenic cells.

In again another embodiment, a method is provided for increasing the C18:1 levels in seed oil, comprising the steps of treating seeds or plant material with a mutagenic chemical substance or with ionizing radiation; identifying plants with a mutated ROD1 gene, wherein the ROD1 gene, prior to being mutated, encodes a polypeptide having at least 90% sequence identity to SEQ ID No. 3 or to SEQ ID No. 6; and selecting a plant with an increased level of C18:1 in the seeds compared to a plant in which the ROD1 gene is not mutated.

In a further embodiment, a method is provided for obtaining a *Brassica* plant with increased levels of C18:1 in the seeds comprising the step of introducing a knock-out allele of a ROD1 gene in said *Brassica* plant, and selecting said *Brassica* plant with increased levels of C18:1 levels in the seeds for the presence of said knock-out allele of a ROD1 gene by analyzing genomic DNA from said plant for the presence of at least one molecular marker, wherein said at least one molecular marker is linked to said knock-out allele of a ROD1 gene.

In another embodiment, a method is provided to determine the presence or absence of a knock-out allele of a ROD1 gene in a biological sample, comprising providing genomic DNA from said biological sample, and analyzing said DNA for the presence of at least one molecular marker, wherein the at least one molecular marker is linked to said knock-out allele of a ROD1 gene.

Yet another embodiment provides a kit for the detection of a knock-out allele of a ROD1 gene in *Brassica* DNA samples, wherein said kit comprises one or more PCR primer pairs, which are able to amplify a DNA marker linked to said knock-out allele of a ROD1 gene.

In a further embodiment, a method is provided for determining the zygosity status of a mutant ROD1 allele in a plant, or a cell, part, seed or progeny thereof, comprising determining the presence of a mutant and/or a corresponding wild type ROD1 specific region in the genomic DNA of said plant, or a cell, part, seed or progeny thereof.

Yet a further embodiment provides method for transferring at least one knock-out ROD1 allele from one plant to another plant comprising the steps of: identifying a first plant comprising at least one knock-out ROD1 allele; crossing the first plant with a second plant not comprising the at least one knock-out ROD1 allele and collecting F1 hybrid seeds from the cross; optionally, identifying F1 plants comprising the at least one knock-out ROD1 allele; backcrossing F1 plants comprising the at least one knock-out ROD1 allele with the second plant not comprising the at least one knock-out ROD1 allele for at least one generation and collecting back cross seeds from the crosses; identifying in every generation back cross plants comprising the at least one knock-out ROD1 allele by analyzing genomic DNA of said back cross plants for the presence of at least one molecular marker, wherein the at least one molecular marker is linked to said knock-out ROD1 allele.

Another embodiment provides a chimeric gene comprising the following operably linked elements: a plant-expressible promoter; a DNA region, which when transcribed yields an RNA molecule inhibitory to at least one ROD1 gene; and optionally a transcription termination and polyadenylation region functional in plant cells.

In again another embodiment, a knock-out allele of an ROD1 gene is provided, wherein the knock-out ROD1 allele is a mutated version of the native ROD1 gene selected from the group consisting of: a nucleic acid molecule which comprises at least 90% sequence identity to SEQ ID No. 1, SEQ ID No. 4, SEQ ID No. 7, SEQ ID No. 10, SEQ ID No.

13, SEQ ID No. 16, SEQ ID No. 19, SEQ ID No. 22, SEQ ID No. 25, SEQ ID No. 28, SEQ ID No. 31, SEQ ID No. 34, SEQ ID No. 84, SEQ ID No. 86, SEQ ID No. 88, or SEQ ID No. 90; or a nucleic acid molecule encoding an amino acid sequence comprising at least 90% sequence identity to SEQ ID No. 3, SEQ ID No. 6, SEQ ID No. 9, SEQ ID No. 12, SEQ ID No. 15, SEQ ID No. 18, SEQ ID No. 21, SEQ ID No. 24, SEQ ID No. 27, SEQ ID No. 30, SEQ ID No. 33, SEQ ID No. 36, SEQ ID No. 85, SEQ ID No. 87, SEQ ID No. 89, or SEQ ID No. 91, wherein said mutant rod1 allele comprises a mutated DNA region consisting of one or more inserted, deleted or substituted nucleotides compared to a corresponding wild-type DNA region in the functional ROD1 gene and wherein said mutant rod1 allele encodes no functional ROD1 protein or encodes a ROD1 protein with reduced activity.

In a further embodiment, a method is provided for producing oil, comprising harvesting seeds from the plants according to the invention, i.e. plants comprising an inactivated or knock-out ROD1 gene or an RNA inhibitory to a ROD1 gene, and extracting the oil from said seeds.

In yet a further embodiment, a method is provided of producing food or feed, such as oil, meal, grain, starch, flour or protein, or an industrial product, such as biofuel, fiber, industrial chemicals, a pharmaceutical or a neutraceutical, comprising obtaining the plant or a part thereof according to the invention, and preparing the food, feed or industrial product from the plant or part thereof.

GENERAL DEFINITIONS

Figure 1:
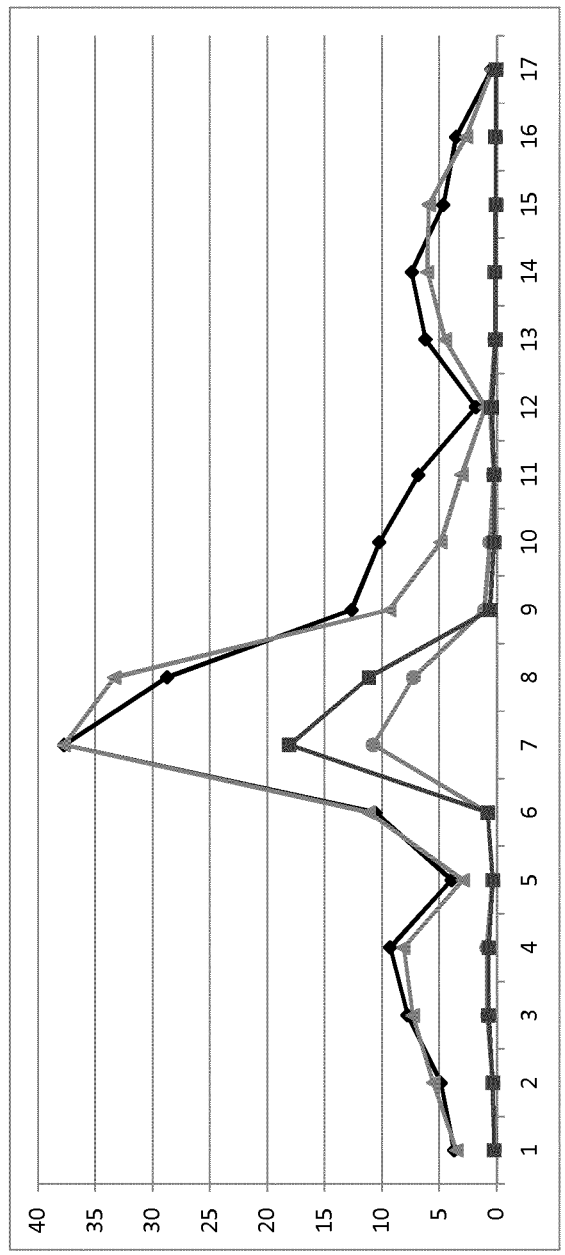
FIG. 1. Gene expression level in 17 tissue-stage combinations for BnROD1-A1 (black diamonds), BnROD1-C1 (gray triangles), BnROD1-A2 (gray circles) and BnROD1-C2 (black squares). 1: cotyledons 10 days after sowing (DAS); 2: Stem 2 weeks, 14 DAS; 3: Roots 14 DAS; 4: Apical meristem 33 DAS; 5: young leaf 33 DAS; 6: Stem 5 weeks, 33 DAS; 7: Small flower bud (≤5 mm) 42 DAS; 8: Big flower bud (≥5 mm) 42 DAS; 9: Open flower 52 DAS; 10: Pod valves stage 2, 14-20 days after fertilization (DAF); 11: Pod valves stage 3, 21-25 DAF; 12: Seed stage 2, 14-20 DAF; 13: Seed stage 3, 21-25 DAF; 14: Seed stage 4, 26-30 DAF; 15: Seed stage 5, 31-35 DAF; 16: Seed stage 6, 42 DAF; 17: Seed stage 7, 49 DAF.

A "ROD1 gene" or "ROD1 allele", as used herein, is a gene or allele comprising a sequence having at least 60% sequence identity to the coding sequence of the ROD1 gene of *Arabidopsis thaliana*, as described in WO2009/111587.

A ROD1 gene or ROD1 allele can, but does not need to encode a functional ROD1 protein. Functionality of the ROD1 protein can be tested, for example, in yeast as described in example 4 or as described by Lu et al. (2009) Proc Natl Acad Sci USA 106:18839.

A "knock-out rod1 gene" or "knock-out rod1 allele" as used herein is a rod1 gene or a rod1 allele which encodes no functional ROD1 protein, or which encodes a ROD1 protein with reduced activity. Said "knock-out rod1 gene" can be a full knock-out rod1 gene, encoding no functional ROD1 protein, or can be a partial knock-out rod1 gene, encoding a ROD1 protein with reduced activity. Said "knock-out rod1 gene" or "knock-out rod1 allele" can be a mutant rod1 allele or a mutant rod1 gene, which may encode no functional ROD1 protein, or which may encode a mutant ROD1 protein with reduced activity. The gene or allele may also be referred to as an inactivated gene or allele.

A "functional ROD1 gene" or "functional ROD1 allele" as used herein is a ROD1 gene or a ROD1 allele which encodes a functional ROD1 protein.

A "mutant rod1 gene" or "mutant rod1 allele" as used herein refers to any rod1 gene or rod1 allele which is not found in plants in the natural population or breeding population, but which is produced by human intervention such as mutagenesis or gene targeting. A mutant rod1 allele comprises knock-out rod1 alleles, and functional rod1 alleles.

Functional ROD1 protein is a ROD1 protein which has at least 10%, or at least 15%, or at least 20%, or at least 25%, or at least 30% of the activity of the protein encoded by a reference *Brassica napus* ROD1-A1 gene, as tested, for example, in yeast as described in example 4, wherein the reference *Brassica napus* ROD1-A1 gene encodes the protein with the amino acid sequence as depicted in SEQ ID No. 3.

A mutant ROD1 protein with reduced functionality is a ROD1 protein encoded by a mutant rod1 gene which has reduced activity as compared to the corresponding wild-type ROD1 protein encoded by the wild-type ROD1 gene. Said activity may be reduced with at least 10%, or at least 20%, or at least 30%, or at least 40%, or at least 50%, or at least 60%, or at least 70%, or at least 80%, or at least 90%.

The term "nucleic acid sequence" (or nucleic acid molecule) refers to a DNA or RNA molecule in single or double stranded form, particularly a DNA encoding a protein or protein fragment according to the invention. An "endogenous nucleic acid sequence" refers to a nucleic acid sequence within a plant cell, e.g. an endogenous allele of an ROD1 gene present within the nuclear genome of a *Brassica* cell. An "isolated nucleic acid sequence" is used to refer to a nucleic acid sequence that is no longer in its natural environment, for example in vitro or in a recombinant bacterial or plant host cell.

The term "gene" means a DNA sequence comprising a region (transcribed region), which is transcribed into an RNA molecule (e.g. into a pre-mRNA, comprising intron sequences, which is then spliced into a mature mRNA, or directly into a mRNA without intron sequences) in a cell, operably linked to regulatory regions (e.g. a promoter). A gene may thus comprise several operably linked sequences, such as a promoter, a 5' leader sequence comprising e.g. sequences involved in translation initiation, a (protein) coding region (cDNA or genomic DNA) and a 3' non-translated sequence comprising e.g. transcription termination sites. "Endogenous gene" is used to differentiate from a "foreign gene", "transgene" or "chimeric gene", and refers to a gene from a plant of a certain plant genus, species or variety, which has not been introduced into that plant by transformation (i.e. it is not a "transgene"), but which is normally present in plants of that genus, species or variety, or which is introduced in that plant from plants of another plant genus, species or variety, in which it is normally present, by normal breeding techniques or by somatic hybridization, e.g., by protoplast fusion. Similarly, an "endogenous allele" of a gene is not introduced into a plant or plant tissue by plant transformation, but is, for example, generated by plant mutagenesis and/or selection or obtained by screening natural populations of plants.

"Expression of a gene" or "gene expression" refers to the process wherein a DNA region, which is operably linked to appropriate regulatory regions, particularly a promoter, is transcribed into an RNA molecule. The RNA molecule is then processed further (by post-transcriptional processes) within the cell, e.g. by RNA splicing and translation initiation and translation into an amino acid chain (polypeptide), and translation termination by translation stop codons. The term "functionally expressed" is used herein to indicate that a functional protein is produced; the term "not functionally expressed" to indicate that a protein with significantly reduced or no functionality (biological activity) is produced or that no protein is produced (see further below).

The terms "protein" or "polypeptide" are used interchangeably and refer to molecules consisting of a chain of amino acids, without reference to a specific mode of action, size, 3-dimensional structure or origin. A "fragment" or "portion" of an ROD1 protein may thus still be referred to as a "protein". An "isolated protein" is used to refer to a protein that is no longer in its natural environment, for example in vitro or in a recombinant bacterial or plant host cell.

As used herein, the term "allele(s)" means any of one or more alternative forms of a gene at a particular locus. In a diploid (or amphidiploid) cell of an organism, alleles of a given gene are located at a specific location or locus (loci plural) on a chromosome. One allele is present on each chromosome of the pair of homologous chromosomes.

As used herein, the term "homologous chromosomes" means chromosomes that contain information for the same biological features and contain the same genes at the same loci but possibly different alleles of those genes. Homologous chromosomes are chromosomes that pair during meiosis. "Non-homologous chromosomes", representing all the biological features of an organism, form a set, and the number of sets in a cell is called ploidy. Diploid organisms contain two sets of non-homologous chromosomes, wherein each homologous chromosome is inherited from a different parent. In amphidiploid species, essentially two sets of diploid genomes exist, whereby the chromosomes of the two genomes are referred to as "homeologous chromosomes" (and similarly, the loci or genes of the two genomes are referred to as homeologous loci or genes). A diploid, or amphidiploid, plant species may comprise a large number of different alleles at a particular locus.

As used herein, the term "heterozygous" means a genetic condition existing when two different alleles reside at a specific locus, but are positioned individually on corresponding pairs of homologous chromosomes in the cell. Conversely, as used herein, the term "homozygous" means a genetic condition existing when two identical alleles reside at a specific locus, but are positioned individually on corresponding pairs of homologous chromosomes in the cell.

As used herein, the term "locus" (loci plural) means a specific place or places or a site on a chromosome where for example a gene or genetic marker is found.

"Wild type" (also written "wildtype" or "wild-type"), as used herein, refers to a typical form of a plant or a gene as it most commonly occurs in nature. A "wild type plant" refers to a plant in the natural population or in a breeding population. A "wild type allele" refers to an allele of a gene occurring in wild-type plants.

Whenever reference to a "plant" or "plants" according to the invention is made, it is understood that also plant parts (cells, tissues or organs, seed pods, seeds, severed parts such as roots, leaves, flowers, pollen, etc.), progeny of the plants which retain the distinguishing characteristics of the parents (especially the fruit dehiscence properties), such as seed obtained by selfing or crossing, e.g. hybrid seed (obtained by crossing two inbred parental lines), hybrid plants and plant parts derived there from are encompassed herein, unless otherwise indicated.

"Creating propagating material", as used herein, relates to any means know in the art to produce further plants, plant parts or seeds and includes inter alia vegetative reproduction methods (e.g. air or ground layering, division, (bud) grafting, micropropagation, stolons or runners, storage organs such as bulbs, corms, tubers and rhizomes, striking or cutting, twin-scaling), sexual reproduction (crossing with another plant) and asexual reproduction (e.g. apomixis, somatic hybridization).

"Mutagenesis", as used herein, refers to the process in which plant cells (e.g., a plurality of Brassica seeds or other parts, such as pollen, etc.) are subjected to a technique which induces mutations in the DNA of the cells, such as contact with a mutagenic agent, such as a chemical substance (such as ethylmethylsulfonate (EMS), ethylnitrosourea (ENU), etc.) or ionizing radiation (neutrons (such as in fast neutron mutagenesis, etc.), alpha rays, gamma rays (such as that supplied by a Cobalt 60 source), X-rays, UV-radiation, etc.), T-DNA insertion mutagenesis (Azpiroz-Leehan et al. (1997) Trends Genet. 13:152-156), transposon mutagenesis (McKenzie et al. (2002) Theor Appl Genet. 105:23-33), or tissue culture mutagenesis (induction of somaclonal variations), or a combination of two or more of these. Thus, the desired mutagenesis of one or more ROD1 alleles may be accomplished by one of the above methods. While mutations created by irradiation are often large deletions or other gross lesions such as translocations or complex rearrangements, mutations created by chemical mutagens are often more discrete lesions such as point mutations. For example, EMS alkylates guanine bases, which results in base mispairing: an alkylated guanine will pair with a thymine base, resulting primarily in G/C to A/T transitions. Following mutagenesis, Brassica plants are regenerated from the treated cells using known techniques. For instance, the resulting Brassica seeds may be planted in accordance with conventional growing procedures and following self-pollination seed is formed on the plants. Alternatively, doubled haploid plantlets may be extracted to immediately form homozygous plants, for example as described by Coventry et al. (1988, Manual for Microspore Culture Technique for Brassica napus. Dep. Crop Sci. Techn. Bull. OAC Publication 0489. Univ. of Guelph, Guelph, Ontario, Canada). Additional seed that is formed as a result of such self-pollination in the present or a subsequent generation may be harvested and screened for the presence of mutant rod1 alleles. Several techniques are known to screen for specific mutant alleles, e.g., Delete-agene™ (Delete-a-gene; Li et al., 2001, Plant J 27: 235-242) uses polymerase chain reaction (PCR) assays to screen for deletion mutants generated by fast neutron mutagenesis, TILLING (targeted induced local lesions in genomes; McCallum et al., 2000, Nat Biotechnol 18:455-457) identifies EMS-induced point mutations, etc. Additional techniques to screen for the presence of specific mutant rod1 alleles are described in the Examples below.

The term "gene targeting" refers herein to directed gene modification that uses mechanisms such as homologous recombination, mismatch repair or site-directed mutagenesis. The method can be used to replace, insert and delete endogenous sequences or sequences previously introduced in plant cells. Methods for gene targeting can be found in, for example, WO 2006/105946 or WO2009/002150. Gene targeting can be used to create mutant rod1 alleles, such as knock-out rod1 alleles.

A "variety" is used herein in conformity with the UPOV convention and refers to a plant grouping within a single botanical taxon of the lowest known rank, which grouping can be defined by the expression of the characteristics resulting from a given genotype or combination of genotypes, can be distinguished from any other plant grouping by the expression of at least one of the said characteristics and is considered as a unit with regard to its suitability for being propagated unchanged (stable).

The term "comprising" is to be interpreted as specifying the presence of the stated parts, steps or components, but does not exclude the presence of one or more additional parts, steps or components. A plant comprising a certain trait may thus comprise additional traits.

It is understood that when referring to a word in the singular (e.g. plant or root), the plural is also included herein (e.g. a plurality of plants, a plurality of roots). Thus, reference to an element by the indefinite article "a" or "an" does not exclude the possibility that more than one of the element is present, unless the context clearly requires that there be one and only one of the elements. The indefinite article "a" or "an" thus usually means "at least one".

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The "optimal alignment" of two sequences is found by aligning the two sequences over the entire length according to the Needleman and Wunsch global alignment algorithm (Needleman and Wunsch, 1970, J Mol Biol 48(3):443-53) in The European Molecular Biology Open Software Suite (EMBOSS, Rice et al., 2000, Trends in Genetics 16(6): 276-277; see e.g. http://www.ebi.ac.uk/emboss/align/index.html) using default settings (gap opening penalty=10 (for nucleotides)/10 (for proteins) and gap extension penalty=0.5 (for nucleotides)/0.5 (for proteins)). For nucleotides the default scoring matrix used is EDNAFULL and for proteins the default scoring matrix is EBLOSUM62.

"Substantially identical" or "essentially similar", as used herein, refers to sequences, which, when optimally aligned as defined above, share at least a certain minimal percentage of sequence identity (as defined further below).

"Stringent hybridization conditions" can be used to identify nucleotide sequences, which are substantially identical to a given nucleotide sequence. Stringent conditions are sequence dependent and will be different in different circumstances. Generally, stringent conditions are selected to be about 5° C. lower than the thermal melting point ($T_m$) for the specific sequences at a defined ionic strength and pH. The $T_m$ is the temperature (under defined ionic strength and pH) at which 50% of the target sequence hybridizes to a perfectly matched probe. Typically stringent conditions will be chosen in which the salt concentration is about 0.02 molar at pH 7 and the temperature is at least 60° C. Lowering the salt concentration and/or increasing the temperature increases stringency. Stringent conditions for RNA-DNA hybridizations (Northern blots using a probe of e.g. 100 nt) are for example those which include at least one wash in 0.2×SSC at 63° C. for 20 min, or equivalent conditions.

"High stringency conditions" can be provided, for example, by hybridization at 65° C. in an aqueous solution containing 6×SSC (20×SSC contains 3.0 M NaCl, 0.3 M Na-citrate, pH 7.0), 5×Denhardt's (100×Denhardt's contains 2% Ficoll, 2% Polyvinyl pyrollidone, 2% Bovine Serum Albumin), 0.5% sodium dodecyl sulphate (SDS), and 20 µg/ml denaturated carrier DNA (single-stranded fish sperm DNA, with an average length of 120-3000 nucleotides) as non-specific competitor. Following hybridization, high stringency washing may be done in several steps, with a final wash (about 30 min) at the hybridization temperature in 0.2-0.1×SSC, 0.1% SDS.

"Moderate stringency conditions" refers to conditions equivalent to hybridization in the above described solution but at about 60-62° C. Moderate stringency washing may be done at the hybridization temperature in 1×SSC, 0.1% SDS.

"Low stringency" refers to conditions equivalent to hybridization in the above described solution at about 50-52° C. Low stringency washing may be done at the hybridization temperature in 2×SSC, 0.1% SDS. See also Sambrook et al. (1989) and Sambrook and Russell (2001).

DETAILED DESCRIPTION

The current invention is based on the identification of four ROD1 genes in *Brassica rapa* and in *Brassica oleracea*, and of 8 ROD1 genes in *Brassica napus*, and of the role of the *Brassica* ROD1 gene products in fatty acid desaturation.

It is a first embodiment of the invention to provide a *Brassica* plant or plant cell, part, seed or progeny thereof, comprising at least one ROD1 gene, characterized in that at least one ROD1 gene is an inactivated or knock-out rod1 gene. Said at least one ROD1 gene can be, for example, one ROD1 gene, or two ROD1 genes, or four ROD1 genes, or eight ROD1 genes. In a further embodiment, said *Brassica* plant is *Brassica rapa*, and said knock-out rod1 gene is a knock-out allele of the ROD1 gene encoding a protein having at least 90% sequence identity to SEQ ID No. 15, to SEQ ID No. 18, to SEQ ID No. 21, or to SEQ ID No. 24, such as a *Brassica rapa* plant comprising a knock-out allele of the ROD1 gene encoding a protein having at least 90% sequence identity to SEQ ID No. 15. In yet a further embodiment, said *Brassica* plant is *Brassica oleracea*, and said knock-out rod1 gene is a knock-out allele of the ROD1 gene encoding a protein having at least 90% sequence identity to SEQ ID No. 27, to SEQ ID No. 30, to SEQ ID No. 33, or to SEQ ID No. 36, such as a *Brassica oleracea* plant comprising a knock-out allele of the ROD1 gene encoding a protein having at least 90% sequence identity to SEQ ID No. 30. In yet another embodiment, said *Brassica* plant is *Brassica napus*, and said knock-out rod1 gene is a knock-out allele of a ROD1 gene encoding a protein having at least 90% sequence identity to SEQ ID No. 3 or SEQ ID No. 6, such as *Brassica napus* which is obtainable from seeds obtainable from seeds selected from the group consisting of seed comprising HIOL306 having been deposited at NCIMB under accession number NCIMB 41995, seed comprising HIOL307 having been deposited at NCIMB under accession number NCIMB 42000, seed comprising HIOL310 having been deposited at NCIMB under accession number NCIMB 41996, seed comprising HIOL313 having been deposited at NCIMB under accession number NCIMB 42001, seed comprising HIOL316 having been deposited at NCIMB under accession number NCIMB 41997, seed comprising HIOL318 having been deposited at NCIMB under accession number NCIMB 41998, and seed comprising HIOL319 having been deposited at NCIMB under accession number NCIMB 41999, or such as *Brassica napus* comprising two knock-out rod1 alleles, one of said knock-out alleles being a knock-out allele of a ROD1 gene encoding a protein having at least 90% sequence identity to SEQ ID No. 3, and one of said knock-out alleles being a knock-out allele of a ROD1 gene encoding a protein having at least 90% sequence identity to SEQ ID No. 6.

In a further embodiment, said *Brassica* plant is homozygous for said knock-out rod1 gene.

At least 90% sequence identity as used herein can be at least 90% sequence identity, or at least 95% sequence identity, or at least 98% sequence identity, or can be 100% sequence identity.

A knock-out allele of the ROD1 gene encoding a protein having at least 90% sequence identity to SEQ ID No. 15 can be a knock-out allele of the ROD1 gene having at least 90% sequence identity, or at least 95% sequence identity, or at least 98% sequence identity or having 100% sequence identity to SEQ ID No. 13.

A knock-out allele of the ROD1 gene encoding a protein having at least 90% sequence identity to SEQ ID No. 27 can be a knock-out allele of the ROD1 gene having at least 90% sequence identity, or at least 95% sequence identity, or at least 98% sequence identity, or having 100% sequence identity to SEQ ID No. 25.

A knock-out allele of the ROD1 gene encoding a protein having at least 90% sequence identity to SEQ ID No. 3 or to SEQ ID No. 6 can be a knock-out allele of the ROD1 gene having at least 90% sequence identity, or at least 95% sequence identity, or at least 98% sequence identity, or having 100% sequence identity to SEQ ID No. 1, SEQ ID No. 4, respectively.

Said knock-out allele of said ROD1 gene can be a mutant ROD1 gene comprising one or more nucleotide deletions, insertions or substitutions relative to the wild type nucleic acid sequences. The mutation(s) can result in one or more changes (deletions, insertions and/or substitutions) in the amino acid sequence of the encoded protein is not a functional ROD1 protein.

Nucleic Acid Sequences According to the Invention

Provided are both wild type ROD1 nucleic acid sequences encoding functional ROD1 proteins and mutant rod1 nucleic acid sequences (comprising one or more mutations, preferably mutations which result in no or a significantly reduced biological activity of the encoded ROD1 protein or in no ROD1 protein being produced) of ROD1 genes from *Brassica*, especially from *Brassica napus*, *Brassica rapa*, and *Brassica*.

However, isolated ROD1 and rod1 nucleic acid sequences (e.g. isolated from the plant by cloning or made synthetically by DNA synthesis), as well as variants thereof and fragments of any of these are also provided herein, as these can be used to determine which sequence is present endogenously in a plant or plant part, whether the sequence encodes a functional, a non-functional or no protein (e.g. by expression in a recombinant host cell as described below) and for selection and transfer of specific alleles from one plant into another, in order to generate a plant having the desired combination of functional and mutant alleles.

Nucleic acid sequences of ROD1-A1, ROD1-C1, ROD1-A2, ROD1-C2, ROD1-A3, and ROD1-C4 have been isolated from *Brassica napus*, nucleic acid sequences of ROD1-1, ROD1-2, ROD1-3 and ROD1-4 have been isolated from *Brassica oleracea* and from *Brassica rapa* as depicted in the sequence listing. The wild type ROD1 sequences are depicted, while the mutant rod1 sequences of these sequences, and of sequences essentially similar to these, are described herein below and in the Examples, with reference to the wild type ROD1 sequences. The genomic ROD1 protein-encoding DNA from *Brassica napus*, *Brassica oleracea*, and *Brassica rapa* do comprise any introns. The coding sequences or cDNA sequences, of the *Brassica* ROD1 genes, not comprising the introns, are also depicted in the sequence listing.

A "*Brassica napus* ROD1-A1 gene", "BnROD1-A1 gene", *Brassica napus* ROD1-A1 allele", "BnROD1-A1 allele" or "ROD1-A1 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 1.

A "*Brassica napus* ROD1-C1 gene", "BnROD1-C1 gene", *Brassica napus* ROD1-C1 allele", "BnROD1-C1 allele" or "ROD1-C1 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 4.

A "*Brassica napus* ROD1-A2 gene", "BnROD1-A2 gene", *Brassica napus* ROD1-A2 allele", "BnROD1-A2 allele" or "ROD1-A2 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 7.

A "*Brassica napus* ROD1-C2 gene", "BnROD1-C2 gene", *Brassica napus* ROD1-C2 allele", "BnROD1-C2 allele" or "ROD1-C2 from *Brassica napus*", or variant nucleic acid sequences thereof as used herein refers to a gene, allele or a sequence having at least 90%, or at least 95%, or at least 98%, or at least 99%, or 100% sequence identity SEQ ID No. 10.

A "*Brassica napus* ROD1-A3 gene", "BnROD1-A3 gene", *Brassica napus* ROD1-A3 allele", "BnROD1-A3 allele" or "ROD1-A3 from *Brassica napus*", or variant nucleic acid sequences thereof as used herein refers to a gene, allele or a sequence of which the cDNA sequence has at least 90%, or at least 95%, or at least 98%, or at least 99%, or 100% sequence identity SEQ ID No. 84.

A "*Brassica napus* ROD1-C3 gene", "BnROD1-C3 gene", *Brassica napus* ROD1-C3 allele", "BnROD1-C3 allele" or "ROD1-C3 from *Brassica napus*", or variant nucleic acid sequences thereof as used herein refers to a gene, allele or a sequence of which the cDNA sequence has at least 90%, or at least 95%, or at least 98%, or at least 99%, or 100% sequence identity SEQ ID No. 86.

A "*Brassica napus* ROD1-A4 gene", "BnROD1-A4 gene", *Brassica napus* ROD1-A4 allele", "BnROD1-A4 allele" or "ROD1-A4 from *Brassica napus*", or variant nucleic acid sequences thereof as used herein refers to a gene, allele or a sequence of which the cDNA sequence has at least 90%, or at least 95%, or at least 98%, or at least 99%, or 100% sequence identity SEQ ID No. 88.

A "*Brassica napus* ROD1-C4 gene", "BnROD1-C4 gene", *Brassica napus* ROD1-C4 allele", "BnROD1-C4 allele" or "ROD1-C4 from *Brassica napus*", or variant nucleic acid sequences thereof as used herein refers to a gene, allele or a sequence of which the cDNA sequence has at least 90%, or at least 95%, or at least 98%, or at least 99%, or 100% sequence identity SEQ ID No. 90.

A "*Brassica rapa* ROD1-1 gene", "BrROD1-1 gene", *Brassica rapa* ROD1-1 allele", "BrROD1-1 allele" or "ROD1-1 from *Brassica rapa*", or variant nucleic acid sequences thereof as used herein refers to a gene, allele or a sequence having at least 90%, or at least 95%, or at least 98%, or at least 99%, or 100% sequence identity SEQ ID No. 13.

A "*Brassica rapa* ROD1-2 gene", "BrROD1-2 gene", *Brassica rapa* ROD1-2 allele", "BrROD1-2 allele" or "ROD1-2 from *Brassica rapa*", or variant nucleic acid sequences thereof as used herein refers to a gene, allele or a sequence having at least 90%, or at least 95%, or at least 98%, or at least 99%, or 100% sequence identity SEQ ID No. 16.

A "*Brassica rapa* ROD1-3 gene", "BrROD1-3 gene", *Brassica rapa* ROD1-3 allele", "BrROD1-3 allele" or "ROD1-3 from *Brassica rapa*", or variant nucleic acid sequences thereof as used herein refers to a gene, allele or a sequence having at least 90%, or at least 95%, or at least 98%, or at least 99%, or 100% sequence identity SEQ ID No. 19.

A "*Brassica rapa* ROD1-4 gene", "BrROD1-4 gene", *Brassica rapa* ROD1-4 allele", "BrROD1-4 allele" or "ROD1-4 from *Brassica rapa*", or variant nucleic acid sequences thereof as used herein refers to a gene, allele or a sequence having at least 90%, or at least 95%, or at least 98%, or at least 99%, or 100% sequence identity SEQ ID No. 22.

A "*Brassica oleracea* ROD1-1 gene", "BoROD1-1 gene", *Brassica oleracea* ROD1-1 allele", "BoROD1-1 allele" or "ROD1-1 from *Brassica oleracea*", or variant nucleic acid sequences thereof as used herein refers to a gene, allele or a sequence having at least 90%, or at least 95%, or at least 98%, or at least 99%, or 100% sequence identity SEQ ID No. 25.

A "*Brassica oleracea* ROD1-2 gene", "BoROD1-2 gene", *Brassica oleracea* ROD1-2 allele", "BoROD1-2 allele" or "ROD1-2 from *Brassica oleracea*", or variant nucleic acid sequences thereof as used herein refers to a gene, allele or a sequence having at least 90%, or at least 95%, or at least 98%, or at least 99%, or 100% sequence identity SEQ ID No. 28.

A "*Brassica oleracea* ROD1-3 gene", "BoROD1-3 gene", *Brassica oleracea* ROD1-3 allele", "BoROD1-3 allele" or "ROD1-3 from *Brassica oleracea*", or variant nucleic acid sequences thereof as used herein refers to a gene, allele or a sequence having at least 90%, or at least 95%, or at least 98%, or at least 99%, or 100% sequence identity SEQ ID No. 31.

A "*Brassica oleracea* ROD1-4 gene", "BoROD1-4 gene", *Brassica oleracea* ROD1-4 allele", "BoROD1-4 allele" or "ROD1-4 from *Brassica oleracea*", or variant nucleic acid sequences thereof as used herein refers to a gene, allele or a sequence having at least 90%, or at least 95%, or at least 98%, or at least 99%, or 100% sequence identity SEQ ID No. 34.

Thus the invention provides both nucleic acid sequences encoding wild type, functional ROD1 proteins, including variants and fragments thereof (as defined further below), as well as mutant nucleic acid sequences of any of these, whereby the mutation in the nucleic acid sequence preferably results in one or more amino acids being inserted, deleted or substituted in comparison to the wild type ROD1 protein. Preferably the mutation(s) in the nucleic acid sequence result in one or more amino acid changes (i.e. in relation to the wild type amino acid sequence one or more amino acids are inserted, deleted and/or substituted) whereby the biological activity of the ROD1 protein is significantly reduced or completely abolished.

Functionality of the ROD1 protein can be tested, for example, in yeast as described in example 4 or as described by Lu et al. (2009) Proc Natl Acad Sci USA 106:18839.

Both endogenous and isolated nucleic acid sequences are provided herein. Also provided are fragments of the ROD1 sequences and ROD1 variant nucleic acid sequences defined above, for use as primers or probes and as components of kits according to another aspect of the invention (see further below). A "fragment" of a ROD1 or rod1 nucleic acid sequence or variant thereof (as defined) may be of various lengths, such as at least 10, 12, 15, 18, 20, 50, 100, 200, 500, 600 contiguous nucleotides of the ROD1 or rod1 sequence (or of the variant sequence).

Wild-Type Nucleic Acid Sequences Encoding Wild-Type ROD1 Proteins

The nucleic acid sequences depicted in the sequence listing encode wild type ROD1 proteins from *Brassica napus*, from *Brassica rapa*, and from *Brassica oleracea*. Thus, these sequences are endogenous to the *Brassica* plants from which they were isolated.

Other *Brassica* crop species, varieties, breeding lines or wild accessions may be screened for other ROD1 alleles, encoding the same ROD1 proteins or variants thereof. For example, nucleic acid hybridization techniques (e.g. Southern blot analysis, using for example stringent hybridization conditions) or nucleic acid amplification-based techniques such as PCR techniques may be used to identify ROD1 alleles endogenous to other *Brassica* plants, such as various *Brassica napus*, *Brassica rapa*, or *Brassica oleracea* varieties, lines or accessions. To screen such plants, plant organs or tissues for the presence of ROD1 alleles, the ROD1 nucleic acid sequences provided in the sequence listing, or variants or fragments of any of these, may be used. For example whole sequences or fragments may be used as probes or primers. For example specific or degenerate primers may be used to amplify nucleic acid sequences encoding ROD1 proteins from the genomic DNA of the plant, plant organ or tissue. These ROD1 nucleic acid sequences may be isolated and sequenced using standard molecular biology techniques. Bioinformatics analysis may then be used to characterize the allele(s), for example in order to determine which ROD1 allele the sequence corresponds to and which ROD1 protein or protein variant is encoded by the sequence.

In addition, it is understood that ROD1 nucleic acid sequences and variants thereof (or fragments of any of these) may be identified in silico, by screening nucleic acid databases for essentially similar sequences. Likewise, a nucleic acid sequence may be synthesized chemically. Fragments of nucleic acid molecules according to the invention are also provided, which are described further below.

Mutant Nucleic Acid Sequences Encoding Mutant ROD1 Proteins

Nucleic acid sequences comprising one or more nucleotide deletions, insertions or substitutions relative to the wild type nucleic acid sequences are another embodiment of the invention, as are fragments of such mutant nucleic acid molecules. Such mutant nucleic acid sequences (referred to as rod1 sequences) can be generated and/or identified using various known methods, as described further below. Again, such nucleic acid molecules are provided both in endogenous form and in isolated form. In one embodiment, the mutation(s) result in one or more changes (deletions, insertions and/or substitutions) in the amino acid sequence of the encoded ROD1 protein (i.e. it is not a "silent mutation"). In another embodiment, the mutation(s) in the nucleic acid sequence result in a significantly reduced or completely abolished biological activity of the encoded ROD1 protein relative to the wild type protein.

The knock-out ROD1 genes may, thus, comprise one or more mutations, such as:

(a) a "missense mutation", which is a change in the nucleic acid sequence that results in the substitution of an amino acid for another amino acid;

(b) a "nonsense mutation" or "STOP codon mutation", which is a change in the nucleic acid sequence that results in the introduction of a premature STOP codon and thus the termination of translation (resulting in a truncated protein); plant genes contain the translation stop codons "TGA" (UGA in RNA), "TAA" (UAA in RNA) and "TAG" (UAG in RNA); thus any nucleotide substitution, insertion, deletion which results in one of these codons to be in the mature mRNA being translated (in the reading frame) will terminate translation;

(c) an "insertion mutation" of one or more amino acids, due to one or more codons having been added in the coding sequence of the nucleic acid;

(d) a "deletion mutation" of one or more amino acids, due to one or more codons having been deleted in the coding sequence of the nucleic acid;

(e) a "frameshift mutation", resulting in the nucleic acid sequence being translated in a different frame downstream of the mutation. A frameshift mutation can have various causes, such as the insertion, deletion or duplication of one or more nucleotides;

(f) a splice site mutation, resulting in altered splicing, which results in an altered mRNA processing and, consequently, in an altered encoded protein which contains either deletions, substitutions or insertions of various lengths, possibly combined with premature translation termination.

Thus in one embodiment, nucleic acid sequences comprising one or more of any of the types of mutations described above are provided. In another embodiment, rod1 sequences comprising one or more stop codon (nonsense) mutations, one or more missense mutations, one or more frameshift mutations, and/or one or more splice site mutations are provided. Any of the above mutant nucleic acid sequences are provided per se (in isolated form), as are plants and plant parts comprising such sequences endogenously. In the tables herein below the most preferred rod1 alleles are described and seed deposits of *Brassica napus* seeds comprising one or more mutant rod1 alleles have been deposited as indicated.

A range of possible EMS stop codon mutations in the BnROD1-A1, BnROD1-C1, BnROD1-A2, BnROD1-C2, BoROD1-1, BrROD1-1, BoROD1-2, BrROD1-2, BoROD1-3, BrROD1-3, BoROD1-4, and BrROD1-4 genes are shown in Tables 1a-p, respectively, and a range of possible EMS splice site mutations in the BnROD1-A1, BnROD1-C1, BnROD1-A2, BnROD1-C2, BoROD1-1, BrROD1-1, BoROD1-2, BrROD1-2, BoROD1-3, BrROD1-3, BoROD1-4, and BrROD1-4 genes are shown in Tables 1q-ab, respectively.

TABLE 1a possible stop codon mutations in BnROD1-A1

| position relative to the genomic sequence (SEQ ID No. 1) | WT codon | AA | position relative to the protein (SEQ ID No. 3) | stop codon | AA |
|---|---|---|---|---|---|
| 811-813 | TGG | TRP | 56 | TAG | STOP |
|  |  |  |  | TAA | STOP |
|  |  |  |  | TGA | STOP |
| 850-852 | TGG | TRP | 69 | TAG | STOP |
|  |  |  |  | TAA | STOP |
|  |  |  |  | TGA | STOP |
| 910-912 | CAG | GLN | 89 | TAG | STOP |
|  |  |  |  | TAA | STOP |
| 1782-1784 | CAA | GLN | 133 | TAA | STOP |
| 1800-1802 | TGG | TRP | 139 | TGA | STOP |
|  |  |  |  | TAA | STOP |
|  |  |  |  | TAG | STOP |

TABLE 1a-continued possible stop codon mutations in BnROD1-A1

| position relative to the genomic sequence (SEQ ID No. 1) | WT codon | WT AA | position relative to the protein (SEQ ID No. 3) | stop codon | stop AA |
|---|---|---|---|---|---|
| 1806-1808 | TGG | TRP | 141 | TGA | STOP |
|  |  |  |  | TAA | STOP |
|  |  |  |  | TAG | STOP |
| 1827-1829 | CGA | ARG | 148 | TGA | STOP |
|  |  |  |  | TAA | STOP |
| 1887-1889 | CAG | GLN | 168 | TAA | STOP |
|  |  |  |  | TAG | STOP |
| 1902-1904 | CAG | GLN | 173 | TAA | STOP |
|  |  |  |  | TAG | STOP |
| 2872-2874 | CAG | GLN | 211 | TAG | STOP |
|  |  |  |  | TAA | STOP |
| 2917-2919 | CAA | GLN | 226 | TAA | STOP |

TABLE 1b possible stop codon mutations in BnROD1-C1

| position relative to the genomic sequence (SEQ ID No. 4) | WT codon | WT AA | position relative to the protein (SEQ ID No. 6) | stop codon | stop AA |
|---|---|---|---|---|---|
| 1381-1383 | TGG | TRP | 54 | TAG | STOP |
|  |  |  |  | TAA | STOP |
|  |  |  |  | TGA | STOP |
| 1420-1422 | TGG | TRP | 67 | TAG | STOP |
|  |  |  |  | TAA | STOP |
|  |  |  |  | TGA | STOP |
| 1480-1482 | CAG | GLN | 87 | TAA | STOP |
|  |  |  |  | TAG | STOP |
| 2923-2925 | CAA | GLN | 131 | TAA | STOP |
| 2941-2943 | TGG | TRP | 137 | TGA | STOP |
|  |  |  |  | TAA | STOP |
|  |  |  |  | TAG | STOP |
| 2947-2949 | TGG | TRP | 139 | TGA | STOP |
|  |  |  |  | TAG | STOP |
|  |  |  |  | TAA | STOP |
| 2968-2970 | CGA | ARG | 146 | TGA | STOP |
|  |  |  |  | TAA | STOP |
| 3028-3030 | CAG | GLN | 166 | TAA | STOP |
|  |  |  |  | TAG | STOP |
| 3043-3045 | CAG | GLN | 171 | TAG | STOP |
|  |  |  |  | TAA | STOP |
| 10056-10058 | CAG | GLN | 209 | TAG | STOP |
|  |  |  |  | TAA | STOP |
| 10101-10103 | CAA | GLN | 224 | TAA | STOP |

TABLE 1c possible stop codon mutations in BnROD1-A2

| position relative to the genomic sequence (SEQ ID No. 7) | WT codon | WT AA | position relative to the protein (SEQ ID No. 9) | stop codon | stop AA |
|---|---|---|---|---|---|
| 1756-1758 | TGG | TRP | 57 | TAG | STOP |
|  |  |  |  | TGA | STOP |
|  |  |  |  | TAA | STOP |
| 1795-1797 | TGG | TRP | 70 | TGA | STOP |
|  |  |  |  | TAG | STOP |
|  |  |  |  | TAA | STOP |
| 1855-1857 | CAA | GLN | 90 | TAA | STOP |
| 2557-2559 | CAA | GLN | 134 | TAA | STOP |
| 2575-2577 | TGG | TRP | 140 | TAA | STOP |
|  |  |  |  | TGA | STOP |
|  |  |  |  | TAG | STOP |
| 2581-2583 | TGG | TRP | 142 | TGA | STOP |
|  |  |  |  | TAG | STOP |
|  |  |  |  | TAA | STOP |
| 2602-2604 | CGA | ARG | 149 | TGA | STOP |
|  |  |  |  | TAA | STOP |
| 2662-2664 | CAG | GLN | 169 | TAA | STOP |
|  |  |  |  | TAG | STOP |
| 2677-2679 | CAG | GLN | 174 | TAG | STOP |
|  |  |  |  | TAA | STOP |
| 3315-3317 | CAG | GLN | 212 | TAG | STOP |
|  |  |  |  | TAA | STOP |
| 3360-3362 | CAA | GLN | 227 | TAA | STOP |
| 3369-3371 | CGG | ARG | 230 | TAG | STOP |
|  |  |  |  | TGA | STOP |
|  |  |  |  | TAA | STOP |

TABLE 1d possible stop codon mutations in BnROD1-C2

| position relative to the genomic sequence (SEQ ID No. 10) | WT codon | WT AA | position relative to the protein (SEQ ID No. 12) | stop codon | stop AA |
|---|---|---|---|---|---|
| 1490-1492 | TGG | TRP | 57 | TAG | STOP |
|  |  |  |  | TGA | STOP |
|  |  |  |  | TAA | STOP |
| 1529-1531 | TGG | TRP | 70 | TAA | STOP |
|  |  |  |  | TAG | STOP |
|  |  |  |  | TGA | STOP |
| 1589-1591 | CAG | GLN | 90 | TAA | STOP |
|  |  |  |  | TAG | STOP |
| 3211-3213 | CAA | GLN | 134 | TAA | STOP |
| 3229-3231 | TGG | TRP | 140 | TGA | STOP |
|  |  |  |  | TAG | STOP |
|  |  |  |  | TAA | STOP |
| 3235-3237 | TGG | TRP | 142 | TAA | STOP |
|  |  |  |  | TGA | STOP |
|  |  |  |  | TAG | STOP |
| 3256-3258 | CGA | ARG | 149 | TGA | STOP |
|  |  |  |  | TAA | STOP |
| 3316-3318 | CAG | GLN | 169 | TAA | STOP |
|  |  |  |  | TAG | STOP |
| 3331-3333 | CAG | GLN | 174 | TAG | STOP |
|  |  |  |  | TAA | STOP |
| 3967-3969 | CAG | GLN | 212 | TAG | STOP |
|  |  |  |  | TAA | STOP |
| 4012-4014 | CAA | GLN | 227 | TAA | STOP |

TABLE 1e possible stop codon mutations in BnROD1-A3

| position relative to the cDNA sequence (SEQ ID No. 84) | WT codon | WT AA | position relative to the protein (SEQ ID No. 85) | stop codon codon | stop codon AA |
|---|---|---|---|---|---|
| 235-237 | CAA | GLN | 37 | TAA | STOP |
| 256-258 | CAA | GLN | 44 | TAA | STOP |
| 322-324 | TGG | TRP | 66 | TGA | STOP |
|  |  |  |  | TAG | STOP |
|  |  |  |  | TAA | STOP |
| 361-363 | TGG | TRP | 79 | TAA | STOP |
|  |  |  |  | TGA | STOP |
|  |  |  |  | TAG | STOP |
| 424-426 | CAG | GLN | 100 | TAA | STOP |
|  |  |  |  | TAG | STOP |
| 556-558 | CAA | GLN | 144 | TAA | STOP |
| 574-576 | TGG | TRP | 150 | TAG | STOP |
|  |  |  |  | TGA | STOP |
|  |  |  |  | TAA | STOP |
| 580-582 | TGG | TRP | 152 | TGA | STOP |
|  |  |  |  | TAA | STOP |
|  |  |  |  | TAG | STOP |
| 595-597 | CGA | ARG | 157 | TGA | STOP |
|  |  |  |  | TAA | STOP |
| 601-603 | CGA | ARG | 159 | TGA | STOP |
|  |  |  |  | TAA | STOP |
| 661-663 | CAG | GLN | 179 | TAG | STOP |
|  |  |  |  | TAA | STOP |
| 676-678 | CAG | GLN | 184 | TAG | STOP |
|  |  |  |  | TAA | STOP |
| 835-837 | CAA | GLN | 237 | TAA | STOP |
| 865-867 | CAA | GLN | 247 | TAA | STOP |

TABLE 1f possible stop codon mutations in BnROD1-C3

| position relative to the cDNA sequence (SEQ ID No. 86) | WT codon | WT AA | position relative to the protein (SEQ ID No. 87) | stop codon codon | stop codon AA |
|---|---|---|---|---|---|
| 261-263 | CAA | GLN | 37 | TAA | STOP |
| 282-284 | CAA | GLN | 44 | TAA | STOP |
| 348-350 | TGG | TRP | 66 | TAG | STOP |
|  |  |  |  | TAA | STOP |
|  |  |  |  | TGA | STOP |
| 369-371 | CAG | GLN | 73 | TAA | STOP |
|  |  |  |  | TAG | STOP |
| 387-389 | TGG | TRP | 79 | TGA | STOP |
|  |  |  |  | TAG | STOP |
|  |  |  |  | TAA | STOP |
| 450-452 | CAG | GLN | 100 | TAG | STOP |
|  |  |  |  | TAA | STOP |
| 582-584 | CAA | GLN | 144 | TAA | STOP |
| 600-602 | TGG | TRP | 150 | TGA | STOP |
|  |  |  |  | TAA | STOP |
|  |  |  |  | TAG | STOP |
| 606-608 | TGG | TRP | 152 | TGA | STOP |
|  |  |  |  | TAG | STOP |
|  |  |  |  | TAA | STOP |
| 621-623 | CGA | ARG | 157 | TAA | STOP |
|  |  |  |  | TGA | STOP |
| 627-629 | CGA | ARG | 159 | TAA | STOP |
|  |  |  |  | TGA | STOP |
| 687-689 | CAG | GLN | 179 | TAA | STOP |
|  |  |  |  | TAG | STOP |
| 702-704 | CAG | GLN | 184 | TAA | STOP |
|  |  |  |  | TAG | STOP |
| 861-863 | CAA | GLN | 237 | TAA | STOP |
| 891-893 | CAA | GLN | 247 | TAA | STOP |

TABLE 1g possible stop codon mutations in BnROD1-A4

| position relative to the cDNA sequence (SEQ ID No. 88) | WT codon | WT AA | position relative to the protein (SEQ ID No. 89) | stop codon codon | stop codon AA |
|---|---|---|---|---|---|
| 276-278 | CAA | GLN | 3 | TAA | STOP |
| 312-314 | TGG | TRP | 15 | TGA | STOP |
|  |  |  |  | TAG | STOP |
|  |  |  |  | TAA | STOP |
| 339-341 | TGG | TRP | 24 | TAA | STOP |
|  |  |  |  | TAG | STOP |
|  |  |  |  | TGA | STOP |
| 378-380 | TGG | TRP | 37 | TAA | STOP |
|  |  |  |  | TGA | STOP |
|  |  |  |  | TAG | STOP |
| 570-572 | CAA | GLN | 101 | TAA | STOP |
| 588-590 | TGG | TRP | 107 | TAG | STOP |
|  |  |  |  | TAA | STOP |
|  |  |  |  | TGA | STOP |
| 594-596 | TGG | TRP | 109 | TAG | STOP |
|  |  |  |  | TAA | STOP |
|  |  |  |  | TGA | STOP |
| 609-611 | CGG | ARG | 114 | TGA | STOP |
|  |  |  |  | TAG | STOP |
|  |  |  |  | TAA | STOP |
| 615-617 | CGA | ARG | 116 | TGA | STOP |
|  |  |  |  | TAA | STOP |
| 675-677 | CAG | GLN | 136 | TAA | STOP |
|  |  |  |  | TAG | STOP |
| 804-806 | CAG | GLN | 179 | TAA | STOP |
|  |  |  |  | TAG | STOP |
| 849-851 | CAG | GLN | 194 | TAA | STOP |
|  |  |  |  | TAG | STOP |
| 969-971 | CAA | GLN | 234 | TAA | STOP |

TABLE 1h possible stop codon mutations in BnROD1-C4

| position relative to the cDNA sequence (SEQ ID No. 90) | WT codon | WT AA | position relative to the protein (SEQ ID No. 91) | stop codon codon | stop codon AA |
|---|---|---|---|---|---|
| 30-32 | CAA | GLN | 3 | TAA | STOP |
| 66-68 | TGG | TRP | 15 | TAA | STOP |
|  |  |  |  | TGA | STOP |
|  |  |  |  | TAG | STOP |
| 93-95 | TGG | TRP | 24 | TAG | STOP |
|  |  |  |  | TGA | STOP |
|  |  |  |  | TAA | STOP |
| 132-134 | TGG | TRP | 37 | TAA | STOP |
|  |  |  |  | TAG | STOP |
|  |  |  |  | TGA | STOP |
| 324-326 | CAA | GLN | 101 | TAA | STOP |
| 342-344 | TGG | TRP | 107 | TAG | STOP |
|  |  |  |  | TAA | STOP |
|  |  |  |  | TGA | STOP |
| 348-350 | TGG | TRP | 109 | TAA | STOP |
|  |  |  |  | TGA | STOP |
|  |  |  |  | TAG | STOP |
| 363-365 | CGG | ARG | 114 | TGA | STOP |
|  |  |  |  | TAG | STOP |
|  |  |  |  | TAA | STOP |
| 369-371 | CGA | ARG | 116 | TAA | STOP |
|  |  |  |  | TGA | STOP |
| 429-431 | CAG | GLN | 136 | TAA | STOP |
|  |  |  |  | TAG | STOP |

TABLE 1h-continued possible stop codon mutations in BnROD1-C4

| position relative to the cDNA sequence (SEQ ID No. 90) | WT codon | WT AA | position relative to the protein (SEQ ID No. 91) | stop codon codon | stop codon AA |
|---|---|---|---|---|---|
| 558-560 | CAG | GLN | 179 | TAG | STOP |
|  |  |  |  | TAA | STOP |
| 603-605 | CAG | GLN | 194 | TAG | STOP |
|  |  |  |  | TAA | STOP |
| 723-725 | CAA | GLN | 234 | TAA | STOP |

TABLE 1i possible stop codon mutations in BoROD1-1

| position relative to the genomic sequence (SEQ ID No. 25) | WT codon | WT AA | position relative to the protein (SEQ ID No. 27) | stop codon codon | stop codon AA |
|---|---|---|---|---|---|
| 1972-1974 | TGG | TRP | 54 | TGA | STOP |
|  |  |  |  | TAG | STOP |
|  |  |  |  | TAA | STOP |
| 2011-2013 | TGG | TRP | 67 | TAA | STOP |
|  |  |  |  | TGA | STOP |
|  |  |  |  | TAG | STOP |
| 2071-2073 | CAG | GLN | 87 | TAA | STOP |
|  |  |  |  | TAG | STOP |
| 2932-2934 | CAA | GLN | 131 | TAA | STOP |
| 2950-2952 | TGG | TRP | 137 | TGA | STOP |
|  |  |  |  | TAA | STOP |
|  |  |  |  | TAG | STOP |
| 2956-2958 | TGG | TRP | 139 | TAA | STOP |
|  |  |  |  | TGA | STOP |
|  |  |  |  | TAG | STOP |
| 2977-2979 | CGA | ARG | 146 | TGA | STOP |
|  |  |  |  | TAA | STOP |
| 3037-3039 | CAG | GLN | 166 | TAG | STOP |
|  |  |  |  | TAA | STOP |
| 3052-3054 | CAG | GLN | 171 | TAG | STOP |
|  |  |  |  | TAA | STOP |
| 4245-4247 | CAG | GLN | 209 | TAA | STOP |
|  |  |  |  | TAG | STOP |
| 4290-4292 | CAA | GLN | 224 | TAA | STOP |

TABLE 1j possible stop codon mutations in BrROD1-1

| position relative to the genomic sequence (SEQ ID No. 13) | WT codon | WT AA | position relative to the protein (SEQ ID No. 15) | stop codon codon | stop codon AA |
|---|---|---|---|---|---|
| 1045-1047 | TGG | TRP | 54 | TAA | STOP |
|  |  |  |  | TGA | STOP |
|  |  |  |  | TAG | STOP |
| 1084-1086 | TGG | TRP | 67 | TGA | STOP |
|  |  |  |  | TAA | STOP |
|  |  |  |  | TAG | STOP |
| 1144-1146 | CAG | GLN | 87 | TAG | STOP |
|  |  |  |  | TAA | STOP |
| 2013-2015 | CAA | GLN | 131 | TAA | STOP |
| 2031-2033 | TGG | TRP | 137 | TGA | STOP |
|  |  |  |  | TAA | STOP |
|  |  |  |  | TAG | STOP |
| 2037-2039 | TGG | TRP | 139 | TGA | STOP |
|  |  |  |  | TAA | STOP |
|  |  |  |  | TAG | STOP |

TABLE 1j-continued possible stop codon mutations in BrROD1-1

| position relative to the genomic sequence (SEQ ID No. 13) | WT codon | WT AA | position relative to the protein (SEQ ID No. 15) | stop codon codon | stop codon AA |
|---|---|---|---|---|---|
| 2058-2060 | CGA | ARG | 146 | TAA | STOP |
|  |  |  |  | TGA | STOP |
| 2118-2120 | CAG | GLN | 166 | TAA | STOP |
|  |  |  |  | TAG | STOP |
| 2133-2135 | CAG | GLN | 171 | TAA | STOP |
|  |  |  |  | TAG | STOP |
| 3101-3103 | CAG | GLN | 209 | TAA | STOP |
|  |  |  |  | TAG | STOP |
| 3146-3148 | CAA | GLN | 224 | TAA | STOP |

TABLE 1k possible stop codon mutations in BoROD1-2

| position relative to the genomic sequence (SEQ ID No. 28) | WT codon | WT AA | position relative to the protein (SEQ ID No. 30) | stop codon codon | stop codon AA |
|---|---|---|---|---|---|
| 2016-2018 | TGG | TRP | 57 | TAG | STOP |
|  |  |  |  | TAA | STOP |
|  |  |  |  | TGA | STOP |
| 2055-2057 | TGG | TRP | 70 | TGA | STOP |
|  |  |  |  | TAG | STOP |
|  |  |  |  | TAA | STOP |
| 2115-2117 | CAG | GLN | 90 | TAG | STOP |
|  |  |  |  | TAA | STOP |
| 2823-2825 | CAA | GLN | 134 | TAA | STOP |
| 2841-2843 | TGG | TRP | 140 | TAA | STOP |
|  |  |  |  | TAG | STOP |
|  |  |  |  | TGA | STOP |
| 2847-2849 | TGG | TRP | 142 | TAG | STOP |
|  |  |  |  | TAA | STOP |
|  |  |  |  | TGA | STOP |
| 2868-2870 | CGA | ARG | 149 | TAA | STOP |
|  |  |  |  | TGA | STOP |
| 2928-2930 | CAG | GLN | 169 | TAG | STOP |
|  |  |  |  | TAA | STOP |
| 2943-2945 | CAG | GLN | 174 | TAA | STOP |
|  |  |  |  | TAG | STOP |
| 3578-3580 | CAG | GLN | 212 | TAG | STOP |
|  |  |  |  | TAA | STOP |
| 3623-3625 | CAA | GLN | 227 | TAA | STOP |

TABLE 1l possible stop codon mutations in BrROD1-2

| position relative to the genomic sequence (SEQ ID No. 16) | WT codon | WT AA | position relative to the protein (SEQ ID No. 18) | stop codon codon | stop codon AA |
|---|---|---|---|---|---|
| 1302-1304 | TGG | TRP | 57 | TAA | STOP |
|  |  |  |  | TAG | STOP |
|  |  |  |  | TGA | STOP |
| 1341-1343 | TGG | TRP | 70 | TAA | STOP |
|  |  |  |  | TAG | STOP |
|  |  |  |  | TGA | STOP |
| 1401-1403 | CAA | GLN | 90 | TAA | STOP |
| 2104-2106 | CAA | GLN | 134 | TAA | STOP |
| 2122-2124 | TGG | TRP | 140 | TAA | STOP |
|  |  |  |  | TGA | STOP |
|  |  |  |  | TAG | STOP |

TABLE 1l-continued possible stop codon mutations in BrROD1-2

| position relative to the genomic sequence (SEQ ID No. 16) | WT codon | WT AA | position relative to the protein (SEQ ID No. 18) | stop codon | stop AA |
|---|---|---|---|---|---|
| 2128-2130 | TGG | TRP | 142 | TAG | STOP |
|  |  |  |  | TAA | STOP |
|  |  |  |  | TGA | STOP |
| 2149-2151 | CGA | ARG | 149 | TAA | STOP |
|  |  |  |  | TGA | STOP |
| 2209-2211 | CAG | GLN | 169 | TAG | STOP |
|  |  |  |  | TAA | STOP |
| 2224-2226 | CAG | GLN | 174 | TAG | STOP |
|  |  |  |  | TAA | STOP |
| 2862-2864 | CAG | GLN | 212 | TAA | STOP |
|  |  |  |  | TAG | STOP |
| 2907-2909 | CAA | GLN | 227 | TAA | STOP |
| 2916-2918 | CGG | ARG | 230 | TAA | STOP |
|  |  |  |  | TAG | STOP |
|  |  |  |  | TGA | STOP |

TABLE 1m possible stop codon mutations in BoROD1-3

| position relative to the genomic sequence (SEQ ID No. 31) | WT codon | WT AA | position relative to the protein (SEQ ID No. 33) | stop codon | stop AA |
|---|---|---|---|---|---|
| 1194-1196 | CAA | GLN | 37 | TAA | STOP |
| 1215-1217 | CAA | GLN | 44 | TAA | STOP |
| 1281-1283 | TGG | TRP | 66 | TAG | STOP |
|  |  |  |  | TAA | STOP |
|  |  |  |  | TGA | STOP |
| 1302-1304 | CAG | GLN | 73 | TAA | STOP |
|  |  |  |  | TAG | STOP |
| 1320-1322 | TGG | TRP | 79 | TAA | STOP |
|  |  |  |  | TGA | STOP |
|  |  |  |  | TAG | STOP |
| 1383-1385 | CAG | GLN | 100 | TAG | STOP |
|  |  |  |  | TAA | STOP |
| 1446-1448 | CGA | ARG | 121 | TGA | STOP |
|  |  |  |  | TAA | STOP |
| 2017-2019 | CAA | GLN | 144 | TAA | STOP |
| 2035-2037 | TGG | TRP | 150 | TAA | STOP |
|  |  |  |  | TGA | STOP |
|  |  |  |  | TAG | STOP |
| 2041-2043 | TGG | TRP | 152 | TAG | STOP |
|  |  |  |  | TGA | STOP |
|  |  |  |  | TAA | STOP |
| 2056-2058 | CGA | ARG | 157 | TAA | STOP |
|  |  |  |  | TGA | STOP |
| 2062-2064 | CGA | ARG | 159 | TAA | STOP |
|  |  |  |  | TGA | STOP |
| 2122-2124 | CAG | GLN | 179 | TAA | STOP |
|  |  |  |  | TAG | STOP |
| 2137-2139 | CAG | GLN | 184 | TAG | STOP |
|  |  |  |  | TAA | STOP |
| 2540-2542 | CAA | GLN | 237 | TAA | STOP |
| 2570-2572 | CAA | GLN | 247 | TAA | STOP |

TABLE 1n possible stop codon mutations in BrROD1-3

| position relative to the genomic sequence (SEQ ID No. 19) | WT codon | WT AA | position relative to the protein (SEQ ID No. 21) | stop codon | stop AA |
|---|---|---|---|---|---|
| 1217-1219 | CAA | GLN | 37 | TAA | STOP |
| 1238-1240 | CAA | GLN | 44 | TAA | STOP |
| 1304-1306 | TGG | TRP | 66 | TGA | STOP |
|  |  |  |  | TAG | STOP |
|  |  |  |  | TAA | STOP |
| 1343-1345 | TGG | TRP | 79 | TGA | STOP |
|  |  |  |  | TAA | STOP |
|  |  |  |  | TAG | STOP |
| 1406-1408 | CAG | GLN | 100 | TAA | STOP |
|  |  |  |  | TAG | STOP |
| 2017-2019 | CAA | GLN | 144 | TAA | STOP |
| 2035-2037 | TGG | TRP | 150 | TAG | STOP |
|  |  |  |  | TGA | STOP |
|  |  |  |  | TAA | STOP |
| 2041-2043 | TGG | TRP | 152 | TGA | STOP |
|  |  |  |  | TAG | STOP |
|  |  |  |  | TAA | STOP |
| 2056-2058 | CGA | ARG | 157 | TAA | STOP |
|  |  |  |  | TGA | STOP |
| 2062-2064 | CGA | ARG | 159 | TAA | STOP |
|  |  |  |  | TGA | STOP |
| 2122-2124 | CAG | GLN | 179 | TAA | STOP |
|  |  |  |  | TAG | STOP |
| 2137-2139 | CAG | GLN | 184 | TAG | STOP |
|  |  |  |  | TAA | STOP |
| 2553-2555 | CAA | GLN | 237 | TAA | STOP |
| 2583-2585 | CAA | GLN | 247 | TAA | STOP |

TABLE 1o possible stop codon mutations in BoROD1-4

| position relative to the genomic sequence (SEQ ID No. 34) | WT codon | WT AA | position relative to the protein (SEQ ID No. 36) | stop codon | stop AA |
|---|---|---|---|---|---|
| 1825-1827 | CAA | GLN | 3 | TAA | STOP |
| 1861-1863 | TGG | TRP | 15 | TAG | STOP |
|  |  |  |  | TAA | STOP |
|  |  |  |  | TGA | STOP |
| 1888-1890 | TGG | TRP | 24 | TAG | STOP |
|  |  |  |  | TAA | STOP |
|  |  |  |  | TGA | STOP |
| 1927-1929 | TGG | TRP | 37 | TAG | STOP |
|  |  |  |  | TAA | STOP |
|  |  |  |  | TGA | STOP |
| 2994-2996 | CAA | GLN | 101 | TAA | STOP |
| 3012-3014 | TGG | TRP | 107 | TGA | STOP |
|  |  |  |  | TAG | STOP |
|  |  |  |  | TAA | STOP |
| 3018-3020 | TGG | TRP | 109 | TAA | STOP |
|  |  |  |  | TGA | STOP |
|  |  |  |  | TAG | STOP |
| 3033-3035 | CGG | ARG | 114 | TAA | STOP |
|  |  |  |  | TAG | STOP |
|  |  |  |  | TGA | STOP |
| 3039-3041 | CGA | ARG | 116 | TGA | STOP |
|  |  |  |  | TAA | STOP |
| 3099-3101 | CAG | GLN | 136 | TAA | STOP |
|  |  |  |  | TAG | STOP |
| 3780-3782 | CAG | GLN | 179 | TAA | STOP |
|  |  |  |  | TAG | STOP |
| 3825-3827 | CAG | GLN | 194 | TAG | STOP |
|  |  |  |  | TAA | STOP |
| 3945-3947 | CAA | GLN | 234 | TAA | STOP |

TABLE 1p possible stop codon mutations in BrROD1-4

| position relative to the genomic sequence (SEQ ID No. 22) | WT codon | WT AA | position relative to the protein (SEQ ID No. 24) | stop codon | stop AA |
|---|---|---|---|---|---|
| 1830-1832 | CAA | GLN | 3 | TAA | STOP |
| 1866-1868 | TGG | TRP | 15 | TAG | STOP |
|  |  |  |  | TGA | STOP |
|  |  |  |  | TAA | STOP |
| 1893-1895 | TGG | TRP | 24 | TAG | STOP |
|  |  |  |  | TAA | STOP |
|  |  |  |  | TGA | STOP |
| 1932-1934 | TGG | TRP | 37 | TAG | STOP |
|  |  |  |  | TAA | STOP |
|  |  |  |  | TGA | STOP |
| 2994-2996 | CAA | GLN | 101 | TAA | STOP |
| 3012-3014 | TGG | TRP | 107 | TAA | STOP |
|  |  |  |  | TGA | STOP |
|  |  |  |  | TAG | STOP |
| 3018-3020 | TGG | TRP | 109 | TAG | STOP |
|  |  |  |  | TGA | STOP |
|  |  |  |  | TAA | STOP |
| 3033-3035 | CGG | ARG | 114 | TAA | STOP |
|  |  |  |  | TAG | STOP |
|  |  |  |  | TGA | STOP |
| 3039-3041 | CGA | ARG | 116 | TAA | STOP |
|  |  |  |  | TGA | STOP |
| 3099-3101 | CAG | GLN | 136 | TAG | STOP |
|  |  |  |  | TAA | STOP |
| 3856-3858 | CAG | GLN | 179 | TAG | STOP |
|  |  |  |  | TAA | STOP |
| 3901-3903 | CAG | GLN | 194 | TAA | STOP |
|  |  |  |  | TAG | STOP |
| 4021-4023 | CAA | GLN | 234 | TAA | STOP |

TABLE 1q possible splice site mutations in BnROD1-A1

| position relative to the genomic sequence (SEQ ID No. 1) | Splice site | WT | mutant |
|---|---|---|---|
| 1026 | Intron 1 - donor | g[gt | a[gt |
| 1027 | Intron 1 - donor | g[gt | g[at |
| 1766 | Intron 1 - acceptor | ag]g | aa]g |
| 1767 | Intron 1 - acceptor | ag]g | ag]a |
| 1904 | Intron 2 - donor | g[gt | a[gt |
| 1905 | Intron 2 - donor | g[gt | g[at |
| 2760 | Intron 2 - acceptor | ag]g | aa]g |
| 2761 | Intron 2 - acceptor | ag]g | ag]a |

TABLE 1r possible splice site mutations in BnROD1-C1

| position relative to the genomic sequence (SEQ ID No. 4) | Splice site | WT | mutant |
|---|---|---|---|
| 1596 | Intron 1 - donor | g[gt | a[gt |
| 1597 | Intron 1 - donor | g[gt | g[at |
| 2907 | Intron 1 - acceptor | ag]g | aa]g |
| 2908 | Intron 1 - acceptor | ag]g | ag]a |
| 3045 | Intron 2 - donor | g[gt | a[gt |
| 3046 | Intron 2 - donor | g[gt | g[at |
| 9944 | Intron 2 - acceptor | ag]g | aa]g |
| 9945 | Intron 2 - acceptor | ag]g | ag]a |

TABLE 1s possible splice site mutations in BnROD1-A2

| position relative to the genomic sequence (SEQ ID No. 7) | Splice site | WT | mutant |
|---|---|---|---|
| 1971 | Intron 1 - donor | g[gt | a[gt |
| 1972 | Intron 1 - donor | g[gt | g[at |
| 2541 | Intron 1 - acceptor | ag]g | aa]g |
| 2542 | Intron 1 - acceptor | ag]g | ag]a |
| 2679 | Intron 2 - donor | g[gt | a[gt |
| 2680 | Intron 2 - donor | g[gt | g[at |
| 3203 | Intron 2 - acceptor | ag]g | aa]g |
| 3204 | Intron 2 - acceptor | ag]g | ag]a |

TABLE 1t possible splice site mutations in BnROD1-C2

| position relative to the genomic sequence (SEQ ID No. 10) | Splice site | WT | mutant |
|---|---|---|---|
| 1705 | Intron 1 - donor | g[gt | a[gt |
| 1706 | Intron 1 - donor | g[gt | g[at |
| 3195 | Intron 1 - acceptor | ag]g | aa]g |
| 3196 | Intron 1 - acceptor | ag]g | ag]a |
| 3333 | Intron 2 - donor | g[gt | a[gt |
| 3334 | Intron 2 - donor | g[gt | g[at |
| 3855 | Intron 2 - acceptor | ag]g | aa]g |
| 3856 | Intron 2 - acceptor | ag]g | ag]a |

TABLE 1u possible splice site mutations in BoROD1-1

| position relative to the genomic sequence (SEQ ID No. 25) | Splice site | WT | mutant |
|---|---|---|---|
| 2187 | Intron 1 - donor | g[gt | a[gt |
| 2188 | Intron 1 - donor | g[gt | g[at |
| 2916 | Intron 1 - acceptor | ag]g | aa]g |
| 2917 | Intron 1 - acceptor | ag]g | ag]a |
| 3054 | Intron 2 - donor | g[gt | a[gt |
| 3055 | Intron 2 - donor | g[gt | g[at |
| 4133 | Intron 2 - acceptor | ag]g | aa]g |
| 4134 | Intron 2 - acceptor | ag]g | ag]a |

TABLE 1v possible splice site mutations in BrROD1-1

| position relative the genomic sequence (SEQ ID No. 13) | Splice site | WT | mutant |
|---|---|---|---|
| 1260 | Intron 1 - donor | g[gt | a[gt |
| 1261 | Intron 1 - donor | g[gt | g[at |
| 1997 | Intron 1 - acceptor | ag]g | aa]g |
| 1998 | Intron 1 - acceptor | ag]g | ag]a |
| 2135 | Intron 2 - donor | g[gt | a[gt |
| 2136 | Intron 2 - donor | g[gt | g[at |
| 2989 | Intron 2 - acceptor | ag]g | aa]g |
| 2990 | Intron 2 - acceptor | ag]g | ag]a |

TABLE 1w possible splice site mutations in BoROD1-2

| position relative to the genomic sequence (SEQ ID No. 28) | Splice site | WT | mutant |
|---|---|---|---|
| 2231 | Intron 1 - donor | g[gt | a[gt |
| 2232 | Intron 1 - donor | g[gt | g[at |
| 2807 | Intron 1 - acceptor | ag]g | aa]g |
| 2808 | Intron 1 - acceptor | ag]g | ag]a |
| 2945 | Intron 2 - donor | g[gt | a[gt |
| 2946 | Intron 2 - donor | g[gt | g[at |
| 3466 | Intron 2 - acceptor | ag]g | aa]g |
| 3467 | Intron 2 - acceptor | ag]g | ag]a |

TABLE 1x possible splice site mutations in BrROD1-2

| position relative to the genomic sequence (SEQ ID No. 16) | Splice site | WT | mutant |
|---|---|---|---|
| 1517 | Intron 1 - donor | g[gt | a[gt |
| 1518 | Intron 1 - donor | g[gt | g[at |
| 2088 | Intron 1 - acceptor | ag]g | aa]g |
| 2089 | Intron 1 - acceptor | ag]g | ag]a |
| 2226 | Intron 2 - donor | g[gt | a[gt |
| 2227 | Intron 2 - donor | g[gt | g[at |
| 2750 | Intron 2 - acceptor | ag]g | aa]g |
| 2751 | Intron 2 - acceptor | ag]g | ag]a |

TABLE 1y possible splice site mutations in BoROD1-3

| position relative to the genomic sequence (SEQ ID No. 31) | Splice site | WT | mutant |
|---|---|---|---|
| 1499 | Intron 1 - donor | g[gt | a[gt |
| 1500 | Intron 1 - donor | g[gt | g[at |
| 2001 | Intron 1 - acceptor | ag]g | aa]g |
| 2002 | Intron 1 - acceptor | ag]g | ag]a |
| 2139 | Intron 2 - donor | g[gt | a[gt |
| 2140 | Intron 2 - donor | g[gt | g[at |
| 2383 | Intron 2 - acceptor | ag]g | aa]g |
| 2384 | Intron 2 - acceptor | ag]g | ag]a |

TABLE 1y-continued possible splice site mutations in BoROD1-3

| position relative to the genomic sequence (SEQ ID No. 31) | Splice site | WT | mutant |
|---|---|---|---|

TABLE 1z possible splice site mutations in BrROD1-3

| position relative to the genomic sequence (SEQ ID No. 19) | Splice site | WT | mutant |
|---|---|---|---|
| 1522 | Intron 1 - donor | g[gt | a[gt |
| 1523 | Intron 1 - donor | g[gt | g[at |
| 2001 | Intron 1 - acceptor | ag]g | aa]g |
| 2002 | Intron 1 - acceptor | ag]g | ag]a |
| 2139 | Intron 2 - donor | g[gt | a[gt |
| 2140 | Intron 2 - donor | g[gt | g[at |
| 2396 | Intron 2 - acceptor | ag]g | aa]g |
| 2397 | Intron 2 - acceptor | ag]g | ag]a |

TABLE 1aa possible splice site mutations in BoROD1-4

| position relative to the genomic sequence (SEQ ID No. 34) | Splice site | WT | mutant |
|---|---|---|---|
| 2103 | Intron 1 - donor | g[gt | a[gt |
| 2104 | Intron 1 - donor | g[gt | g[at |
| 2978 | Intron 1 - acceptor | ag]g | aa]g |
| 2979 | Intron 1 - acceptor | ag]g | ag]a |
| 3116 | Intron 2 - donor | g[gt | a[gt |
| 3117 | Intron 2 - donor | g[gt | g[at |
| 3668 | Intron 2 - acceptor | ag]g | aa]g |
| 3669 | Intron 2 - acceptor | ag]g | ag]a |

TABLE 1ab possible splice site mutations in BrROD1-4

| position relative the genomic sequence (SEQ ID No. 22) | Splice site | WT | mutant |
|---|---|---|---|
| 2108 | Intron 1 - donor | g[gt | a[gt |
| 2109 | Intron 1 - donor | g[gt | g[at |
| 2978 | Intron 1 - acceptor | ag]g | aa]g |
| 2979 | Intron 1 - acceptor | ag]g | ag]a |
| 3116 | Intron 2 - donor | g[gt | a[gt |
| 3117 | Intron 2 - donor | g[gt | g[at |
| 3744 | Intron 2 - acceptor | ag]g | aa]g |
| 3745 | Intron 2 - acceptor | ag]g | ag]a |

Obviously, mutations are not limited to the ones shown in the above tables and it is understood that analogous STOP mutations may be present in rod1 alleles other than those depicted in the sequence listing and referred to in the tables above. Not only stopcodon mutations, but also mutations resulting in an amino acid substitution may lead to proteins with reduced functionality or with no detectable activity.

In another embodiment, said knock-out rod1 gene in *Brassica napus* is selected from the group consisting of nucleic acids comprising:

a G to A mutation at position 1802 of SEQ ID No. 1;
a G to A mutation at position 1822 of SEQ ID No. 1;
a C to T mutation at position 1834 of SEQ ID No. 1;
a G to A mutation at position 1866 of SEQ ID No. 1;
a G to A mutation at position 2956 of SEQ ID No. 4;
a G to A mutation at position 3005 of SEQ ID No. 4;
a G to A mutation at position 3008 of SEQ ID No. 4;
a C to T mutation at position 3040 of SEQ ID No. 4;
a G to A mutation at position 3046 of SEQ ID No. 4;
a C to T mutation at position 2968 of SEQ ID No. 4.

In a specific embodiment, said knock-out rod1 gene in *Brassica napus* is selected from the group consisting of nucleic acids comprising:

a C to T mutation at position in 1834 of SEQ ID No. 1;
a G to A mutation at position 1866 of SEQ ID No. 1;
a G to A mutation at position 2380 of SEQ ID No. 4;
a G to A mutation at position 2429 of SEQ ID No. 4;
a G to A mutation at position 2470 of SEQ ID No. 4;
a C to T mutation at position 2392 of SEQ ID No. 4.

Wild-type and mutant ROD1 nucleic acid sequences from the A-genome as described herein, such as BnROD1-A1, BnROD1-A2, BnROD1-A3, BnROD1-A4, BrROD1-1, BrROD1-2, BrROD1-3 and BrROD1-4 are also suitable to use in other *Brassica* species comprising an A genome, such as *Brassica juncea*.

Wild-type and mutant ROD1 nucleic acid sequences from the C-genome as described herein, such as BnROD1-C1, BnROD1-C2, BnROD1-C3, BnROD1-C4, BoROD1-1, BoROD1-2, BoROD1-3 and BoROD1-4 are also suitable to use in other *Brassica* species comprising a C genome, such as *Brassica carinata*.

Amino Acid Sequences According to the Invention

Provided are both wild type ROD1 amino acid sequences and mutant ROD1 amino acid sequences (comprising one or more mutations, preferably mutations which result in a significantly reduced or no biological activity of the ROD1 protein) from Brassicaceae, particularly from *Brassica* species, especially from *Brassica napus, Brassica rapa*, and *Brassica oleracea*. In addition, mutagenesis methods can be used to generate mutations in wild type ROD1 alleles, thereby generating mutant alleles which can encode further mutant ROD1 proteins. In one embodiment the wild type and/or mutant ROD1 amino acid sequences are provided within a *Brassica* plant (i.e. endogenously). However, isolated ROD1 amino acid sequences (e.g. isolated from the plant or made synthetically), as well as variants thereof and fragments of any of these are also provided herein.

Amino acid sequences of ROD1-A1, ROD1-C1, ROD1-A2 and ROD1-C2 proteins from *Brassica napus*, ROD1-1, ROD1-2, ROD1-3 and ROD1-4 proteins from *Brassica rapa*, and ROD1-1, ROD1-2, ROD1-3 and ROD1-4 proteins from *Brassica oleracea*, have been isolated as depicted in the sequence listing. The wild type ROD1 sequences are depicted, while the mutant ROD1 sequences of these sequences, and of sequences essentially similar to these, are described herein below, with reference to the wild type ROD1 sequences.

"*Brassica napus* ROD1-A1 amino acid sequences" or "BnROD1-A1 amino acid sequences" or variant amino acid sequences thereof according to the invention are amino acid sequences having at least 95%, 98%, 99% or 100% sequence identity with SEQ ID NO: 3. These amino acid sequences may also be referred to as being "essentially similar" or "essentially identical" to the ROD1 sequences provided in the sequence listing.

"*Brassica napus* ROD1-C1 amino acid sequences" or "BnROD1-C1 amino acid sequences" or variant amino acid sequences thereof according to the invention are amino acid sequences having at least 95%, 98%, 99% or 100% sequence identity with SEQ ID NO: 6. These amino acid sequences may also be referred to as being "essentially similar" or "essentially identical" to the ROD1 sequences provided in the sequence listing.

"*Brassica napus* ROD1-A2 amino acid sequences" or "BnROD1-A2 amino acid sequences" or variant amino acid sequences thereof according to the invention are amino acid sequences having at least 95%, 98%, 99% or 100% sequence identity with SEQ ID NO: 9. These amino acid sequences may also be referred to as being "essentially similar" or "essentially identical" to the ROD1 sequences provided in the sequence listing.

"*Brassica napus* ROD1-C2 amino acid sequences" or "BnROD1-C2 amino acid sequences" or variant amino acid sequences thereof according to the invention are amino acid sequences having at least 95%, 98%, 99% or 100% sequence identity with SEQ ID NO: 12. These amino acid sequences may also be referred to as being "essentially similar" or "essentially identical" to the ROD1 sequences provided in the sequence listing.

"*Brassica napus* ROD1-A3 amino acid sequences" or "BnROD1-A3 amino acid sequences" or variant amino acid sequences thereof according to the invention are amino acid sequences having at least 95%, 98%, 99% or 100% sequence identity with SEQ ID NO: 85. These amino acid sequences may also be referred to as being "essentially similar" or "essentially identical" to the ROD1 sequences provided in the sequence listing.

"*Brassica napus* ROD1-C3 amino acid sequences" or "BnROD1-C3 amino acid sequences" or variant amino acid sequences thereof according to the invention are amino acid sequences having at least 95%, 98%, 99% or 100% sequence identity with SEQ ID NO: 87a. These amino acid sequences may also be referred to as being "essentially similar" or "essentially identical" to the ROD1 sequences provided in the sequence listing.

"*Brassica napus* ROD1-A4 amino acid sequences" or "BnROD1-A4 amino acid sequences" or variant amino acid sequences thereof according to the invention are amino acid sequences having at least 95%, 98%, 99% or 100% sequence identity with SEQ ID NO: 89. These amino acid sequences may also be referred to as being "essentially similar" or "essentially identical" to the ROD1 sequences provided in the sequence listing.

"*Brassica napus* ROD1-C4 amino acid sequences" or "BnROD1-C4 amino acid sequences" or variant amino acid sequences thereof according to the invention are amino acid sequences having at least 95%, 98%, 99% or 100% sequence identity with SEQ ID NO: 91. These amino acid sequences may also be referred to as being "essentially similar" or "essentially identical" to the ROD1 sequences provided in the sequence listing.

"*Brassica rapa* ROD1-1 amino acid sequences" or "BrROD1-1 amino acid sequences" or variant amino acid sequences thereof according to the invention are amino acid sequences having at least 95%, 98%, 99% or 100% sequence identity with SEQ ID NO: 15. These amino acid sequences may also be referred to as being "essentially similar" or "essentially identical" to the ROD1 sequences provided in the sequence listing.

"*Brassica rapa* ROD1-2 amino acid sequences" or "BrROD1-2 amino acid sequences" or variant amino acid sequences thereof according to the invention are amino acid sequences having at least 95%, 98%, 99% or 100% sequence identity with SEQ ID NO: 18. These amino acid sequences may also be referred to as being "essentially similar" or "essentially identical" to the ROD1 sequences provided in the sequence listing.

"*Brassica rapa* ROD1-3 amino acid sequences" or "BrROD1-3 amino acid sequences" or variant amino acid sequences thereof according to the invention are amino acid sequences having at least 95%, 98%, 99% or 100% sequence identity with SEQ ID NO: 21. These amino acid sequences may also be referred to as being "essentially similar" or "essentially identical" to the ROD1 sequences provided in the sequence listing.

"*Brassica rapa* ROD1-4 amino acid sequences" or "BrROD1-4 amino acid sequences" or variant amino acid sequences thereof according to the invention are amino acid sequences having at least 95%, 98%, 99% or 100% sequence identity with SEQ ID NO: 24. These amino acid sequences may also be referred to as being "essentially similar" or "essentially identical" to the ROD1 sequences provided in the sequence listing.

"*Brassica oleracea* ROD1-1 amino acid sequences" or "BoROD1-1 amino acid sequences" or variant amino acid sequences thereof according to the invention are amino acid sequences having at least 95%, 98%, 99% or 100% sequence identity with SEQ ID NO: 27. These amino acid sequences may also be referred to as being "essentially similar" or "essentially identical" to the ROD1 sequences provided in the sequence listing.

"*Brassica oleracea* ROD1-2 amino acid sequences" or "BoROD1-2 amino acid sequences" or variant amino acid sequences thereof according to the invention are amino acid sequences having at least 95%, 98%, 99% or 100% sequence identity with SEQ ID NO: 30. These amino acid sequences may also be referred to as being "essentially similar" or "essentially identical" to the ROD1 sequences provided in the sequence listing.

"*Brassica oleracea* ROD1-3 amino acid sequences" or "BoROD1-3 amino acid sequences" or variant amino acid sequences thereof according to the invention are amino acid sequences having at least 95%, 98%, 99% or 100% sequence identity with SEQ ID NO: 33. These amino acid sequences may also be referred to as being "essentially similar" or "essentially identical" to the ROD1 sequences provided in the sequence listing.

"*Brassica oleracea* ROD1-4 amino acid sequences" or "BoROD1-4 amino acid sequences" or variant amino acid sequences thereof according to the invention are amino acid sequences having at least 95%, 98%, 99% or 100% sequence identity with SEQ ID NO: 36. These amino acid sequences may also be referred to as being "essentially similar" or "essentially identical" to the ROD1 sequences provided in the sequence listing.

Thus, the invention provides both amino acid sequences of wild type proteins, including variants and fragments thereof (as defined further below), as well as mutant amino acid sequences of any of these, whereby the mutation in the amino acid sequence preferably results in a significant reduction in or a complete abolishment of the biological activity of the ROD1 protein as compared to the biological activity of the corresponding wild type ROD1 protein.

Both endogenous and isolated amino acid sequences are provided herein. Also provided are fragments of the ROD1 amino acid sequences and ROD1 variant amino acid sequences defined above. A "fragment" of a ROD1 amino acid sequence or variant thereof (as defined) may be of various lengths, such as at least 10, 12, 15, 18, 20, 50, 100, 150, 175, 180 contiguous amino acids of the ROD1 sequence (or of the variant sequence).

Amino Acid Sequences of Wild-Type ROD1 Proteins

The amino acid sequences depicted in the sequence listing are wild type ROD1 proteins from *Brassica napus*. Thus, these sequences are endogenous to the *Brassica napus* plants from which they were isolated. Other *Brassica*, varieties, breeding lines or wild accessions may be screened for other functional ROD1 proteins with the same amino acid sequences or variants thereof, as described above.

In addition, it is understood that ROD1 amino acid sequences and variants thereof (or fragments of any of these) may be identified in silico, by screening amino acid databases for essentially similar sequences. Fragments of amino acid molecules according to the invention are also provided.

Amino Acid Sequences of Mutant ROD1 Proteins

Amino acid sequences comprising one or more amino acid deletions, insertions or substitutions relative to the wild type amino acid sequences are another embodiment of the invention, as are fragments of such mutant amino acid molecules. Such mutant amino acid sequences can be generated and/or identified using various known methods, as described above. Again, such amino acid molecules are provided both in endogenous form and in isolated form.

In one embodiment, the mutation(s) in the amino acid sequence result in a significantly reduced or completely abolished biological activity of the ROD1 protein relative to the wild type protein. As described above, basically, any mutation which results in a protein comprising at least one amino acid insertion, deletion and/or substitution relative to the wild type protein can lead to significantly reduced or no biological activity.

Thus in one embodiment, mutant ROD1 proteins are provided comprising one or more deletion or insertion mutations, whereby the deletion(s) or insertion(s) result(s) in a mutant protein which has significantly reduced or no activity. Such mutant ROD1 proteins are ROD1 proteins wherein at least 1, at least 2, 3, 4, 5, 10, 20, 30, 50, 100, 150, 200 or more amino acids are deleted, inserted or substituted as compared to the wild type ROD1 protein, whereby the deletion(s) or insertion(s) result(s) in a mutant protein which has significantly reduced or no activity.

In another embodiment, mutant ROD1 proteins are provided which are truncated whereby the truncation results in a mutant protein that has significantly reduced or no activity.

In yet another embodiment, mutant ROD1 proteins are provided comprising one or more substitution mutations, whereby the substitution(s) result(s) in a mutant protein that has significantly reduced or no activity.

In a further embodiment, said mutant ROD1 proteins from *Brassica napus* are selected from the group consisting of proteins comprising:
  SEQ ID No. 3 truncated after the amino acid at position 138;
  an R to K substitution at position 146 of SEQ ID No. 3;
  a T to I substitution at position 150 of SEQ ID No. 3;
  a G to S substitution at position 161 of SEQ ID No. 3;
  an E to K substitution at position 142 of SEQ ID No. 6;
  an R to H substitution at position 158 of SEQ ID No. 6;
  an G to D substitution at position 159 of SEQ ID No. 6;
  an P to S substitution at position 170 of SEQ ID No. 6;
  SEQ ID No. 6 truncated after the amino acid at position 145.

In a specific embodiment, said knock-out rod1 gene in *Brassica napus* is selected from the group consisting of nucleic acids comprising:

a T to I substitution at position 150 of SEQ ID No. 3;
a G to S substitution at position 161 of SEQ ID No. 3;
an E to K substitution at position 142 of SEQ ID No. 6;
an R to H substitution at position 158 of SEQ ID No. 6;
SEQ ID No. 6 truncated after the amino acid at position 145.

In a further embodiment, a transgenic *Brassica* plant is provided comprising a chimeric gene, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells. In another embodiment, said transgenic *Brassica* plant is *Brassica napus*, and said RNA molecule is inhibitory to a ROD1 gene encoding a protein having at least 90% sequence identity to SEQ ID No. 3 and to a ROD1 gene encoding a protein having at least 90% sequence identity to SEQ ID No. 6.

An RNA molecule inhibitory to at least one ROD1 gene can be an RNA that downregulates ROD1 gene expression by decreasing the levels of ROD1 mRNAs available for translation. Said RNA can downregulate ROD1 gene expression through, for example, co-suppression (sense RNA suppression), antisense RNA, double-stranded RNA (dsRNA) or microRNA (miRNA), or ta-siRNA.

Said RNA molecule inhibitory to at least one ROD1 gene is characterized tin that said RNA molecule comprises a region with sufficient homology to said ROD1 genes to be downregulated.

Sufficient homology to the ROD1 genes to be downregulated as used herein means that the transcribed DNA region (and resulting RNA molecule) comprises at least 20 consecutive nucleotides having at least 95% sequence identity to the nucleotide sequence or the complement of the nucleotide of the ROD1 gene to be downregulated.

Said RNA molecule inhibitory to at least one ROD1 gene may be a sense RNA molecule capable of down-regulating expression of one or more functional ROD1 genes by co-suppression. Said RNA molecule comprises at least 20 consecutive nucleotides having at least 95% sequence identity to the nucleotide sequence of one or more ROD1 genes present in the plant cell or plant.

Said RNA molecule inhibitory to at least one ROD1 gene may further be an antisense RNA molecule capable of down-regulating expression of one or more functional ROD1 genes. Said RNA molecule comprises at least 20 consecutive nucleotides having at least 95% sequence identity to the complement of the nucleotide sequence of one or more functional ROD1 genes present in the plant cell or plant.

The minimum nucleotide sequence of the antisense or sense RNA region of about 20 nt of the ROD1 gene may be comprised within a larger RNA molecule, varying in size from 20 nt to a length equal to the size of the target gene. The mentioned antisense or sense nucleotide regions may thus be about from about 21 nt to about 1300 nt long, such as 21 nt, 40 nt, 50 nt, 100 nt, 200 nt, 300 nt, 500 nt, 1000 nt, or even about 1300 nt or larger in length. Moreover, it is not required for the purpose of the invention that the nucleotide sequence of the used inhibitory ROD1 RNA molecule or the encoding region of the transgene, is completely identical or complementary to the endogenous ROD1 gene the expression of which is targeted to be reduced in the plant cell. The longer the sequence, the less stringent the requirement for the overall sequence identity is. Thus, the sense or antisense regions may have an overall sequence identity of about 40% or 50 or 60% or 70% or 80% or 90% or 100% to the nucleotide sequence of the endogenous ROD1 gene or the complement thereof. However, as mentioned, antisense or sense regions should comprise a nucleotide sequence of 20 consecutive nucleotides having about 95 to about 100% sequence identity to the nucleotide sequence of the endogenous ROD1 gene. The stretch of about 95 to about 100% sequence identity may be about 50, 75 or 100 nt. It will be clear that all combinations between mentioned length and sequence identity can be made, both in sense and/or antisense orientation.

The abovementioned chimeric gene may further comprise DNA elements which result in the expression of aberrant, non-polyadenylated ROD1 inhibitory RNA molecules. One such DNA element suitable for that purpose is a DNA region encoding a self-splicing ribozyme, as described in WO 00/01133. The efficiency may also be enhanced by providing the generated RNA molecules with nuclear localization or retention signals as described in WO 03/076619.

Said RNA molecule inhibitory to at least one ROD1 gene may further be a double-stranded RNA molecule capable of down-regulating ROD1 gene expression. Upon transcription of the DNA region the RNA is able to form dsRNA molecule through conventional base paring between a sense and antisense region, whereby the sense and antisense region are nucleotide sequences as hereinbefore described. dsRNA-encoding ROD1 expression-reducing chimeric genes according to the invention may further comprise an intron, such as a heterologous intron, located e.g. in the spacer sequence between the sense and antisense RNA regions in accordance with the disclosure of WO 99/53050. To achieve the construction of such a transgene, use can be made of the vectors described in WO 02/059294 A1.

Said RNA molecule inhibitory to at least one ROD1 gene may further be a pre-miRNA molecule which is processed into a miRNA capable of guiding the cleavage of ROD1 mRNA. miRNAs are small endogenous RNAs that regulate gene expression in plants, but also in other eukaryotes. In plants, these about 21 nucleotide long RNAs are processed from the stem-loop regions of long endogenous pre-miRNAs by the cleavage activity of DICERLIKE1 (DCL1). Plant miRNAs are highly complementary to conserved target mRNAs, and guide the cleavage of their targets. miRNAs appear to be key components in regulating the gene expression of complex networks of pathways involved inter alia in development.

As used herein, a "miRNA" is an RNA molecule of about 20 to 22 nucleotides in length which can be loaded into a RISC complex and direct the cleavage of a target RNA molecule, wherein the target RNA molecule comprises a nucleotide sequence essentially complementary to the nucleotide sequence of the miRNA molecule whereby one or more of the following mismatches may occur:

A mismatch between the nucleotide at the 5' end of said miRNA and the corresponding nucleotide sequence in the target RNA molecule;
A mismatch between any one of the nucleotides in position 1 to position 9 of said miRNA and the corresponding nucleotide sequence in the target RNA molecule;
Three mismatches between any one of the nucleotides in position 12 to position 21 of said miRNA and the corresponding nucleotide sequence in the target RNA molecule provided that there are no more than two consecutive mismatches.

No mismatch is allowed at positions 10 and 11 of the miRNA (all miRNA positions are indicated starting from the 5' end of the miRNA molecule).

As used herein, a "pre-miRNA" molecule is an RNA molecule of about 100 to about 200 nucleotides, preferably about 100 to about 130 nucleotides which can adopt a secondary structure comprising a dsRNA stem and a single stranded RNA loop and further comprising the nucleotide sequence of the miRNA and its complement sequence of the miRNA* in the double-stranded RNA stem. Preferably, the miRNA and its complement are located about 10 to about 20 nucleotides from the free ends of the miRNA dsRNA stem. The length and sequence of the single stranded loop region are not critical and may vary considerably, e.g. between 30 and 50 nt in length. Preferably, the difference in free energy between unpaired and paired RNA structure is between −20 and −60 kcal/mole, particularly around −40 kcal/mole. The complementarity between the miRNA and the miRNA* do not need to be perfect and about 1 to 3 bulges of unpaired nucleotides can be tolerated. The secondary structure adopted by an RNA molecule can be predicted by computer algorithms conventional in the art such as mFold, UNAFold and RNAFold. The particular strand of the dsRNA stem from the pre-miRNA which is released by DCL activity and loaded onto the RISC complex is determined by the degree of complementarity at the 5' end, whereby the strand which at its 5' end is the least involved in hydrogen bounding between the nucleotides of the different strands of the cleaved dsRNA stem is loaded onto the RISC complex and will determine the sequence specificity of the target RNA molecule degradation. However, if empirically the miRNA molecule from a particular synthetic pre-miRNA molecule is not functional because the "wrong" strand is loaded on the RISC complex, it will be immediately evident that this problem can be solved by exchanging the position of the miRNA molecule and its complement on the respective strands of the dsRNA stem of the pre-miRNA molecule. As is known in the art, binding between A and U involving two hydrogen bounds, or G and U involving two hydrogen bounds is less strong that between G and C involving three hydrogen bounds.

miRNA molecules may be comprised within their naturally occurring pre-miRNA molecules but they can also be introduced into existing pre-miRNA molecule scaffolds by exchanging the nucleotide sequence of the miRNA molecule normally processed from such existing pre-miRNA molecule for the nucleotide sequence of another miRNA of interest. The scaffold of the pre-miRNA can also be completely synthetic. Likewise, synthetic miRNA molecules may be comprised within, and processed from, existing pre-miRNA molecule scaffolds or synthetic pre-miRNA scaffolds.

Said RNA molecule inhibitory to at least one ROD1 gene may further be a ta-siRNAs as described in WO2006/074400.

Said RNA molecule may be inhibitory to all ROD1 genes present in said Brassica plant. For example, said transgenic Brassica plant is Brassica rapa, and said RNA molecule is inhibitory to a ROD1 gene encoding a protein having at least 90% sequence identity to SEQ ID No. 15, and to a ROD1 gene encoding a protein having at least 90% sequence identity to SEQ ID No. 18, and to a ROD1 gene encoding a protein having at least 90% sequence identity to SEQ ID No. 21, and to a ROD1 gene encoding a protein having at least 90% sequence identity to SEQ ID No. 24, such as a ROD1 gene having at least 90% sequence identity, or at least 95% sequence identity, or at least 98% sequence identity or having 100% sequence identity to SEQ ID No. 13, SEQ ID No. 16, SEQ ID No. 19, or SEQ ID No. 22, respectively. Further, said transgenic Brassica plant can be Brassica oleracea, and said RNA molecule can be inhibitory to a ROD1 gene encoding a protein having at least 90% sequence identity to SEQ ID No. 27, and to a ROD1 gene encoding a protein having at least 90% sequence identity to SEQ ID No. 30, and to a ROD1 gene encoding a protein having at least 90% sequence identity to SEQ ID No. 33, and to a ROD1 gene encoding a protein having at least 90% sequence identity to SEQ ID No. 36, such as a ROD1 gene having at least 90% sequence identity, or at least 95% sequence identity, or at least 98% sequence identity or having 100% sequence identity to SEQ ID No. 25, SEQ ID No. 28, SEQ ID No. 31, or SEQ ID No. 34, respectively. Alternatively, said transgenic Brassica plant can be Brassica napus, and said RNA molecule can be inhibitory to a ROD1 gene encoding a protein having at least 90% sequence identity to SEQ ID No. 3, and to a ROD1 gene encoding a protein having at least 90% sequence identity to SEQ ID No. 6, and to a ROD1 gene encoding a protein having at least 90% sequence identity to SEQ ID No. 9, and to a ROD1 gene encoding a protein having at least 90% sequence identity to SEQ ID No. 12, and to a ROD1 gene encoding a protein having at least 90% sequence identity to SEQ ID No. 85, and to a ROD1 gene encoding a protein having at least 90% sequence identity to SEQ ID No. 87, and to a ROD1 gene encoding a protein having at least 90% sequence identity to SEQ ID No. 89, and to a ROD1 gene encoding a protein having at least 90% sequence identity to SEQ ID No. 91, such as a ROD1 gene having at least 90% sequence identity, or at least 95% sequence identity, or at least 98% sequence identity or having 100% sequence identity to SEQ ID No. 1, SEQ ID No. 4, SEQ ID No. 7, SEQ ID No. 10, SEQ ID No. 84, SEQ ID No. 86, SEQ ID No. 88, or SEQ ID No. 90, respectively. Said RNA molecule inhibitory to at least one ROD1 gene can, for example, comprise the sequence of nt 1405-3650 of SEQ ID No. 48.

Said RNA molecule may further be inhibitory to ROD1 genes encoding a functional protein only, such as the Brassica napus ROD1 genes encoding a protein having at least 90% sequence identity to SEQ ID No. 3 and SEQ ID No. 6, such as a ROD1 gene having at least 90% sequence identity, or at least 95% sequence identity, or at least 98% sequence identity or having 100% sequence identity to SEQ ID No. 1 and to SEQ ID No. 4, respectively. Said RNA molecule inhibitory to at least one ROD1 gene can, for example, comprise the sequence of nt 1405-3072 of SEQ ID No. 47.

Said RNA molecule may further be inhibitory to only one ROD1 gene, such as, for example, to the Brassica rapa ROD1 gene encoding a protein having at least 90% sequence identity to SEQ ID No. 15, such as a ROD1 gene having at least 90% sequence identity, or at least 95% sequence identity, or at least 98% sequence identity or having 100% sequence identity to SEQ ID No. 13, or such as the Brassica oleracea ROD1 gene encoding a protein having at least 90% sequence identity to SEQ ID No. 27, such as a ROD1 gene having at least 90% sequence identity, or at least 95% sequence identity, or at least 98% sequence identity or having 100% sequence identity to SEQ ID No. 25.

As used herein, the term "plant-expressible promoter" means a DNA sequence that is capable of controlling (initiating) transcription in a plant cell. This includes any promoter of plant origin, but also any promoter of non-plant origin which is capable of directing transcription in a plant cell, i.e., certain promoters of viral or bacterial origin such as the CaMV35S (Harpster et al. (1988) *Mol Gen Genet.* 212(1):182-90, the subterranean clover virus promoter No 4 or No 7 (WO9606932), or T-DNA gene promoters but also tissue-specific or organ-specific promoters including but not limited to seed-specific promoters (e.g., WO89/03887), organ-primordia specific promoters (An et al. (1996) *Plant Cell* 8(1):15-30), stem-specific promoters (Keller et al., (1988) *EMBO J.* 7(12): 3625-3633), leaf specific promoters (Hudspeth et al. (1989) *Plant Mol Biol.* 12: 579-589), mesophyl-specific promoters (such as the light-inducible Rubisco promoters), root-specific promoters (Keller et al. (1989) *Genes Dev.* 3: 1639-1646), tuber-specific promoters (Keil et al. (1989) *EMBO J.* 8(5): 1323-1330), vascular tissue specific promoters (Peleman et al. (1989) *Gene* 84: 359-369), stamen-selective promoters (WO 89/10396, WO 92/13956), dehiscence zone specific promoters (WO 97/13865) and the like.

A "heterologous promoter" as used herein refers to a promoter which is not normally associated in its natural context with the coding DNA region operably linked to it in the DNA molecules according to the invention.

Said plant-expressible promoter can, for example, be a constitutive promoter, such as the CaMV35S promoter (Harpster et al. (1988) *Mol Gen Genet.* 212(1):182-90), or a seed-specific promoter, such as the *Arabidopsis* oleosin promoter (WO1998/045461).

Constitutive promoters are well known in the art, and include the CaMV35S promoter (Harpster et al. (1988) *Mol Gen Genet.* 212(1):182-90), Actin promoters, such as, for example, the promoter from the Rice Actin gene (McElroy et al., 1990, Plant Cell 2:163), the promoter of the Cassava Vein Mosaic Virus (Verdaguer et al., 1996 Plant Mol. Biol. 31: 1129), the GOS promoter (de Pater et al., 1992, Plant J. 2:837), the Histone H3 promoter (Chaubet et al., 1986, Plant Mol Biol 6:253), the *Agrobacterium tumefaciens* Nopaline Synthase (Nos) promoter (Depicker et al., 1982, J. Mol. Appl. Genet. 1: 561), or Ubiquitin promoters, such as, for example, the promoter of the maize Ubiquitin-1 gene (Christensen et al., 1992, Plant Mol. Biol. 18:675).

Seed specific promoters are well known in the art, including the *Arabidopsis* oleosin promoter (WO1998/045461), the USP promoter from *Vicia faba* described in DE10211617; the promoter sequences described in WO2009/073738; promoters from *Brassica napus* for seed specific gene expression as described in WO2009/077478; the plant seed specific promoters described in US2007/0022502; the plant seed specific promoters described in WO03/014347; the seed specific promoter described in WO2009/125826; the promoters of the omega_3 fatty acid desaturase family described in WO2006/005807 and the like.

A "transcription termination and polyadenylation region" as used herein is a sequence that drives the cleavage of the nascent RNA, whereafter a poly(A) tail is added at the resulting RNA 3' end, functional in plants. Transcription termination and polyadenylation signals functional in plants include, but are not limited to, 3'nos, 3'35S, 3'his and 3'g7.

In a further embodiment, the seeds of the plants according to the invention have increased levels of C18:1, or increased levels of C18:1 and decreased levels of C18:2, or increased levels of C18:1 and decreased levels of SATS.

In a further embodiment, seeds are provided from the plants according to the invention, i.e. plants comprising a knock-out ROD1 gene or an RNA inhibitory to a ROD1 gene. In yet another embodiment, oil from the seeds of the plants according to the invention is provided.

In another embodiment, a method is provided for increasing the C18:1 levels in seed oil, comprising modulating the expression of a ROD1 gene. In yet another embodiment, a method is provided for increasing the C18:1 levels in seed oil, comprising the steps of introducing or providing an chimeric gene to a *Brassica* plant cell, to create transgenic cells, said chimeric gene comprising the following operably linked DNA fragments: a plant-expressible promoter, a DNA region, which when transcribed yields an RNA molecule inhibitory to at least one ROD1 gene; and optionally a transcription termination and polyadenylation region functional in plant cells; and regenerating transgenic plants from said transgenic cells.

"C18:1", also referred to as "oleic acid", "cis-9-octadecenoic", "18:1", "18:1 (n-9)", "9c-18:1" or "18:1cis $\Delta^9$" as used herein, refers to a monounsaturated omega-9 fatty acid, with the IUPAC name (9Z)-Octadec-9-enoic acid.

"C18:2", also referred to as" linoleic acid", "cis-9,12-octadecadienoic acid", "18:2", "18:2 (n-6)", "9c12c-18:1 or "18:2cis $\Delta^{9,12}$", as used herein, refers to a carboxylic acid with an 18-carbon chain and two double bonds with the IUPAC name cis, cis-9,12-Octadecadienoic acid.

SATS, as used herein, refers to saturated fatty acids, which refers to the sum of the levels of C12:0, C14:0, C16:0, C18:0, C20:0, C22:0 and C24:0.

Increasing the C18:1 levels or increased C18:1 levels in seed oil can be an increase of C18:1 levels with at least 2%, or at least 5%, or at least 8%, or at least 10%, or at least 12%. Said increase is an increase with respect to C18:1 levels as obtained in control plants.

Decreased levels of C18:2 can be a decrease of C18:2 levels in seed oil with at least 2%, or at least 5%, or at least 8%, or at least 10%, or at least 20%, or at least 30%.

Decreased levels of SATS can be a decrease in the levels of SATS in seed oil with at least 2%, or at least 3%, or at least 5%. A decrease in the levels of SATS refers to a decrease in the total levels of the sum of C16:0, C18:0, C20:0, C22:0 and C24:0. As such, a decrease in the levels of SATS can be a decrease in the levels of only one of the saturated fatty acids, or of more than one of the saturated fatty acids.

Optionally, the increase of the C18:1 levels or decrease of the C18:2 or SATS in seeds or in seed oil is higher than an increase in C18:1 levels or decrease of the C18:2 or SATS in membrane lipids. For example, the levels of C18:1 are increased, or the C18:2 levels or SATS are increased in the seeds, but the C18:1, C18:2 and SATS levels are unchanged in membrane lipids.

C18:1, C18:2 and SATS levels can be measured as described herein, such as, for example, using the methods as described in Examples 5 and 6.

The "control plant" as used herein is generally a plant of the same species which has wild-type levels of ROD1. "Wild-type levels of ROD1" as used herein refers to the typical levels of ROD1 protein in a plant as it most commonly occurs in nature. Said control plant does contain an RNA molecule inhibitory to ROD1, and in which the ROD1 genes are wild-type ROD1 genes.

A chimeric gene can be provided to a plant or plant cell using methods well-known in the art. Methods to provide plant cells with a chimeric are not deemed critical for the current invention and any method to provide plant cells with a chimeric gene suitable for a particular plant species can be used. Such methods are well known in the art and include *Agrobacterium*-mediated transformation, particle gun delivery, microinjection, electroporation of intact cells, polyethyleneglycol-mediated protoplast transformation, electroporation of protoplasts, liposome-mediated transformation, silicon-whiskers mediated transformation etc. Said chimeric can be transiently introduced into the plant cell or plant cell nucleus. Said chimeric may be stably integrated into the genome of said plant cell, resulting in a transformed plant cell. The transformed plant cells obtained in this way may then be regenerated into mature fertile transformed plants.

The obtained transformed plant, comprising the RNA molecule inhibitory to at least one ROD1 gene, can be used in a conventional breeding scheme to produce more transformed plants with the same characteristics or to introduce the transgene according to the invention in other varieties of the same or related plant species, or in hybrid plants. Seeds obtained from the transformed plants contain the chimeric genes of the invention as a stable genomic insert and are also encompassed by the invention.

In again another embodiment, a method is provided for increasing the C18:1 levels in seed oil, comprising the steps of treating seeds or plant material with a mutagenic chemical substance or with ionizing radiation; identifying plants with a mutated rod1 gene, wherein the ROD1 gene, prior to being mutated, encodes a polypeptide having at least 90% sequence identity to SEQ ID No. 3, to SEQ ID No. 6, to SEQ ID No. 15 or to SEQ ID No. 27; and selecting a plant with an increased level of C18:1 in the seeds compared to a plant in which the ROD1 gene is not mutated.

Said ROD1 gene, prior to being mutated, can be, for example, a ROD1 gene having at least 90% sequence identity, or at least 95% sequence identity, or at least 98% sequence identity or having 100% sequence identity to SEQ ID No. 1, or SEQ ID no. 4, or SEQ ID No. 13, or SEQ ID No. 25.

In a further embodiment, a method is provided for obtaining a *Brassica* plant with increased levels of C18:1 in the seeds comprising the step of introducing a knock-out allele of a ROD1 gene in said *Brassica* plant, and selecting said *Brassica* plant with increased levels of C18:1 in the seeds for the presence of said knock-out allele of a ROD1 gene by analyzing genomic DNA from said plant for the presence of at least one molecular marker, wherein said at least one molecular marker is linked to said knock-out allele of a ROD1 gene.

Introducing said knock-out allele of ROD1 can occur through mutagenesis or gene targeting as described above. Introducing said knock-out allele can also occur through introduction of a knock-out ROD1 allele from one plant into another.

In another embodiment, a method is provided to determine the presence or absence of a knock-out allele of a ROD1 gene in a biological sample, comprising providing genomic DNA from said biological sample, and analyzing said DNA for the presence of at least one molecular marker, wherein the at least one molecular marker is linked to said knock-out allele of a ROD1 gene.

Said genomic DNA can be provided by isolating genomic DNA from said biological sample. Isolating genomic DNA refers to isolating a biological sample comprising genomic DNA from, such as isolating part of a tissue, such as, for example part of a leaf. Isolating genomic DNA from said biological sample can, but does not need to comprise, purification of genomic DNA from said sample.

Yet another embodiment provides a kit for the detection of a knock-out allele of a ROD1 gene in *Brassica* DNA samples, wherein said kit comprises one or more PCR primer pairs, which are able to amplify a DNA marker linked to said knock-out allele of a ROD1 gene. In yet another embodiment, said kit further comprises one or more probes.

In a specific embodiment, said knock-out allele of a ROD1 gene is a mutant ROD1 allele.

In a further embodiment, a method is provided for determining the zygosity status of a mutant ROD1 allele in a plant, or a cell, part, seed or progeny thereof, comprising determining the presence of a mutant and/or a corresponding wild type ROD1 specific region in the genomic DNA of said plant, or a cell, part, seed or progeny thereof.

Yet a further embodiment provides method for transferring at least one knock-out ROD1 allele from one plant to another plant comprising the steps of: identifying a first plant comprising at least one knock-out ROD1 allele; crossing the first plant with a second plant not comprising the at least one knock-out ROD1 allele and collecting F1 hybrid seeds from the cross; optionally, identifying F1 plants comprising the at least one knock-out ROD1 allele; backcrossing F1 plants comprising the at least one knock-out ROD1 allele with the second plant not comprising the at least one knock-out ROD1 allele for at least one generation and collecting back cross seeds from the crosses; identifying in every generation back cross plants comprising the at least one knock-out ROD1 allele by analyzing genomic DNA of said back cross plants for the presence of at least one molecular marker, wherein the at least one molecular marker is linked to said knock-out ROD1 allele.

A molecular marker which is linked to said knock-out allele of a ROD1 gene or said mutant ROD1 allele can comprise on or more primers or probes that specifically detect said knock-out allele of said ROD1 gene as described herein below.

Methods According to the Invention

Mutant rod1 alleles may be generated (for example induced by mutagenesis) and/or identified using a range of methods, which are conventional in the art, for example using nucleic acid amplification based methods to amplify part or all of the rod1 genomic or cDNA.

Following mutagenesis, plants are grown from the treated seeds, or regenerated from the treated cells using known techniques. For instance, mutagenized seeds may be planted in accordance with conventional growing procedures and following self-pollination seed is formed on the plants. Alternatively, doubled haploid plantlets may be extracted from treated microspore or pollen cells to immediately form homozygous plants, for example as described by Coventry et al. (1988, Manual for Microspore Culture Technique for *Brassica napus*. Dep. Crop Sci. Techn. Bull. OAC Publication 0489. Univ. of Guelph, Guelph, Ontario, Canada). Additional seed which is formed as a result of such self-pollination in the present or a subsequent generation may be harvested and screened for the presence of mutant ROD1 alleles, using techniques which are conventional in the art, for example nucleic acid amplification based techniques, such as polymerase chain reaction (PCR) based techniques (amplification of the rod1 alleles) or hybridization based techniques, e.g. Southern blot analysis, BAC library screening, and the like, and/or direct sequencing of rod1 alleles. To screen for the presence of point mutations (so called Single Nucleotide Polymorphisms or SNPs) in mutant ROD1 alleles, SNP detection methods conventional in the art can be used, for example oligoligation-based techniques, single base extension-based techniques or techniques based on differences in restriction sites, such as TILLING.

As described above, mutagenization (spontaneous as well as induced) of a specific wild-type ROD1 allele results in the presence of one or more deleted, inserted, or substituted nucleotides (hereinafter called "mutation region") in the resulting mutant ROD1 allele. The mutant ROD1 allele can thus be characterized by the location and the configuration of the one or more deleted, inserted, or substituted nucleotides in the wild type ROD1 allele. The site in the wild type ROD1 allele where the one or more nucleotides have been inserted, deleted, or substituted, respectively, is herein also referred to as the "mutation region or sequence". A "5' or 3' flanking region or sequence" as used herein refers to a DNA region or sequence in the mutant (or the corresponding wild type) ROD1 allele of at least 20 bp, preferably at least 50 bp, at least 750 bp, at least 1500 bp, and up to 5000 bp of DNA different from the DNA containing the one or more deleted, inserted, or substituted nucleotides, preferably DNA from the mutant (or the corresponding wild type) ROD1 allele which is located either immediately upstream of and contiguous with (5' flanking region or sequence") or immediately downstream of and contiguous with (3' flanking region or sequence") the mutation region in the mutant ROD1 allele (or in the corresponding wild type ROD1 allele). A "joining region" as used herein refers to a DNA region in the mutant (or the corresponding wild type) ROD1 allele where the mutation region and the 5' or 3' flanking region are linked to each other. A "sequence spanning the joining region between the mutation region and the 5' or 3' flanking region thus comprises a mutation sequence as well as the flanking sequence contiguous therewith.

The tools developed to identify a specific mutant ROD1 allele or the plant or plant material comprising a specific mutant ROD1 allele, or products which comprise plant material comprising a specific mutant ROD1 allele are based on the specific genomic characteristics of the specific mutant ROD1 allele as compared to the genomic characteristics of the corresponding wild type ROD1 allele, such as, a specific restriction map of the genomic region comprising the mutation region, molecular markers comprising primers and/or probes as described below, or the sequence of the flanking and/or mutation regions.

Once a specific mutant ROD1 allele has been sequenced, molecular markers, such as primers and probes can be developed which specifically recognize a sequence within the 5' flanking, 3' flanking and/or mutation regions of the mutant ROD1 allele in the nucleic acid (DNA or RNA) of a sample by way of a molecular biological technique. For instance an amplification method can be developed to identify the mutant ROD1 allele in biological samples (such as samples of plants, plant material or products comprising plant material). Such an amplification is based on at least two specific "primers": one recognizing a sequence within the 5' or 3' flanking region of the mutant ROD1 allele and the other recognizing a sequence within the 3' or 5' flanking region of the mutant ROD1 allele, respectively; or one recognizing a sequence within the 5' or 3' flanking region of the mutant ROD1 allele and the other recognizing a sequence within the mutation region of the mutant ROD1 allele; or one recognizing a sequence within the 5' or 3' flanking region of the mutant ROD1 allele and the other recognizing a sequence spanning the joining region between the 3' or 5' flanking region and the mutation region of the specific mutant ROD1 allele (as described further below), respectively.

The primers preferably have a sequence of between 15 and 35 nucleotides which under optimized amplification conditions "specifically recognize" a sequence within the 5' or 3' flanking region, a sequence within the mutation region, or a sequence spanning the joining region between the 3' or 5' flanking and mutation regions of the specific mutant ROD1 allele, so that a specific fragment ("mutant ROD1 specific fragment" or discriminating amplicon) is amplified from a nucleic acid sample comprising the specific mutant ROD1 allele. This means that only the targeted mutant ROD1 allele, and no other sequence in the plant genome, is amplified under optimized amplification conditions.

PCR primers suitable for the invention may be the following:

oligonucleotides ranging in length from 17 nt to about 200 nt, comprising a nucleotide sequence of at least 17 consecutive nucleotides, preferably 20 consecutive nucleotides selected from the 5' or 3' flanking sequence of a specific mutant ROD1 allele or the complement thereof (i.e., for example, the sequence 5' or 3' flanking the one or more nucleotides deleted, inserted or substituted in the mutant ROD1 alleles of the invention, such as the sequence 5' or 3' flanking the non-sense, mis-sense, frameshift or splice site mutations described above or the sequence 5' or 3' flanking the STOP codon mutations indicated in the above Tables or the substitution mutations indicated above or the complement thereof) (primers recognizing 5' flanking sequences); or oligonucleotides ranging in length from 17 nt to about 200 nt, comprising a nucleotide sequence of at least 17 consecutive nucleotides, preferably 20 nucleotides selected from the sequence of the mutation region of a specific mutant ROD1 allele or the complement thereof (i.e., for example, the sequence of nucleotides inserted or substituted in the ROD1 genes of the invention or the complement thereof) (primers recognizing mutation sequences).

The primers may of course be longer than the mentioned 17 consecutive nucleotides, and may e.g. be 18, 19, 20, 21, 30, 35, 50, 75, 100, 150, 200 nt long or even longer. The primers may entirely consist of nucleotide sequence selected from the mentioned nucleotide sequences of flanking and mutation sequences. However, the nucleotide sequence of the primers at their 5' end (i.e. outside of the 3'-located 17 consecutive nucleotides) is less critical. Thus, the 5' sequence of the primers may consist of a nucleotide sequence selected from the flanking or mutation sequences, as appropriate, but may contain several (e.g. 1, 2, 5, 10) mismatches. The 5' sequence of the primers may even entirely consist of a nucleotide sequence unrelated to the flanking or mutation sequences, such as e.g. a nucleotide sequence representing restriction enzyme recognition sites. Such unrelated sequences or flanking DNA sequences with mismatches should preferably be no longer than 100, more preferably not longer than 50 or even 25 nucleotides.

Moreover, suitable primers may comprise or consist of a nucleotide sequence spanning the joining region between flanking and mutation sequences (i.e., for example, the joining region between a sequence 5' or 3' flanking one or more nucleotides deleted, inserted or substituted in the mutant ROD1 alleles of the invention and the sequence of the one or more nucleotides inserted or substituted or the sequence 3' or 5', respectively, flanking the one or more nucleotides deleted, such as the joining region between a sequence 5' or 3' flanking non-sense, missense, frameshift or splice site mutations in the ROD1 genes of the invention described above and the sequence of the non-sense, missense, frameshift or splice site mutations, or the joining region between a sequence 5' or 3' flanking a potential STOP codon mutation as indicated in the above Tables or the substitution mutations indicated above and the sequence of the potential STOP codon mutation or the substitution mutations, respectively), provided the nucleotide sequence is not derived exclusively from either the mutation region or flanking regions.

It will also be immediately clear to the skilled artisan that properly selected PCR primer pairs should also not comprise sequences complementary to each other.

For the purpose of the invention, the "complement of a nucleotide sequence represented in SEQ ID No: X" is the nucleotide sequence which can be derived from the represented nucleotide sequence by replacing the nucleotides through their complementary nucleotide according to Chargaff's rules (A↔T; G↔C) and reading the sequence in the 5' to 3' direction, i.e. in opposite direction of the represented nucleotide sequence.

Examples of primers suitable to identify specific mutant ROD1 alleles are described in the Examples.

As used herein, "the nucleotide sequence of SEQ ID No. Z from position X to position Y" indicates the nucleotide sequence including both nucleotide endpoints.

Preferably, the amplified fragment has a length of between 50 and 1000 nucleotides, such as a length between 50 and 500 nucleotides, or a length between 100 and 350 nucleotides. The specific primers may have a sequence which is between 80 and 100% identical to a sequence within the 5' or 3' flanking region, to a sequence within the mutation region, or to a sequence spanning the joining region between the 3' or 5' flanking and mutation regions of the specific mutant ROD1 allele, provided the mismatches still allow specific identification of the specific mutant ROD1 allele with these primers under optimized amplification conditions. The range of allowable mismatches however, can easily be determined experimentally and are known to a person skilled in the art.

Detection and/or identification of a "mutant ROD1 specific fragment" can occur in various ways, e.g., via size estimation after gel or capillary electrophoresis or via fluorescence-based detection methods. The mutant ROD1 specific fragments may also be directly sequenced. Other sequence specific methods for detection of amplified DNA fragments are also known in the art.

Standard nucleic acid amplification protocols, such as PCR protocols are described in the art, such as in 'PCR Applications Manual" (Roche Molecular Biochemicals, 2nd Edition, 1999) and other references. The optimal conditions for the amplification, including the sequence of the specific primers, is specified in a "PCR identification protocol" for each specific mutant ROD1 allele. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase, $MgCl_2$ concentration or annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Alternatively, specific primers can be used to amplify a mutant ROD1 specific fragment that can be used as a "specific probe" for identifying a specific mutant ROD1 allele in biological samples. Contacting nucleic acid of a biological sample, with the probe, under conditions that allow hybridization of the probe with its corresponding fragment in the nucleic acid, results in the formation of a nucleic acid/probe hybrid. The formation of this hybrid can be detected (e.g. labeling of the nucleic acid or probe), whereby the formation of this hybrid indicates the presence of the specific mutant ROD1 allele. Such identification methods based on hybridization with a specific probe (either on a solid phase carrier or in solution) have been described in the art. The specific probe is preferably a sequence that, under optimized conditions, hybridizes specifically to a region within the 5' or 3' flanking region and/or within the mutation region of the specific mutant ROD1 allele (hereinafter referred to as "mutant ROD1 specific region"). Preferably, the specific probe comprises a sequence of between 10 and 1000 bp, 50 and 600 bp, between 100 to 500 bp, between 150 to 350 bp, which is at least 80%, preferably between 80 and 85%, more preferably between 85 and 90%, especially preferably between 90 and 95%, most preferably between 95% and 100% identical (or complementary) to the nucleotide sequence of a specific region. Preferably, the specific probe will comprise a sequence of about 13 to about 100 contiguous nucleotides identical (or complementary) to a specific region of the specific mutant ROD1 allele.

Specific probes suitable for the invention may be the following:
  oligonucleotides ranging in length from 13 nt to about 1000 nt, comprising a nucleotide sequence of at least 13 consecutive nucleotides selected from the 5' or 3' flanking sequence of a specific mutant ROD1 allele or the complement thereof (i.e., for example, the sequence 5' or 3' flanking the one or more nucleotides deleted, inserted or substituted in the mutant ROD1 alleles of the invention, such as the sequence 5' or 3' flanking the non-sense, mis-sense, frameshift or splice site mutations described above or the sequence 5' or 3' flanking the potential STOP codon mutations indicated in the above Tables or the substitution mutations indicated above), or a sequence having at least 80% sequence identity therewith (probes recognizing 5' flanking sequences); or
  oligonucleotides ranging in length from 13 nt to about 1000 nt, comprising a nucleotide sequence of at least 13 consecutive nucleotides selected from the mutation sequence of a specific mutant ROD1 allele or the complement thereof (i.e., for example, the sequence of nucleotides inserted or substituted in the ROD1 genes of the invention, or the complement thereof), or a sequence having at least 80% sequence identity therewith (probes recognizing mutation sequences).

The probes may entirely consist of nucleotide sequence selected from the mentioned nucleotide sequences of flanking and mutation sequences. However, the nucleotide sequence of the probes at their 5' or 3' ends is less critical. Thus, the 5' or 3' sequences of the probes may consist of a nucleotide sequence selected from the flanking or mutation sequences, as appropriate, but may consist of a nucleotide sequence unrelated to the flanking or mutation sequences. Such unrelated sequences should preferably be no longer than 50, more preferably not longer than 25 or even no longer than 20 or 15 nucleotides.

Moreover, suitable probes may comprise or consist of a nucleotide sequence spanning the joining region between flanking and mutation sequences (i.e., for example, the joining region between a sequence 5' or 3' flanking one or more nucleotides deleted, inserted or substituted in the mutant ROD1 alleles of the invention and the sequence of the one or more nucleotides inserted or substituted or the sequence 3' or 5', respectively, flanking the one or more nucleotides deleted, such as the joining region between a sequence 5' or 3' flanking non-sense, mis-sense, frameshift or splice site mutations in the ROD1 genes of the invention described above and the sequence of the non-sense, mis-sense, frameshift or splice site mutations, or the joining region between a sequence 5' or 3' flanking a potential STOP codon mutation as indicated in the above Tables or the substitution mutations indicated above and the sequence of the potential STOP codon or substitution mutation, respectively), provided the mentioned nucleotide sequence is not derived exclusively from either the mutation region or flanking regions.

Detection and/or identification of a "mutant ROD1 specific region" hybridizing to a specific probe can occur in various ways, e.g., via size estimation after gel electrophoresis or via fluorescence-based detection methods. Other sequence specific methods for detection of a "mutant ROD1 specific region" hybridizing to a specific probe are also known in the art.

Alternatively, plants or plant parts comprising one or more mutant rod1 alleles can be generated and identified using other methods, such as the "Delete-a-gene™" method which uses PCR to screen for deletion mutants generated by fast neutron mutagenesis (reviewed by Li and Zhang, 2002, Funct Integr Genomics 2:254-258), by the TILLING (Targeting Induced Local Lesions IN Genomes) method which identifies EMS-induced point mutations using denaturing high-performance liquid chromatography (DHPLC) to detect base pair changes by heteroduplex analysis (McCallum et al., 2000, Nat Biotech 18:455, and McCallum et al. 2000, Plant Physiol. 123, 439-442), etc. As mentioned, TILLING uses high-throughput screening for mutations (e.g. using Cel 1 cleavage of mutant-wildtype DNA heteroduplexes and detection using a sequencing gel system). Thus, the use of TILLING to identify plants or plant parts comprising one or more mutant rod1 alleles and methods for generating and identifying such plants, plant organs, tissues and seeds is encompassed herein. Thus in one embodiment, the method according to the invention comprises the steps of mutagenizing plant seeds (e.g. EMS mutagenesis), pooling of plant individuals or DNA, PCR amplification of a region of interest, heteroduplex formation and high-throughput detection, identification of the mutant plant, sequencing of the mutant PCR product. It is understood that other mutagenesis and selection methods may equally be used to generate such mutant plants.

Instead of inducing mutations in ROD1 alleles, natural (spontaneous) mutant alleles may be identified by methods known in the art. For example, ECOTILLING may be used (Henikoff et al. 2004, Plant Physiology 135(2):630-6) to screen a plurality of plants or plant parts for the presence of natural mutant rod1 alleles. As for the mutagenesis techniques above, preferably Brassica species are screened which comprise an A and/or a C genome, so that the identified rod1 allele can subsequently be introduced into other Brassica species, such as Brassica napus, by crossing (inter- or intraspecific crosses) and selection. In ECOTILLING natural polymorphisms in breeding lines or related species are screened for by the TILLING methodology described above, in which individual or pools of plants are used for PCR amplification of the rod1 target, heteroduplex formation and high-throughput analysis. This can be followed by selecting individual plants having a required mutation that can be used subsequently in a breeding program to incorporate the desired mutant allele.

The identified mutant alleles can then be sequenced and the sequence can be compared to the wild type allele to identify the mutation(s). Optionally functionality can be tested as indicated above. Using this approach a plurality of mutant rod1 alleles (and Brassica plants comprising one or more of these) can be identified. The desired mutant alleles can then be combined with the desired wild type alleles by crossing and selection methods as described further below. Finally a single plant comprising the desired number of mutant rod1 and the desired number of wild type ROD1 alleles is generated.

Oligonucleotides suitable as PCR primers or specific probes for detection of a specific mutant ROD1 allele can also be used to develop methods to determine the zygosity status of the specific mutant ROD1 allele.

To determine the zygosity status of a specific mutant ROD1 allele, a nucleic acid amplification-based assay can be developed to determine the presence of a mutant and/or corresponding wild type ROD1 specific allele:

To determine the zygosity status of a specific mutant ROD1 allele, two primers specifically recognizing the wild-type ROD1 allele can be designed in such a way that they are directed towards each other and have the mutation region located in between the primers. These primers may be primers specifically recognizing the 5' and 3' flanking sequences, respectively. This set of primers allows simultaneous diagnostic amplification of the mutant, as well as of the corresponding wild type ROD1 allele.

Alternatively, to determine the zygosity status of a specific mutant ROD1 allele, two primers specifically recognizing the wild-type ROD1 allele can be designed in such a way that they are directed towards each other and that one of them specifically recognizes the mutation region. These primers may be primers specifically recognizing the sequence of the 5' or 3' flanking region and the mutation region of the wild type ROD1 allele, respectively. This set of primers, together with a third primer which specifically recognizes the sequence of the mutation region in the mutant ROD1 allele, allow simultaneous diagnostic amplification of the mutant ROD1 gene, as well as of the wild type ROD1 gene.

Alternatively, to determine the zygosity status of a specific mutant ROD1 allele, two primers specifically recognizing the wild-type ROD1 allele can be designed in such a way that they are directed towards each other and that one of them specifically recognizes the joining region between the 5' or 3' flanking region and the mutation region. These primers may be primers specifically recognizing the 5' or 3' flanking sequence and the joining region between the mutation region and the 3' or 5' flanking region of the wild type ROD1 allele, respectively. This set of primers, together with a third primer which specifically recognizes the joining region between the mutation region and the 3' or 5' flanking region of the mutant ROD1 allele, respectively, allow simultaneous diagnostic amplification of the mutant ROD1 gene, as well as of the wild type ROD1 gene.

Alternatively, the zygosity status of a specific mutant ROD1 allele can be determined by using alternative primer sets that specifically recognize mutant and wild type ROD1 alleles.

If the plant is homozygous for the mutant ROD1 gene or the corresponding wild type ROD1 gene, the diagnostic amplification assays described above will give rise to a single amplification product typical, preferably typical in length, for either the mutant or wild type ROD1 allele. If the plant is heterozygous for the mutant ROD1 allele, two specific amplification products will appear, reflecting both the amplification of the mutant and the wild tvae ROD1 allele.

Identification of the wild type and mutant ROD1 specific amplification products can occur e.g. by size estimation after gel or capillary electrophoresis (e.g. for mutant ROD1 alleles comprising a number of inserted or deleted nucleotides which results in a size difference between the fragments amplified from the wild type and the mutant ROD1 allele, such that said fragments can be visibly separated on a gel); by evaluating the presence or absence of the two different fragments after gel or capillary electrophoresis, whereby the diagnostic amplification of the mutant ROD1 allele can, optionally, be performed separately from the diagnostic amplification of the wild type ROD1 allele; by direct sequencing of the amplified fragments; or by fluorescence-based detection methods.

Examples of primers suitable to determine the zygosity of specific mutant ROD1 alleles are described in the Examples.

Alternatively, to determine the zygosity status of a specific mutant ROD1 allele, a hybridization-based assay can be developed to determine the presence of a mutant and/or corresponding wild type ROD1 specific allele:

To determine the zygosity status of a specific mutant ROD1 allele, two specific probes recognizing the wild-type ROD1 allele can be designed in such a way that each probe specifically recognizes a sequence within the ROD1 wild type allele and that the mutation region is located in between the sequences recognized by the probes. These probes may be probes specifically recognizing the 5' and 3' flanking sequences, respectively. The use of one or, preferably, both of these probes allows simultaneous diagnostic hybridization of the mutant, as well as of the corresponding wild type ROD1 allele.

Alternatively, to determine the zygosity status of a specific mutant ROD1 allele, two specific probes recognizing the wild-type ROD1 allele can be designed in such a way that one of them specifically recognizes a sequence within the ROD1 wild type allele upstream or downstream of the mutation region, preferably upstream of the mutation region, and that one of them specifically recognizes the mutation region. These probes may be probes specifically recognizing the sequence of the 5' or 3' flanking region, preferably the 5' flanking region, and the mutation region of the wild type ROD1 allele, respectively. The use of one or, preferably, both of these probes, optionally, together with a third probe which specifically recognizes the sequence of the mutation region in the mutant ROD1 allele, allow diagnostic hybridization of the mutant and of the wild type ROD1 gene.

Alternatively, to determine the zygosity status of a specific mutant ROD1 allele, a specific probe recognizing the wild-type ROD1 allele can be designed in such a way that the probe specifically recognizes the joining region between the 5' or 3' flanking region, preferably the 5' flanking region, and the mutation region of the wild type ROD1 allele. This probe, optionally, together with a second probe that specifically recognizes the joining region between the 5' or 3' flanking region, preferably the 5' flanking region, and the mutation region of the mutant ROD1 allele, allows diagnostic hybridization of the mutant and of the wild type ROD1 gene.

Alternatively, the zygosity status of a specific mutant ROD1 allele can be determined by using alternative sets of probes that specifically recognize mutant and wild type ROD1 alleles.

If the plant is homozygous for the mutant ROD1 gene or the corresponding wild type ROD1 gene, the diagnostic hybridization assays described above will give rise to a single specific hybridization product, such as one or more hybridizing DNA (restriction) fragments, typical, preferably typical in length, for either the mutant or wild type ROD1 allele. If the plant is heterozygous for the mutant ROD1 allele, two specific hybridization products will appear, reflecting both the hybridization of the mutant and the wild type ROD1 allele.

Identification of the wild type and mutant ROD1 specific hybridization products can occur e.g. by size estimation after gel or capillary electrophoresis (e.g. for mutant ROD1 alleles comprising a number of inserted or deleted nucleotides which results in a size difference between the hybridizing DNA (restriction) fragments from the wild type and the mutant ROD1 allele, such that said fragments can be visibly separated on a gel); by evaluating the presence or absence of the two different specific hybridization products after gel or capillary electrophoresis, whereby the diagnostic hybridization of the mutant ROD1 allele can, optionally, be performed separately from the diagnostic hybridization of the wild type ROD1 allele; by direct sequencing of the hybridizing DNA (restriction) fragments; or by fluorescence-based detection methods.

Furthermore, detection methods specific for a specific mutant ROD1 allele that differ from PCR- or hybridization-based amplification methods can also be developed using the specific mutant ROD1 allele specific sequence information provided herein. Such alternative detection methods include linear signal amplification detection methods based on invasive cleavage of particular nucleic acid structures, also known as Invader™ technology, (as described e.g. in U.S. Pat. No. 5,985,557 "Invasive Cleavage of Nucleic Acids", U.S. Pat. No. 6,001,567 "Detection of Nucleic Acid sequences by Invader Directed Cleavage, incorporated herein by reference), RT-PCR-based detection methods, such as Taqman, or other detection methods, such as SNPlex. Briefly, in the Invader™ technology, the target mutation sequence may e.g. be hybridized with a labeled first nucleic acid oligonucleotide comprising the nucleotide sequence of the mutation sequence or a sequence spanning the joining region between the 5' flanking region and the mutation region and with a second nucleic acid oligonucleotide comprising the 3' flanking sequence immediately downstream and adjacent to the mutation sequence, wherein the first and second oligonucleotide overlap by at least one nucleotide. The duplex or triplex structure that is produced by this hybridization allows selective probe cleavage with an enzyme (Cleavase®) leaving the target sequence intact. The cleaved labeled probe is subsequently detected, potentially via an intermediate step resulting in further signal amplification.

A "kit", as used herein, refers to a set of reagents for the purpose of performing the method of the invention, more particularly, the identification of a specific mutant ROD1 allele in biological samples or the determination of the zygosity status of plant material comprising a specific mutant ROD1 allele. More particularly, a preferred embodiment of the kit of the invention comprises at least two specific primers, as described above, for identification of a specific mutant ROD1 allele, or at least two or three specific primers for the determination of the zygosity status. Optionally, the kit can further comprise any other reagent described herein in the PCR identification protocol. Alternatively, according to another embodiment of this invention, the kit can comprise at least one specific probe, which specifically hybridizes with nucleic acid of biological samples to identify the presence of a specific mutant ROD1 allele therein, as described above, for identification of a specific mutant ROD1 allele, or at least two or three specific probes for the determination of the zygosity status. Optionally, the kit can further comprise any other reagent (such as but not limited to hybridizing buffer, label) for identification of a specific mutant ROD1 allele in biological samples, using the specific probe.

The kit of the invention can be used, and its components can be specifically adjusted, for purposes of quality control (e.g., purity of seed lots), detection of the presence or absence of a specific mutant ROD1 allele in plant material or material comprising or derived from plant material, such as but not limited to food or feed products.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in a specific mutant ROD1 allele under the conditions set forth in the method (such as the conditions of the PCR identification protocol), whereby the specificity is determined by the presence of positive and negative controls.

The term "hybridizing", as used herein when referring to specific probes, refers to the fact that the probe binds to a specific region in the nucleic acid sequence of a specific mutant ROD1 allele under standard stringency conditions. Standard stringency conditions as used herein refers to the conditions for hybridization described herein or to the conventional hybridizing conditions as described by Sambrook et al., 1989 (Molecular Cloning: A Laboratory Manual, Second Edition, Cold Spring Harbour Laboratory Press, NY) which for instance can comprise the following steps: 1) immobilizing plant genomic DNA fragments or BAC library DNA on a filter, 2) prehybridizing the filter for 1 to 2 hours at 65° C. in 6×SSC, 5×Denhardt's reagent, 0.5% SDS and 20 µg/ml denatured carrier DNA, 3) adding the hybridization probe which has been labeled, 4) incubating for 16 to 24 hours, 5) washing the filter once for 30 min. at 68° C. in 6×SSC, 0.1% SDS, 6) washing the filter three times (two times for 30 min. in 30 ml and once for 10 min in 500 ml) at 68° C. in 2×SSC, 0.1% SDS, and 7) exposing the filter for 4 to 48 hours to X-ray film at −70° C.

As used in herein, a "biological sample" is a sample of a plant, plant material or product comprising plant material. The term "plant" is intended to encompass plant tissues, at any stage of maturity, as well as any cells, tissues, or organs taken from or derived from any such plant, including without limitation, any seeds, leaves, stems, flowers, roots, single cells, gametes, cell cultures, tissue cultures or protoplasts. "Plant material", as used herein refers to material that is obtained or derived from a plant. Products comprising plant material relate to food, feed or other products that are produced using plant material or can be contaminated by plant material. It is understood that, in the context of the present invention, such biological samples are tested for the presence of nucleic acids specific for a specific mutant ROD1 allele, implying the presence of nucleic acids in the samples. Thus the methods referred to herein for identifying a specific mutant ROD1 allele in biological samples, relate to the identification in biological samples of nucleic acids that comprise the specific mutant ROD1 allele.

Another embodiment provides a chimeric gene comprising the following operably linked elements: a plant-expressible promoter; a DNA region, which when transcribed yields an RNA molecule inhibitory to at least one ROD1 gene; and optionally a transcription termination and polyadenylation region functional in plant cells.

In again another embodiment, a knock-out allele of an ROD1 gene is provided, wherein the knock-out ROD1 allele is a mutated version of the native ROD1 gene selected from the group consisting of: a nucleic acid molecule which comprises at least 90% sequence identity to SEQ ID No. 1, SEQ ID No. 4, SEQ ID No. 7, SEQ ID No. 10, SEQ ID No. 13, SEQ ID No. 16, SEQ ID No. 19, SEQ ID No. 22, SEQ ID No. 25, SEQ ID No. 28, SEQ ID No. 31, SEQ ID No. 34, SEQ ID No. 84, SEQ ID No. 86, SEQ ID No. 88, or SEQ ID No. 90; or a nucleic acid molecule encoding an amino acid sequence comprising at least 90% sequence identity to SEQ ID No. 3, SEQ ID No. 6, SEQ ID No. 9, SEQ ID No. 12, SEQ ID No. 15, SEQ ID No. 18, SEQ ID No. 21, SEQ ID No. 24, SEQ ID No. 27, SEQ ID No. 30, SEQ ID No. 33, SEQ ID No. 36, SEQ ID No. 85, SEQ ID No. 87, SEQ ID No. 89, or SEQ ID No. 91, wherein said mutant rod1 allele comprises a mutated DNA region consisting of one or more inserted, deleted or substituted nucleotides compared to a corresponding wild-type DNA region in the functional ROD1 gene and wherein said mutant rod1 allele encodes no functional ROD1 protein or encodes a ROD1 protein with reduced activity.

The chimeric gene according to the invention can be used to produce plants, such as *Brassica* plants, with increased levels of C18:1 in the seeds, or with decreased levels of C18:2 or SATS in the seeds, or to produce seed oil with increased levels of C18:1, or with decreased levels of C18:2 or SATS.

In a further embodiment, a method is provided for producing oil, comprising harvesting seeds from the plants according to the invention, i.e. plants comprising a knock-out ROD1 gene or an RNA inhibitory to a ROD1 gene, and extracting the oil from said seeds.

In yet a further embodiment, a method is provided of producing food or feed, such as oil, meal, grain, starch, flour or protein, or an industrial product, such as biofuel, fiber, industrial chemicals, a pharmaceutical or a neutraceutical, comprising obtaining the plant or a part thereof according to the invention, and preparing the food, feed or industrial product from the plant or part thereof.

Plants according to the invention, such as plants comprising at least one knock-out ROD1 gene or plants comprising an RNA molecule inhibitory to at least one ROD1 gene can further be used to produce seeds, such as seeds with increased levels of C18:1, or seeds with decreased levels of C18:2 or SATS, or to produce seed oil with increased levels of C18:1, or with decreased levels of C18:2 or SATS.

The plants according to the invention may additionally contain an endogenous or a transgene, which confers herbicide resistance, such as the bar or pat gene, which confer resistance to glufosinate ammonium (Liberty®, Basta® or Ignite®) [EP 0 242 236 and EP 0 242 246 incorporated by reference]; or any modified EPSPS gene, such as the 2mEPSPS gene from maize [EPO 508 909 and EP 0 507 698 incorporated by reference], or glyphosate acetyltransferase, or glyphosate oxidoreductase, which confer resistance to glyphosate (RoundupReady®), or bromoxynitril nitrilase to confer bromoxynitril tolerance, or any modified AHAS gene, which confers tolerance to sulfonylureas, imidazolinones, sulfonylamino carbonyltriazolinones, triazolopyrimidines or pyrimidyl(oxy/thio)benzoates, such as oilseed rape imidazolinone-tolerant mutants PM1 and PM2, currently marketed as Clearfield® canola. Further, the plants according to the invention may additionally contain an endogenous or a transgene which confers increased oil content or improved oil composition, such as a 12:0 ACP thioesteraseincrease to obtain high laureate, which confers pollination control, such as barnase under control of an anther-specific promoter to obtain male sterility, or barstar under control of an anther-specific promoter to confer restoration of male sterility, or such as the Ogura cytoplasmic male sterility and nuclear restorer of fertility.

The plants and seeds according to the invention may be further treated with a chemical compound, such as a chemical compound selected from the following lists:

Herbicides: Clethodim, Clopyralid, Diclofop, Ethametsulfuron, Fluazifop, Glufosinate, Glyphosate, Metazachlor, Quinmerac, Quizalo fop, Tepraloxydim, Trifluralin.

Fungicides/PGRs: Azoxystrobin, N-[9-(dichloromethylene)-1,2,3,4-tetrahydro-1,4-methanonaphthalen-5-yl]-3-(difluoromethyl)-1-methyl-1H-pyrazole-4-carboxamide (Benzovindiflupyr, Benzodiflupyr), Bixafen, Boscalid, Carbendazim, Carboxin, Chlormequat-chloride, Coniothryrium minitans, Cyproconazole, Cyprodinil, Difenoconazole, Dimethomorph, Dimoxystrobin, Epoxiconazole, Famoxadone, Fluazinam, Fludioxonil, Fluopicolide, Fluopyram, Fluoxastrobin, Fluquinconazole, Flusilazole, Fluthianil, Flutriafol, Fluxapyroxad, Iprodione, Isopyrazam, Mefenoxam, Mepiquat-chloride, Metalaxyl, Metconazole, Metominostrobin, Paclobutrazole, Penflufen, Penthiopyrad, Picoxystrobin, Prochloraz, Prothioconazole, Pyraclostrobin, Sedaxane, Tebuconazole, Tetraconazole, Thiophanate-methyl, Thiram, Triadimenol, Trifloxystrobin, *Bacillus firmus, Bacillus firmus* strain 1-1582, *Bacillus subtilis, Bacillus subtilis* strain GB03, *Bacillus subtilis* strain QST 713, *Bacillus pumulis, Bacillus. pumulis* strain GB34.

Insecticides: Acetamiprid, Aldicarb, Azadirachtin, Carbofuran, Chlorantraniliprole (Rynaxypyr), Clothianidin, Cyantraniliprole (Cyazypyr), (beta-)Cyfluthrin, gamma-Cyhalothrin, lambda-Cyhalothrin, Cypermethrin, Deltamethrin, Dimethoate, Dinetofuran, Ethiprole, Flonicamid, Flubendiamide, Fluensulfone, Fluopyram, Flupyradifurone, tau-Fluvalinate, Imicyafos, Imidacloprid, Metaflumizone, Methiocarb, Pymetrozine, Pyrifluquinazon, Spinetoram, Spinosad, Spirotetramate, Sulfoxaflor, Thiacloprid, Thiamethoxam, 1-(3-chloropyridin-2-yl)-N-[4-cyano-2-methyl-6-(methylcarbamoyl)phenyl]-3-{[5-(trifluoromethyl)-2H-tetrazol-2-yl]methyl}-1H-pyrazole-5-carboxamide, 1-(3-chloropyridin-2-yl)-N-[4-cyano-2-methyl-6-(methylcarbamoyl)phenyl]-3-{[5-(trifluoromethyl)-1H-tetrazol-1-yl]methyl}-1H-pyrazole-5-carboxamide, 1-{2-fluoro-4-methyl-5-[(2,2,2-trifluoroethyl)sulfinyl]phenyl}-3-(trifluoromethyl)-1H-1,2,4-triazol-5-amine, (1E)-N-[(6-chloropyridin-3-yl)methyl]-N'-cyano-N-(2,2-difluoroethyl)ethanimidamide, *Bacillus firmus, Bacillus firmus* strain I-1582, *Bacillus subtilis, Bacillus subtilis* strain GB03, *Bacillus subtilis* strain QST 713, *Metarhizium anisopliae* F52.

In some embodiments, the plant cells of the invention, i.e. a plant cell comprising a knock-out rod1 gene or an RNA inhibitory to a ROD1 gene, as well as plant cells generated according to the methods of the invention, may be non-propagating cells.

The obtained plants according to the invention can be used in a conventional breeding scheme to produce more plants with the same characteristics or to introduce the characteristic according to the invention in other varieties of the same or related plant species, or in hybrid plants. The obtained plants can further be used for creating propagating material. Plants according to the invention can further be used to produce gametes, seeds (including crushed seeds and seed cakes), seed oil, embryos, either zygotic or somatic, progeny, or to produce food or feed, such as oil, meal, grain, starch, flour or protein, or an industrial product, such as bio fuel, fiber, industrial chemicals, a pharmaceutical or a neutraceutical, or to produce hybrids of plants obtained by methods of the invention.

All patents, patent applications, and publications or public disclosures (including publications on internet) referred to or cited herein are incorporated by reference in their entirety.

The sequence listing contained in the file named "BCS12-2010-US1_ST25.txt", which is 216 kilobytes (size as measured in Microsoft Windows®), contains 91 sequences SEQ ID NO: 1 through SEQ ID NO: 91 and was created on 2 Jul. 2012 is filed herewith by electronic submission and is incorporated by reference herein.

In the description and examples, reference is made to the following sequences:

Sequences

SEQ ID No. 1: Genomic DNA sequence of ROD1-A1 from *Brassica napus*.

SEQ ID No. 2: cDNA sequence of ROD1-A1 from *Brassica napus*.

SEQ ID No. 3: protein sequence of ROD1-A1 from *Brassica napus*.

SEQ ID No. 4: Genomic DNA sequence of ROD1-C1 from *Brassica napus*.

SEQ ID No. 5: cDNA sequence of ROD1-C1 from *Brassica napus*.

SEQ ID No. 6: protein sequence of ROD1-C1 from *Brassica napus*.

SEQ ID No. 7: Genomic DNA sequence of ROD1-A2 from *Brassica napus*.

SEQ ID No. 8: cDNA sequence of ROD1-A2 from *Brassica napus*.

SEQ ID No. 9: protein sequence of ROD1-A2 from *Brassica napus*.

SEQ ID No. 10: Genomic DNA sequence of ROD1-C2 from *Brassica napus*.

SEQ ID No. 11: cDNA sequence of ROD1-C2 from *Brassica napus*.

SEQ ID No. 12: protein sequence of ROD1-C2 from *Brassica napus*.

SEQ ID No. 13: Genomic DNA sequence of ROD1-1 from *Brassica rapa*.

SEQ ID No. 14: cDNA sequence of ROD1-1 from *Brassica rapa*.

SEQ ID No. 15: protein sequence of ROD1-1 from *Brassica rapa*.

SEQ ID No. 16: Genomic DNA sequence of ROD1-2 from *Brassica rapa*.

SEQ ID No. 17: cDNA sequence of ROD1-2 from *Brassica rapa*.

SEQ ID No. 18: protein sequence of ROD1-2 from *Brassica rapa*.

SEQ ID No. 19: Genomic DNA sequence of ROD1-3 from *Brassica rapa*.

SEQ ID No. 20: cDNA sequence of ROD1-3 from *Brassica rapa*.

SEQ ID No. 21: protein sequence of ROD1-3 from *Brassica rapa*.

SEQ ID No. 22: Genomic DNA sequence of ROD1-4 from *Brassica rapa*.

SEQ ID No. 23: cDNA sequence of ROD1-4 from *Brassica rapa*.

SEQ ID No. 24: protein sequence of ROD1-4 from *Brassica rapa*.

SEQ ID No. 25: Genomic DNA sequence of ROD1-1 from *Brassica oleracea*.

SEQ ID No. 26: cDNA sequence of ROD1-1 from *Brassica oleracea*.

SEQ ID No. 27: protein sequence of ROD1-1 from *Brassica oleracea*.
SEQ ID No. 28: Genomic DNA sequence of ROD1-2 from *Brassica oleracea*.
SEQ ID No. 29: cDNA sequence of ROD1-2 from *Brassica oleracea*.
SEQ ID No. 30: protein sequence of ROD1-2 from *Brassica oleracea*.
SEQ ID No. 31: Genomic DNA sequence of ROD1-3 from *Brassica oleracea*.
SEQ ID No. 32: cDNA sequence of ROD1-3 from *Brassica oleracea*.
SEQ ID No. 33: protein sequence of ROD1-3 from *Brassica oleracea*.
SEQ ID No. 34: Genomic DNA sequence of ROD1-4 from *Brassica oleracea*.
SEQ ID No. 35: cDNA sequence of ROD1-4 from *Brassica oleracea*.
SEQ ID No. 36: protein sequence of ROD1-4 from *Brassica oleracea*.
SEQ ID No. 37: Primer BnROD1_A1/C1 Forward.
SEQ ID No. 38: Primer BnROD1_A1/C1 Reverse.
SEQ ID No. 39: Primer BnROD1_A2 Forward.
SEQ ID No. 40: Primer BnROD1_A2 Reverse.
SEQ ID No. 41: Primer BnROD1_C2 Forward.
SEQ ID No. 42: Primer BnROD1_C2 Reverse.
SEQ ID No. 43: Primer BnROD1 F1.
SEQ ID No. 44: Primer BnROD1 R1.
SEQ ID No. 45: Primer BnROD1 F2.
SEQ ID No. 46: Primer BnROD1 R2.
SEQ ID No. 47: expression cassette of the ROD1-Bn1 hairpin of pTCO363.
SEQ ID No. 48: expression cassette of the ROD1-Bn2 hairpin of pTCO364.
SEQ ID No. 49: FAM primer HIOL302.
SEQ ID No. 50: VIC primer HIOL302.
SEQ ID No. 51: Reverse primer HIOL302.
SEQ ID No. 52: FAM primer HIOL303.
SEQ ID No. 53: VIC primer HIOL303.
SEQ ID No. 54: Reverse primer HIOL303.
SEQ ID No. 55: FAM primer HIOL304.
SEQ ID No. 56: VIC primer HIOL304.
SEQ ID No. 57: Reverse primer HIOL304.
SEQ ID No. 58: FAM primer HIOL306.
SEQ ID No. 59: VIC primer HIOL306.
SEQ ID No. 60: Reverse primer HIOL306.
SEQ ID No. 61: FAM primer HIOL307.
SEQ ID No. 62: VIC primer HIOL307.
SEQ ID No. 63: Reverse primer HIOL307.
SEQ ID No. 64: FAM primer HIOL308.
SEQ ID No. 65: VIC primer HIOL308.
SEQ ID No. 66: Reverse primer HIOL308.
SEQ ID No. 67: FAM primer HIOL309.
SEQ ID No. 68: VIC primer HIOL309.
SEQ ID No. 69: Reverse primer HIOL309.
SEQ ID No. 70: FAM primer HIOL310.
SEQ ID No. 71: VIC primer HIOL310.
SEQ ID No. 72: Reverse primer HIOL310.
SEQ ID No. 73: FAM primer HIOL311.
SEQ ID No. 74: VIC primer HIOL311.
SEQ ID No. 75: FAM primer HIOL313.
SEQ ID No. 76: VIC primer HIOL313.
SEQ ID No. 77: FAM primer HIOL315.
SEQ ID No. 78: VIC primer HIOL315.
SEQ ID No. 79: Reverse primer HIOL315.
SEQ ID No. 80: FAM primer HIOL316.
SEQ ID No. 81: VIC primer HIOL316.
SEQ ID No. 82: FAM primer HIOL318-319.
SEQ ID No. 83: VIC primer HIOL318-319.
SEQ ID No. 84: cDNA sequence of ROD1-A3 from *Brassica napus*.
SEQ ID No. 85: protein sequence of ROD1-A3 from *Brassica napus*.
SEQ ID No. 86: cDNA sequence of ROD1-C3 from *Brassica napus*.
SEQ ID No. 87: protein sequence of ROD1-C3 from *Brassica napus*.
SEQ ID No. 88: cDNA sequence of ROD1-A4 from *Brassica napus*.
SEQ ID No. 89: protein sequence of ROD1-A4 from *Brassica napus*.
SEQ ID No. 90: cDNA sequence of ROD1-C4 from *Brassica napus*.
SEQ ID No. 91: protein sequence of ROD1-C4 from *Brassica napus*.

EXAMPLES

Unless stated otherwise in the Examples, all recombinant DNA techniques are carried out according to standard protocols as described in Sambrook and Russell (2001) Molecular Cloning: A Laboratory Manual, Third Edition, Cold Spring Harbor Laboratory Press, NY, in Volumes 1 and 2 of Ausubel et al. (1994) Current Protocols in Molecular Biology, Current Protocols, USA and in Volumes I and II of Brown (1998) Molecular Biology LabFax, Second Edition, Academic Press (UK). Standard materials and methods for plant molecular work are described in Plant Molecular Biology Labfax (1993) by R. D. D. Croy, jointly published by BIOS Scientific Publications Ltd (UK) and Blackwell Scientific Publications, UK. Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany. Standard procedures for AFLP analysis are described in Vos et al. (1995, NAR 23:4407-4414) and in published EP patent application EP 534858.

Example 1—Isolation of the DNA Sequences of *Brassica* ROD1 Genes

A TBLASTN homology search using the *A. thaliana* ROD1 gene sequence (At3g15280) as the query resulted in the identification of the unigene sequence Bna.6194 from a *B. napus* EST database as the homolog of *A. thaliana* ROD1. Subsequently, Bna.6194 was used as the query in a BLAST homology search of in-house databases of *Brassica rapa* coding sequences and of *Brassica oleracea* coding sequences. The contigs in these databases were obtained by assembly of short sequence reads using the software package SOAPdenovo. The BLAST analyses resulted in the identification of 4 ROD1 gene homologs for *B. rapa* (BrROD1-1 (SEQ ID No. 13), BrROD1-2 (SEQ ID No. 16), BrROD1-3 (SEQ ID No. 19) and BrROD1-4 (SEQ ID No. 22)) and 4 ROD1 gene homologs for *B. oleracea* (BoROD1-1 (SEQ ID No. 25), BoROD1-2 (SEQ ID No. 28), BoROD1-3 (SEQ ID No. 31) and BoROD1-4 (SEQ ID No. 34)). cDNAs corresponding to these sequences were predicted using FgeneSH software, and are depicted in SEQ ID No. 14, SEQ ID No. 17, SEQ ID No. 20, SEQ ID No. 23, SEQ ID No. 26, SEQ ID No. 29, SEQ ID No. 32, and SEQ ID No. 35, respectively. A BLAST homology search of an in-house database containing *Brassica napus* mRNA sequences using the *B. rapa* BrROD1 gene sequences resulted in the identification of the cDNA sequences of *B. napus* BnROD1-A1 (SEQ ID No. 2), BnROD1-A2 (SEQ ID No. 8), BnROD1-A3 (SEQ ID No. 84), and BnROD1-A4 (SEQ ID No. 88). Based on gene structure predictions using the Fgenesh software or mRNA derived sequencing read abundance the corresponding coding sequences were identified. Similarly, a BLAST homology search of the in-house database containing *Brassica napus* mRNA sequences using the *B. oleracea* BoROD1 gene sequences as a query resulted in the identification of the cDNA sequences of BnROD1-C1 (SEQ ID No. 5), BnROD1-C2 (SEQ ID No. 11), BnROD1-C3 (SEQ ID No. 86), and BnROD1-C4 (SEQ ID No. 90). The corresponding coding sequences were obtained following the above-mentioned gene structure prediction methods.

In order to retrieve the *B. napus* ROD1 gene sequences a BAC library was screened. Following standard GS-FLX sequencing of the positive library clones and de novo contig assembly using the 454 assembly software Newbler the gene sequences for BnROD1-A1 (SEQ ID No. 1), BnROD1-A2 (SEQ ID No. 7), BnROD1-C1 (SEQ ID No. 4) and BnROD1-C2 (SEQ ID No. 10) were identified.

Example 2—Expression Analysis of *Brassica napus* ROD1 Genes

The relative gene expression levels of *Brassica* spp. ROD1 genes were determined through analysis of Illumina mRNAseq derived transcriptome databases obtained for multiple tissues and developmental stages. Gene expression levels were calculated taking into account a normalization step for the sequencing depth per database (target reads per million reads in the database) and for the target gene length (reads per kilobase per million reads in the database [RPKM; Mortazavi A, Williams B A, McCue K, Schaeffer L, Wold B: Mapping and quantifying mammalian transcriptomes by RNA-Seq. Nature Methods (2008), 5(7):621-628].

The result of the expression analysis is shown in FIG. 1. From this figure it can be seen that BnROD1-A1 and BnROD1-C1 have the highest levels of expression, and that the expression is highest in flower buds. Moreover, there is some expression of BnROD1-A1 and BnROD1-C1 in seeds from 21-25 days after fertilization till about 42 days after fertilization.

Example 3—Generation and Isolation of Mutant *Brassica napus* Rod1 Alleles

Mutations in the ROD1 genes from *Brassica napus* identified in Example 1 were generated and identified as follows: 30,000 seeds from an elite spring oilseed rape breeding line (M0 seeds) were preimbibed for two hours on wet filter paper in deionized or distilled water. Half of the seeds were exposed to 0.8% EMS and half to 1% EMS (Sigma: M0880) and incubated for 4 hours.

The mutagenized seeds (M1 seeds) were rinsed 3 times and dried in a fume hood overnight. 30,000 M1 plants were grown in soil and selfed to generate M2 seeds. M2 seeds were harvested for each individual M1 plant.

Two times 4800 M2 plants, derived from different M1 plants, were grown and DNA samples were prepared from leaf samples of each individual M2 plant according to the CTAB method (Doyle and Doyle, 1987, Phytochemistry Bulletin 19:11-15).

The DNA samples were screened for the presence of point mutations in the ROD1 genes causing the introduction of STOP codons in the protein-encoding regions of the ROD1 genes, amino acid substitutions, or the disruption of splice sites in the ROD1 mRNA, by direct sequencing by standard sequencing techniques and analyzing the sequences for the presence of the point mutations using the NovoSNP software.

The following mutant rod1 alleles were thus identified:

TABLE 2a mutations in BnROD1-A1

| Plant name | Allele | Nt pos Genomic SEQ ID 1 | Nt pos. cDNA SEQ ID 2 | AA pos. SEQ ID 3 | WT → mut codon | WT → mut AA |
|---|---|---|---|---|---|---|
| HIOL301 | EMS01 | 1786 | 652 | 134 | ACG→ATG | T→M |
| HIOL302 | EMS02 | 1802 | 668 | 139 | TGG→TGA | W→Stop |
| HIOL303 | EMS03 | 1804 | 670 | 140 | ACA→ATA | T→I |
| HIOL304 | EMS04 | 1818 | 684 | 145 | GGA→AGA | G→R |
| HIOL305 | EMS05 | 1822 | 688 | 146 | AGA→AAA | R→K |
| HIOL306* | EMS06 | 1834 | 700 | 150 | ACT→ATT | T→I |
| HIOL307* | EMS07 | 1866 | 732 | 161 | GGC→AGC | G→S |

TABLE 2b mutations in BnROD1-C1

| Plant name | Allele | Nt pos Genomic SEQ ID 4 | Nt pos. cDNA SEQ ID 5 | AA pos. SEQ ID 6 | WT → mut codon | WT → mut AA |
|---|---|---|---|---|---|---|
| HIOL308 | EMS01 | 2917 | 636 | 129 | GCG→ACG | A→T |
| HIOL309 | EMS02 | 2930 | 649 | 133 | ACG→ATG | T→M |
| HIOL310* | EMS03 | 2956 | 675 | 142 | GAA→AAA | E→K |
| HIOL311 | EMS04 | 2963 | 682 | 144 | AGA→AAA | R→K |
| HIOL312 | EMS05 | 2981 | 700 | 150 | TCG→TTG | S→L |
| HIOL313* | EMS06 | 3005 | 724 | 158 | CGC→CAC | R→H |
| HIOL314 | EMS07 | 3008 | 727 | 159 | GGT→GAT | G→D |
| HIOL315 | EMS08 | 3040 | 759 | 170 | CCA→TCA | P→S |
| HIOL316* | EMS09 | 3046 | — | SPLICE | -GT-→-AT | SPLICE |

TABLE 2b-continued mutations in BnROD1-C1

| Plant name | Allele | Nt pos Genomic SEQ ID 4 | Nt pos. cDNA SEQ ID 5 | AA pos. SEQ ID 6 | WT → mut codon | WT → mut AA |
| --- | --- | --- | --- | --- | --- | --- |
| HIOL317 | EMS10 | 2907 | — | SPLICE | AG-→AA- | SPLICE |
| HIOL318* | EMS11 | 2968 | 687 | 146 | CGA→TGA | R→STOP |
| HIOL319* | EMS12 | 2968 | 687 | 146 | CGA→TGA | R→STOP |

Footnotes*: Seeds comprising a mutant BnROD1-A1 allele comprising the HIOL306 mutation in homozygous state or the HIOL307 mutation in homozygous state have been deposited at the NCIMB (NCIMB Ltd, Ferguson Building, Craibstone Estate, Bucksburn, Aberdeen AB21 9YA, Scotland, UK) on 28 June 2012, under accession number NCIMB 41995 and NCIMB 42000, respectively. Seeds comprising a mutant BnROD1-C1 allele comprising the HIOL310 mutation in homozygous state, the HIOL313 mutation in homozygous state, the HIOL316 mutation in homozygous state, the HIOL318 mutation in homozygous state, or the HIOL319 mutation in homozygous state have been deposited at the NCIMB (NCIMB Ltd, Ferguson Building, Craibstone Estate, Bucksburn, Aberdeen AB21 9YA, Scotland, UK) on 28 June 2012, under accession number NCIMB 41996, NCIMB 42001, NCIMB 41997, NCIMB 41998, and NCIMB 41999, respectively.

Example 4—Activity of BnROD1 Alleles in Yeast

The activity of the Brassica napus ROD1-A1, ROD1-A2, ROD1-C1 and ROD1-C2 alleles, as well as mutant alleles of BnROD1-A1 and BnROD1-C1, were tested in yeast.

Cloning of the ROD1 Alleles in East Expression Vectors

BnROD1-A1, BnROD1-C1, BnROD1-A2 and BnROD1-C2 and their mutant alleles were amplified by KOD DNA polymerase (Toyobo Life Science Department, http://www-.toyobo-global.com), using primers that created 5' BamHI and 3' EcoRI restriction sites.

BnROD1-A1 and BnROD1-C1 and their mutant alleles were amplified with the primers BnROD1_A1/C1 Forward (SEQ ID No. 37) and BnROD1_A1/C1 Reverse (SEQ ID No. 38). BnROD1-A2 (with codon usage optimized for yeast) was amplified with the primers BnROD1_A2 Forward (SEQ ID No. 39) and BnROD1_A2 Reverse (SEQ ID No. 40), and BnROD1-C2 (with codon usage optimized for yeast) was amplified with the primers BnROD1_C2 Forward (SEQ ID No. 41) and BnROD1_C2 Reverse (SEQ ID No. 42). Following BamHI and EcoRI double digestion, each product was ligated into the p424GPD vector (ATCC, http://www.atcc.org/), in which the cDNA is expressed under control of the constitutive Glyceraldehyde-3-P dehydrogenase promoter, and then transformed into E. coli competent cells (TOP10, Invitrogen). Plasmids with correct inserts confirmed by sequencing were transformed into yeast HJ091 cells (cpt1::LEU2 ept1-), and transformants were selected by synthetic minimal media (SD base) with dropout leucine and tryptophan (DO-Leu/-Trp) (Clontech, http://www.clontech.com).

Activity Testing of the ROD1 Alleles in Yeast

ROD1 activity assay was modified based on Supplementary Information in Lu et al., 2009 (PNAS, 2009, 106 (44):18837-18842, S1 Materials and Methods). Yeast cells were inoculated from overnight cultures and grown to mid-log phase (OD600=0.5–1.5) at 30° C. in liquid media SD/-Leu/-Trp. To prepare a total membrane fraction, 100 ml yeast cells were harvested by centrifugation at 1500 g for 5 min. Each cell pellet was washed once with sterile water and then resuspended in ice-cold glucose-Tris-EDTA (GTE) buffer [20% glycerol, 50 mM glucose, 25 mM Tris-HCl, pH 7.4, 10 mM EDTA]. Cells were then vortexed for 30 seconds×8 times with 30 seconds gaps on ice. The resulting homogenate was centrifuged at 2,500 g at 4° C. for 10 min to pellet cell debris. The supernatant was centrifuged at 100,000 g at 4° C. for 1 h and the membrane pellet was resuspended in 200 µL GTE buffer. The protein concentration was determined by Bradford assay.

The PDCT activities in membrane preparations of HJ091 cells transformed with p424GPD (control) or p424BnROD1 and mutant alleles were determined as the amount of [14C] dioleoyl-PC produced from 1,2-dioleoyl-rac-glycerol [14C (U)] ([14C-glycerol]diolein). The substrates of 1.8 nmol (200,000 cpm) [14C-glycerol]diolein (American Radiolabeled Chemicals, Inc. (http://www.arcinc.com) and 0.1 µmmol dioleoyl-PC were dried under nitrogen gas and resuspended in 50 µL of 4× reaction buffer [final concentrations: 50 mM 3-(N-morpholino)propanesulfonic acid (MOPS)/NaOH (pH 7.5), 20 mM $MgCl_2$, 0.45% Triton X-100] by 2 minutes sonication in a bath sonicator. Reactions (200 µL) were started by adding 50 ng of microsomal proteins suspended in the GTE buffer. Assays were incubated at 15° C. for 15 min and were terminated by the addition of 3 mL of chloroform/ethanol (2:1, vol./vol.), followed by 1.5 mL of 0.9% KCl. Tubes were mixed by vortexing, and phase separation was facilitated by centrifugation at 2,000 g for 2 min. The aqueous phase was aspirated, and the organic phase was washed twice with 1.5 mL of 40% (vol./vol.) ethanol. Samples were analyzed by TLC on Whatman Partisil® K6 silica gel 60 Å 20×20 cm glass plates (Whatman, http://www.whatman.com) in a solvent system of chloroform/methanol/water (65:25:4, by volume), followed by phosphorimaging analysis (phosphorimager 445 SI, Lab Extreme, Inc, http://www.labextreme.com). Corresponding bands were scraped, and radioactivity was determined by scintillation counting on a TRI-CARB® liquid scintillation analyzer (Packard Instrument Company).

Figure 2:
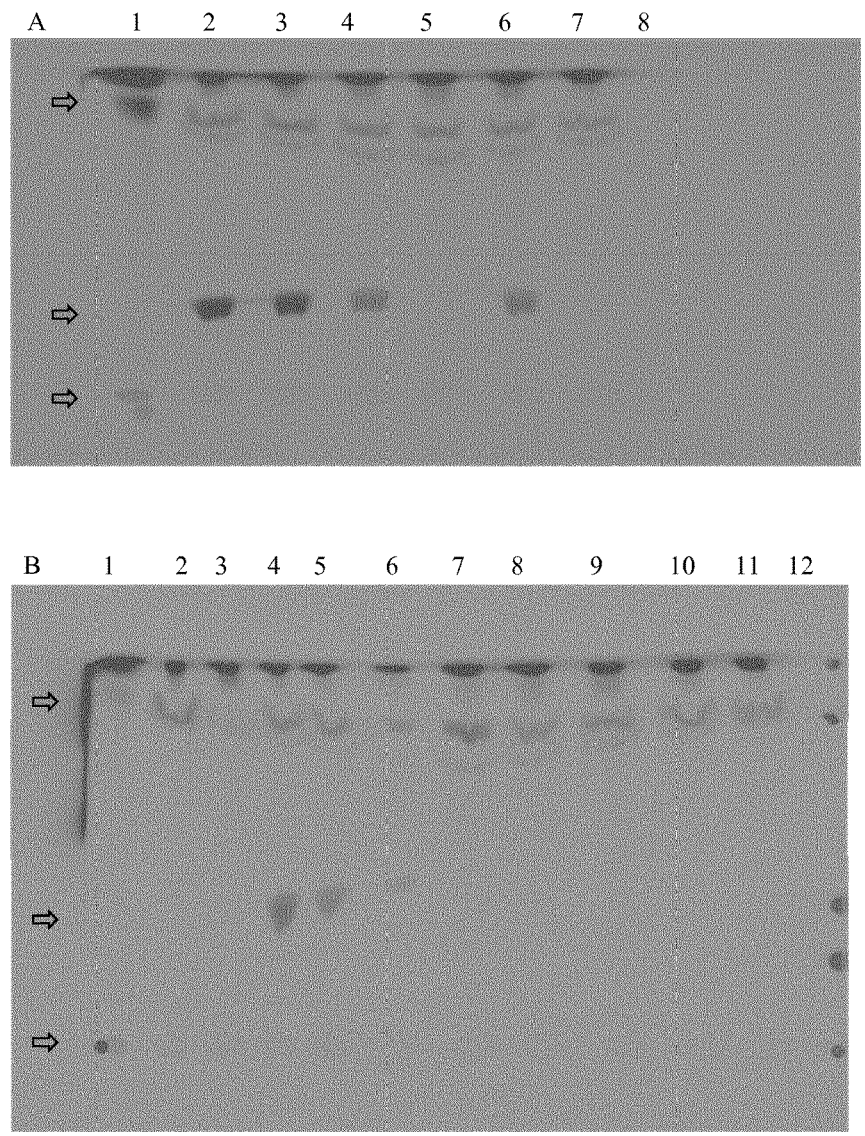
FIG. 2. Activity of the ROD1 alleles in yeast. A: activity of wild-type BnROD1 homologues. Lane 1: DAG; Lane 2: *Arabidopsis* ROD1, Lane 3: *Arabidopsis* ROD1; lane 4: BnROD1-A1; lane 5: BnROD1-A2; Lane 6: BnROD1-C1; Lane7: BnROD1-C2, lane 8: PC. B: Activity of mutants of BnROD1-A1. Lane 1: DAG; Lane 2: Negative control (empty vector), Lane 3: Boiled *Arabidopsis* ROD1; lane 4: *Arabidopsis* ROD1; lane 5: BnROD1-A1; Lane 6: BnROD1-A1 mutant HIOL305; Lane7: BnROD1-A1 mutant HIOL306; lane 8: BnROD1-A1 mutant HIOL307; lane 9: BnROD1-A1 mutant HIOL302; lane 10: BnROD1-A2; lane 11: BnROD1-C2; lane 12: PC. C: Activity of mutants of BnROD1-C1. Lane 1: DAG; Lane 2: BnROD1-A1; Lane 3: BnROD1-C1; lane 4: BnROD1-C1 mutant HIOL311; lane 5: BnROD1-C1 mutant HIOL314; Lane 6: BnROD1-C1 mutant HIOL315; Lane7: BnROD1-C1 mutant HIOL310; lane 8: BnROD1-C1 mutant HIOL313; lane 9: BnROD1-C1 mutant HIOL309; lane 10: PC. Arrows at the left: upper arrows indicate $^{14}$C Di 18:1-DAG; middle arrows indicate $^{14}$C Di 18:1-PC; lower arrows indicate the origin.

The results of the activity assays of the ROD1 alleles are shown in FIGS. 2a, b and c and Table 3. From FIG. 2a and Table 3, Experiment I, it can be seen that BnROD1-A1 and BnROD1-C1 have activity, whereas no activity of the BnROD1-A2 and BnROD1-C2 could be detected. These results indicate that BnROD1-A1 and BnROD1-C1 are the only functional homologs of the Arabidopsis ROD1 in Brassica napus. As the BnROD1-A3, BnROD1-C3, BnROD1-A4 and BnROD1-C4 have an even lower sequence identity to BnROD1-A1 and BnROD1-C1, it is likely that these copies also represent non-functional homologs of ROD1. Consequently, it is conceivable that BrROD1-1, which is the B. rapa ortholog of BnROD1-A1, and BoROD1-1, which is the B. oleracea ortholog of BnROD1-C1, are the functional homologs of the Arabidopsis ROD1 in B. rapa and B. oleracea, respectively.

From FIG. 2b and Table 3, Experiment II, it can be seen that the mutants of BnROD1-A1 HIOL306, HOIL307, and HIOL302 have no detectable activity, whereas the BnROD1-A1 mutant HIOL305 has reduced activity as compared to BnROD1-A1. FIG. 2c and Table 3, Experiment III show that the mutants of BnROD1-C1 HIOL311 and HIOL309 have activities comparable to wild-type BnROD1-C1, that HIOL315 has reduced activity, and that HIOL310, HIOL314, and HIOL313 have no detectable activity.

TABLE 3

Relative activity of Brassica ROD1 wild-type and mutant alleles. Values represent counts per minute (cpm) in PC.
AtROD1 = ROD1 from *Arabidopsis thaliana*.
BnROD1 = ROD1 from *Brassica napus*.
DAG = Diacylglycerol; PC = phosphatidylcholine

| Experiment I | | Experiment II | | Experiment III | |
|---|---|---|---|---|---|
| DAG | 304 | DAG | 270 | DAG | 93 |
| AtROD1 (1) | 12490 | Neg. control | 415 | BnROD1-A1 | 3306 |
| AtROD1 (2) | 9212 | AtROD1 boiled | 99 | BnROD1-C1 | 2554 |
| BnROD1-A1 | 3538 | AtROD1 | 8160 | HIOL311 | 3425 |
| BnROD1-A2 | 95 | BnROD1-A1 | 3519 | HIOL314 | 66 |
| BnROD1-C1 | 1191 | HIOL305 | 455 | HIOL315 | 387 |
| BnROD1-C2 | 79 | HIOL306 | 116 | HIOL310 | 84 |
| PC | 60 | HIOL307 | 92 | HIOL313 | 55 |
| | | HIOL302 | 96 | HIOL309 | 4434 |
| | | BnROD1-A2 | 75 | PC | 65 |
| | | BnROD1-C2 | 66 | | |

Example 5—Downreulation of BnROD1 in *Brassica napus*

The *Brassica* ROD1 genes were downregulated in *Brassica napus* using hairpin constructs of ROD1.

Construction of the ROD1 Hairpin Constructs

Host *Escherichia coli* strains were TOP10 (with Gateway entry and expression clones) or DB3.1 (with pHELLS-GATE12 destination vector; Invitrogen). Bacterial cultures were grown at 37° C. in Luria broth medium with appropriate antibiotics.

Generation of BnROD1 hpRNA Suppression Constructs:

To specifically knock down the expression of BnROD1-A1 and BnROD1-C1, a hairpin construct was generated (ROD1-Bn1) which contains no more than 20 bp identical between BnROD1-A1 or C1 and other BnROD1 homologs. Therefore, a 278 bp fragment from 29 to 300 of BnROD1 was amplified by PCR using primers BnROD1 F1 (29-53): caccGTCGCAGATCTAACGGATATCACAC (forward) (SEQ ID No. 43) and BnROD1 R1 (276-300): AATATC-GAACGGCTCAGACTTCGCC (reverse) (SEQ ID No. 44). For knocking down all BnROD1 members, a hairpin construct ROD1-Bn2 was created. Therefore, a 561 bp fragment from 289 to 849 of BnROD1 was amplified by PCR using primers: BnROD1 F2 (289-311): caccCCGTTCGATAT-TGGGTTTGTG (SEQ ID No. 45) and BnROD1 R2 (827-849): TTAATTGACTAGCGAGTCTTTAG (SEQ ID No. 46).

Each DNA fragment was amplified by PCR on BnROD1-A1 DNA as template: The PCR reaction (50 µl) contained 0.3 µM of each primer, 2 ng/µL template DNA, 0.2 mM of dNTP mix, 0.02 unit/µL of KOD DNA polymerase (Toyobo), 5 µl of 10×PCR buffer, and 1.5 mM MgSO4. Programmed cycles were as follows: 2 min initial denaturing step at 95° C.; 40 cycles of 20 s denaturation at 95° C., 15 s annealing at 55° C., 20 s extension at 70° C. PCR products were purified with QIAquick Gel Extraction Kit (QIAGEN) and ligated into the pENTR™/D-TOPO® cloning vector (Invitrogen) to generate entry clones according to the manual's instruction. To generate hairpin constructs, 100 ng BnROD1 entry clone and 150 ng pHELLSGATE12 destination vector were mixed, and LR recombination reaction was conducted using Gateway® LR Clonase™ Enzyme following the manual's instruction (Invitrogen). After transformation into TOP10 competent cells, clones were screened by restriction analysis to identify plasmids with the expected insert in the correct orientation, and then were validated by sequencing.

Transformation vectors were obtained by extracting the hairpin region from the above hairpin constructs and placing this cassette into a transformation vector under control of the Cauliflower Mosaic Virus 35S promoter containing bar as selectable marker. The resulting vector pTCO363 contains the ROD1-Bn1 hairpin construct (to specifically knock down the expression of BnROD1-A1 and BnROD1-C1), and the resulting vector pTCO364 contains the ROD1-Bn2 hairpin construct (to knock down all *Brassica napus* ROD1 members).

The sequence of the expression cassette of the ROD1-Bn1 hairpin of pTCO363 is given in SEQ ID No. 47, and the sequence of the expression cassette of the ROD1-Bn2 hairpin of pTCO364 is given in SEQ ID No. 48.

Additional transformation vectors were obtained by extracting the hairpin region from the above hairpin constructs and placing this cassette into a transformation vector under control of the seed-specific Oleosin promoter containing bar as selectable marker.

Transformation of *Brassica napus* with the ROD1 Hairpin Constructs

The above-mentioned vectors pTCO363 and pTCO364 were used for transformation of *Brassica napus* using the hypocotyl transformation protocol essentially as described by De Block et al. (1989), Plant Physiol. 91: 694).

Single-copy regenerated *B. napus* transformation events were back-crossed with a *B. napus* (elite) line. Following 2 rounds of selfing seeds from both homozygous transformation events and wild type segregants were harvested for subsequent seed oil analysis.

Oil Composition in Seeds from *Brassica napus* Transformed with the ROD1 Hairpin Constructs The fatty acid composition of the seed oil of individual progeny *Brassica* plants for homozygous transformation events and the corresponding wild type segregants as well as the non-transformed reference line grown in the greenhouse was determined by extracting the fatty acyls from the seeds and analyzing their relative levels in the seed oil by capillary gas-liquid chromatography as described in WO09/007,091.

Figure 3:
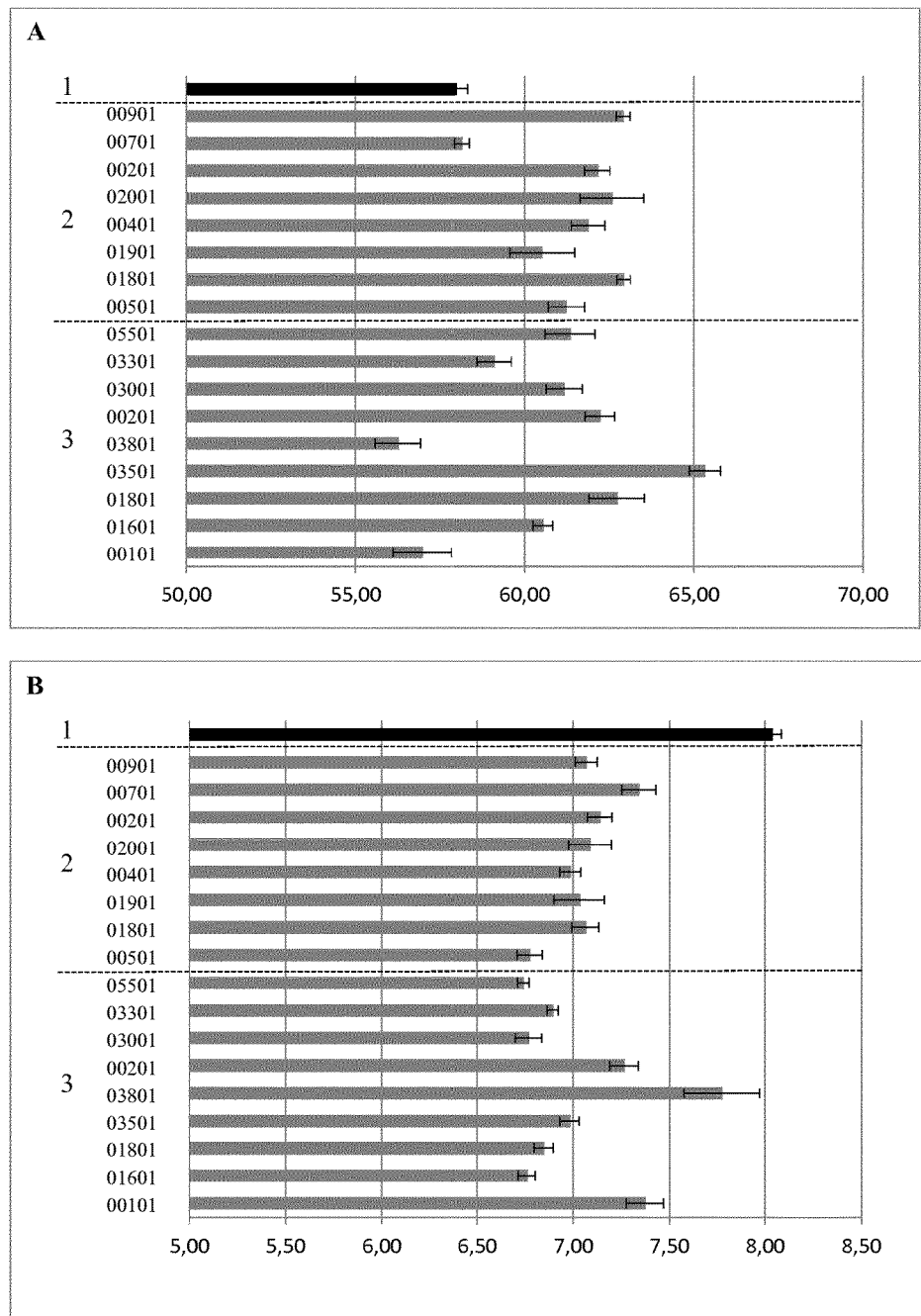
FIG. 3. Levels of C18:1, SATS (C16:0, C18:0, C20:0, C22:0 and C24:0), and correlation between C18:1 and C18:2 in transformants with ROD1 hairpin constructs, T1S1 seeds. All levels are in weight percentages. A: Levels of C18:1. 1: wild-type control, 2: Different lines transformed with ROD1-Bn2 (general) hairpin constructs; 3: Different lines transformed with ROD1-Bn1 (specific) hairpin. B: Levels of SATS (C16:0, C18:0, C20:0, C22:0 and C24:0). 1: wild-type control, 2: Different lines transformed with ROD1-Bn2 (general) hairpin constructs; 3: Different lines transformed with ROD1-Bn1 (specific) hairpin. C: correlation between C18:1 and C18:2. C18:2 levels are plotted against C18:1 levels in seeds from different transformants with ROD1-Bn2 (general) hairpin or ROD1-Bn1 (specific) hairpin constructs. Linear regression was calculated having the equation y=−0.6961x+63.183, with R square value of 0.8643.

FIG. 3a shows that in the T1S1 generation of seeds, which contains a mixture of homozygous, hemizygous seeds and wild-type segregants, both for the ROD1-Bn1 (specific) and ROD1-Bn2 (general) hairpin constructs, most of the plants have significantly increased levels of C18:1 in their seeds. The levels of saturated fatty acids (SATS; C16:0, C18:0, C20:0, C22:0, C24:0) in seeds of most plants containing ROD1-Bn1 (specific) and ROD1-Bn2 (general) hairpin constructs are decreased (FIG. 3b). When the C18:2 levels are plotted against the C18:1 levels of the different plants, it is clear that there is a negative correlation between C18:1 and C18:2 levels: the higher the levels of C18:1, the lower the levels of C18:2 (FIG. 3c).

Figure 4:
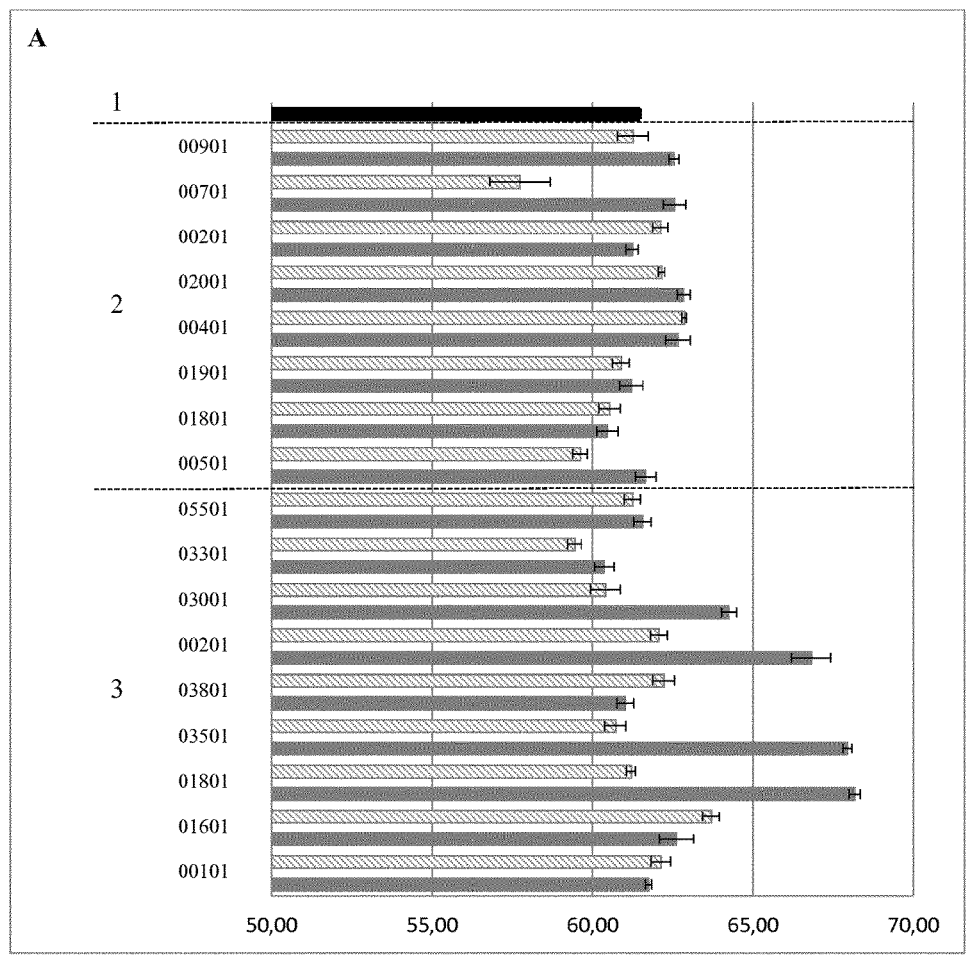
FIG. 4. Levels of C18:1 and SATS (C16:0, C18:0, C20:0, C22:0 and C24:0) in transformants with ROD1 hairpin constructs, T1S2 seeds. All levels are in weight percentages. A: Levels of C18:1 of transformed plants (gray bars) as compared to their wild-type segregants (diagonally striped bars). 1: wild-type control, 2: Different lines transformed with ROD1-Bn2 (general) hairpin constructs; 3: Different lines transformed with ROD1-Bn1 (specific) hairpin. B: Levels of SATS (C16:0, C18:0, C20:0, C22:0 and C24:0) of transformed plants (gray bars) as compared to their wild-type segregants (diagonally striped bars). 1: wild-type control, 2: Different lines transformed with ROD1-Bn2 (general) hairpin constructs; 3: Different lines transformed with ROD1-Bn1 (specific) hairpin.

In the T1S2 generation of seeds, in which all seeds are homozygous for the hairpin constructs, use of both hairpin constructs results in transformation events with increased levels of C18:1 in the seed lipids compared to the wild type segregant or the reference line. However, surprisingly, transformation with the ROD1-Bn1 (specific) hairpin construct resulted in events with seed C18:1 levels exceeding those in any of the events obtained with the ROD1-Bn1 (general) (FIG. 4a and Table 4). Further, in the T1S2 generation of seeds, the levels of SATS were reduced in seeds of some of the plants containing the ROD1-Bn1 (specific) and in some of the plants containing the ROD1-Bn2 (general) hairpin construct (FIG. 4b and Table 4).

These results show that downregulation of the BnROD1-A1 and/or BnROD1-C1 alleles contributes significantly to the increase of C18:1 levels in the seed lipid fraction, whereas downregulation of the other ROD1 alleles of *Brassica napus* does not result in a further increase of C18:1 levels. In support to this, no increase in C18:1 levels was observed in homozygous seeds where all *B. napus* ROD1 alleles were downregulated as compared to homozygous seeds in which only the ROD1-A1 and ROD1-C1 alleles were downregulated.

TABLE 4a levels of C18:1, C18:2 and SATS in greenhouse homozygous plants (HH) and wild-type segregants (WTS) transformed with ROD1 hairpin constructs in weight percentages (Wt %) of total weight of seed fatty acids

|   | Line | C18:1 (Wt %) | C18:2 (Wt %) | SATS (Wt %) |
|---|---|---|---|---|
| BnROD1-Bn1 (specific) hairpin construct | 00101-HH | 61.75 | 19.34 | 7.22 |
| | 00101-WTS | 62.13 | 18.91 | 7.31 |
| | 01601-HH | 62.61 | 18.07 | 7.03 |
| | 01601-WTS | 63.69 | 16.87 | 7.05 |
| | 01801-HH | 68.17 | 13.01 | 7.20 |
| | 01801-WTS | 61.20 | 19.11 | 7.39 |
| | 03501-HH | 67.95 | 13.52 | 7.09 |
| | 03501-WTS | 60.72 | 19.96 | 7.25 |
| | 03801-HH | 61.02 | 19.32 | 7.40 |
| | 03801-WTS | 62.22 | 18.43 | 7.38 |
| | 00201-HH | 66.82 | 14.73 | 7.27 |
| | 00201-WTS | 62.06 | 18.83 | 7.38 |
| | 03001-HH | 64.25 | 15.27 | 7.29 |
| | 03001-WTS | 60.40 | 19.41 | 7.14 |
| | 03301-HH | 60.37 | 19.69 | 7.20 |
| | 03301-WTS | 59.45 | 20.46 | 7.21 |
| | 05501-HH | 61.56 | 19.83 | 6.99 |
| | 05501-WTS | 61.24 | 19.76 | 7.15 |
| BnROD1-Bn2 (general) hairpin construct | 00501-HH | 61.65 | 19.84 | 7.17 |
| | 00501-WTS | 59.62 | 21.32 | 7.49 |
| | 01801-HH | 60.46 | 20.79 | 7.44 |
| | 01801-WTS | 60.53 | 20.62 | 7.44 |
| | 01901-HH | 61.21 | 20.26 | 7.28 |
| | 01901-WTS | 60.89 | 20.74 | 7.15 |
| | 00401-HH | 62.66 | 18.30 | 7.06 |
| | 00401-WTS | 62.85 | 17.84 | 7.53 |
| | 02001-HH | 62.84 | 18.12 | 7.30 |
| | 02001-WTS | 62.14 | 18.39 | 7.42 |
| | 00201-HH | 61.24 | 19.58 | 7.47 |
| | 00201-WTS | 62.12 | 18.76 | 7.46 |
| | 00701-HH | 62.56 | 18.43 | 7.14 |
| | 00701-WTS | 57.75 | 21.83 | 7.51 |
| | 00901-HH | 62.54 | 18.44 | 7.32 |
| | 00901-WTS | 61.25 | 19.35 | 7.22 |
| | Wild-type control | 61.45 | 19.05 | 7.45 |

TABLE 4b

Change in C18:1, C18:2 and SATS levels in homozygous plants transformed with ROD1 hairpin constructs relative to wild-type segregants (% versus wild-type segregant level)

|   | Line | C18:1 (%) | C18:2 (%) | SATS (%) |
|---|---|---|---|---|
| BnROD1-Bn1 (specific) hairpin | 00101 | −0.61 | 2.27 | −1.30 |
| | 01601 | −1.69 | 7.11 | −0.31 |
| | 01801 | 11.39 | −31.96 | −2.54 |
| | 03501 | 11.91 | −32.28 | −2.23 |
| | 03801 | −1.93 | 4.83 | 0.35 |
| | 00201 | 7.67 | −21.79 | −1.54 |
| | 03001 | 6.37 | −21.35 | 2.10 |
| | 03301 | 1.54 | −3.75 | −0.22 |
| | 05501 | 0.51 | 0.34 | −2.24 |
| BnROD1-Bn2 (general) hairpin construct | 00501 | 3.41 | −6.94 | −4.30 |
| | 01801 | −0.11 | 0.82 | 0.11 |
| | 01901 | 0.52 | −2.31 | 1.90 |
| | 00401 | −0.31 | 2.57 | −6.29 |
| | 02001 | 1.11 | −1.48 | −1.64 |
| | 00201 | −1.41 | 4.39 | 0.08 |
| | 00701 | 8.33 | −15.56 | −4.82 |
| | 00901 | 2.10 | −4.73 | 1.41 |

Example 6—Oil Composition in Seeds from *Brassica napus* Comprising BnROD1-A1 and BnROD1-C1 Knock-Out Alleles Grown in the Greenhouse

*Brassica* plants comprising mutant ROD1-A1 and ROD1-C1 alleles were crossed. Following 2 rounds of selfing seeds from plants homozygous for ROD1-A1 and ROD1-C1 mutations, for the ROD1-A1 mutation, for the ROD1-C1 mutation or wild type segregants (i.e. not comprising any mutant ROD1 allele that would impact the normal function of a ROD1 protein) were obtained based on molecular marker based selection of plants (see below).

Fatty acid composition was determined from plants grown in the greenhouse as described above in F1S2 seeds of the *Brassica* lines with mutant BnROD1-A1, BnROD1-C1, and combinations thereof. For each combination of mutants, oil composition was determined in wild-type segregants not comprising the respective mutations in BnROD1-A1 and BnROD1-C1, in lines homozygous for either the mutant BnROD1-A1 or for the mutant BnROD1-C1 allele, and in lines homozygous for both mutants BnROD1-A1 and BnROD1-C1.

Figure 5:
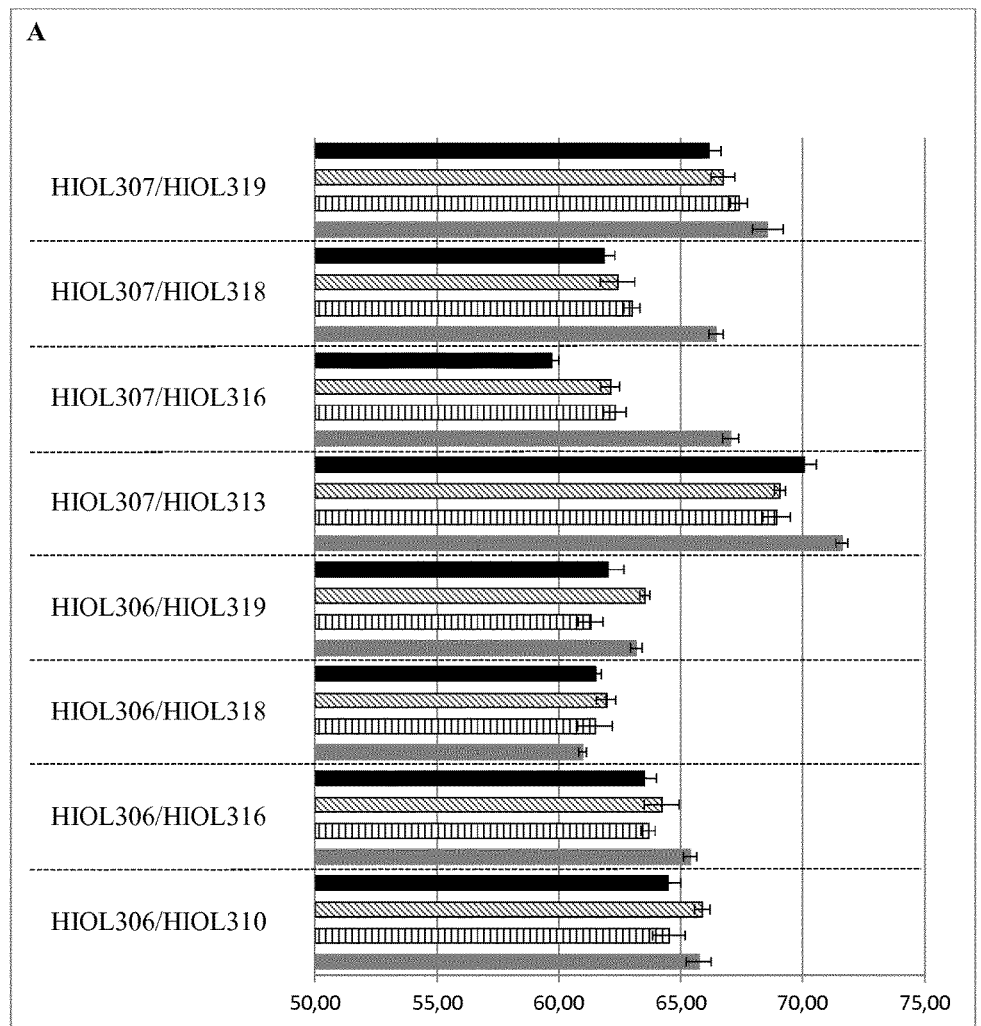
FIG. 5. Levels of C18:1 and SATS (C16:0, C18:0, C20:0, C22:0 and C24:0) in ROD1 in T1S2 seeds of EMS mutants of ROD1-A1 and ROD1-C1 and combinations thereof. All levels are in weight percentages. A: Levels of C18:1 of wild-type segregants (black bars), homozygous single mutants, C1 only (diagonally striped bars), homozygous single mutants A1 only (vertically striped bars), and homozygous double mutants A1 and C1 (gray bars). Mutant alleles in ROD1-A1 and ROD1-C1 are indicated at the left. B: Levels of SATS (C16:0, C18:0, C20:0, C22:0 and C24:0) of wild-type segregants (black bars), homozygous single mutants, C1 only (diagonally striped bars), homozygous single mutants A1 only (vertically striped bars), and homozygous double mutants A1 and C1 (gray bars). Mutant alleles in ROD1-A1 and ROD1-C1 are indicated at the left.

FIG. 5a shows the levels of C18:1 in the mutant and wild-type lines (see also Table 5a and 4b). It can be seen that in several lines with homozygous single mutants, both in BnROD1-A1 and in BnROD1-C1, levels of C18:1 are significantly increased as compared to the wild-type segregant. Furthermore, this figure shows that in all double mutant lines except one (HIOL306/HIOL318), the levels of C18:1 are significantly increased as compared to wild-type. The highest level of C18:1, 71.6%, is observed in lines comprising the HIOL307/HIOL313 mutant.

FIG. 5b shows the levels of SATS in the different mutant and wild-type lines (see also Table 5a and 5b). In some of the mutant lines, a significant reduction of SATS is observed as compared to wild-type.

TABLE 5a

Levels of C18:1, C18:2 and SATS in F1S2 seeds of EMS mutants of BnROD1-A1 and BnROD1-C1 and combinations thereof grown in the greenhouse. All levels are in weight percentages. (--/--) refers to wild-type segregant; (--/C1C1) refers to homozygous single mutant, C1 only; (A1A1/--) refers to homozygous single mutant, A1 only; (A1A1/C1C1) refers to double homozygous mutant A1 and C1

| Mutant | | C18:1 (WT %) | C18:2 (WT %) | SATS (WT %) |
|---|---|---|---|---|
| HIOL306/HIOL310 | (A1A1/C1C1) | 65.72 | 17.94 | 7.04 |
| | (A1A1/--) | 64.50 | 18.88 | 7.23 |
| | (--/C1C1) | 65.86 | 17.24 | 7.40 |
| | (--/--) | 64.48 | 18.49 | 7.30 |
| HIOL306/HIOL316 | (A1A1/C1C1) | 65.38 | 17.14 | 6.89 |
| | (A1A1/--) | 63.66 | 18.72 | 7.00 |
| | (--/C1C1) | 64.21 | 18.36 | 6.97 |
| | (--/--) | 63.52 | 18.86 | 7.02 |
| HIOL306/HIOL318 | (A1A1/C1C1) | 60.97 | 20.69 | 7.00 |
| | (A1A1/--) | 61.48 | 20.73 | 7.03 |
| | (--/C1C1) | 61.94 | 19.82 | 7.31 |
| | (--/--) | 61.50 | 20.45 | 7.37 |
| HIOL306/HIOL319 | (A1A1/C1C1) | 63.16 | 19.91 | 7.44 |
| | (A1A1/--) | 61.30 | 21.10 | 7.47 |
| | (--/C1C1) | 63.52 | 20.11 | 7.58 |
| | (--/--) | 62.02 | 21.38 | 7.50 |
| HIOL307/HIOL313 | (A1A1/C1C1) | 71.60 | 10.84 | 7.73 |
| | (A1A1/--) | 68.93 | 13.84 | 7.37 |
| | (--/C1C1) | 69.06 | 13.70 | 7.15 |
| | (--/--) | 70.07 | 13.17 | 7.29 |
| HIOL307/HIOL316 | (A1A1/C1C1) | 67.03 | 13.84 | 8.01 |
| | (A1A1/--) | 62.29 | 19.08 | 7.71 |
| | (--/C1C1) | 62.10 | 19.44 | 7.85 |
| | (--/--) | 59.71 | 20.72 | 7.82 |
| HIOL307/HIOL318 | (A1A1/C1C1) | 66.43 | 16.08 | 7.34 |
| | (A1A1/--) | 63.00 | 19.57 | 7.03 |
| | (--/C1C1) | 62.40 | 19.37 | 7.60 |
| | (--/--) | 61.87 | 20.34 | 7.41 |
| HIOL307/HIOL319 | (A1A1/C1C1) | 68.56 | 14.47 | 7.01 |
| | (A1A1/--) | 67.37 | 15.75 | 6.96 |
| | (--/C1C1) | 66.70 | 16.56 | 7.01 |
| | (--/--) | 66.15 | 16.87 | 6.90 |

TABLE 5b

Change in C18:1, C18:2 and SATS levels in ROD1 mutants relative to wild-type segregants in F1S2 seeds of EMS mutants of BnROD1-A1 and BnROD1-C1 and combinations thereof grown in the greenhouse. (--/C1C1) refers to homozygous single mutant, C1 only; (A1A1/--) refers to homozygous single mutant, A1 only; (A1A1/C1C1) refers to double homozygous mutant A1 and C1. Changes are expressed as % relative to the wild-type segregant

| Mutant | | C18:1 (WT%) | C18:2 (WT%) | SATS (WT%) |
|---|---|---|---|---|
| HIOL306/HIOL310 | (A1A1/C1C1) | 1.92 | -2.96 | -3.62 |
| | (A1A1/--) | 0.03 | 2.08 | -0.99 |
| | (--/C1C1) | 2.14 | -6.76 | 1.40 |
| HIOL306/HIOL316 | (A1A1/C1C1) | 2.93 | -9.09 | -1.77 |
| | (A1A1/--) | 0.22 | -0.72 | -0.29 |
| | (--/C1C1) | 1.10 | -2.65 | -0.60 |
| HIOL306/HIOL318 | (A1A1/C1C1) | -0.87 | 1.14 | -5.10 |
| | (A1A1/--) | -0.04 | 1.35 | -4.67 |
| | (--/C1C1) | 0.72 | -3.08 | -0.84 |
| HIOL306/HIOL319 | (A1A1/C1C1) | 1.84 | -6.90 | -0.75 |
| | (A1A1/--) | -1.16 | -1.31 | -0.37 |
| | (--/C1C1) | 2.42 | -5.96 | 1.12 |
| HIOL307/HIOL313 | (A1A1/C1C1) | 2.20 | -17.64 | 6.03 |
| | (A1A1/--) | -1.63 | 5.15 | 1.07 |
| | (--/C1C1) | -1.43 | 4.04 | -2.03 |
| HIOL307/HIOL316 | (A1A1/C1C1) | 12.27 | -33.20 | 2.43 |
| | (A1A1/--) | 4.33 | -7.91 | -1.36 |
| | (--/C1C1) | 4.01 | -6.20 | 0.36 |
| HIOL307/HIOL318 | (A1A1/C1C1) | 7.37 | -20.91 | -0.94 |
| | (A1A1/--) | 1.82 | -3.76 | -5.13 |
| | (--/C1C1) | 0.85 | -4.74 | 2.56 |
| HIOL307/HIOL319 | (A1A1/C1C1) | 3.65 | -14.22 | 1.51 |
| | (A1A1/--) | 1.85 | -6.64 | 0.81 |
| | (--/C1C1) | 0.84 | -1.85 | 1.54 |

Taken together, the data show that C18:1 levels can be increased, and the levels of SATS can be decreased in *Brassica* seeds by downregulation of expression of the *Brassica napus* ROD1-A1 and ROD1-C1 gene, or by knocking out the *Brassica napus* ROD1-A1 gene, the *Brassica napus* ROD1-C1 gene, or both.

Example 7—Oil Composition in Seeds from *Brassica napus* Comprising BnROD1-A1 and BnROD1-C1 Knock-Out Alleles Grown in the Field Fatty acid composition was determined from plants grown in the field as described above in seeds of the *Brassica* lines with mutant BnROD1-A1, BnROD1-C1, and combinations thereof. For each combination of mutants, oil composition was determined in wild-type segregants not comprising the respective mutations in BnROD1-A1 and BnROD1-C1, in lines homozygous for either the mutant BnROD1-A1 or for the mutant BnROD1-C1 allele, and in lines homozygous for both mutants BnROD1-A1 and BnROD1-C1. The mutant genotypes were tested at 3 different geographic locations. Three repeats per location were produced. Seed quality parameters were obtained through GC analysis. For the statistical analysis an ANOVA test was run. Contrasts between the mutant lines versus the corresponding null-segregants were subject to significance testing. For the statistical analysis of the key parameter, oleic acid (C18:1), a mixed model with heterogeneous variances between locations was applied. Control refers to a reference *B. napus* genotype that was not subject to EMS treatment.

Table 6a shows the levels of C18:1 in the mutant and wild-type lines. Table 6b shows the differences in C18:1 content in the mutant *B. napus* lines versus the corresponding wild type segregants (average of all locations and blocks).

TABLE 6a

C18:1 levels for genotype effects from plants grown in the field (average for all locations and blocks). (--/--) refers to wild-type segregant; (--/C1C1) refers to homozygous single mutant, C1 only; (A1A1/--) refers to homozygous single mutant, A1 only; (A1A1/C1C1) refers to double homozygous mutant A1 and C1

| Genotype | C18:1 (% of oil weight) | SE | Cl. lower | Cl. upper |
|---|---|---|---|---|
| HIOL306/310 (--/--) | 60.36 | 0.31 | 59.76 | 60.97 |
| HIOL306/310 (--/C1C1) | 60.36 | 0.31 | 59.75 | 60.96 |
| HIOL306/310 (A1A1/--) | 61.77 | 0.31 | 61.16 | 62.37 |
| HIOL306/310 (A1A1/C1C1) | 61.23 | 0.31 | 60.62 | 61.83 |
| HIOL306/316 (--/--) | 60.29 | 0.31 | 59.68 | 60.89 |

TABLE 6a-continued

C18:1 levels for genotype effects from plants grown in the field (average for all locations and blocks). (--/--) refers to wild-type segregant; (--/C1C1) refers to homozygous single mutant, C1 only; (A1A1/--) refers to homozygous single mutant, A1 only; (A1A1/C1C1) refers to double homozygous mutant A1 and C1

| Genotype | C18:1 (% of oil weight) | SE | Cl. lower | Cl. upper |
|---|---|---|---|---|
| HIOL306/316 (--/C1C1) | 60.68 | 0.31 | 60.07 | 61.28 |
| HIOL306/316 (A1A1/--) | 59.52 | 0.31 | 58.91 | 60.12 |
| HIOL306/316 (A1A1/C1C1) | 61.49 | 0.31 | 60.89 | 62.10 |
| HIOL306/318 (--/--) | 56.45 | 0.31 | 55.85 | 57.06 |
| HIOL306/318 (--/C1C1) | 58.11 | 0.31 | 57.50 | 58.71 |
| HIOL306/318 (A1A1/--) | 56.92 | 0.31 | 56.32 | 57.53 |
| HIOL306/318 (A1A1/C1C1) | 57.04 | 0.31 | 56.43 | 57.64 |
| HIOL306/319 (--/--) | 57.50 | 0.31 | 56.89 | 58.10 |
| HIOL306/319 (--/C1C1) | 60.68 | 0.31 | 60.08 | 61.28 |
| HIOL306/319 (A1A1/--) | 56.29 | 0.31 | 55.68 | 56.89 |
| HIOL306/319 (A1A1/C1C1) | 58.74 | 0.31 | 58.13 | 59.34 |
| HIOL307/313 (--/--) | 64.54 | 0.31 | 63.93 | 65.14 |
| HIOL307/313 (--/C1C1) | 65.56 | 0.31 | 64.96 | 66.17 |
| HIOL307/313 (A1A1/--) | 65.41 | 0.31 | 64.80 | 66.01 |
| HIOL307/313 (A1A1/C1C1) | 67.70 | 0.31 | 67.10 | 68.31 |
| HIOL307/316 (--/--) | 57.72 | 0.31 | 57.12 | 58.33 |
| HIOL307/316 (--/C1C1) | 59.99 | 0.31 | 59.39 | 60.59 |
| HIOL307/316 (A1A1/--) | 59.50 | 0.31 | 58.90 | 60.11 |
| HIOL307/316 (A1A1/C1C1) | 63.63 | 0.31 | 63.02 | 64.23 |
| HIOL307/318 (--/--) | 56.99 | 0.31 | 56.38 | 57.59 |
| HIOL307/318 (--/C1C1) | 57.79 | 0.31 | 57.19 | 58.40 |
| HIOL307/318 (A1A1/--) | 60.15 | 0.31 | 59.55 | 60.75 |
| HIOL307/318 (A1A1/C1C1) | 62.72 | 0.31 | 62.12 | 63.33 |
| HIOL307/319 (--/--) | 62.64 | 0.31 | 62.03 | 63.24 |
| HIOL307/319 (--/C1C1) | 63.77 | 0.31 | 63.17 | 64.38 |
| HIOL307/319 (A1A1/--) | 62.91 | 0.31 | 62.31 | 63.51 |
| HIOL307/319 (A1A1/C1C1) | 65.42 | 0.31 | 64.82 | 66.03 |
| 98-55-013 | 61.09 | 0.22 | 60.66 | 61.52 |

TABLE 6b

Differences in C18:1 content in the mutant *B. napus* lines versus the corresponding wild type segregants from plants grown in the field (average of all locations and blocks)

| Genotype | C18_1 difference (% of oil weight) | SE | CI.lower | CI.upper |
|---|---|---|---|---|
| HIOL306/310 (--/C1C1) vs HIOL306/310 (--/--) | 0.00 | 0.44 | −0.86 | 0.85 |
| HIOL306/310 (A1A1/--) vs HIOL306/310 (--/--) | 1.40 | 0.44 | 0.55 | 2.26 |
| HIOL306/310 (A1A1/C1C1) vs HIOL306/310 (--/--) | 0.86 | 0.44 | 0.01 | 1.72 |
| HIOL306/316 (--/C1C1) vs HIOL306/316 (--/--) | 0.39 | 0.44 | −0.46 | 1.25 |
| HIOL306/316 (A1A1/--) vs HIOL306/316 (--/--) | −0.77 | 0.44 | −1.62 | 0.09 |
| HIOL306/316 (A1A1/C1C1) vs HIOL306/316 (--/--) | 1.21 | 0.44 | 0.35 | 2.06 |
| HIOL306/318 (--/C1C1) vs HIOL306/318 (--/--) | 1.66 | 0.44 | 0.80 | 2.51 |
| HIOL306/318 (A1A1/--) vs HIOL306/318 (--/--) | 0.47 | 0.44 | −0.38 | 1.33 |
| HIOL306/318 (A1A1/C1C1) vs HIOL306/318 (--/--) | 0.59 | 0.44 | −0.27 | 1.44 |
| HIOL306/319 (--/C1C1) vs HIOL306/319 (--/--) | 3.18 | 0.44 | 2.33 | 4.03 |
| HIOL306/319 (A1A1/--) vs HIOL306/319 (--/--) | −1.21 | 0.44 | −2.07 | −0.36 |
| HIOL306/319 (A1A1/C1C1) vs HIOL306/319 (--/--) | 1.24 | 0.44 | 0.39 | 2.09 |
| HIOL307/313 (--/C1C1) vs HIOL307/313 (--/--) | 1.02 | 0.44 | 0.17 | 1.88 |
| HIOL307/313 (A1A1/--) vs HIOL307/313 (--/--) | 0.87 | 0.44 | 0.02 | 1.72 |
| HIOL307/313 (A1A1/C1C1) vs HIOL307/313 (--/--) | 3.17 | 0.44 | 2.31 | 4.02 |
| HIOL307/316 (--/C1C1) vs HIOL307/316 (--/--) | 2.27 | 0.44 | 1.41 | 3.12 |
| HIOL307/316 (A1A1/--) vs HIOL307/316 (--/--) | 1.78 | 0.44 | 0.93 | 2.64 |
| HIOL307/316 (A1A1/C1C1) vs HIOL307/316 (--/--) | 5.90 | 0.44 | 5.05 | 6.76 |
| HIOL307/318 (--/C1C1) vs HIOL307/318 (--/--) | 0.81 | 0.44 | −0.05 | 1.66 |
| HIOL307/318 (A1A1/--) vs HIOL307/318 (--/--) | 3.16 | 0.44 | 2.31 | 4.02 |
| HIOL307/318 (A1A1/C1C1) vs HIOL307/318 (--/--) | 5.74 | 0.44 | 4.88 | 6.59 |
| HIOL307/319 (--/C1C1) vs HIOL307/319 (--/--) | 1.14 | 0.44 | 0.28 | 1.99 |
| HIOL307/319 (A1A1/--) vs HIOL307/319 (--/--) | 0.27 | 0.44 | −0.58 | 1.13 |
| HIOL307/319 (A1A1/C1C1) vs HIOL307/319 (--/--) | 2.79 | 0.44 | 1.93 | 3.64 |

The data obtained in the field confirm the data obtained in the greenhouse that the presence of a mutant allele of BnROD1-A1 and BnROD1-C1 can increase the levels of C18:1. The combination of the BnROD1-A1 allele HIOL307 with a BnROD1-C1 mutant allele even has a synergistic effect on the level of C18:1 in the seed oil. The highest increase in levels of C18:1 is observed in lines with a combination of HIOL307 and HIOL316 mutations (5.90% increase), and in lines with a combination of HIOL307 and HIOL318 mutations (5.74% increase).

Example 8—Detection and/or Transfer of Mutant ROD1 Alleles into (Elite) *Brassica* Lines The mutant ROD1 genes are transferred into (elite) *Brassica* breeding lines by the following method: A plant containing a mutant ROD1 gene (donor plant), is crossed with an (elite) *Brassica* line (elite parent/recurrent parent) or variety lacking the mutant ROD1 gene. The following introgression scheme is used (the mutant ROD1 allele is abbreviated to rod1 while the wild type is depicted as ROD1):

BC1 cross: rod1/rod1 (donor plant)×ROD1/ROD1 (elite parent)
F1 plant: ROD1/rod1
BC2 cross: ROD1/rod1×ROD1/ROD1 (recurrent parent)
BC2 plants: 50% ROD1/rod1 and 50% ROD1/ROD1

The 50% ROD1/rod1 are selected using molecular markers (e.g. AFLP, PCR, Invader™, TaqMan®, KASP assay, and the like; see also below) for the mutant ROD1 allele (rod1).
BC3 cross: ROD1/rod1 (BC1 plant)×ROD1/ROD1 (recurrent parent)
BC3 plants: 50% ROD1/rod1 and 50% ROD1/ROD1

The 50% ROD1/rod1 are selected using molecular markers for the mutant ROD1 allele (rod1).
Backcrossing is repeated until BC4 to BC7.
BC4-7 plants: 50% ROD1/rod1 and 50% ROD1/ROD1
The 50% ROD1/rod1 are selected using molecular markers for the mutant ROD1 allele (rod1). To reduce the number of backcrossings (e.g. until BC4 instead of BC7), molecular markers can be used specific for the genetic background of the elite parent.
BC4-7 S1 cross: ROD1/rod1×ROD1/rod1
BC4-7 S1 plants: 25% ROD1/ROD1 and 50% ROD1/rod1 and 25% rod1/rod1
Plants containing rod1 are selected using molecular markers for the mutant ROD1 allele (rod1). Individual BC4-7 S1 or BC4-7 S2 plants that are homozygous for the mutant ROD1 allele (rod1/rod1) are selected using molecular markers for the mutant and the wild-type ROD1 alleles. These plants are then used for seed production.

To select for plants comprising a point mutation in a ROD1 allele, direct sequencing by standard sequencing techniques known in the art can be used.

Alternatively, Invader™ technology (Third Wave Agbio) can be used to discriminate plants comprising a specific point mutation in an ROD1 allele from plants not comprising that specific point mutation. Discriminating Invader™ probes are thus developed to detect the presence or absence and the zygosity status of mutant alleles identified in Example 3, based on the single nucleotide difference between the mutant and wildtype allele. Briefly, probes specific for the mutant or corresponding wild-type target ROD1 gene and "invading" probes which can be used in combination with them are developed. Generally, each probe set consists of one probe specific for the mutant or the wild type target gene of which the first nucleotide after the "5' flap" sequence matches with the nucleotide difference (the so-called "primary probe") and one probe specific for the nucleotides upstream of the nucleotide difference (the so-called "Invader® oligo"). The last nucleotide of the latter primer may match with the nucleotide difference in the mutant, but other nucleotides may be used as well for this last nucleotide as long as the primary probe and the Invader® oligo are still able to form a single base overlap when hybridized to the target DNA to generate the specific invasive structure recognized by the Cleavase® enzymes (Third Wave Agbio). The Invader™ assay procedure and interpretation of the data are performed as prescribed by the manufacturer (Third Wave Agbio). Briefly, 5' "flap" nucleotide sequences (flap1 for the mutant allele and flap2 for the wild-type allele) are cleaved from the primary probes in the primary phase of the Invader™ assay and are complementary to sequences in FRET™ cassette 1 and 2, respectively, and not complementary to the target mutant or wild type sequences. If the primary probes are cleaved in the primary phase and the flap1-probe and/or flap2-probe hybridise to FRET™ cassette 1 and 2, respectively, in the secondary phase, a signal is generated indicative of the presence in the sample of the mutant or corresponding wild-type target ROD1 gene, respectively.

Alternatively, KASP assays (KBioscience) can be used to discriminate plants comprising a specific point mutation in an ROD1 allele from plants not comprising that specific point mutation. Discriminating primers were developed to detect the presence or absence and the zygosity status of mutant alleles identified in Example 3, in particular of HIOL302, HIOL303, HIOL304, HIOL306, HIOL307, HIOL308, HIOL309, HIOL310, HIOL311, HIOL313, HIOL315 and HIOL316, HIOL318, and HIOL319.

Briefly, forward primers specific for the mutant or corresponding wild-type target ROD1 gene and a reverse primer that can be used in combination with them were developed. The nucleotide at the 3' end of the forward primers corresponds to the nucleotide which differs between the mutant and the corresponding wild-type allele. The primers can be used in combination with fluorescent dyes, such as FAM and VIC according to the protocol as described by the manufacturer (KBioscience).

Primers to detect the presence or absence and the zygosity status of the mutant ROD1 alleles are shown in Table 7.

TABLE 7

Forward (Fw) and reverse (Rv) primers to detect mutant ROD1 alleles and the corresponding wild-type alleles. FAM probe: wild-type allele, VIC probe: mutant allele

| Name | Primer | | SEQ ID |
|---|---|---|---|
| HIOL302 | Fw FAM | GTCTTCCTTCCATCAACCATGTCG | 49 |
|  | Fw VIC | GGTCTTCCTTCCATCAACCATGTTA | 50 |
|  | Rv | GTAGCGATGCAAACGACGTATATTGTAT | 51 |
| HIOL303 | Fw FAM | ATGCAAACGACGTATATTGTATGGACC | 52 |
|  | Fw VIC | GATGCAAACGACGTATATTGTATGGATT | 53 |
|  | Rv | TCGTGGTCTTCCTTCCATCAACCAT | 54 |
| HIOL304 | Fw FAM | AGATAGTGGCTCGTGGTCTTCCG | 55 |
|  | Fw VIC | GAGATAGTGGCTCGTGGTCTTCTA | 56 |
|  | Rv | CGTATATTGTATGGACATGGTTGATGGAA | 57 |
| HIOL306 | Fw FAM | GAAGGTGACCAAGTTCATGCTGGAAGGAAGACC ACGAGCCAC | 58 |
|  | Fw VIC | GAAGGTCGGAGTCAACGGATTGGAAGGAAGACC ACGAGCCAT | 59 |
|  | Rv | GAGCTGAGTAGAGTAACCAAGAATG | 60 |
| HIOL307 | Fw FAM | TGCTTCATGTTTACTTGTCGCGG | 61 |
|  | Fw VIC | GCTTGCTTCATGTTTACTTGTCGCAA | 62 |
|  | Rv | GGGAGCTGAGTAGAGTAACCAAGAA | 63 |

TABLE 7-continued

Forward (Fw) and reverse (Rv) primers to detect mutant ROD1 alleles and the corresponding wild-type alleles. FAM probe: wild-type allele, VIC probe: mutant allele

| Name | Primer | | SEQ ID |
|---|---|---|---|
| HIOL308 | Fw FAM | CATACAATATACGTCGTTTGCATCGCG | 64 |
| | Fw VIC | CATACAATATACGTCGTTTGCATCGTA | 65 |
| | Rv | TGGATGATGGGGACAGGTATTCGTA | 66 |
| HIOL309 | Fw FAM | GTATTCGTAGCGATGCAAACGACC | 67 |
| | Fw VIC | AGGTATTCGTAGCGATGCAAACGATT | 68 |
| | Rv | CCTTCCATCAACCATGTCCATACAATATA | 69 |
| HIOL310 | Fw FAM | GAAGGTGACCAAGTTCATGCTGTATATTGTATGGACATGGTTGATGG | 70 |
| | Fw VIC | GAAGGTCGGAGTCAACGGATTCGTATATTGTATGGACATGGTTGATGA | 71 |
| | Rv | AATATAAATATATTATAAGAGTGAGAGGTAGTATAATAT | 72 |
| HIOL311 | Fw FAM | ATGGACATGGTTGATGGAAGGAAGG | 73 |
| | Fw VIC | GTATGGACATGGTTGATGGAAGGAAAA | 74 |
| | Rv | ACAAGTAAACATGAAGCAAGCCGAGATA | 60 |
| HIOL313 | Fw FAM | GGCTTGCTTCATGTTTACTTGTCGG | 75 |
| | Fw VIC | CGGCTTGCTTCATGTTTACTTGTCAA | 76 |
| | Rv | GGGAGCTGAGTAGAGTAACCAAGAA | 63 |
| HIOL315 | Fw FAM | AAAGAGGTGGGAGACCTGTGGC | 77 |
| | Fw VIC | GTAAAGAGGTGGGAGACCTGTGAT | 78 |
| | Rv | TGGTTACTCTACTCAGCTCCCTCTA | 79 |
| HIOL316 | Fw FAM | AATATTTGTGTAAAGAGGTGGGAGACG | 80 |
| | Fw VIC | ATATAATATTTGTGTAAAGAGGTGGGAGATA | 81 |
| | Rv | TGGTTACTCTACTCAGCTCCCTCTA | 79 |
| HIOL318-HIOL319 | Fw FAM | ATGGTTGATGGAAGGAAGACCACC | 82 |
| | Fw VIC | ACATGGTTGATGGAAGGAAGACCATT | 83 |
| | Rv | ACAAGTAAACATGAAGCAAGCCGAGATA | 60 |

Example 9—Generation and Isolation of Mutant Brassica rapa ROD1 Alleles

Mutations in the ROD1 genes from Brassica rapa identified in Example 1 are generated and identified as described above for Brassica napus.

The DNA samples are screened for the presence of point mutations in the ROD1 genes causing the introduction of STOP codons in the protein-encoding regions of the BrROD1-1 gene, amino acid substitutions, or the disruption of splice sites in the BrROD1-1 mRNA, by direct sequencing by standard sequencing techniques and analyzing the sequences for the presence of the point mutations using the NovoSNP software.

Mutant Alleles of BrROD1-1 are Identified.

Oil composition is determined in seeds of the Brassica rapa lines with mutant BrROD1-1. The levels of C18:1 are increased in seeds of mutant Brassica rapa lines as compared to those of the wild-types, whereas levels of C18:2 and SATS are reduced.

Example 10—Generation and Isolation of Mutant Brassica oleracea ROD1 Alleles

Mutations in the ROD1 genes from Brassica oleracea identified in Example 1 are generated and identified as described above for Brassica napus.

The DNA samples are screened for the presence of point mutations in the ROD1 genes causing the introduction of STOP codons in the protein-encoding regions of the BoROD1-1 gene, amino acid substitutions, or the disruption of splice sites in the BoROD1-1 mRNA, by direct sequencing by standard sequencing techniques and analyzing the sequences for the presence of the point mutations using the NovoSNP software.

Mutant Alleles of BoROD1-1 are Identified.

Oil composition is determined in seeds of the Brassica oleracea lines with mutant BoROD1-1. The levels of C18:1 are increased in seeds of mutant Brassica oleracea lines as compared to those of the wild-types, whereas levels of C18:2 and SATS are reduced.

The invention claimed is:

1. Seed of *Brassica napus* line selected from the group consisting of:
   a) HIOL306, wherein representative samples of seeds of said line have been deposited at NCIMB under accession number NCIMB 41995,
   b) HIOL307, wherein representative samples of seeds of said line have been deposited at NCIMB under accession number NCIMB 42000,
   c) HIOL310, wherein representative samples of seeds of said line have been deposited at NCIMB under accession number NCIMB 41996,
   d) HIOL313, wherein representative samples of seeds of said line have been deposited at NCIMB under accession number NCIMB 42001,
   e) HIOL316, wherein representative samples of seeds of said line have been deposited at NCIMB under accession number NCIMB 41997,
   f) HIOL318, wherein representative samples of seeds of said line have been deposited at NCIMB under accession number NCIMB 41998, and
   g) HIOL319, wherein representative samples of seeds of said line have been deposited at NCIMB under accession number NCIMB 41999.

2. A plant grown from the seed of claim 1.

3. A cell of the plant of claim 2.

4. A method for producing oil, comprising harvesting seeds from the plant according to claim 2 and extracting the oil from said seeds.

5. A method of producing food, feed, or an industrial product comprising
   (a) obtaining the plant or a part thereof, of claim 1; and
   (b) preparing the food, feed or industrial product from the plant or part thereof.

6. The method of claim 5, wherein
   (a) the food or feed is oil, meal, grain, starch, flour or protein; or
   (b) the industrial product is biofuel, fiber, industrial chemicals, a pharmaceutical or a nutraceutical.

7. A method for determining the zygosity status of the mutant allele in a plant, cell, part, seed, or progeny produced from the seed of claim 1, comprising determining the presence of the induced mutation in the genomic DNA of said plant, cell, part, seed or progeny, wherein the induced mutation is selected from the group consisting of:
   ACT->ATT at corresponding position 700 of SEO ID NO: 2 (HIOL306),
   GGC-+AGC at corresponding position 732 of SEO ID NO: 2 (HIOL307),
   GAA-+AAA at corresponding position 675 of SEO ID NO: 5 (HIOL310),
   CGC-+CAC at corresponding position 724 of SEO ID NO: 5 (HIOL313),
   -GT->-AT at corresponding position 3046 of SEO ID NO: 4 (HIOL316),
   CGA->TGA at corresponding position 687 of SEO ID NO: 5 (HIOL318),
   CGA->TGA at corresponding position 687 of SEQ ID NO: S (HIOL319), or
   a combination thereof.

8. A method for transferring the knock-out allele from the plant of claim 2 to another plant comprising:
   (a) crossing the plant of claim 2 with a second plant not comprising the knock-out allele to produce seeds comprising the knock-out allele, (b) growing the seeds from step (a) to produce plants comprising the knock-out allele,
(c) backcrossing the plants comprising the knock-out allele with the second plant not comprising the knock-out allele for at least one generation (x) and collecting BCx seeds from the crosses, and
(d) identifying in every generation BCx plants comprising the knock-out allele and analyzing genomic DNA from the plants identified in step (d) for the presence of at least one molecular marker, wherein the at least one molecular marker is linked to said knock-out allele.

* * * * *